United States Patent [19]

Schmidt

[11] Patent Number: 5,699,268

[45] Date of Patent: Dec. 16, 1997

[54] COMPUTATIONAL METHOD FOR DESIGNING CHEMICAL STRUCTURES HAVING COMMON FUNCTIONAL CHARACTERISTICS

[75] Inventor: Jonathan M. Schmidt, Elora, Canada

[73] Assignee: University of Guelph, Guelph, Canada

[21] Appl. No.: 485,272

[22] Filed: Jun. 7, 1995

[30] Foreign Application Priority Data

Mar. 24, 1995 [GB] United Kingdom .................. 9506048
May 9, 1995 [GB] United Kingdom .................. 9509320

[51] Int. Cl.$^6$ .................................................. G06F 17/50
[52] U.S. Cl. .................................... 364/496; 364/578
[58] Field of Search ........................ 364/496, 497, 364/498, 499, 578

[56] References Cited

U.S. PATENT DOCUMENTS 5,434,796  7/1995  Weininger .............................. 364/496
5,526,281  6/1996  Chapman et al. ....................... 364/496

OTHER PUBLICATIONS

Clark et al., Pro_Ligand: An Approach to De Novo Molecular Design. 1. Application to the Design of Organic Molecules, Journal of Computer-Aided Molecular Design, 1995, pp. 13–32.

Walters et al., Genetically Evolved Receptor Models: A Computational Approach to Construction of Receptor Models, American Chemical Society, 1994.

Carneiro et al., Rethinking "Shape Space": Evidence from Simulated Docking Suggests That Steric Shape Complementarity is Not Limiting for Antibody–Antigen Recognition . . . , J. Theor. Biol., 1994, 169, pp. 391–402.

Blanco, Molecular Silverware. I. General Solutions to Excluded Volume Constrained Problems, Journal of Computational Chemistry, 1991, vol. 12, No. 2, pp. 237–247.

Dean, Molecular Recognition: The Measurement and Search for Molecular Similarity in Ligand–Receptor Interaction, Concepts and Applications of Molecular Similarity, pp. 211–238.

Primary Examiner—Emanuel T. Voeltz
Assistant Examiner—M. Kemper
Attorney, Agent, or Firm—Lynn C. Schumacher

[57] ABSTRACT

The present invention relates to computational methods for designing chemical structures sharing common useful, functional properties based on specific combinations of steric configuration and binding affinity. More particularly the present invention provides a method for producing computer-simulated receptors which functionally mimic biological receptors. The simulated receptors are designed to exhibit optimized selective affinity for known target molecules. Chemical structures are then generated and evolved to exhibit selective affinity for the simulated receptors.

52 Claims, 4 Draw

BENZALDEHYDE  CYCLOHEXANONE  2-OCTANONE  MENTHONE

LIGAND 1.1  LIGAND 1.2  LIGAND 1.3  LIGAND 1.4

LIGAND 2.1  LIGAND 2.2  LIGAND 2.3  LIGAND 2.4

COMPUTATIONAL METHOD FOR DESIGNING CHEMICAL STRUCTURES HAVING COMMON FUNCTIONAL CHARACTERISTICS

FIELD OF THE INVENTION

The present invention relates to a computer-based methods for designing chemical structures sharing common useful, functional properties based on specific combinations of steric configuration and binding affinity. More particularly the present invention provides a method for producing computer-simulated receptors which functionally mimic biological receptors. The simulated receptors are designed to exhibit optimized selective affinity for known target molecules. Chemical structures are then generated and evolved to exhibit selective affinity for the simulated receptors.

BACKGROUND OF THE INVENTION

Biological receptors are linear polymers of either amino acids or nucleotides that are folded to create three-dimensional envelopes for substrate binding. The specific three-dimensional arrangements of these linear arrays, and the placement of charged sites on the envelope surface are the products of evolutionary selection on the basis of functional efficacy. Biological receptors including antibodies, enzymes, ribozymes and transport proteins to mention just a few bind selectively to specific sets of compounds and the stereospecific and selective interactions between the relevant molecular species forms the basis of antibody-antigen interactions, biological toxicity and drug design. Although non-specific binding occurs, the functionality of receptors is generally dependent on their capacity to bind with high affinity to a limited set of substrates. For example, the immune system of vertebrates relies on the ability of antibodies to bind to a specific set of antigens.

The selectivity of biological receptors depends upon differences in the strength of attractive and repulsive forces generated between the receptor and the substrate. The magnitude of these forces varies in part with the magnitude and proximity of charged sites on the receptor and substrate surfaces. Charge sites can be formed by ionization of the substrate due to the addition or removal of electrons. Charge sites also arise in neutral, polar molecules due to asymmetrical sharing of electrons in covalent bonds. Electronegative atoms acquire partial negative charges by displacement of electrons away from less electronegative atoms. The resulting charge asymmetry generates a local or atomic dipole moment. Charge sites can also be induced when an uncharged molecule is brought into close proximity with a charged site on the receptor surface. Under these conditions a partial displacement of the electron orbitals in the portion of the substrate close to the charge site on the receptor may induce a net local charge. The strength of these induced charges varies with the susceptibility of the electrons in the affected portion of the substrate to displacement (polarizability), as well as the strength and proximity of the charged site on the receptor.

Because substrates differ in the number and magnitude of the charged sites present or induced on their surfaces, as well as the spatial arrangement of these sites, binding affinity can vary with substrate structure. Substrates with similar binding affinities for the same receptor have a high likelihood of sharing a common spatial arrangement of at least some of their induced and fixed charged sites. If the function of the receptor is correlated with binding affinity, then substrates with similar binding affinities will also be functionally similar in their effects. It is in this sense the receptor can be said to recognize or quantify similarities between the substrates.

Recent advances in molecular theory have made numerous contributions to the design of drugs, pesticides and polymers. Molecular theory provides tools based on quantum chemical techniques and a variety of methods that make use of molecular dynamics and Monte Carlo simulations based on empirical potential energy functions. These methods are applied to the determination of the geometric and electronic structural properties of bioactive molecules and polymers. Two principal concerns in the development of these methods are the electronic characteristics (e.g. charge-distribution, dipole and quadrapole moments and molecular electrostatic potential) and the nature of the active or functional conformation of a molecule.

A significant computational tool in this field is high-resolution force-field simulation based on data from simple experimental systems or ab initio quantum mechanical calculations. Similar approaches can be used to generate models of the distribution of charges over a molecular surface. Such quantum chemical approaches can be applied to a wide variety of small molecules. However, these methods are limited by the significant number of torsional degrees of freedom and corresponding conformational complexity of large molecules.

An important focus of these studies is the description of stereospecific and selective interactions between two molecular species, including antigens and antibodies or pharmacophores and target proteins. Such analyses at the level of individual molecules can be critical steps in the design of novel compounds with specific properties or functions. Descriptions of molecular interactions can be made by empirical description of the participating molecular species, for example by NMR or X-ray crystallography. Alternatively, one or both of the participating molecules may be modeled by a chemical or computational surrogate or model. Antibodies generated for various pharmacophores and toxophores are used as structural models of the active sites of their targets. Phage display of antibody proteins can also be used to develop structural models of receptors and the identification of selective ribozymes generated by combinatorial techniques represents a similar approach to the indirect description of biological target sites.

The structures of many protein receptor molecules have been determined by x-ray crystallography and NMR. This data is the basis for structure-based design of novel pharmaceutical agents (Kuntz, I. D. et al. (1982) J. Mol. Biol. 161: 269). When the proposed target protein cannot be identified or characterised directly, alternative computational techniques, including homology modelling (Blundell, T. L. et al. (1987) Nature, 326: 347), pharmacophore mapping (Martin, Y. C. et al. (1993) J. Comput.-Aided Design 7: 83) and comparative molecular field analysis (ComFA) (Cramer, R. D. et al. (1988) J. Am. Chem. Soc. 110: 5959) have been used to design pharmacophores that can interact with the receptor.

Traditional methods used in molecular recognition to identify or discover novel chemical compounds or substrates for selective binding affinity to receptors are based on finding molecular common subgraphs of active substrates and using these to predict new, similar compounds. A drawback to this technique is that it presupposes substrates exhibiting a similar efficacy for binding are structurally similar. In many cases however structurally dissimilar substrates can exhibit similar binding affinities for the same receptor. More current techniques based on quantitative structure-activity relationships (QSAR) are suited only to developing novel compounds within the same structural class and is largely inadequate at developing new molecular structures exhibiting the desired selective affinity, see for example Dean, Philip M., "Molecular Recognition: The Measurement and Search For Molecular Similarity in Ligand-Receptor Interaction", in Concepts and Applications of Molecular Similarity, Ed. Mark A. Johnson and Gerald M. Maggiora, pp. 211–238 (1990).

Recent efforts have been directed at the construction of atomic models of either pseudoreceptors, in which atoms and functional groups are connected, or minireceptors, comprised of unconnected sets of atoms or functional groups (Snyder, J. P. (1993) In 3D QSAR in Drug Design: Theory, Methods and Applications; Kubinyi, H. Ed.; Escom, Leiden. P. 336). Related methods involve surrounding known target ligands with a number of model atoms and calculation of the intermolecular forces generated between the ligand and the receptor model. Such models have a high correlation between calculated binding energy and biological activity (Walters, D. E. and Hinds, R. M. (1994) J. Medic. Chem. 37: 2527) but have not been developed to the point where novel chemical structures exhibiting selective affinity for the receptor models can be produced.

Therefore, it would be very advantageous to provide a method for identifying non-trivial similarities between different chemical structures which are both sufficient and necessary to account for their shared properties which can then be used as the basis for the design of new chemical structures with useful functional properties based on specific combinations of steric configuration and binding affinity.

SUMMARY OF THE INVENTION

The present invention provides a method for identifying non-trivial similarities between different chemical structures which are both necessary and sufficient to account for their shared functional properties. The process also provides a method of generating novel chemical structures that display similar functional properties.

The basic concept underlying the present invention is the use of a two-step computational process to design or discover chemical structures with useful functional properties based on specific combinations of steric configuration and binding affinity. In the first step of this process an algorithmic emulation of antibody formation is used to create a population of computer-generated simulated receptors that mimic biological receptors with optimized binding affinity for selected target substrates. In the second stage of the process the simulated or virtual receptors are used to evaluate the binding affinity of existing compounds or to design novel substrates with optimal binding.

The method described herein provides simulated receptors which mimic selected features of biological receptors, including the evolutionary processes that optimize their binding selectivity. The mimics or simulated receptors generated by the method can be used to recognize specific similarities between molecules. Like antibodies and other biological receptors, the simulated receptors generated by this invention are feature extraction mechanisms: they can be used to identify or recognize common or similar structural features of target substrates. Binding affinity between the receptors and the target substrates is used as a metric for feature recognition. Target substrates can be quantitatively categorized on the basis of binding affinity with a specific simulated receptor. Compounds sharing specific structural features will also share similar binding affinities for the same virtual receptor.

Binding affinity between biological receptors and substrates is determined by the steric goodness of fit between the adjacent receptor and substrate surfaces, the exclusion of water between non-polar regions of the two surfaces and the strength of electrostatic forces generated between neighbouring charged sites. In some cases the formation of covalent bonds between the substrate and the receptor may also contribute to binding affinity. The simulated receptors generated by this process mimic the binding mechanisms of their biological counterparts. Average proximity of the receptor and target surfaces and the strength of electrostatic attractions developed between charged sites on both surfaces are used to calculate a measurement of binding affinity. The resulting values for binding affinity are used to evaluate substrate molecular similarities.

Binding affinity can be globally determined, that is, dependent upon interactions between the entire substrate surface and a closed receptor or receptor envelope that completely surrounds the substrate. In this case analysis of global similarities between substrates is appropriate as a basis for developing useful quantitative structure-activity relationships. However, in most, if not all, biological systems, affinity is locally rather than globally determined. Interactions between substrate molecules and biological receptors are generally limited to contacts between isolated fragments of the receptor and the substrate surface. In this situation, analysis of global similarities between substrates is inappropriate as a method of developing structure-activity relationships, since only fragments of the substrate are directly involved in the generation of binding affinity.

Locally similar structures share similar structural fragments in similar relative positions and orientations. Locally similar structures are not necessarily globally similar. Sampling of molecular properties may be achieved by a total sampling strategy involving evaluation of global similarity; a fragment sampling strategy involving evaluation of local similarity; and multiple fragments sampling strategies involving evaluation of both local and global similarity.

The analysis of local similarities relies on sampling discrete regions of substrates for similar structures and charge distributions. In biological receptors, localized sampling arises due to the irregularity or bumpiness of the adjacent substrate and receptor surfaces. Interactions between closely opposed surfaces will predominant over interactions between more separated regions in the determination of binding affinity. The proximity of the adjacent surfaces will also determine the strength of hydrophobic binding. The effective simulated receptors generated by the present method must exploit discrete local sampling of target substrates (molecules) in order to evaluate functionally relevant similarities between compounds.

Analysis of local similarities is complicated by two factors: 1) the number, location and identity of the relevant fragments sufficient and necessary for specific binding affinity cannot usually be established by simple deduction from the chemical structure of the substrate; and 2) the positions and orientations of the sampled fragments are dependent upon the underlying structure of the whole molecule.

The part of the present method directed to the generation of simulated receptors capable of categorizing similarities between chemical substrates is essentially a search for receptors that sample the relevant fragments of the substrates at the relevant locations in space. The optimization process relies on four features of simulated receptors: 1) generality: wherein the receptors are able to bind with more than one substrate; 2) specificity: the binding affinity of the receptors varies with substrate structure; 3) parsimony: the receptors differentiate among substrates on the basis of a minimal set of local structural features; and 4) mutability: alteration of the structure of a receptor can change its binding affinity for a specific substrate. Encoding of the receptor phenotype in the form of a linear genotype represented by a character string facilitates the processes of mutation, recombination and inheritance of the structural characteristics of the simulated receptors.

Simulated receptors that satisfy these fundamental criteria can be optimized to obtain specific binding affinities for locally similar substrates using evolutionary selective breeding strategies. This is accomplished by encoding the spatial configuration and charge site distribution of the receptor in an inheritable format that can undergo alterations or mutations. Like biological receptors, the simulated receptors generated by this method define a three-dimensional exclusion space. Such a three-dimensional space can be outlined to an arbitrary degree of resolution by a one-dimensional path of sufficient length and tortuosity. Proteins formed from linear polymers of amino acids are examples of such structures. Similarly the three-dimensional structure of simulated receptors can be encoded as a linear array of turning instructions. This one-dimensional encoded form of the receptor constitutes its genotype. The decoded form used to assess binding affinity constitutes its phenotype. During the optimization process alterations (mutations) are made to the receptor genotype. The effects of these changes on the binding affinity of the phenotype are subsequently evaluated. Genotypes that generate phenotypes with desirable binding affinities are retained for further alteration, until, by iteration of the mutation and selection process, a selected degree of optimization of the phenotype is achieved. A variety of evolutionary strategies, including classical genetic algorithms, may be used to generate populations of simulated receptors with optimal binding characteristics.

Receptors generated by this method are then used to generate or identify novel chemical structures (compounds) which share the specific, useful properties of the molecular target species used as selection criteria in producing the simulated receptors. Using interaction with the receptors as selection criteria, novel chemical structures are evolved to optimally fit the receptors. Because these structures must meet the necessary and sufficient requirements for receptor selectivity, they are likely to also possess biological activity similar to that of the original molecular targets. The population of simulated receptors with enhanced selectivity may also be used to screen existing chemical structures for compounds with high affinity that may share these useful properties. The same process may also be used to screen for compounds with selected toxicological or immunological properties.

In one aspect of the invention there is provided a computer-based method of designing chemical structures having a preselected functional characteristic, comprising the steps of:

(a) producing a physical model of a simulated receptor phenotype encoded in a linear charater sequence, and providing a set of target molecules sharing at least one quantifiable functional characteristic;

(b) for each target molecule;
(i) calculating an affinity between the receptor and the target molecule in each of a plurality of orientations using an effective affinity calculation;
(ii) calculating a sum affinity by summing the calculated affinities;
(iii) identifying a maximal affinity;

(c) using the calculated sum and maximal affinities to:
(i) calculate a maximal affinity correlation coefficient between the maximal affinities and the quantifiable functional characteristic;
(ii) calculate a sum affinity correlation coefficient between the sum affinities and the quantifiable functional characteristic;

(d) using the maximal correlation coefficient and sum correlation coefficient to calculate a fitness coefficient;

(e) altering the structure of the receptor and repeating steps (b) through (d) until a population of receptors having a preselected fits coefficient are obtained;

(f) providing a physical model of a chemical structure encoded in a molecular linear character sequence, calculating an affinity between the chemical structure and each receptor in a plurality of orientations using said effective affinity calculation, using the calculated affinities to calculate an affinity fitness score;

(g) altering the chemical structure to produce a variant of the chemical structure and repeating step (f); and (h) retaining and further altering those variants of the chemical structure whose affinity score approaches a preselected affinity score.

In another aspect of the invention there is provided a method of screening chemical structures for preselected functional characteristics, comprising:

a) producing a simulated receptor genotype by generating a receptor linear character sequence which codes for spatial occupancy and charge;

b) decoding the genotype to produce a receptor phenotype, providing at least one target molecule exhibiting a selected functional characteristic, calculating an affinity between the receptor and each target molecule in a plurality of orientations using an effective affinity calculation, calculating a sum and maximal affinity between each target molecule and receptor, calculating a sum affinity correlation coefficient for sum affinity versus said functional characteristic of the target molecule and a maximal affinity correlation coefficient for maximal affinity versus said functional characteristic, and calculating a fitness coefficient dependent on said sum and maximal affinity correlation coefficients;

c) mutating the receptor genotype and repeating step b) and retaining and mutating those receptors exhibiting increased fitness coefficients until a population of receptors with preselected fitness coefficients are obtained; thereafter d) calculating an affinity between a chemical structure being screened and each receptor in a plurality of orientations using said effective affinity calculation, calculating an affinity fitness score which includes calculating a sum and maximal affinity between the compound and each receptor and comparing at least one of said sum and maximal affinity to the sum and maximal affinities between said at least one target and said population of receptors whereby said comparison is indicative of the level of functional activity of said chemical structure relative to said at least one target molecule.

In another aspect of the invention there is provided a method of designing simulated receptors mimicking biological receptors exhibiting selective affinity for compounds with similar functional characteristics, comprising the steps of:

a) producing a simulated receptor genotype by generating a receptor linear character sequence which codes for spatial occupancy and charge;

b) decoding the genotype to produce a receptor phenotype, providing a set of target molecules sharing similar functional characteristics, calculating an affinity between the receptor and each target molecule in a plurality of orientations using an effective affinity calculation, calculating a sum and maximal affinity between each target molecule and receptor, calculating a sum affinity correlation coefficient for sum affinity versus a functional characteristic for each target molecule and a maximal affinity correlation coefficient for maximal affinity versus said functional characteristic for each target molecule, and calculating a fitness coefficient dependent on said sum and maximal affinity correlation coefficients for each target molecule; and c) mutating the genotype and repeating step b) and retaining and mutating those receptors exhibiting increased fitness coefficients until a population of receptors with preselected fitness coefficients are obtained.

In another aspect of the invention there is provided a computer-based method of designing chemical structures having a preselected functional characteristic, comprising the steps of:

(a) providing a physical model of a receptor and a set of target molecules, the target molecules sharing at least one quantifiable functional characteristic;

(b) for each target molecule;
  (i) calculating an affinity between the receptor and the target molecule in each of a plurality of orientations using an effective affinity calculation;
  (ii) calculating a sum affinity by summing the calculated affinities;
  (iii) identifying a maximal affinity;

(c) using the calculated sum and maximal affinities to:
  (i) calculate a maximal affinity correlation coefficient between the maximal affinities and the quantifiable functional characteristic;
  (ii) calculate a sum affinity correlation coefficient between the sum affinities and the quantifiable functional characteristic;

(d) using the maximal correlation coefficient and sum correlation coefficient to calculate a fitness coefficient;

(e) altering the structure of the receptor and repeating steps (b) through (d) until a population of receptors having a preselected fitness coefficient are obtained;

(f) providing a physical model of a chemical structure, calculating an affinity between the chemical structure and each receptor in a plurality of orientations using said effective affinity calculation, using calculated affinities to calculate an affinity fitness score;

(g) altering the chemical strucutre to produce a variant of the chemical structure and repeating step (f); and (h) retaining and further altering those variants of the chemical structure whose affinity score approaches a preselected affinity score.

In yet another aspect of the invention there is provided a method of encoding chemical structures comprising atomic elements, the method comprising providing a linear character sequence which codes for spatial occupancy and charge for each atom of said chemical structure.

BRIEF DESCRIPTION OF THE DRAWINGS

The method of the present invention will now be described, by example only, reference being had to the accompanying drawings in which.

DESCRIPTION OF THE PREFERRED EMBODIMENTS

Figure 1:
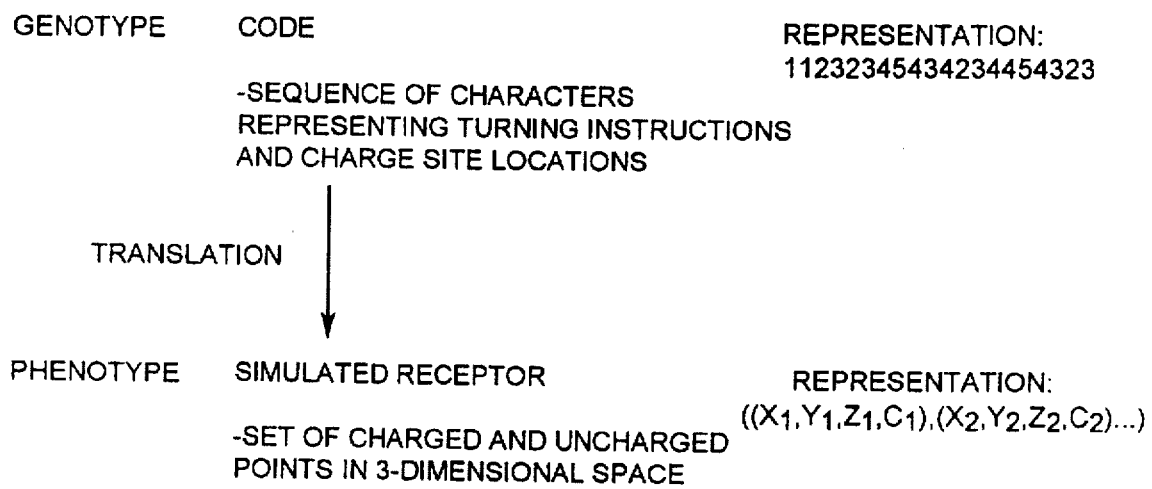
FIG. 1 is a flow chart showing relationship between genotype code creation and translation to produce a corresponding phenotype forming part of the present invention.

The method can be broken into two parts: (A) evolution of a population of simulated receptors with selective affinity for compounds with shared functional characteristics and (B) generation of novel chemical structures having the shared functional characteristics. Part (A) comprises several steps including 1) receptor genotype and phenotype generation; 2) presentation of the known chemical structure(s) to the receptor; 4) evaluation of affinity of the receptor for the chemical structure(s); 5) assessing the selectivity of the receptor for the chemical structure(s); 6) stochastically evolving a family of related receptors with optimized selective affinity for the chemical structure(s); screening chemical substrates for toxicological and pharmacological activity and using the optimized receptors to design novel chemical structure(s) with selective binding affinity for the receptors.

The following description of the best mode of the invention refers to various tables of molecular and atomic radius, polarizabilities, effective dipole values, and transition states and addition factors which values are found in Tables I to V located at the end of the description. Flowcharts giving non-limiting examples of process calculations are attached to the end of the description in Modules 1 to 15.

PART A: EVOLUTION OF POPULATION OF SIMULATED RECEPTORS EXHIBITING SELECTIVE AFFINITY FOR TARGET MOLECULES SHARING COMMON FUNCTIONAL CHARACTERISTICS (1) Genotype Code and Receptor Phenotype Generation Both the simulated receptor genotypes and phenotype are computational objects. The phenotypes of the simulated receptors consist of folded, unbranched polymers of spherical subunits whose diameter is equal in length to the van der Waals radius of atomic hydrogen ($\cong 110$ pm). The radius of the hydrogen atom was chosen as the lower limit of spatial resolution. In many biological receptors, the majority of the receptor surface is formed by projecting hydrogen atoms.

Subunits can be connected to each other at any two of the six points corresponding to the intercepts of the spheres with each of their principal axes. In the present implementation connections between subunits cannot be stretched or rotated and the centers of two connected subunits are always separated by a distance equal to the length of their sides (i.e. 1 hydrogen radius). Turns occur when two subunits are not attached to the opposite faces of their common neighbour. Four kinds of orthogonal turns are possible: left, right, up and down. Turns must be made parallel to one of the principal axes. For computational simplicity, if turns result in intersection with other subunits in the polymer, subunits are permitted to occupy the same space with other subunits.

A complete simulated receptor consists of one or more discrete polymers. In the case of receptors consisting of multiple polymers, the individual polymers can originate at different points in space. For computational simplicity, all polymers comprising a single receptor are chosen to be of the same length in this implementation (=number of subunits). This restriction is not a requirement for functionality, and sets of polymers differing in length may be useful for modelling specific systems.

The structure of each polymer is encoded as a sequential set of turning instructions. The instructions identify individual turns with respect to an internal reference frame based on the initial orientation of the first subunit in each polymer. Encoding on the basis of an internal reference frame mimics the assembly of proteins and ribozymes more closely than encoding on the basis of an external coordinate system.

Hydration of the receptor and substrate are not treated explicitly in the current implementation, instead, it is assumed that any water molecules present at the binding site are attached permanently to the receptor surface and comprise an integral part of its structure. This is an arbitrary approximation and those skilled in the art will appreciate that it could be replaced by a more exact treatment (see, for example, VanOss, 1995, *Molecular Immunology* 32:199–211).

With reference to FIG. 1, the code creation module generates random strings of characters. Each character represents either a turning instruction or determines the charge characteristics or reactivity of a point in the three-dimensional shape comprising the virtual receptor. A minimum of five different characters are required to create a string describing the three-dimensional shape of a receptor based on Cartesian (rectangular) coordinate framework. Other frameworks, e.g. tetrahedral structures can also be constructed using different sets of turning instructions. The characters represent turning instructions which are defined with respect to the current path of the virtual receptor structure in three-dimensional space (i.e. the instructions refer to the intrinsic reference frame of the virtual receptor and not an arbitrary external reference frame). An external reference frame is defined arbitrarily outside the receptor structure as a three-dimensional coordinate system (rectangular, cylindrical or spherical). The position of each subunit is specified by a triplet of coordinates (e.g. (x, y, z)) and turns are specified by the resulting unit changes to these coordinates. For example x, y, z→x, y+1, z+1 could specify a turn in an external rectangular coordinate system.

An intrinsic reference frame is defined with respect to the path of the polymer, and without reference to an external coordinate system. In place of turning instructions defined in terms of incremental changes in coordinates, turning instructions are given with respect to the current direction and orientation of the polymer. Only left, right, up and down turns are permitted. If a turn does not occur the polymer can either terminate or continue in its current direction. The virtual receptors generated in the current implementation are based upon an intrinsic reference frame.

While the receptor could be encoded using either an external or internal coordinate system, and codes can be interconverted, an internal coordinate system is preferred since the effects of mutation and recombination differ between coordinate systems. Particularly, mutations of codes based on external reference frames cause more restricted changes in phenotype architecture than similar mutations applied to codes based on internal reference frames. Specifically, the spatial orientations of the portions of the phenotype derived from unmutated sections of the code are unaffected (conserved) when the code is based on an external coordinate system. In contrast, the orientation of the portion of the phenotype distal to both the attachment site of the polymer and the mutation site will be affected by mutation if an internal reference frame is employed. As a result, the impact of point mutations on the receptor phenotype is generally greater when codes based on an internal reference frame are used. The three-dimensional tertiary structures of both proteins and ribozymes are partially based on internal reference frames (bond angles between adjacent peptides).

For a rectangular system the minimum character set is: $C_1$=no turn; $C_2$=right turn; $C_3$=left turn; $C_4$=up turn; and $C_5$=down turn. It will be understood that instructions could be combined to create diagonal turns e.g. $A_{1,2}=C_1C_2$; $A_{2,1}=C_2C_1$, etc. The number of different characters that determine different charge or reactivity states is unrestricted and may be adjusted according to empirical evidence. Codes may differ both in length (number of characters) and frequency with which specific characters appear in the series.

Example Of Genotype Creation

The following example of a genotype code creation and phenotype expression will be understood by those skilled in the art to be illustrative only. In this example the following conventions are employed.

(1) The character set used to generate the codes consists of five characters referring to turning instructions and two characters identifying a charged site: "0"=no turn; "1"=right turn; "2"=up turn; "3"=left turn; "4"=down turn; "5"= positively charged site (no turn); and "6"=negatively charged site (no turn).

(2) Subunits are of two types: charged or uncharged. All charged subunits are assumed to carry a unitary positive or negative charge. The uniform magnitude of charges is an arbitrary convention. It will be understood that receptors may also be constructed using subunits with different charges. The use of uniform charges in the present instance is a computational simplification. It also reduces the number of factors influencing the strength of electrostatic interactions between the receptor and substrate to two: the magnitude of the charge on the substrate; and the distance between the charge sites.

(3) The receptors comprise 15 discrete polymers. The length of the complete code is always a multiple of fifteen. The length of each polymer is equal to the total code length divided by fifteen. It will be understood that receptors can be constructed from any number of discrete polymers of varying or constant length.

(4) The following parameters are set by the user: (a) total code length (and polymer length); (b) the frequency with which each character occurs in the code string; and (c) the occurrence of character combinations. Module I gives a flowchart of a sample of genotype code creation.

Example of Receptor phenotype Creation

Each genotype code is translated to create the three-dimensional description of its corresponding phenotype or virtual receptor. From a predefined starting point a translation algorithm is used to convert the turning instructions into a series of coordinate triplets which describe the position in space of the successive subunits comprising the receptor polymers. The starting coordinates for each polymer must be given prior to translation. The translation assumes that centers of successive subunits are separated by a distance equal to the covalent diameter of a hydrogen atom.

The translation algorithm reads the code string sequentially to generate successive turns and straight path sections. The interpretation of successive turns with respect to an external coordinate system depends upon the preceding sequence of turns. For each polymer comprising the receptor, the initial orientation is assumed to be the same.

In the current implementation, the translation algorithm is described by TABLE I giving the input and output states. If no turn occurs, the most recent values for $\Delta x, \Delta y, \Delta z$ and new state are used to calculate the new coordinate triplet. Charge sites are treated as straight (no turn) sections. The initial value of old state is 20. The following parameters can be set by the user:

a. Starting coordinates for each polymer comprising the receptor.

Output is stored as a. Three vectors (one for each axes: $\{x_1, x_2, x_3 \ldots x_n\}$, $\{y_1 \ldots y_n\}$, $\{z_1 \ldots z_n\}$).

b: A three-dimensional binary matrix.

c. Separate vectors for charge site coordinates. A sample process of code translation is give in module 2.

(2) Target Generation

Targets are represented as molecules consisting of spherical atoms. The atoms are considered to be hard spheres with fixed radii characteristic for each atomic species. The hard sphere radius at which the repulsive force between the target atoms and the virtual receptor is considered to be infinite is approximated by the exposed van der Waals radius given in TABLE 2. Other estimated values of the van der Waals radius can be used in place of those in TABLE 2.

The distance between the atomic centers of two atoms connected by a covalent bond is expressed as the sum of their covalent bond radii. Covalent bond radii vary with bond order and atomic species. Examples of suitable values of bond radii are given in TABLE 3. As a first approximation, bond length is assumed to be fixed (i.e. bond vibrations are ignored). Bond rotation is permitted, and multiple configurations of the same structure are required to sample representative rotational states. Configurational stability is not considered because binding with the virtual receptor may stabilize otherwise energetically unstable configurations. Various enery minimization algorithms can be applied to the generation of target ligands.

Electrical charges arising due to bond dipole moments are considered to be localized at the atomic nuclei. The negative charge is carried by the atom with the larger electronegativity. The dipole values used in the current implementation are given in TABLE 4.

(3) Target Presentation

The affinity of the each target for the simulated receptor(s) is tested for several orientations of the target relative to the upper surface of the receptor. The upper surface is defined by the translation algorithm. Prior to the evaluation of binding affinity, the target and receptor must be brought into contact. Contact occurs when the distance between the centers of at least one subunit of the receptor and at least one atom of the target is equal to their combined radii. In order to determine the relative positions of the target and receptor at the point of contact, the target is shifted incrementally towards the receptor surface along a path perpendicular to the surface and passing through the geometric centers of both the receptor and the target. When contact occurs, the target has reached its collision position relative to the receptor. The translated positions of the target atoms when the collision position is reached are used to calculate distances between the atoms of the target and the subunits of the receptor. These distances are used to calculate the strength of electrostatic interactions and proximity.

In the current implementation, the target is assumed to travel in a straight line towards the receptor, and to retain its starting orientation at the time of contact. An alternative approach would allow the target to incrementally change its orientation as it approached the receptor so that the maximal affinity position was achieved at the point of contact. Although this method is functionally similar to that implemented, it is much more computationally complex. In the current implementation, multiple orientations are tested at lower computational effort. The current implementation allows for adjustable displacement of the path along the x and/or y axis of the receptor to accommodate larger molecules. This feature is required to enhance selectivity when molecules differing in size are tested on the same receptor.

Prior to the calculation of the collision position, the orientation of the target is randomized by random rotation in 6° increments around the x, y, and z axes. Each of these random orientations of the target is unique in a given test series. The reliability of the optimization process is dependent upon the number of target orientations tested as well as the number of target compounds evaluated. A sample process for target presentation is given in Module 4.

(4) Calculation of Affinity

Approximation Strategy

An exact calculation of the interaction energy between the targets and virtual receptor is neither practical nor desirable. The optimization of the simulated receptors requires multiple testing of numerous target-receptor pairs. The number of pairs tested per unit time is dependent on the time required to evaluate the affinity of each pair. Although the use of more accurate affinity calculations may result in greater discriminatory capacity, this gain will be at the price of increased computational effort. Furthermore, some components of the total interaction energy do not yet have an exact quantitative treatment, for example hydrogen bonding and hydrophobic interactions. The current implementation is based on a simplified approximation that evaluates the principal components of affinity with relatively little computational effort. The approximation is developed in the following sections. However, it will be appreciated by those skilled in the art that more exact affinity calculation procedures may be utilized which give a more exact affinity value. Known computational packages for calculating more accurate affinity values may be used directly in the present process.

Quantitative evaluation of the electrostatic interactions between receptor and ligand (or host and guest molecular complexes) requires a detailed description of the electron density distributions of the interacting molecules. However, in general the size of the molecules involved, particularly polypeptides, makes ab initio calculations of the electronic structure very difficult. This problem is often aggravated by the large number of torsional degrees of freedom and lack of knowledge concerning the conformations of the interacting molecules during binding.

Studies of crown ethers indicate that the electron density distribution of small molecules can be used to describe the electron densities of larger compounds (Bruning, H. And Feil, D. (1991) J. Comput. Chem. 12: 1). Hirshfeld's stockholder method can be used to define strictly local charge distributions that are subsequently characterized by charge and dipole moment (Hirshfeld, F. L. (1977) Theor. Chim. Acta 44: 129). The result is the division of the total electron density distribution of the molecule into overlapping atomic parts, the sizes of which are related to the free atomic radii.

Unfortunately these methods do not yield reliable values for binding energies and are largely restricted to electrostatic interactions that can be derived from electron density distributions. However, it is possible to demonstrate in crown ethers that the major components of electrostatic interactions are determined by local rather than global transfers of charge between atoms. Charge distribution is mainly determined by short range effects due to different chemical bonds. In particular, non-neighbouring atoms contribute little to atomic dipole moments. In addition, although charge transfer between atoms is also influenced by the electrostatic field of the whole molecule, calculations for crown ethers show only a very small influence on the charge distribution.

Calculated stockholder atomic charges and dipole moments can be used to describe electrostatic interactions (Bruning, H. And Feil, D. (1991) J. Comput. Chem. 12: 1). Beyond the van der Waals radius there is only a minor contribution from the atomic quadrapole moments. Calculations of the electrostatic potential that take only atomic charges into account give very poor results, whereas use of the dipole moments generates improved values.

Based on these considerations, the method of the present invention incorporates an approximation of affinity between the target ligand and the simulated receptor(s) and between the simulated receptor(s) and chemical structure(s) being designed based on two measures.

1. The magnitude of the electrostatic forces generated between the charged subunits of the simulated receptor(s) and the atomic dipoles of the target ligand (chemical structure). Because the charged subunits are assumed to carry non-transferrable unit charges, the magnitude of these forces is directly proportional to the magnitude of the atomic dipole and inversely proportional to the distance between the simulated receptor and the atomic dipole of the ligand.

2. The proportion of the non-polar or uncharged subunits of the simulated receptor sufficiently close to the non-polar regions of the ligand for the generation of significant London dispersion forces.

Assumptions Used For Affinity Calculation In The Current Implementation:

1. The chemical substrate targets evaluated by the current implementation are assumed to be neutral (i.e. not ionized) molecules. This is an arbitrary limitation, and an implementation applicable to charged and uncharged targets can be developed using the same methodology.
2. The dipole moments are assumed to be localised at the atomic nuclei. A similar analysis of affinity could be made assuming the dipole moment to be centered on the covalent bond. According to Allingham et al. (1989), these assumptions are functionally equivalent.
3. The environment surrounding the virtual receptor is assumed to be a solvent system in which the target occurs as a solute. The target is effectively partitioned between the solvent and the virtual receptor.
4. At the instant for which the affinity is calculated, the target and receptor are assumed to be stationary with respect to each other, and in a specific, fixed orientation.
5. The targets are assumed to interact with only two types of site on the receptor surface: fixed charge sites (either negatively or positively charged) and non-polar sites.

On the basis of these assumptions, it is only necessary to consider the following contributions to the strength of the interaction:
1. Charge-Dipole $-Q^2\mu^2/6(4\pi\epsilon)^2 kTr^4$
2. Charge-Non-polar $-Q^2\alpha/2(4\pi\epsilon)^2 r^4$
3. Dipole-Non-polar (Debye energy) $-\mu^2\alpha/(4\pi\epsilon)^2 r^6$
4. Non-polar-Non-polar (London energy) $-0.75[h\nu\alpha^2/(4\pi\epsilon)^2 r^6]$ In the current implementation, only relative strengths are considered by the approximation, therefore all constants are ignored. In addition the fixed charge site is assumed to be unitary and either positive or negative. On this basis, the four components can be rewritten in simplified form:

1. Charge-Dipole $-\mu^2/r^4$ or $-\mu/r^2$
2. Charge-Non-polar $-\alpha/r^4$
3. Dipole-Non-polar (Debye energy) $-\mu^2\alpha/r^6$ or $-\alpha^{0.5}/r^3$
4. Non-polar-Non-polar (London energy) $-\alpha^2/r^6$ or $-\alpha/r^3$ In general, terms 2 and 3 make only small contributions to long-range interactions. However, both 1 and 4 contribute significantly to the interaction energy. In the current implementation, most interactions between non-polar fragments are assumed to occur between adjacent alkyl and aromatic hydrogens and the non-polar subunits of the receptor. Under these conditions the value of $\alpha$ is assumed to be approximately constant.

Hydrophobic Strength and Water Exclusion Contribution

Solvation effects are important considerations in the generation of binding affinity. For example, hydrophobic bond formation relies upon the close spatial association of non-polar, hydrophobic groups so that contact between the hydrophobic regions and water molecules is minimized. Hydrophobic bond formation may contribute as much as half of the total strength of antibody-antigen bonds. Hydration of the receptor and substrate surfaces is also a significant factor. Water bound to polar sites of either the receptor or substrate surface can interfere with binding or increase affinity by forming cross-bridges between the surfaces.

The hydrophobic interaction describes the strong attraction between hydrophobic molecules in water. In the case of receptor-target interactions it is taken to refer to the attraction between the non-polar fragments of the target and adjacent domains of non-polar receptor subunits. The effect arises primarily from entropic effects resulting in rearrangements of the surfaces so that water is excluded between adjacent non-polar domains. Exact theoretical treatments of the hydrophobic interaction are unavailable, however, it is estimated that hydrophobic forces contribute as much as 50% of the total attraction between antibodies and antigens. In order to estimate the hydrophobic interaction between targets and virtual receptors, the present implementation evaluates the proportion of the receptor that is effectively shielded from solvation by binding with the target. All non-polar (uncharged) subunits that are within a fixed distance of non-polar atoms on the target are considered to be shielded from solvation by solvent molecules of diameter equal to or greater than the limiting distance.

Combined Affinity Calculation

The combined affinity calculation used in the current implementation combines two measures of interaction: the summed strengths of the charge-dipole interactions and a proximity measure. These affinities are assumed in the current implementation to be isotropic. It will be appreciated by those skilled in the art that greater discriminatory power may be obtained if anisotropic calculations of affinity are used, although these are computationally much more complex.

The charge-dipole interaction is calculated as $D=\Sigma\mu_i/r_{ij}^v$, where $\mu_i$=the dipole moment of the ith atom of the target and $r_{ij}$=the distance between the ith atom and the jth charge site on the receptor, and the coefficient v can be set to 2, 3, or 4. The contribution of D to the total affinity is more sensitive to charge separation for larger value of v.

The proximity measure is calculated as $P=\Sigma n_i/N$, where $n_i$=the number of uncharged subunits of the receptor that are separated by a maximum distance of $\partial$, from the ith atom of the target with a dipole moment $\leq 0.75$ Debye. In the current implementation, $\partial$ can range from 1 to 4 subunit diameters (this approximates the van der Waals radius of water). N is the total number of subunits comprising the receptor.

An affinity value A is calculated from D and P using the following relationship $A=[P(D+NP/k)]^{0.5}$, where k is a fitting constant (in the current implementation, k=10000). The value of P in the equation serves two roles. In the first instance it is a weighting factor. As a measure of "goodness of fit" it is use to bias the affinity value in favour of those configurations in which the non-polar regions of the target and receptor are in close contact. Under these conditions, hydrophobic interactions and non-polar interaction energies will be large and will contribute significantly to the stability and strength of the bond. Under these conditions the target has fewer possible trajectories to escape from the receptor and its retention time will be prolonged. In the second instance P is used to estimate the contribution of the dispersion energy to the strength of the interaction. It is assumed that the dispersion energy will only be significant for uncharged, non-polar regions, and that it is only significant when the target and receptor are close to each other (i.e. within a $\partial$ of each other). The values of k and $\partial$ can be adjusted to alter the relative contribution of P and D. In general, P dominates for non-polar targets, whereas D is more significant for targets with large local dipoles. Hydrogen bonding is approximated by paired negatively and positively charged receptor units interacting simultaneously with target hydroxyl, carboxylic or amine functional groups.

Alternative Approaches to Affinity Calculation-Bond Polarizability

It may be advantageous is certain cases to introduce a parameter corresponding to the relative polarizability of the target atoms into the affinity calculation. In this case the equation for calculating $P_2$ in $A=[P(D+NP_2/k)]^{0.5}$ is not $P_2=\Sigma n_i/N$. Instead, $P_2$ is calculated as $P_2=\Sigma\alpha_i n_i/N$; where $n_i$=the number of either charged or uncharged subunits of the receptor that are separated by a maximum distance of $\partial$ from the ith atom of the target and $\alpha_i$ is the relative polarizability of the ith atom of the target. For simplicity $\alpha_H$ could be set to 1.0 for aliphatic hydrogen. The value of k must be adjusted if polarizabilities are used. Sample polarizabilities based on the sums of adjacent bond polarizabilities are given in TABLE V.

Since polarizability is associated with displacement of the electron cloud, the polarizability of a molecule can be calculated as the sum of the characteristic polarizabilities of its covalent bonds. This additivity holds for non-aromatic molecules that do not have delocalized electrons.

Alternative Techniques-Functional Group Specificity

The affinity approximation used in the current implementation could be replaced by functionally similar computations that preserve the relationship between local charges, dispersion energy and target-receptor separation. In addition, affinity measures for charged targets could be constructed. The present implementation evaluates only non-covalent interactions, however, the method could be expanded by including in the virtual receptor subunits capable of specific covalent bond-forming reactions with selected target functional groups. Module 5 provides a sample flowchart of the preferred effective affinity calculation used in the present invention.

(5) Assessment of Selective Affinity

Figure 2:
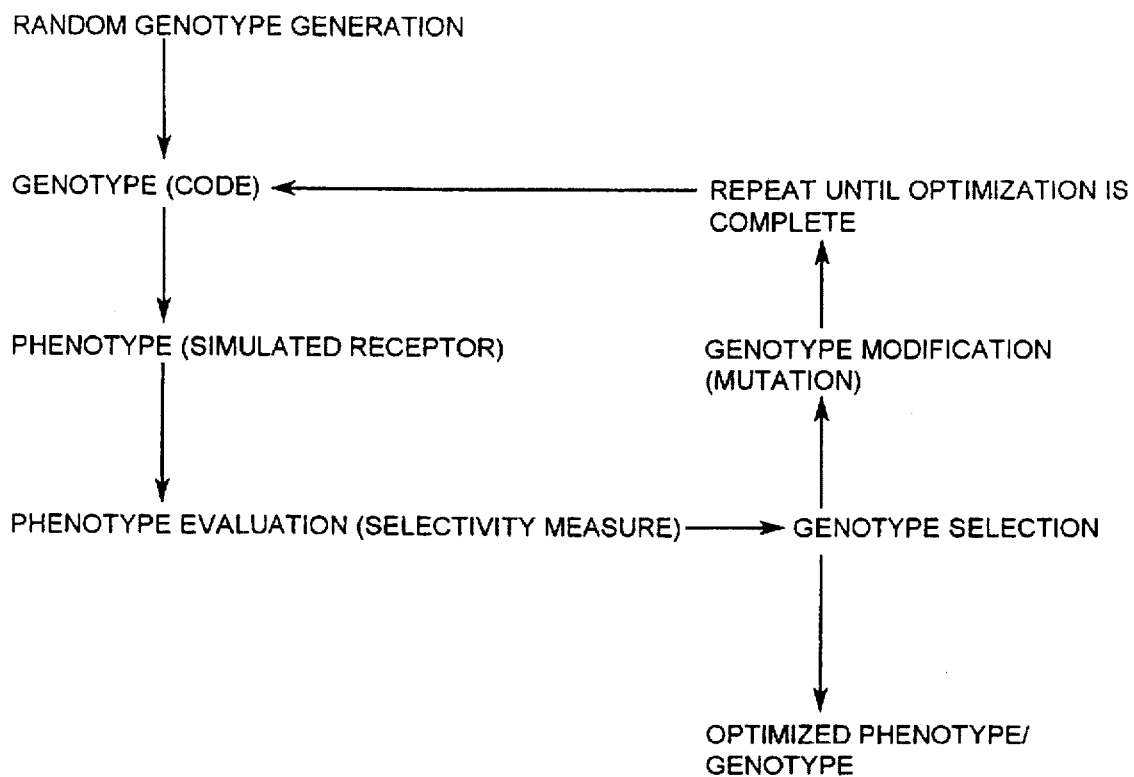
FIG. 2 is a flow chart showing an overview of the steps in the optimization of a receptor for selectively binding to a set of substrates using point mutations forming part of the present invention.
Figure 3:
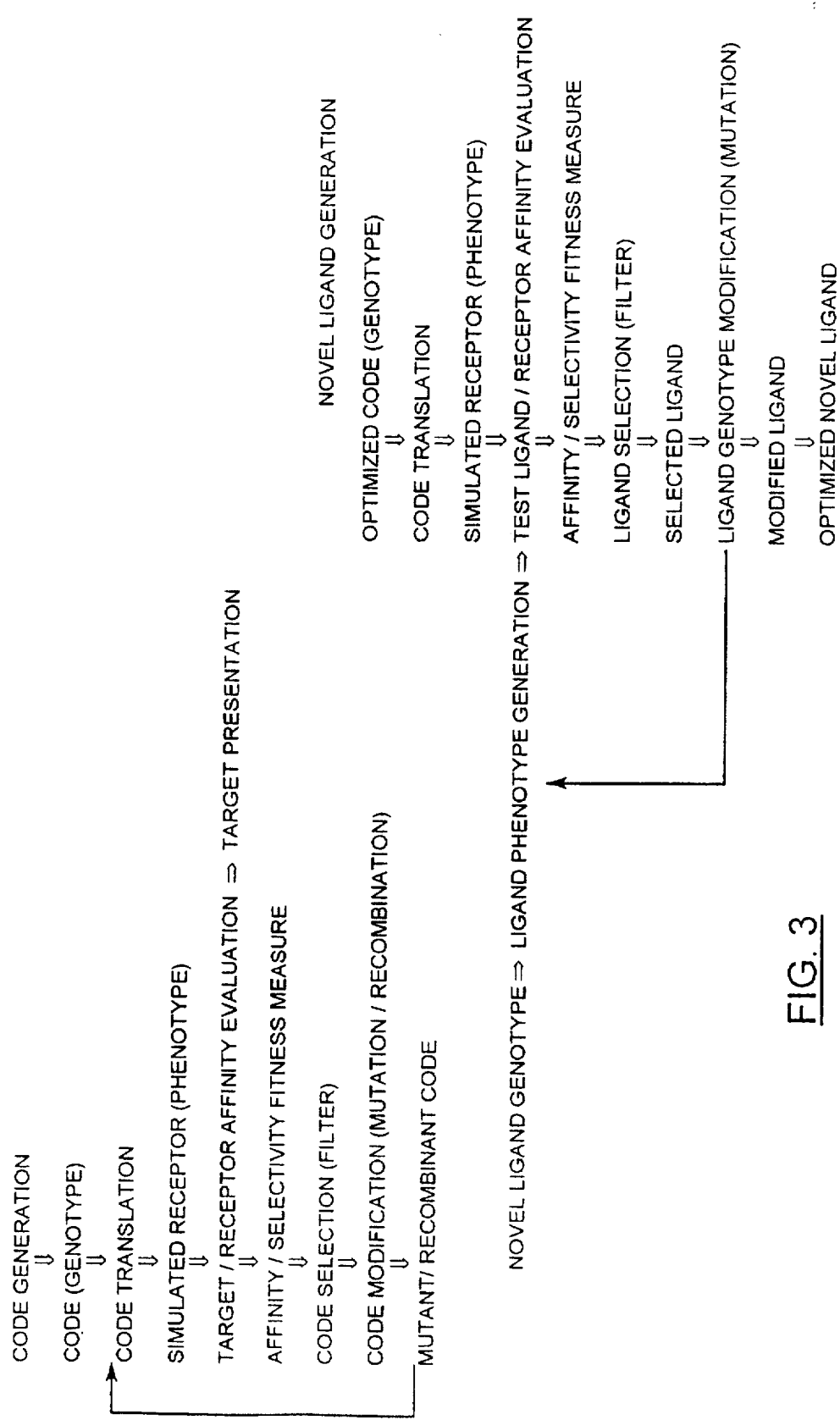
FIG. 3 is a flow chart showing an overview of the steps in the process of producing a population of related receptors with optimized selective binding affinity for a set of chemical substrates and using these optimized receptors for producing a set of novel chemical substrates with common shared functional characteristics.

Goodness of fit between a virtual receptor and a set of target substrates is evaluated by comparing the known activity or affinity values for the targets with those obtained for the virtual receptor-target complex. The maximal affinities of an optimally selective virtual receptor should be strongly correlated with known affinity measures. Successive iterations of point mutations can be used to enhance this correlation between a set of substrates and a virtual receptor (FIG. 2) or for optimizing selectivity of a population of virtual receptors successive iterations of the evolutionary process may used to enhance this correlation (FIG. 3).

Known values can be any index known or suspected to be dependent upon binding affinity, including (but not limited to) $ED_{50}$, $ID_{50}$, binding affinity, and cohesion measures. The values tested must be positive. Logarithmic transformation of the data may be required. Unweighted rank data cannot be used.

The optimal orientation of the targets for maximal binding affinity is unknown prior to testing. In order to obtain a representative measure of the range of receptor-target affinity, each target must be tested repeatedly using different random orientations relative to the receptor surface. Each test uses Module 5 to evaluate affinity. In general, the reliability of the maximal affinity values obtained depends upon the sample size, since it becomes increasingly likely that the sample will contain the true maximal value. The same set of target orientations is used for testing each receptor.

Two techniques are employed in the current implementation to circumvent the need for large sample sets for the generation of optimized receptors: 1) the use of a measure combining average (or sum) affinity and maximal affinity to select for receptors with higher selectivity; and 2) incremental increases in the number of orientations tested with successive iterations of the optimization process (optimization begins with a small set of target orientations, as receptors of greater fitness are generated, more orientations are tested).

In the current implementation, the sum is calculated for the affinity values obtained for all the tested orientations of each target. This sum affinity score is a measure of the average affinity between the receptor and the target. At the same time, the maximal affinity value is also determined.

Correlations between the known values and both the sum affinity $r_{SA}^2$ and the maximal affinities $r_{MA}^2$ are calculated. The origin (0,0) is included in the correlation, based on the assumption that target compounds showing no activity should have little or no affinity for the virtual receptor. This assumption may not always be valid, and other intercept values may be required in some tests.

The correlation of using sum affinity is a measure of the average goodness of fit. If this correlation is large, but the correlation between maximal affinity and known affinity is weak, the result suggests that the virtual receptor is not selective, i.e. multiple orientations of the target can interact effectively with the receptor. Conversely, if the maximal affinity is highly correlated with known affinity values and the correlation with sum affinity is weak, the virtual receptor my be highly selective. If both sum affinity and maximal affinity are highly correlated with known affinity, it is probable that the orientations sampled have identified the response characteristics of the receptor with limited error (both type I and type II errors are reduced: the likelihood of either a false positive or false negative result). In some cases it may be more appropriate to minimize the correlation between the known affinities and the sum affinity, while selecting for an increased correlation between maximal affinity and known affinity. Such a selection would require subtraction of the maximal affinity values from the sum total in order to remove these values as a source of confounding bias.

In the current implementation, a joint correlation value is used as the basis for receptor selection. This value is calculated as the square root of the product of the sum affinity and maximal affinity $$F=(r_{MA}^2 \times r_{SA}^2)^{0.5}$$

This value is optimized by the evolutionary process applied to the virtual receptors. Note: If $r_{MA}^2$ and $r_{SA}^2$ are strongly correlated with each other, then the values contributing to $r_{SA}^2$ must either individually correlate closely with the maximal affinity value or contribute negligibly to the sum. Alternatively the correlation ($r_{SA-MA}$) for the (sum affinity–the maximal affinity) vs known affinity can be calculated and the measure $$F=(r_{MA}^2 \times (1-r_{SA-MA}^2))^{0.5}$$

is maximized. Use of this measure will select for receptors that have high affinity for a very limited set of target orientations. Module 6 provides a flowchart of a sample goodness of fit calculation.

(6) The Optimization Process

The objective of the optimization process is to evolve a virtual receptor that has selective affinity for a set of target receptors. A highly efficient mechanism for finding solutions is required, since the total number of possible genotypes containing 300 instructions is $7^{300}$ or about $10^{253}$. The following four phases summarize the steps in the optimization process whereinafter each phase is discussed in more detail and example calculations given.

PHASE 1: Generate a set of random genotypes and screen for a minimal level of activity. Use selected genotype as basis for further optimization using genetic algorithm (recombination) and unidirectional mutation techniques.

PHASE 2: Mutate selected genotype to generate a breeding population of distinct but related genotypes for recombinations. Chose most selective mutants from population from population for recombination.

PHASE 3: Generate new genotypes by recombination of selective mutants. Select from the resulting genotypes those with the highest affinity fitness. Use this subpopulation for the next recombinant or mutation generation.

PHASE 4: Take best recombination products and apply repeated point mutations to enhance selectivity.

Phase I: Evolution-generation of Primary Code

The Genetic Algorithm developed by Holland (Holland, J. H. (1975) Adaptation in Natural and Artificial Systems. U. Michigan Press. Ann Arbour) can be used to search for optimal solutions to a variety of problems. Normally this technique is applied using large, initially random sets of solutions. In the present implementation the technique is significantly modified in order to reduce the number of tests and iterations required to find virtual receptors with high selectivity. This has been accomplished by using a set of closely related genotypes as the initial population and the application of high rates of mutation at each iteration. For any set of target compounds it is possible to develop distinct receptors with optimal affinity characteristics. For example, receptors may bind optimally to the same targets but in different orientations. The use of an initial population of closely related genotypes increases the likelihood that the optimization process is converging on a single solution. Recombination of unrelated genotypes, although it may generate novel genotypes of increased fitness, is more likely to result in divergence.

The objective of the first stage in the optimization process is to generate a genotype with a minimal level of affinity for the target set. This genotype is subsequently used to generate a population of related genotypes. A flowchart of a sample process for generation of a genotype with a minimum level of affinity is given in Module 7.

Phase 2: Evolution-Mutation of Primary Code

Mutation of the genotype comprises changing one or more characters in the code. Mutations in the current implementation do not alter the number of subunits comprising the receptor polymers and do not affect the length of the genotype. It will be appreciated that these conventions are arbitrary, and it will be understood that variants may have utility in some systems.

Mutations can alter the folding pattern of the phenotype, with resulting changes in the receptor shape space and the location or exposure of binding sites. Mutations that affect the configuration of peripheral regions of the phenotype can result in shifts of the receptor center relative to the target center.

Neutral mutations

All mutations alter the structure of the phenotype, however, not all mutations result in changes in the functionality of the receptor. Such neutral mutations may alter components of the receptor that do not affect affinity. In some cases these neutral mutations can combine with subsequent mutations to exert a synergistic affect.

The Breeding Population

The objective of the second phase of the evolutionary process is the generation of a population of distinct but related genotypes derived from the primary genotype. Members of this population are subsequently used to generate recombinants. This breeding population is created by multiple mutation of the primary genotype. The resulting genotypes are translated and screened for selectivity. The most selective products are retained for recombination. Module 8 gives a flowchart for a sample process for multiple mutation of a genotype.

Phase 3: Evolution-Recombination

The objective of recombination is the generation of novel genotypes with increased fitness. Recombination facilitates the conservation of genotype fragments that are essential for phenotypic fitness, while at the same time introducing novel combinations of instructions. In general, recombination coupled with selection results in rapid optimization of selectivity. Module 9 gives a flowchart for a sample process for multiple mutation of a genotype.

The current implementation retains the population used for recombination for testing in step 7 of Module 9. This ensures that genotypes with high selectivity are not replaced by genotypes with lower selectivity. In addition, in the current implementation, mutations (Module 7) are applied to 50% of the recombinant genotypes prior to testing (Step 7-module 9). This step increases the variability within the recombinant population. The test populations used in the current implementation range in size from 10 to 40 genotypes. This is a relatively small population size. Under some conditions, larger populations may be required.

Phase 4: Evolution-Maturation

Progressive Micromutation Technique

The final stage in the optimization process mimics the maturation of antibodies in the mammalian immune system. A series of single point mutations are applied to the genotype, and the effect on phenotypic fitness is evaluated. Unlike recombination, this process generally results in only small incremental changes to the selectivity of the phenotype. The maturation process uses a Rechenberg (1+1) evolutionary strategy (Rechenberg, I. (1973), Evolutionsstrategie. F. Frommann. Stuttgart). At each generation the fitness of the parental genotype is compared to that of its mutation product, and the genotype with the greater selectivity is retained for the next generation. As a result, this process is strictly unidirectional, since less selective mutants do not replace their parents.

During each iteration of the maturation process, only a single instruction in the code is changed. If a parent and its mutation product have the same selectivity, the parent is replaced by its product in the next generation. This method results in the accumulation of neutral mutations that may have synergistic effects with subsequent mutations. This convention is arbitrary. Module 10 provides a flowchart for a sample maturation process.

If recombination or maturation do not generate improved selectivity after repeated iterations, it may be necessary to repeat Phase 2 in order to increase the variability of the breeding population genome.

Selected Applications

The process of the present invention can be used in several areas including: 1) screening for compounds with selected pharmacological or toxicological activity; and 2) development of novel chemical structures with selected functional characteristics. Both applications and examples are provided hereinafter.

1A) Screening Method

A population of receptors that have been evolved for selective affinity for a specific group of compounds sharing similar pharmacological properties can be used as probes for the identification of other compounds with similar activity, provided this activity is dependent upon binding affinity. For example, a population of receptors could be evolved to display specific affinity for salicylates. If the affinity of these receptors for salicylates closely correlates with the affinity of cyclooxygenase for salicylates, the receptors must at least partially mimic functionally relevant features of the binding site of the cyclooxygenase molecule. These receptors can therefore be used to screen other compounds for possible binding affinity with cyclooxygenase.

This technique can also be applied to screening compounds for potential toxicological or carcinogenic activity. For example, receptors could be evolved that mimic the specific binding affinity of steroid hormone receptors. These receptors could then be used to evaluate the affinity of pesticides, solvents, food additives and other synthetic materials for possible binding affinity prior to in vitro or in vivo testing. Simulated receptors may also be constructed to detect affinity for alternate target sites, transport proteins or non-target binding.

1B) Screening For Sub-Maximal Activity

In some instances compounds with high affinity may have deleterious side effects or may be unsuitable for chronic administration. In this case, compounds with lower binding affinity may be required. Techniques such as combinatorial synthesis do not readily generate or identify such compounds. In contrast, simulated receptors could be used to effectively screen for structures that display binding affinity of any specified level.

1C) Measuring Molecular Similarity The selectivity of the simulated receptors can be used as a quantitative measure of molecular similarity.

Example of a Software Implementation

Appendices A, B, and C are attached. Appendix A is a computer program written in Microsoft Visual Basic 3.0 which can be used to generated simulated receptors. Appendix B is a computer program, also written in Microsoft Visual Basic 3.0, which can be used to generate chemical structures. Appendix C is a file which is required to run both programs.

Both programs are merely examples of programs which can be used to carry out a particular implementations of the invention. Those skilled in the art can write other programs which can be used to practice the methods of the invention.

Examples of Simulated Receptors

In the examples, fictitious test values of target affinities were chosen to demonstrate the ability of the receptor generation program to construct simulated receptors mimicking any arbitrarily chosen pattern of activity.

In these examples, all receptors consist of 15 polymers. Width, Length, and Depth values specify origin coordinates of the 15 polymers relative to the center of the receptor.

EXAMPLE 1

A simulated receptor was generated with the following specifications:

---

Number of subunits: 240; Width: 6; Length: 6 +Depth: 25
Code:
"41000331032122041033334240523120133410241240222323340100322
42510144051332434003246204121001313100431121011324120224 2130
24132311243301331003230523000433414010202230214041444 3502652
03413103310220514141410214021340143100102311103312353100 1624
0"

---

Each target was tested 20 times against the receptor

The affinity score for the optimized receptor was 0.9358 which is relatively low.

The target substrates used to optimize the receptor were benzene, phenol, benzoic acid and o-salicylic acid. The aspirin precursor o-salicylic acid is an inhibitor of prostaglandin synthesis by cyclooxygenase. Benzoic acid and phenol have much lower affinity for the same site. The target affinity values and the scores for the receptor are shown in Table A below which shows that the simulated receptor has maximal affinity for o-salicylic acid.

| Target Compound | Target Affinity | Sum Affinity Score | Maximal Affinity Score |
|---|---|---|---|
| Benzene | 0.6 | 20.88 | 3.38 |
| Phenol | 1.2 | 8.03 | 4.99 |
| Benzoic Acid | 1.6 | 42.23 | 12.98 |
| o-Salicylic Acid | 4.4 | 80.33 | 34.71 |

Three test substrates were evaluated using the simulated receptor. Two of the compounds are known to be less active than o-salicylic acid: m-salicylic acid and p-salicylic acid. The third compound, Diflusinal is a fluorinated salicylic acid derivative of efficacy equal to or greater than that of salicylic acid. The results of the evaluation are given in Table B.

| Target Compound | Sum Affinity Score | Maximal Affinity Score |
|---|---|---|
| m-Salicylic acid | 45.9 | 12.3 |
| p-Salicylic acid | 63.5 | 27.5 |
| Diflusinal | 117 | 71.2 |
| o-Salicylic Acid | 80.33 | 34.71 |

The results obtained using the simulated receptor closely match the pharmacological data for these compounds: m-salicylic acid and p-salicylic acid have lower affinity scores than o-salicylic acid and diflusinal is more active than o-salicylic acid. Further refinement of the simulated receptor and the use of additional, independently optimised receptors would be required to increase the certainty of these predictions of activity.

EXAMPLE 2

Simulated receptors selective for Benzodiazepams (Valium analogues).

Code:
"313305423414342402400322214113114321411360531202421110243202
331110133110040211230332143314023304425124121442020351242223
140022112133223241001421200413121023122414302231344123301021
3"

Code Length: 180
Depth: 25 Width: 6 Length: 7
Number of Tests: 40
Population Size for Recombination: 10
Translation Factor: ±2
Optimized Correlation Score: 0.98
Training Targets (used to optimize receptor affinity and selectivity; the target affinity scores are fictitious):

| Compound | Target Affinity | Sum Score | Maximal Affinity Score |
|---|---|---|---|
| Benzene | 0.5 | 64 | 7.5 (inactive) |
| Diazepam | 8.5 | 616 | 263 |
| Chlorodiazepam | 5.6 | 383 | 139 (less active than Diazepam) |
| Methyldiazepam | 4.2 | 354 | 147 (less active than Diazepam) |

Test Targets: (Small molecules not known to interact with the diazepam receptor):

| Compound | Sum Affinity Score | Maximal Affinity Score |
|---|---|---|
| Phenol | −67.7 | 5.6 |
| Benzoic Acid | 198 | 31 |
| o-Salicylic Acid | 168 | 21 |

EXAMPLE 2a

A simulated receptor mimicking affinity of cyclooxygenase for salicylates.

Optimized Correlation Score: 0.95
Training Targets used to optimize selective affinity (Cyclooxygenase as receptor): These targets differ in affinity for cyclooxygenase. The target affinities used are fictitious.

| Compound | Target Affinity | Sum Affinity Score | Maximal Affinity Score |
|---|---|---|---|
| Benzene | 0.9 | 29.5 | 5.8 |
| Phenol | 1.6 | 21.0 | 7.4 |
| Benzoic Acid | 2.1 | 59.3 | 27 |
| o-Salicylic Acid | 5.3 | 134 | 105 |

Test Targets: (Both m-salicylic acid and p-salicylic acid should be less active than o-Salicylic acid)

| Compound Sum | Affinity Score | Maximal Affinity Score |
|---|---|---|
| o-Salicylic Acid | 134 | 105 |
| m-Salicylic Acid | 52 | 28 (less active) |
| p-Salicylic Acid | 28 | 4 (less active) |

Note ordering of scores ortho > meta > para

EXAMPLE 2b

A simulated receptor mimicking affinity of cyclooxygenase for salicylates.

Optimized Correlation Score: 0.98
Training Targets used to optimize selective affinity (Cyclooxygenase as receptor): These targets differ in affinity for cyclooxygenase. The target affinities used are fictitious.

| Compound | Target Affinity | Sum Affinity Score | Maximal Affinity Score |
|---|---|---|---|
| Benzene | 1.1 | 15 | 2.4 |
| Benzoic Acid | 3.0 | 43.6 | 8.0 |
| o-Salicylic Acid | 5.1 | 57.9 | 16.2 |

Test Targets: (Both m-salicylic acid and p-salicylic acid should be less active than o-Salicylic acid and Diflusinal is an active o-salicylate analogue)

| Compound | Sum Affinity Score | Maximal Affinity Score |
|---|---|---|
| o-Salicylic Acid | 57.9 | 16.2 |
| m-Salicylic Acid | 37.7 | 8.0 (less active) |
| p-Salicylic Acid | 35.4 | 4.4 (less active) |
| Diflusinal | 87.5 | 14.1 (similar activity) |

Note ordering of scores ortho > meta > para

EXAMPLE 2c

A simulated receptor mimicking affinity of cyclooxygenase for salicylates.

Optimized Correlation Score: 0.98
Training Targets used to optimize selective affinity (Cyclooxygenase as receptor): These targets differ in affinity for cyclooxygenase. Phenol was not used in this optimization. The target affinities used are fictitious.

| Compound | Target Affinity | Sum Affinity Score | Maximal Affinity Score |
|---|---|---|---|
| Benzene | 1.1 | 15 | 2.4 |
| Benzoic Acid | 3 | 43.6 | 8 |
| o-Salicylic Acid | 5.1 | 57.9 | 16.2 |

Test Targets: (Both m-salicylic acid and p-salicylic acid should be less active than o-Salicylic acid, Diflunisal is as potent as o-Salicylic acid)

| Compound | Sum Affinity Score | Maximal Affinity Score |
|---|---|---|
| o-Salicylic Acid | 57.9 | 16.2 |
| m-Salicylic Acid | 37.7 | 8 (less active) |
| p-Salicylic Acid | 35.4 | 4.4 (less active) |
| Diflunisal | 87.5 | 14.1 (similar activity) |

Note ordering of scores ortho>meta>para

EXAMPLE 3

A simulated receptor with stereospecific affinity for salicylates.

Optimized Correlation Score: 0.98

Training Targets used to optimize selective affinity (Cyclooxygenase as receptor):

These targets differ in affinity for cyclooxygenase. Phenol was not used in this optimization. In this example p-salicylate was assumed to have higher affinity than o-salicylate. The target affinities used are fictitious.

| Compound | Target Affinity | Sum Affinity Score | Maximal Affinity Score |
|---|---|---|---|
| Benzene | 0.9 | 11 | 26.3 |
| o-Salicylic Acid | 2.5 | 48.3 | 40.1 |
| p-Salicylic Acid | 6.2 | 94.8 | 83.8 |

Test Targets:

| Compound | Sum Affinity Score | Maximal Affinity Score |
|---|---|---|
| p-Salicylic Acid | 94.8 | 83.8 |
| m-Salicylic Acid | 68.7 | 61.3 (less active) |
| Benzoic Acid | 73.5 | 63.5 (less active) |
| Phenol | 31.5 | 32.6 (less active) |

Note ordering of scores ortho<meta<para, which reverses the order shown in previous example.

EXAMPLE 4

A simulated receptor with specific affinity for salicylates. This receptor responds equally well to diflunisal and o-Salicylic acid, mainly on the basis of the benzoic acid moiety. It is not strongly specific, probably because of the very small set of optimisation criteria used to generate it.

Optimized Correlation Score: 0.97

Training Targets used to optimize selective affinity (Cyclooxygenase as receptor): These targets differ in affinity for cyclooxygenase. Phenol and benzoic acid were not used in this optimization. In this example o-salicylate and diflunisal were assumed to have similar affinities. The target affinities used are fictitious.

| Compound | Target Affinity | Sum Affinity Score | Maximal Affinity Score |
|---|---|---|---|
| Benzene | 0.6 | 80 | 24 |
| o-Salicylic Acid | 7.4 | 232 | 122.3 |
| Diflunisal | 6.6 | 236 | 121.5 |

Test Targets

| Compound | Sum Affinity Score | Maximal Affinity Score |
|---|---|---|
| p-Salicylic Acid | 196 | 104 (less active) |
| m-Salicylic Acid | 219 | 98.3 (less active) |
| Benzoic Acid | 214 | 108 (less active) |

EXAMPLE 5

A simulated receptor with specific affinity for salicylates. This receptor was optimised first to detect benzoic acid, then o-salicylate. It is selective for the ortho isomer, but equally sensitive to the benzoic acid moieties in p- and m-Salicylic acid.

Optimized Correlation Score: 0.97

Training Targets used to optimize selective affinity. The target affinities used are fictitious.

| Compound | Target Affinity | Sum Affinity Score | Maximal Affinity Score |
|---|---|---|---|
| Benzene | 0.7 | 12.5 | 1.8 |
| Benzoic Acid | 5.9 | 71.9 | 12.5 |
| o-Salicylic Acid | 8.9 | 91 | 17.4 |

Test Targets

| Compound | Sum Affinity Score | Maximal Affinity Score |
|---|---|---|
| p-Salicylic Acid | 56.2 | 12.4 (less active) |
| m-Salicylic Acid | 40.1 | 12.9 (less active) |
| Benzoic Acid | 71.9 | 12.5 |
| o-Salicylic Acid | 91 | 17.4 |

EXAMPLE 6

Two simulated receptors with stereospecific affinity for salicylates. Receptor A is discriminates more strongly between o-salicylic acid and benzoic acid than receptor B. This difference was established by the target affinities assigned during the training process.

Optimized Correlation Score: Receptor A: 0.99; Receptor B: 0.99

Training Targets used to optimize selective affinity. The target affinities used are fictitious.

Receptor A

| Compound | Target Affinity | Sum Affinity Score | Maximal Affinity Score |
|---|---|---|---|
| Benzene | 0.9 | 11.1 | 6.6 |
| Benzoic Acid | 2.4 | 42.9 | 13.1 |
| o-Salicylic Acid | 4.1 | 70.1 | 24.8 |

Test Targets

| Compound Sum | Affinity Score | Maximal Affinity Score |
|---|---|---|
| p-Salicylic Acid | 31.5 | 13.6 (less active) |
| m-Salicylic Acid | 36.6 | 16 (less active) |

Receptor B

| Compound | Target Affinity | Sum Affinity Score | Maximal Affinity Score |
|---|---|---|---|
| Benzene | 0.9 | 20 | 6.2 |
| Benzoic Acid | 2.2 | 41 | 15.5 |
| o-Salicylic Acid | 3.1 | 51 | 19.5 |

Test Targets

| Compound | Sum Affinity Score | Maximal Affinity Score |
|---|---|---|
| p-Salicylic Acid | 34 | 16 (less active) |
| m-Salicylic Acid | 52 | 22 (similar to o-salicylic acid) |

Note that Receptor B is more strongly affected by the similarities between the compounds and benzoic acid.

EXAMPLE 7

Four simulated receptors lacking specific affinity for salicylates. This was established by assigning benzoic acid and o-salicylic acid similar target affinities during the training process. As a result, all four receptors are primarily sensitive to the benzoic acid moiety of the salicylic acids and largely ignore the contribution of the hydroxyl group.

Optimized Correlation Score: Receptor A: 0.997; Receptor B: 0.97; Receptor C: 0.96; Receptor D: 0.995

Training Targets used to optimize selective affinity. The target affinities used are fictitious. Twenty-five tests per target.

Target Affinities for All Receptors

| Compound | Target Affinity |
|---|---|
| Benzene | 0.5 |
| Benzoic Acid | 4.7 |
| o-Salicylic Acid | 5.0 |

Receptor Affinities

| Compound | Sum Score | | | | Maximal Score | | | |
|---|---|---|---|---|---|---|---|---|
|  | A | B | C | D | A | B | C | D |
| Benzene | 7.5 | 28.4 | 1.2 | -2.8 | 5.9 | 5.8 | 2.5 | 2.8 |
| Benzoic Acid | 54.5 | 102 | 29 | 69 | 29.6 | 19.9 | 9.3 | 25.3 |
| o-Salicylic Acid | 53.6 | 97.8 | 22.7 | 73.7 | 32.6 | 17.9 | 10.8 | 26.8 |

Test Targets

| Compound | Sum Score | | | | Maximal Score | | | |
|---|---|---|---|---|---|---|---|---|
|  | A | B | C | D | A | B | C | D |
| m-Salicylic | 15.4 | 106 | 25.2 | 61.5 | 28.0 | 18.9 | 8.6 | 24.7 |
| p-Salicylic Acid | 50.4 | 104 | 18.5 | 59.5 | 28.8 | 20.1 | 9.5 | 23.4 |
| o-Salicylic Acid | 53.6 | 97.8 | 22.7 | 73.7 | 32.6 | 17.9 | 10.8 | 26.8 |

EXAMPLE 8

Three simulated receptors with specific affinity for positional isomers of chlorinated arenes. This was established by assigning chlorobenzene and o-dichlorobenzene very different target affinities during the training process.

Optimized Correlation Score: Receptor A: 0.987, Receptor B: 0.992, Receptor C: 0.996.

Training Targets used to optimize selective affinity. The target affinities used are fictitious. Twenty-five tests per target.

Target Affinities for All Receptors

| Compound | Target Affinity |
|---|---|
| Benzene | 0.9 |
| Chlorobenzene | 2.5 |
| o-Dichlorobenzene | 5.8 |

Receptor Affinities

| Compound | Sum Score | | | Maximal Score | | |
|---|---|---|---|---|---|---|
|  | A | B | C | A | B | C |
| Benzene | 39.7 | 17.1 | 31.0 | 3.7 | 3.2 | 3.4 |
| Chlorobenzene | 81.8 | 45.4 | 76.2 | 9.0 | 11.9 | 12.9 |
| o-Dichlorobenzene | 147.3 | 90.9 | 170.5 | 19.9 | 23.2 | 21.1 |

Test Targets

| Compound | Sum Score | | | Maximal Score | | |
|---|---|---|---|---|---|---|
|  | A | B | C | A | B | C |
| m-Dichlorobenzene | 68.0 | 73.9 | 145.6 | 17.2 | 17.0 | 18.5 |
| p-Dichlorobenzene | 112.4 | 92.5 | 132.6 | 12.0 | 14.6 | 10.7 |
| o-Dichlorobenzene | 147.3 | 90.9 | 170.5 | 19.9 | 23.2 | 21.1 |

PART B: DEVELOPMENT OF NOVEL COMPOUNDS WITH SELECTED FUNCTIONAL CHARACTERISTICS

Evolution of Novel Ligands

A population of simulated receptors evolved for selective affinity to a set of target compounds with similar functional characteristics can be used to devise novel compounds with similar characteristics, provided these characteristics are closely correlated with the structure or binding affinity of the model compounds. Using interaction with the receptors as selection criteria, novel chemical structures can be evolved to optimally fit the receptors. Because these compounds must meet the necessary and sufficient requirements for receptor selectivity, these novel compounds are likely to also possess activity similar to that of the original molecular targets.

Overview of Process

1. Generate a population of simulated receptors with optimized selectivity for a set of characterized target compounds. In some cases it may be desirable to generate several populations with different affinity characteristics. For example, three populations of simulated receptors could be generated, the first mimicking the properties of the selected target site, the second mimicking a site required for transport of the ligand to its primary target and a third population of simulated receptors mimicking a target site mediating undesirable side-effects. The development of a new ligand structure in this instance would require simultaneous optimization of affinity for the first two receptor populations and minimizing affinity for the third population.

2. Determine the affinity of a novel primary structure for the simulated receptor population(s).

3. Modify primary structure and evaluate affinity using simulated receptor population(s). If the modification improves affinity characteristics, the modified structure is retained for further modification. Otherwise a different modification is tested. Previously rejected modifications may be reintroduced in combination with other modifications.

4. Step 3 is repeated until a compound with suitable affinity characteristics is obtained.

Note: Using suitably discriminating simulated receptors it is possible to evolve chemical structures with sub-maximal affinity for a selected target site.

1) Molecular Genotype Code Generation

Encoding of the ligand phonotype (molecular structure) in the form of a linear genotype represented by a character string facilitates the processes of mutation, recombination and inheritance of the structural characteristics of the ligand during the evolutionary process.

The ligands evolved by the current implementation consist of substituted carbon skeletons. Each code consists of three character vectors. The primary code vector contains the turning instructions for the generation of the carbon skeleton and determines the position of each carbon atom in the skeleton. The secondary code vector identifies the functional groups attached to each carbon atom. The tertiary code vector specifies the position of the functional group relative to the host carbon. Molecular skeletons combining atoms other than carbon (e.g. ethers, amides and heterocycles) can be constructed in a homologous fashion using additional characters in the code to specify atomic species replacing carbon atoms in the skeleton.

The carbon skeleton is constructed from a series of points which form the nodes of a three-dimensional tetrahedral coordinate system. During initial skeleton construction, the distance between nearest points is equal to the mean bond length between alkyl carbon atoms.

Primary code vector: ligand skeleton determinants

The primary code vector consists of characters identifying turning direction relative to the current atom position. Each turning direction specifies the coordinates of the next atom in the tetrahedral matrix. Four directions (1,2,3,4) can be taken from each atom, corresponding to the unfilled valences of $sp^3$ carbon. Each of the carbon atoms belongs to one of four possible states (A, B, C, D). These states correspond to the number of distinct nodes in the tetrahedral coordinate system.

The relationship between turn direction and the new coordinates for the next atom in the skeleton is given by the following tables. The two tables B1 and B2 below embody the two turning conventions required to construct the ligands. The boat convention results in the generation of a tetrahedral matrix in which closed 6-member rings (cyclohexanes) assume the boat configuration. The chair convention results in the generation of a matrix in which cyclohexyl rings assume the chair configuration. It is possible to combine both conventions during code generation. Only the boat convention is used in the examples discussed here.

TABLE B1

Boat Convention
Current Position = (x, y, z)

| Current State | New Position Following Turn | | | |
|---|---|---|---|---|
| | Turn = 1 | Turn = 2 | Turn = 3 | Turn = 4 |
| A | (x − .75, y + .433, z − .5) | (x + .75, y + .433, z − .5) | (x, y − .864, z − .5) | (x, y, z + 1) |
| B | (x + .75, y − .433, z + .5) | (x − .75, y − .433, z + .5) | (x, y + .864, z + .5) | (x, y, z − 1) |
| C | (x − .75, y + .433, z + .5) | (x + .75, y + .433, z + .5) | (x y − .864, z + .5) | (x, y, z − 1) |
| D | (x + .75, y − .433, z − .5) | (x − .75, y − .433, z − .5) | (x, y + .864, z − .5) | (x, y, z + 1) |

Each turn also results in the specification of the state of the new atom:

| Current State | New State Following Turn | | | |
|---|---|---|---|---|
| | Turn = 1 | Turn = 2 | Turn = 3 | Turn = 4 |
| A | B | B | B | C |
| B | A | A | A | D |
| C | D | D | D | A |
| D | C | C | C | B |

TABLE B2

Chair Convention
Current Position = (x, y, z)

| Current State | New Position Following Turn | | | |
|---|---|---|---|---|
| | Turn = 1 | Turn = 2 | Turn = 3 | Turn = 4 |
| A | (x − .75, y + .433, z − .5) | (x + .75, y + .433, z − .5) | (x, y − .864, z − .5) | (x, y, z + 1) |
| B | (x + .75, y − .433, z + .5) | x − .75, y − .433, z + .5) | (x, y + .864, z + .5) | (x, y, z − 1) |
| C | (x − .75, y − .433, z + .5) | (x + .75, y − .433, z + .5) | (x y + .864, z + .5) | (x, y, z − 1) |
| D | (x + .75, y + .433, z − .5) | (x − .75, y + .433, z − .5) | (x, y − .864, z − .5) | (x, y, z + 1) |

Each turn also results in the specification of the state of the new atom:

| Current State | New State Following Turn | | | |
|---|---|---|---|---|
| | Turn = 1 | Turn = 2 | Turn = 3 | Turn = 4 |
| A | B | B | B | C |
| B | A | A | A | D |
| C | D | D | D | A |
| D | C | C | C | B |

Using these relationships, primary code vectors consisting of strings of the characters 1,2,3, and 4 can be decoded to create three-dimensional arrangements of carbon atoms. The resulting string of carbon atoms is allowed to fold back on itself or create closed loops, producing short side chains and ring structures. Specific ring structures (for example, cyclohexanes) can be incorporated directly as specific character sequences, as shown below. Secondary Code Vector:

Substituents A secondary code vector, of the same length as the primary code vector, is used to allocate the type of substituent attached to the carbon atom specified by the primary code vector. Each substituent is identified by a single character. Substituents are added singly to the carbon skeleton. A single carbon atom can have more than one substituent, but only if it is specified more than once by the primary code.

In the current implementation, all valences not filled by substituents specified by the secondary code vector are automatically filled with hydrogen atoms during the ligand construction process. Other rules could be applied for filling empty valences with atoms other than hydrogen.

Tertiary Vector: Substituent Bond Vector

A tertiary code vector, of the same length as the primary code vector, is used to allocate the valence used for the attachment of the substituent specified by the secondary code vector. The tertiary code consists of the characters 1, 2, 3, and 4 each of which refers to the turn directions specified for the primary code. Substituents are only allocated if the valence is not already occupied by either a carbon atom specified by the primary code vector or another previously allocated substituent. Alternatively, successive substituents could replace previously allocated substituents.

2) Code Creation

To create carbon skeletons the primary code is constructed by creating a random sequence of characters belonging to the set {"1", "2", "3", "4"}. The creation of heterocyclic structures, ethers, amides, imides and carboxylic compounds is accomplished by substituting a carbon atom in the skeleton by a different atom specified by the secondary code.

The secondary code is generated from a random sequence of characters identifying substituent types. The frequency of the characters can be random or fixed prior to code generation.

The tertiary code consists of characters belonging to the set {"1", "2", "3", "4"}. Ring structures can be deliberately constructed (as opposed to random generation) by adding specific character sequences to the primary code. For example "431413" codes for a cyclohexyl ring. A total of 24 strings code for all possible orientations of cyclohexyl rings in the tetrahedral matrix. Secondary and tertiary code vectors for the ring primary codes are generated as described previously. Module 12 provides a flowchart of an example creation of code generating carbon skeletons with rings.

The relative positions of the entry and exit points from a ring comprising part of the carbon atom skeleton are determined by the length of the character sequences used to generate the ring. Specifically, if the sequences contains six characters, for example 431413, then the entry and exit point will be the same member of the ring. If the sequence is partially repeated and appended to the initial six characters, the entry point and exit point will not be the same member of the ring. For example, the sequences 4314134 and 43141343141 will generate rings with exit points at the members of the rings adjacent to the entry points.

In the current implementation, rings are added to the skeleton by adding sequences of 6 or more characters to the code. For the ring defined by 431413 the possible sequences used are:

```
431413
4314134
43141343
431413431
4314134314
43141343141
431413431413
431413431413
```

The conventions presented for creating a novel ligand genotype can be used to encode other chemical structures in a linear format, either for storage or for introduction into the ligand evolutionary process. For example, a known pharmacophore can be encoded in linear format and used as the starting point for evolving novel ligands with similar or enhanced functional properties. Similarly, sets of pharmacophores interacting with a common target site can be encoded in linear format and used for recombination.

3) Code Translation and Ligand Construction

The code vectors are converted into three-dimensional representations of ligands in a translation process consisting of three discrete steps. In the first step, the carbon atom skeleton is constructed using the primary code. In the second step substituents are added to the carbon skeleton using the instructions from the secondary and tertiary code vectors. Instructions from the secondary and tertiary code vectors may also specify replacement of carbon atoms in the skeleton with different atoms. Instructions from the secondary and tertiary codes may also change the number and orientation of available valences present on a carbon or other atom forming part of the primary skeleton. For example, addition of carbonyl oxygen occupies two empty valences. In the third step, all valences not filled by substituents during the second step are filled with hydrogen atoms (unless otherwise specified).

Primary decoding: Ligand skeleton construction

Primary decoding uses the turning instructions from the primary code vector to specify the positions of each carbon atom. The first atom is assumed to be located at the origin of the coordinate system. The first atom is assumed to occupy state A in the matrix.

Decoding proceeds sequentially. The result of the primary decoding process is a 3×n matrix containing the x, y, and z coordinates of each of the n carbon atoms in the skeleton. Because loops and reversals are permitted, the same position in space may be occupied by more than one carbon. In these cases, only one carbon atom is assumed to occupy the position. As a result, the number of carbon atoms forming the completed skeleton may be less than the number of characters in the primary code vector.

As the primary code is read, a list is constructed from the secondary code that identifies the substituents attached to each carbon position. At the same time a parallel list is constructed using the tertiary code to specify the valence occupied by each substituent.

Secondary decoding: Substituent additions

Substituents are added sequentially to each carbon atom based on the list generated from the secondary code during primary decoding. The corresponding value from the tertiary code is used to specify the valence position of the substituent relative to the host carbon. If the position is already occupied by either an adjacent carbon atom, or a previously specified substituent, the substitution is not carried out. Alternatively, a decoding process could be constructed in which the substitution is carried out at the next unoccupied position or the substitution replcases a previously specified substituent. The distance between the substituent and the carbon atom is calculated from look up tables of bond lengths. The position data and bond lengths are used to calculate the coordinates of the substituent. In the case of multi-component substituents, such as hydroxyl, nitro, and amino groups, the coordinates for each atom in the substituent are calculated relative to the host carbon.

After all the substituents specified by the secondary code vector are added to the skeleton, all unfilled positions remaining on the skeleton are filled with hydrogen atoms. The hydrogen $sp^3$-carbon bond length is used to calculate the coordinates of each hydrogen atom.

A single carbon atom can have more than one non-hydrogen substituent. This can occur if the same position is specified more than once by the primary code vector. The current implementation does not incorporate multiple substitutions using the secondary code directly, although this can be readily implemented.

Substitutions are only allowed at loci not occupied by carbon atoms forming the ligand skeleton. A cumulative list is maintained of all occupied sites in the tetrahedral matrix.

During the secondary decoding process a list is compiled of the type, radius, and position of all the atoms comprising the ligand. This list is the basis for subsequent target generation.

At this stage in the process, the feasibility of the structure generated from the code sequence is not evaluated. In some cases the atomic coordinates may be entered into energy minimization programs to create more realistic structures. However, in the present implementation, no assumptions are made concerning the configuration of the ligand during binding. In addition, the current implementation preserves the structural uniqueness of specific configurations of the same molecule. For example, the current implementation distinguishes between three rotational isomers of butane, and treats each isomer as a unique molecule.

The code vectors constitute the genotype of the corresponding ligand, and can be subjected to mutation and recombination with resulting changes in ligand structure. The ligand structure itself is the phenotype used to evaluate binding affinity with a selected population of virtual receptors.

4) Target Presentation

Chemical structures or target ligands are initially constructed from randomly generated codes. Following decoding, the coordinates, radii, dipole moments and polarizabilities of each atom in the target ligand are obtained from look up tables of value and used to evaluate the binding affinity between the ligand and a selected population of virtual receptors.

The affinity of the target for each of the virtual receptors is tested for many orientations of the target relative to the receptor surfaces. No assumptions are made concerning the relative orientations of the ligand and simulated receptor. Prior to the evaluation of binding affinity, the target and receptor must be brought into contact. The method of target presentation and calculation of affinity between the chemical structures and simulated receptors is essentially the same as discussed above in Module 4 between known target molecules and the simulated receptors.

5) Evaluation of Binding Affinity and Fitness

The binding affinity of the target ligand for each of the simulated receptors used for fitness evaluation is calculated using the same effective affinity calculation method described for simulated receptor generation using the target molecules. As previously noted, affinity calculations using other criteria can be incorporated into the fitness testing process but the efficacy and computational efficiency of the present invention relies in part on using the same effective affinity calculation for virtual receptor generation and generation of the chemical structures using the simulated receptor populations.

6) Ligand Evolution

Testing Goodness of Fit

Goodness of fit between a selected population of simulated receptors and a novel ligand or chemical structure is evaluated by comparing the target activity or affinity values for the ligand with those obtained for the simulated receptor-ligand complexes. The maximal affinities of an optimally selective virtual receptor should be strongly correlated with the target affinity measures. Successive iterations of the evolutionary process are used to enhance this correlation.

The target values can be set to any level of binding affinity. It is not required that the ligand have the same binding affinity for all the virtual receptors used in the selection process. In the current implementation, the maximal binding affinities of the optimized virtual receptors for known substrates are used to calculate target binding affinities. For example, the target affinities may be set to 90% of the binding affinity of each member of the virtual receptor population for a specific substrate. Alternatively, the target binding affinity may be set to zero if the interaction between the ligand and the virtual receptor is to be minimised.

By combining simulated receptors optimized for different sets of substrates and associating selected target affinity values with each receptor, novel ligands can be selected for specific binding affinity profiles. Ligand fitness measures the match between calculated ligand binding affinities and the target affinity values. The optimization process maximizes ligand fitness.

The optimal orientation of the ligands for maximal binding affinity is unknown prior to testing. In order to obtain a representative measure of the range of receptor-ligand affinities, each novel ligand must be tested repeatedly using different random orientations relative to the receptor surface. Each test uses Module 4 discussed in Part A to evaluate affinity. In general, the reliability of the maximal affinity values obtained depends upon the sample size, since it becomes increasingly likely that the sample will contain the true maximal value.

Two techniques are employed in the current implementation to circumvent the need for large sample sets for the generation of optimized novel ligands or chemical structures:

1. The use of a measure combining average (or sum) affinity and maximal affinity to select for ligands with optimized affinity profiles.

2. Incremental increases in the number of orientations tested with successive iterations of the optimization process. (Optimization begins with a small set of target orientations, as ligands of greater fitness are generated, more orientations are tested.)

In the current implementation, the sum is calculated for the affinity values obtained for all the tested orientations of each ligand. This sum affinity score is a measure of the average affinity between the receptor and the ligand. At the same time, the maximal affinity value is also determined.

Both sum and maximal affinities are used to test the goodness of fit between the virtual receptor and the novel ligand. The fitness of each novel ligand is rated according to the difference between the calculated values of sum affinity and maximal affinity and the target values for these parameters. In the current implementation, the value:

$$F = \left\{ \frac{|\text{calculated max affinity} - \text{target max affinity}|}{2 \times \text{target max affinity}} \right\} + \left\{ \frac{|\text{calculated sum affinity} - \text{target sum affinity}|}{2 \times \text{target sum affinity}} \right\}$$

is calculated as the fitness score for each novel ligand-simulated receptor pair. FITNESS IS MAXIMAL WHEN THE FITNESS SCORE IS ZERO. Target maximal affinity and target sum affinities are obtained from the regression functions developed during the evolution of optimised virtual receptors, as described in the previous sections. The target values are obtained as follows:

target max affinity = $f \times$ maximal affinity of the most potent substrate used for virtual receptor generation target sum affinity = $f \times$ sum affinity of the most potent substrate used for virtual receptor generation where $f$ = a scaling factor.

When more than one simulated receptor is used for the evaluation of ligand fitness, the fitness scores of each ligand-simulated receptor pair are summed.

$$F_{tot} = \sum_{i=1}^{n} F_i$$

$$F_i = \left\{ \frac{|\text{calculated max affinity}_i - \text{target max affinity}_i|}{2 \times \text{target max affinity}_i} \right\} + \left\{ \frac{|\text{calculated sum affinity}_i - \text{target sum affinity}_i|}{2 \times \text{target sum affinity}_i} \right\}$$

In this case, fitness is maximized when the sum of the fitness scores is zero. In some cases it may be desirable to use only the maximal affinity scores when testing a novel ligand against a panel of different simulated receptors. In this case the fitness would be given by:

$$F_{tot} = \sum_{i=1}^{n} |\text{calculated max affinity}_i - \text{target max affinity}_i|/\text{target max affinity}_i.$$

In this case, fitness is also maximized when the sum of the fitness scores is zero. Other methods, for example the use of a geometric mean, could also be used to measure the total fitness of a ligand tested against a series of simulated receptors.

Use of both the maximal affinity values and sum affinity values obtained for each simulated receptor ensures that the selectivity of the virtual receptors is implicated in the evaluation of ligand fitness. In this way, the fitness of the ligand reflects not only the affinity of the ligand but also satisfaction of the steric requirements of the virtual receptor that are the basis of selectivity.

6a) The Optimization Process Objective

To evolve a novel ligand that has selected target affinities for a set of simulated receptors. A highly efficient mechanism for finding solutions is required, since the total number of possible genotypes containing 25 instructions is $256^{25}$.

Process (1) PHASE 1. Generate a set of random genotypes coding for ligands and screen against a set of simulated receptors to select ligands exceeding a threshold level of fitness.

(2) PHASE 2. The selected genotype is used as the basis for further optimization using genetic algorithm (recombination) and unidirectional mutation techniques. Mutate selected genotype to generate a breeding population of distinct but related genotypes for recombination.

(3) Choose most selective mutants from population from population for recombination.

(4) PHASE 3. Generate new genotypes by recombination of selective mutants. Select from the resulting genotypes those with the highest affinity fitness. Use this subpopulation for the next recombinant (repeat PHASE 3) or mutation (repeat PHASE 4) generation.

(5) PHASE 4. Take best recombination products and apply repeated point mutations to enhance selectivity.

(6) The optimization process is completed when ligands of desired fitness are generated.

PHASE I: Evolution-generation of Primary Code

The objective of the first stage in the optimization process is to generate a genotype and corresponding ligand phenotype with a minimal level of fitness. This genotype is subsequently used to generate a population of related genotypes.

The Genetic Algorithm developed by Holland can be used to search for optimal solutions to a variety of problems. Normally this technique is applied using large, initially random sets of solutions. In the present implementation the technique is significantly modified in order to reduce the number of tests and iterations required to find ligands with high selective affinity. This has been accomplished by using a set of closely related genotypes as the initial population and the application of high rates of mutation at each iteration. For any set of target compounds it is possible to develop distinct ligands with optimal affinity characteristics. For example, receptors may bind optimally to the same targets but in different orientations. The use of an initial population of closely related genotypes increases the likelihood that the optimization process is converging on a single solution. Recombination of unrelated genotypes, although it may generate novel genotypes of increased fitness, is more likely to result in divergence.

PHASE 2: Ligand Mutation

The objective of the second phase of the evolutionary process is the generation of a population of distinct but related genotypes derived from the primary genotype. Members of this population are subsequently used to generate recombinants. This breeding population is created by multiple mutation of the primary genotype. The resulting genotypes are translated and screened for selectivity. The most selective products are retained for recombination.

Ligands are subjected to mutation by changing characters in the genotypes (code vectors) encoding their structures. These mutations change the shape of the ligand, as well as functional group placement and functional group types present on the ligand. Mutations in the current implementation can alter the number of carbons comprising the ligand skeleton. Module 12 is a flowchart of a sample process for multiple point mutation.

Mutations can alter the folding pattern of the ligand phenotype, with resulting changes in shape and the location or exposure of functional groups. Mutations that affect the configuration of peripheral regions of the ligand phenotype can result in shifts in position relative to the receptor center.

Neutral Mutations

All mutations alter the structure of the phenotype, however, not all mutations result in changes in the functionality of the ligand. Such neutral mutations may alter components of the ligand that do not affect affinity. In some cases these neutral mutations can combine with subsequent mutations to exert a synergistic affect.

Sequence Mutations

Sequence mutations do not change code characters directly. Instead the sequence of characters in the code is rearranged. Sequence mutations can alter the size of the ligand, the structural configuration and presence and location of functional groups. Four types of sequence mutation are used in the current implementation:

a) DELETION: A sequence of characters is removed from the code.

ABCDEA→ABEA b) INVERSION: The order of characters comprising a sequence within the code is reversed.

ABCDEA→ABDCEA c) DUPLICATION: A sequence of characters comprising part of the code is repeated.

ABCDEA→ABCDCDEA d) INSERTION: A sequence of characters is inserted into the code.

ABCDEA→ABCDBCEA

Mutations are applied in combination in the current implementation. Module 13 provides a flowchart of a sample sequence mutation.

PHASE 3: Generation of Recombinant Code

During recombination, randomly chosen, complementary sections are exchanged between selected genotypes. The objective of recombination is the generation of novel genotypes with increased fitness. Recombination facilitates the conservation of genotype fragments that are essential for phenotypic fitness, while at the same time introducing novel combinations of instructions. In general, recombination coupled with selection results in rapid optimization of selectivity. Module 14 provides a flowchart for a sample procedure for recombination.

The current implementation retains the population used for recombination for testing. This ensures that genotypes with high selectivity are not replaced by genotypes with lower fitness. In the current implementation, multiple mutations are applied to 50% of the recombinant genotypes prior to testing. This process increases the variability within the recombinant population. The test populations used in the current implementation range in size from 10 to 40 genotypes. This is a relatively small population size. Under some conditions, larger populations may be required. Module 14 is a flowchart for an example of recombination.

PHASE 4: Ligand Maturation

Progressive micromutation technique

The final stage in the optimization process mimics the maturation of antibodies in the mammalian immune system. A series of single point mutations are applied to the genotype, and the effect on phenotypic fitness is evaluated. Unlike recombination, this process generally results in only small incremental changes to the selectivity of the phenotype. The maturation process uses a Rechenberg (1+1) evolutionary strategy. At each generation the fitness of the parental genotype is compared to that of its mutation product, and the genotype with the greater selectivity is retained for the next generation. As a result, this process is strictly unidirectional, since less selective mutants do not replace their parents. During each iteration of the maturation process, only a single instruction in the code is changed in the present implementation.

If a parent and its mutation product have the same selectivity, the parent is replaced by its product in the next generation. This method results in the accumulation of neutral mutations that may have synergistic effects with subsequent mutations. This convention is arbitrary. Module 15 provides a flowchart for a sample maturation process.

If recombination or maturation do not generate improved selectivity after repeated iterations, it may be necessary to repeat multiple mutations (PHASE 2) in order to increase the variability of the breeding population genome.

EXAMPLES OF LIGAND GENERATION

Overview

The mosquito *Aedes aegypti* is repelled by benzaldehyde and, to a much smaller degree, by benzene and toluene (Table 1). This species is not repelled significantly by cyclohexane or hexane (Table 1). In the following test of novel ligand generation, the method is used to generate, ab initio, compounds that will be similar in repellent activity to benzaldehyde. In the first step of ligand generation, simulated receptors were constructed with high affinity for benzaldehyde and low affinity for benzene. In the second step, ligands are evolved with binding affinities for the simulated receptors similar to that of benzaldehyde.

Mosquito Responses

Mosquitoes were lab-reared, 7-14 days post-emergence and unfed. Experiments were conducted over six day periods at 20° C. under fluorescent lighting. Tests were run between 12:00 and 17:00 EDT. The test populations in the four sets of trials consisted of 200, 175, 105 and 95 females. Mosquitoes were provided with drinking water.

The tests were conducted in a 35×35×35 cm clear Plexiglas box with two screened sides forming opposite walls. The screening consisted of two layers: an inner layer of coarse plastic mesh and an outer layer of fine nylon mesh. The box was placed in a fumehood such that air entered one of the screened sides and exited through the opposite side. Air flow was <0.5 cm/s.

The mosquitoes landed on the walls of the box, oriented head upwards. Triangular pieces (4×4×1 mm) of Whatman #1 filter paper were used to present the stimulant compounds. The tips were dipped into the test solution to a depth of 0.5 cm and used immediately. Responses to the test solutions were determined as follows:

1. A stationary female resting on the interior screen of the upwind wall was selected for testing.
2. The treated filter paper tip was placed against the outside of the screen and positioned opposite the mesothoracic tarsus of the mosquito. In all cases the initial approach was made from below the position of the mosquito.
3. The tip was held in position for a maximum of 3 s and the response of the mosquito was noted.

The procedure was then repeated for a new individual. Mosquitoes were tested only once each day with each compound. Tips were used for five tests each (total duration of use <30 s), then replaced. Compounds were tested in random order, and each compound was tested twice on separate days. Two sets of controls were conducted using untreated (dry) filter paper tips and tips moistened with distilled water positioned in the same manner as treated tips. Tests of these controls were interspersed regularly among tests of the repellent compounds. Responses to the controls did not vary during the course of the experiment ($p>0.25$). Four behavioral responses were recorded:

1. No response: the mosquito remained motionless.
2. Take-off: the mosquito flew away from its resting site.
3. Ipsilateral leg lifting: the mosquito raised the mesothoracic leg on the same side as the stimulus source.
4. Contralateral leg lifting: the mosquito raised the mesothoracic leg on the opposite side from the stimulus source.

Ipsilateral leg lifting was frequently followed by take-off, in which case both behaviours were recorded. Polyethylene gloves were worn during testing an during all phases of compound preparation.

TABLE E1

Mosquito responses to selected volatile compounds

| Compound | Boiling Point (°C.) | N | % Flight Response | % Leg Lifting Response | Relative Repellency* |
|---|---|---|---|---|---|
| Benzaldehyde | 178 | 130 | 90 | 10 | 178 |
| Benzene | 80 | 72 | 72 | 12.5 | 68 |
| Toluene | 110 | 166 | 67 | 27 | 94 |
| Cyclohexane | 81 | 80 | 6 | 0 | 4.9 |
| Heane | 69 | 100 | 4 | 0 | 2.8 |
| Control (blank) | — | 450 | 5 | 0 | |

*Relative repellency = [(% Flight Response + % Leg Response) × Boiling Point]/100

Simulated Receptor and Ligand Generation

Two simulated receptors were generated using the same selection criteria. Each receptor was used independently to generate a set of ligands.

Molecular Assembly 1

PHASE 1: RECEPTOR GENERATION

A receptor was evolved with selective affinity for benzaldehyde.

The training targets were benzene and benzaldehyde. Fifteen orientations of each target were used to calculate affinity values.

Results of the evolutionary process were:

| Target | Activity Level | Sum Affinity | Maximum Affinity |
|---|---|---|---|
| Benzene | 1.0 | 6.87 | 2.21 |
| Benzaldehyde | 5.9 | 75.87 | 13.02 |

The affinity score for the receptor was 0.992
Code for the Optimized 25×6×7 Benzaldehyde Receptor:

| | | | |
|---|---|---|---|
| 231014406145 | 053400324221 | 412100131300 | 063112101132 |
| 412061421302 | 413231124335 | 133100333032 | 300043541401 |
| 022224-31514 | 143431012321 | 341310334122 | 101414141021 |
| 402131114311 | 010233120331 | 260214016321 | |

PHASE 2: LIGAND GENERATION

The optimized simulated receptor was used as a template for the evolution of novel ligands. Four different ligands were assembled by random mutation and selection. Ligands were selected for similarity with benzaldehyde. The affinity values for the ligands were:

| | Benzaldehyde | Ligand 1.1 $C_9H_{12}O$ | Ligand 1.2 $C_8H_{15}Cl$ | Ligand 1.3 $C_8H_{13}Cl(=O)$ | Ligand 1.4 $C_{13}H_{16}OH(=O)$ |
|---|---|---|---|---|---|
| Sum Affinity | 75.87 | 74.03 | 67.88 | 72.25 | 72.94 |
| Max. Affinity | 13.02 | 12.82 | 15.14 | 12.58 | 11.2 |

Figure 4A:
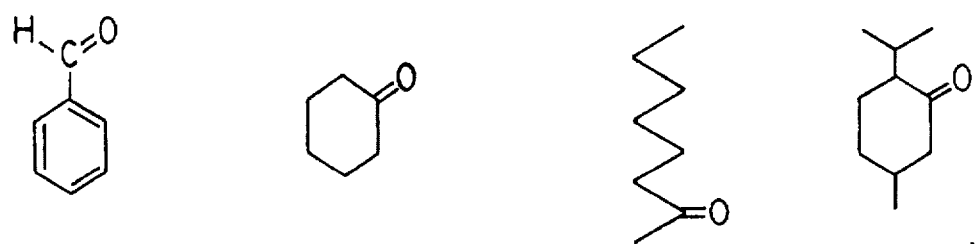
FIG. 4a shows several chemical compounds used in the example relating to examples of ligand generation.
Figure 4B:
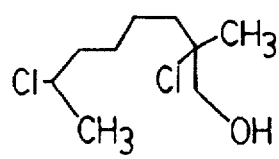
FIG. 4b shows ligands 1.1 to 1.4 generated by the method of the present invention in the example of ligand generation wherein each ligand has at least one orientation wherein it is structurally similar to benzaldehyde.
Figure 4B:
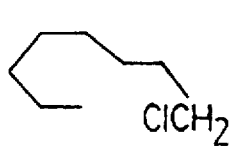
Figure 4B:
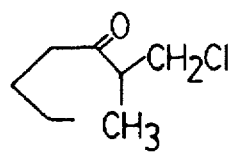
Figure 4B:
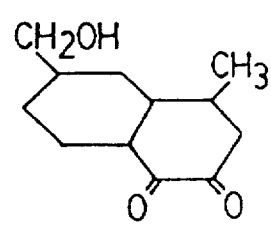

Evolved ligands 1.1 to 1.4 are shown in FIG. 4b. At least one orientation of each ligand was structurally similar to benzaldehyde.

Molecular Assembly 2

PHASE 1: RECEPTOR GENERATION

A 25×6×7 receptor was evolved with selective affinity for benzaldehyde. The training targets were benzene and benzaldehyde. Fifteen orientations of each target were used to calculate affinity values.

Results of the evolutionary process were:

| Target | Activity Level | Sum Affinity | Maximum Affinity |
|---|---|---|---|
| Benzene | 1.0 | 25.88 | 8.53 |
| Benzaldehyde | 5.8 | 162.23 | 42.74 |

The affinity score for the receptor was 0.996
The code for the receptor was:

| | | | |
|---|---|---|---|
| 031264441313 | 004422243042 | 223140112054 | 302122330134 |
| 543301114446 | 210043042311 | 323431131340 | 130020120133 |
| 224223503403 | 432003432122 | 002221221113 | 411440003113 |
| 323030313214 | 002321144010 | 000243013133 | |

PHASE 2: LIGAND GENERATION

The optimized simulated receptor was used as a template for the evolution of novel ligands. Four different ligands were assembled by random mutation and selection. Ligands were selected for similarity with benzaldehyde. The affinity values for the ligands were:

| | Benzaldehye | Ligand 2.1 $C_8H_{13}Cl(=O)$ | Ligand 2.2 $C_9H_{15}Cl(=O)$ | Ligand 2.3 $C_6H_{10}CN(=O)$ | Ligand 2.4 $C_9H_{13}(=)_2$ |
|---|---|---|---|---|---|
| Sum Affinity | 162.33 | 182.4 | 166.5 | 159.7 | 156.8 |
| Max. Affinity | 42.74 | 48.97 | 43.0 | 39.0 | 46.5 |

-continued

|  | Benzaldehye | Ligand 2.1<br>$C_8H_{13}Cl(=O)$ | Ligand 2.2<br>$C_9H_{15}Cl(=O)$ | Ligand 2.3<br>$C_6H_{10}CN(=O)$ | Ligand 2.4<br>$C_9H_{13}(=)_2$ |
|---|---|---|---|---|---|
| Fitness Score |  | 0.135 | 0.02 | 0.05 | 0.06 |

Figure 4C:
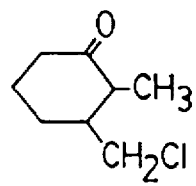
FIG. 4c shows ligands 2.1 to 2.4 generated by the method of the present invention in the example of ligand generation relating to design of chemical structural exhibiting an efficacy for repelling misquitoes.
Figure 4C:
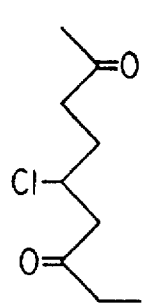
Figure 4C:
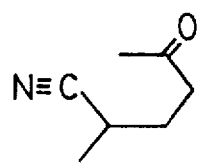
Figure 4C:
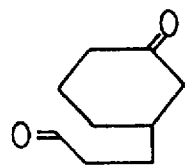

Evolved ligands 2.1 to 2.4 are shown in FIG. 4c. At least one orientation of each ligand was structurally similar to benzaldehyde.

Compounds 2.1 and 2.4 are substituted cyclohexanone derivatives. Ligand 2.2 is 5-Chloro-2, 7-nonadione and ligand 2.3 is 2-cyano-5-hexanone. Ligand 1.4 contains a fragment corresponding in structure to methyl cyclohexyl ketone. Experiments testing the repellency of cyclohexanone, menthone, methyl cyclohexyl ketone and 2-octanone (see FIG. 4a) suggest that these ligands will also be repellent to mosquitoes (Table E2).

TABLE E2

Mosquito responses to selected volatile compounds

| Compound | Boiling Point (°C.) | N | % Flight Response | % Leg Lifting Response | Relative Repellency* |
|---|---|---|---|---|---|
| Benzaldehyde | 178 | 130 | 90 | 10 | 178 |
| 2-Octanone | 173 | 80 | 82 | 12.5 | 162 |
| 2-Acetylcyclo-hexanone | 225 | 100 | 54 | 24 | 175 |
| Cyclohexanone | 156 | 134 | 99 | 1 | ≧154 |
| Menthone | 207 | 110 | 72 | 11 | 172 |
| Control (blank) | — | 450 | 5 | 0 |  |

*Relative repellency = [(% Flight Response + % Leg Response) × Boiling Point]/100

The method disclosed herein of designing new chemical structures exhibiting preselected functional characteristics or properties has been described by example only. For example, the method may be readily practise using other known or acceptable values for polarizabilities, dipole moments, covalent radii and the like. In addition, the flow-charts giving process calculation steps in the modules are meant to be illustrative only. For example, the calculation of affinity may be carried out using available computational packages using fewer approximations than used herein. The method of generating new chemical structures has relied upon first generating one or more simulated receptors exhibiting a preselected affinity for known target compounds with similar functional characteristics and using these receptors to generate the novel structures exhibiting these characteristics to whatever degree is desired. The receptors themselves may be used for other applications besides generating novel chemical structures, for example as a means of screening for pharmaceutical or toxicological properties of known compounds. Thus, it will be appreciated by those skilled in the art that numerous variations of the method disclosed herein may be made without departing from the scope of the invention.

TABLE I

Transition states and addition factors

| Old State | Addition factors | | | New State for Turn = | | | |
|---|---|---|---|---|---|---|---|
|  | Δx | Δy | Δz | Right | Up | Left | Down |
| 1 | 0 | 1 | 0 | 2 | 4 | 3 | 5 |
| 2 | −1 | 0 | 0 | 15 | 6 | 1 | 24 |
| 3 | 1 | 0 | 0 | 1 | 7 | 15 | 22 |
| 4 | 0 | 0 | −1 | 12 | 23 | 14 | 1 |
| 5 | 0 | 0 | 1 | 9 | 1 | 16 | 23 |
| 6 | 0 | 0 | −1 | 11 | 20 | 10 | 2 |
| 7 | 0 | 0 | −1 | 13 | 21 | 8 | 3 |
| 8 | 0 | −1 | 0 | 7 | 9 | 24 | 14 |
| 9 | −1 | 0 | 0 | 17 | 10 | 5 | 8 |
| 10 | 0 | 1 | 0 | 6 | 14 | 22 | 9 |
| 11 | 0 | −1 | 0 | 22 | 16 | 6 | 12 |
| 12 | −1 | 0 | 0 | 18 | 11 | 4 | 13 |
| 13 | 0 | 1 | 0 | 24 | 12 | 7 | 16 |
| 14 | 1 | 0 | 0 | 4 | 8 | 18 | 10 |
| 15 | 0 | −1 | 0 | 3 | 17 | 2 | 18 |
| 16 | 1 | 0 | 0 | 5 | 13 | 17 | 11 |
| 17 | 0 | 0 | −1 | 16 | 19 | 9 | 15 |
| 18 | 0 | 0 | 1 | 14 | 15 | 12 | 19 |
| 19 | 0 | 1 | 0 | 20 | 18 | 21 | 17 |
| 20 | 1 | 0 | 0 | 23 | 24 | 19 | 6 |
| 21 | −1 | 0 | 0 | 19 | 22 | 23 | 7 |
| 22 | 0 | 0 | 1 | 10 | 3 | 11 | 21 |
| 23 | 0 | −1 | 0 | 21 | 5 | 20 | 4 |
| 24 | 0 | 0 | 1 | 8 | 2 | 13 | 20 |

Formula for algorithm: Input (old state, turn) → output (Δx, Δy, Δz, new state)

Example: Initial position (12, 34, −18); Input: old state=10, turn=right:
Output: new state=6, Δx=0, Δy=1, Δz=0; Subsequent position (12, 35, −18)

TABLE 2

| | Van der Waals Raddii | | | | | | | | |
|---|---|---|---|---|---|---|---|---|---|
| Element | H | F | O | N | C | Cl | S | Br | P | I |
| Van der Waals Radius (pm) | 110 | 140 | 150 | 150 | 170 | 180 | 180 | 190 | 190 | 200 |

TABLE 2-continued

Van der Waals Raddii

| Element | H | F | O | N | C | Cl | S | Br | P | I |
|---|---|---|---|---|---|---|---|---|---|---|
| Relative Radius ($H = 0.5$) | 0.5 | 0.64 | 0.68 | 0.68 | 0.77 | 0.82 | 0.82 | 0.86 | 0.86 | 0.91 |

Based on: N. S. Issacs, 1987. Physical Organic Chemistry. Longman Scientific and Technical, New York. 828 pp.

TABLE 3

Covalent Bond Radii (pm)

| Bond Order | | | | | | |
|---|---|---|---|---|---|---|
| First | H | | | | | |
| | 28 | | | | | |
| | B | C | N | O | F | |
| First | 88 | 77 | 70 | 66 | 64 | |
| Second | | | 66.5 | 60 | 55 | |
| Third | | | 60.2 | 55 | | |
| Aromatic | | | 70 | | | |
| First | | Si | P | S | Cl | |
| | | 117 | 110 | 104 | 99 | |
| First | | | | | Br | |
| | | | | | 114 | |

Based on values in N. S. Issacs (1987).

TABLE 4

Sample effective dipole values used for charge site assignments.

| Bond | Atom | Dipole Value (Debye) |
|---|---|---|
| C—H | H | +0.35 or +0.084* |
| | C | no charge assigned |
| ArC—H | H | +0.6 |
| | C | −0.366 or no charge assigned |
| =C—H | H | +0.336 |
| | C | −0.6 or on charge assigned* |
| C=O | O | −2.7 |
| | C | no charge assigned* or +1.35 |
| C—O—C | O | −0.8 |
| C—OH | H | +1.5 or +1.7 |
| | O | −1.1 |
| C—NH$_2$ | H | +1.3 |
| | N | −1.3 |
| C—NO$_2$ | O | −2.0 |
| | N | +4.0 |
| C≡N | N | −3.7 |
| | C | no charge assigned |
| C—S—C | S | in thiophene or dimethyl sulphide +1.5* (may be negatively charged in contexts) |
| C—N=C | N | in pyridine or CH$_3$—N=CH$_2$ +1.5 or +1.3 |
| Ar—F or C=C—F | F | −1.3 |
| C—F | F | −1.8 |
| Ar—Cl or C=C—Cl | C | −1.7 |
| C—Cl | Cl | −2.1 |
| Ar—Br or C=C—Br | Br | −1.7 |
| C—Br | Br | −2.0 |
| C—I | I | −2.0 |

*Preferred uner most conditions

Each target atom is described fully by a set of eight values $\{x_i, y_i, z_i, r_i, br_i, cr_i, d_i, \alpha_i\}$ where $x_i$, $y_i$ and $z_i$ are the positonal coordinates relative to the geometric center of the molecule, $r_i$ = the van der Waals radius, $br_i$ = the bond or covalent radius, $cr_i$ = the collision radius ($=r_i +0.5$), $\alpha_i$ = the polarizability, and $d_i$ = the effective dipole moment value.

TABLE 5

Selected Relative Effective Polarizabilities For Selected Target Atoms

| Atom | Context | Relative Polarizability ($\alpha_i$) |
|---|---|---|
| H | C—H | 1.0 |
| H | N—H | 1.1 |
| H | O—H | 1.1 |
| H | S—H | 3.0* |
| F | C—F | 1.5* |
| Cl | C—Cl | 4.0 |
| Br | C—Br | 5.8 |
| I | C—I | 8.9* |
| C | C—CH$_3$ | 3.7 |
| C | C—CH$_2$—C | 3.5 |
| C | C—CC$_2$—H | 3.2 |
| C | C=CH$_2$ | 4.5 |
| C | C=CH—C | 4.3 |
| C | C=CC$_2$ | 4.0 |
| C | C≡C—H | 4.9* |
| C | C≡C—C | 4.6* |
| C | Arene ring | 4.3* or 2.6 (based on benzene (delocalized electron cloud)) |
| C | C—C≡N | 4.0 |
| C | C$_3$—C—O— | 3.6 |
| C | C$_2$H—C—O— | 3.8 |
| C | CH$_2$—C—O— | 4.1 |
| C | H$_3$—C—O— | 4.4 |
| C | C$_2$—C=O | 3.6 |
| C | CH—C=O | 3.8 |
| C | C$_2$—C=N | ? |
| C | CH—C=N | ? |
| C | C$_3$—C—N | 3.1 |
| C | C$_2$H—C—N | 3.3 |
| C | CH$_2$—C—N | 3.6 |
| C | H$_3$—C—N | 3.8 |
| O | C—O—H | 2.1 |
| O | C=O | 2.1 |
| O | C—O—C | 1.8 |
| O | NO$_2$ | 1.9* |
| N | C—NH$_2$ | 3.1 |
| N | C—NH—C | 2.8* |
| N | C—NC$_2$ | 2.5* |
| N | C—NO$_2$ | 4.6* (may be larger in small molecules) |
| N | C≡N | 3.2 |
| S | C=S | 7.7 |
| S | C—S—C | ? |
| S | C—S—H | 5.0 |

*By calculation from molecular polarizabilites.
? Values can be determined from appropriate molecular data.

MODULE 1: CODE GENERATION FOR SIMULATED RECEPTORS

Step 1

Input code generation parameters: i) code length; and ii) instruction frequency.

Step 2

Initialize empty character string to store code.

Step 3

Generate random number.

Step 4
Based on random number and instruction frequency, select a character {"0", "1", ..., "6"} to concatenate to code string.
Repeat Step 4 until string length equals preset code length.
Step 5
Output code.

MODULE 2: CODE TRANSLATION FOR SIMULATED RECEPTORS
Step 1
Input origin coordinates for polymers comprising receptor.
Step 2
Input code for polymer.
Step 3
Read first character from code.
Step 4
If character is a turning instruction, use translation algorithm to determine subunit coordinates otherwise step 7.
Step 5
Store subunit coordinates. Assign a charge value of 0 to subunit
Step 6
If character is not the last character in code, repeat step 3 otherwise step.
Step 7
If character is a charge instruction, use translation algorithm to determine subunit coordinates assuming no turn.
Step 8
Store subunit coordinates. Assign charge value of +1 or −1 to subunit based on character.
Step 9
If character is not the last character in code, repeat step 3 otherwise step.
Step 10
Repeat steps 2 to 9 for each of the polymers comprising the receptor.
Step 11
Output coordinates and charge values of subunits.

MODULE 4: TARGET PRESENTATION

Step 1
Input coordinates and radii of target atoms $(xt_i, yt_i, zt_i, radius_i)$ (i=number of atoms in target) Input coordinates of receptor $(xr_j, yr_j, zr_j, charge_j)$ (j=number of subunits in receptor)
Step 2
Generate random angular $(\Delta\theta, \Delta\phi)$ and translation values $(k_x, k_y)$.
Step 3
Rotate and translate atomic coordinates by random amounts.
Step 3a
Convert target coordinates to polar form $(xt_i, yt_i, zt_i, radius_i) \rightarrow (\theta_i, \phi_i, \rho_i, radius_i)$
Step 3b
Add random changes to angles $(\theta_i, \phi_i, \rho_i, radius_i) \rightarrow (\theta_i+\Delta\theta, \phi_i+\Delta\phi, \rho_i, radius_i)$
Step 3c
Convert to rectangular coordinates $(\theta_i+\Delta\theta, \phi_i+\Delta\phi, \rho_i, radius_i) \rightarrow (x_i, y_i, z_i, radius_i)$
Step 3d
Add random translation $(xn_i, yn_i, zn_i, radius_i) = (x_i+k_x, y_i+k_y, z_i, radius_i)$
Step 4
Center target coordinates on origin (0,0,0).

Step 4a
Find maximum and minimum values of $xn_i$, $yn_i$ and $zn_i$.
Step 4b
Find geometric center of receptor $xn_{center}=(xn_{maximum}-xn_{minimum})/2$, $yn_{center}=(yn_{maximum}-yn_{minimum})/2$, $zn_{center}=(zn_{maximum}-zn_{minimum})/2$
Step 4c
Calculate centered coordinates: $(xnc_i, ync_i, znc_i)=(xn_i-xn_{center}, yn_i-yn_{center}, zn_i-zn_{maximum})$
Step 5
Use atomic radii and transformed coordinates $(xnc_i, ync_i, znc_i, radius_i)$ to construct collision surface of target $g(x_g, y_g)=z_g$
Step 5a
Create a grid with spacing equal to the diameter of the receptor subunits (=1). Coordinates of grid:

$x_g \in \{Int(xn_{minimum}-xn_{center}), Int(xn_{minimum}-xn_{center})+1 \ldots 0, \ldots Int(xn_{maximum}-xn_{center})-1, Int(xn_{maximum}-xn_{center})\} y_g \in \{Int(yn_{minimum}-yn_{center}), Int(yn_{minimum}-yn_{center})+1 \ldots 0, \ldots Int(yn_{maximum}-yn_{center})-1, Int(yn_{maximum}-yn_{center})\}$ Set the initial values of $g(x_g, y_g)$ to 0 at all points on the grid
Step 5b
For each atom (i) set the $g(x_g, y_g)$ (height) value of each grid point $(x_g, y_g)$ according to the following rule:
For i=1 to number of atoms in target If $(xnc_i-x_p)^2+(ync_i+y_p)^2 < radius_i^2$ then $g(x_g, y_g)=$minimum $(g(x_g, y_g), znc_i, radius_i)$ Else If $(xnc_i-x_p)^2+(ync_i+y_p)^2 < (radius_i+0.5)^2$ then $g(x_g, y_g)=$minimum $(g(x_g, y_g), znc_i-(radius_i/2))$ Else $g(x_g, y_g)=$minimum $(g(x_g, y_g), 0)$ Next i
Step 6
Center receptor coordinates on origin (0,0).
Step 6a
Find maximum and minimum values of $xr_j, yr_j$ and $zr_j$.
Step 6b
Find geometric center of receptor:

$xr_{center}=(xr_{maximum}-xr_{minimum})/2, yr_{center}=(yr_{maximum}-yr_{minimum})/2, zr_{center}=(zr_{maximum}-zr_{minimum})/2$ Step 6c
Calculate centered receptor coordinates:

$(xc_j, yc_j, zc_j)=(xr_j-x_{center}, yr_j-y_{center}, zr_j-z_{minimum})$

Step 7
Construct collision surface of receptor $s(x_s, y_s)=z_s$ using the centered receptor coordinates according to the following rule:
Set all initial values of $s(xc_j, yc_j)$ to 0.
for j=1 to the number of subunits in receptor
if $zc_j > s(xc_j, yc_j)$ then $s(xc_j, yc_j)=zc_j$
next j
Step 8
Find minimal separation between collision surface of receptor and collision surface of the target. Calculate difference matrix $d(x_g, y_g)$ as follows
for all $x_g \in \{Int(xn_{minimum}-xn_{center}), Int(xn_{minimum}-xn_{center})+1 \ldots 0, \ldots$
$Int(xn_{maximum}-xn_{center})-1, Int(xn_{maximum}-xn_{center})\}$ and
$y_g \in \{Int(yn_{minimum}-y_{center}), Int(yn_{minimum}-yn_{center})+1 \ldots 0, \ldots$
$Int(yn_{maximum}-yn_{center})-1, Int(yn_{maximum}-yn_{center})\}$ calculate
$d(x_g,y_g)=(h(x_g,y_g)-zn_{minimum}+zn_{maximum})+(s(x_g,y_g)+zr_{minimum}-zr_{maximum})$ For all $x_g, y_g$ find the minimal value of $d(x_g,y_g)=d_{min}$. $d_{min}$ is the minimal separation distance.

Step 9

Transform target and receptor coordinates for collision configuration

For the receptor:

$(xreceptor_j, yreceptor_j, zreceptor_j) = (xc_j, yc_j, zc_j+zr_{minimum}-zr_{max}$mum$)$ For the target:

$(xtarget_i, ytarget_i, ztarget_i) = (xnc_i, Ync_i, znc_i-zn_{minimum}+zn_{maximum}-d_{min})$.

Step 10

Use $(xtarget_i, ytarget_i, ztarget_i)$ and $(xreceptor_j, yreceptor_j, zreceptor_j)$ for affinity calculations.

Repeat Steps 2–9 for each target configuration tested.

MODULE 5: AFFINITY CALCULATION

Step 1

Input collision coordinates of target and receptor $(xtarget_i, ytarget_i, ztarget_i)$ and $(xreceptor_j, yreceptor_j, zreceptor_j)$ where i=number of atoms in target, j=number of subunits in receptor Step 2

Input dipole moment values for target dip(i) Input charge values for receptor charge(j)

Step 3

Input threshold value for proximity calculation: THRESHOLD

Step 4

Calculate dipole affinity value Step 4a

For each charged subunit (charge(j) ≠0) calculate $e(i,j)= dip(i)/((xtarget_i-xreceptor_j)^2+(ytarget_i-yreceptor_j)^2+(ztarget_i-zreceptor_j)^2)^{1.5}$ Step 4b Calculate the sum of e(i,j) for all combinations of i and j with charge(j) ≠0.

DIPOLE=Σe(i,j)

Step 5

Calculate proximity value (this step could be replaced by a calculation based on polarizability)

Step 5a

For each target atom with $|dip(j)| \leq 0.75$ Calculate $l(i,j)= ((xtarget_i-xreceptor_j)^2+(ytarget_i-yreceptor_j)^2+(ztarget_i-zreceptorc_j)^2)^{0.5}$ If l(i,j)<THRESHOLD then prox(i,j)=1

Step 5b

Calculate the sum of prox(i,j) for all combinations of i and j with $|dip(j)| \leq 0.75$ PROXIMITY=Σprox(i,j)

Step 6

Calculate affinity value for target substrate combination= AFFINITY

AFFINITY=(PROXIMITY/j)((PROXIMITY/10000)+DIPOLE)

MODULE 6: GOODNESS OF FIT CALCULATION

Step 1

Input known target efficacy or affinity values ($y_k$). k=number of targets tested Step 2

Input collision coordinates of targets and receptor $(xtarget_i, ytarget_i, ztarget_i)$ and $(xreceptor_j, yreceptor_j, zreceptorc_j)$ $i_k$=number of atoms in target k j=number of subunits in receptor Step 3

Input number of target orientations to be tested (=m).

Step 4

Use Module 5 to obtain affinity values for each target and target orientation (=AFFINITY$_{k,m}$).

Step 5

Determine maximum affinity (MA$_k$) and sum affinity (SA$_k$) values for each target.

Step 6'

Calculate correlation coefficients $r_{MA}^2$ for maximum affinity (MA$_k$) vs known target efficacy or affinity values ($y_k$) and $r_{SA}^2$ for sum affinity (SA$_k$) vs known target efficacy or affinity values ($y_k$).

Step 7

Calculate fitness coefficient F $$F=(r_{MA}^2 \times r_{SA}^2)^{0.5}$$

Alternate

Step 6'

Calculate correlation coefficients $r_{MA}^2$ for maximum affinity (MA$_k$) vs known target efficacy or affinity values ($y_k$) and $r_{SA-MA}^2$ for sum affinity (SA$_k$)–maximal affinity vs known target efficacy or affinity values ($y_k$).

Step 7'

Calculate fitness coefficient F $$F=(r_{MA}^2 \times (1-r_{SA-MA}^2))^{0.5}$$

MODULE 7: GENERATE GENOTYPE WITH MINIMAL LEVEL OF AFFINITY

Step 1

Set minimal fitness threshold

Step 2

Generate random genotype (Module 1)

Step 3

Translate genotype to construct phenotype (Module 2)

Step 4

Test affinity of phenotype for targets (Modules 3, 4, 5, 6)

Step 5

If the fitness of the phenotype exceeds the fitness threshold then discontinue code generation and pass code to phase 2. Otherwise repeat steps 1–5.

MODULE 8: MULTIPLE MUTATION

Step 1

Input primary code (from phase 1).

Step 2

Set number (=q) of mutations per code (Current implementation mutates 2.5–5% of characters in genotype).

Step 3

Input population size (=p).

Step 4

Select a position in the genotype at random.

Step 5

Replace the code character at that position with a different character chosen at random.

Step 6

Repeat steps 4 and 5 until q times.

Step 7

Repeat steps 4–6 to generate a total of p new codes.

Step 8

Apply Modules 1–6 to test fitness of mutant population. Select subpopulation with highest selectivity for use in Phase 3.

MODULE 9: RECOMBINATION

Step 1

Set population size (=P).

Step 2

Select two codes at random from population generated by Phase 2.

Step 3

Select a position in the genotype at random.

Step 4

Generate a random number for the number of characters to exchange.

Step 5

Swap characters between codes beginning at selected position.

Step 6

Repeat steps 2–5 until P new genotypes have been generated.

Step 7

Apply Modules 2–6 to test fitness of mutant population. Select subpopulation with highest selectivity for next recombination series or for Phase 4 maturation.

MODULE 10: MATURATION

Step 1

Input parental code derived from Phase 3.

Step 2

Set number of iterations.

Step 3

Select a position in the parental genotype at random.

Step 4

Replace the code character at that position with a different character chosen at random.

Step 5

Test selectivity of parental code ($F_p$) and mutation product ($F_M$) using Modules 2–6.

Step 6

If $F_M \geq F_p$ replace parental genotype with mutation product.

Step 7

Repeat steps 3–6 for required number of iterations.

MODULE 11: CREATION OF CODE GENERATING CARBON SKELETONS WITH RINGS (6 Member Rings, Entry point=Exit Point)

Step 1.

Set length of code

Set v1, v2, v3, ... vn (frequencies of substituent groups).

Set prob_ring (frequency of ring code sequence). ($0 \leq$ prob_ring $\leq 1$)

Step 2.

Initialize prime_code=" ".
Initialize second_code=" ".
Initialize third_code=" ".

Step 3

Create character strings.

Repeat step 4 until code length is obtained.

Step 4a.

If prob_ring>random ($0 \leq$ random $\leq 1$) Then Assignment of characters for ring (boat convention).

Set new_character_1 to randomly selected member of {"431413", "314134", "141343", "132132", "321321", "213213", "123123", "231231", "312312", "421412", "214124", "141242", "324234", "242343", "423432"}

Assignment of characters for substituents.

Set new_character_2 to six randomly selected members of {c1, c2, c3, ..., cn} using frequencies v1, v2, v3, ... vn. (c1 ... cn are characters specifying different functional groups)

Assignment of characters for substituent valences.

Set new_character_3 to six randomly selected members of {"1", "2", "3", "4"}.

Else

Step 4b.

Assignment of single (non-ring) characters for primary code. Set new_character_1 to a randomly selected member of {"1", "2", "3", "4"}.

Assignment of characters for substituents.

Set new_character_2 to a randomly selected member of {c1, c2, ..., cn} using frequencies v1, v2, ... vn.

Assignment of characters for substituent valences.

Set new_character_3 to a randomly selected member of {"1", "2", "3", "4"}.

Step 4c.

Concatenate new characters to code strings Prime_code=Prime_code & new_character_1 Second_code=Second_code & new_character_2 Third_code=Third_code & new_character_3

MODULE 12: MULTIPLE POINT MUTATION

Step 1

Input primary code.

Step 2

Set number (=q) of mutations per code (Current implementation mutates 2.5–5% of characters in genotype)

Step 3

Input population size (=p).

Step 4

Select a position in the genotype at random.

Step 5

Replace the code characters at that position in each of the code vectors with different characters chosen at random.

Step 6

Repeat steps 4 and 5 until q times.

Step 7

Repeat steps 4–6 to generate a total of p new codes.

Step 8

Test the fitness of each member of the mutant population. Select subpopulation with highest fitness for use in recombination or additional multiple mutation.

MODULE 13: SEQUENCE MUTATIONS

Step 1

Set $P_{DEL}$, $P_{INV}$, $P_{INS}$, and $P_{DUP}$ as threshold levels for the occurrence of mutations ($0 \leq P_x \leq 1$).

Step 2

Generate a random position (=x) in the code ($0 \leq p \leq$ Length of code).

Step 3

Generate random length of sequence (=L) ($0 \leq L \leq$ Length of code–x).

Step 4

Copy sequence from code starting at x and extending for a total of L characters.

Step 5

If $0 \leq P_{INV} \leq$ Random Number $\leq 1$ Then

Reverse the order of the characters in the string.

Step 6

If $0 \leq P_{DUP} \leq$ Random Number $\leq 1$ Then

Copy the sequence and concatenate copy to sequence.

Step 7

If $0 \leq P_{DEL} \leq$ Random Number $\leq 1$ Then

Eliminate L characters from the code starting at position x

Else

Replace sequence in code with sequence generated in steps 5 and 6.

Step 8

If $0 \leq P_{INS} \leq$ Random Number $\leq 1$ Then

Generate a position (=y) at random in code ($0 \leq y \leq$ Length of code)

Insert sequence generated by steps 5 and 6 at position y.

MODULE 14: RECOMBINATION

Step 1

Set population size (=P)

Step 2

Select two codes at random from population generated by multiple mutation.

Step 3

Select a position in the genotype at random.

Step 4

Generate a random number for the number of characters to exchange.

Step 5

Swap characters between each of the three code vectors beginning at selected position.

Step 6

Repeat steps 2–5 until P new genotypes have been generated.

Step 7

Test the fitness of each ligand in the resulting mutant population. Select subpopulation with highest fitness for next recombination series or for maturation.

MODULE 15: MATURATION

Step 1

Input parental code derived from recombination.

Step 2

Set number of iterations

Step 3

Select a position in the parental genotype at random.

Step 4

Replace the code characters at those positions in each of the code vectors with a different characters chosen at random.

Step 5

Test fitness of parental code ($F_P$) and mutation product ($F_M$) using Modules 4 and 5.

Step 6

If $F_M \geq F_P$ replace parental genotype with mutation product

Step 7

Repeat steps 3–6 for required number of iterations.

APPENDIX A

Simulated Receptor Generation Program

Code: Microsoft Visual Basic 3.0

1. Globally Defined Variables

Global maximals As Double
Global maximalm As Double

Global highaffinity As Double
Global mxtest As Integer
Global mxtarget As Integer
Global mxscore As Double
Global transtarget As Integer
Global transtest As Integer
Global bx As Double
Global alen As Integer
Global codei As Integer
Global coeff As Integer
Global itercount As Integer
Global itermean() As Double
Global itermax() As Double
Global transval As Integer
Global radius1test(40) As Double
Global cradius1test(40) As Double
Global dipm1test(40) As Double
Global xomtest(40) As Double
Global yomtest(40) As Double
Global zomtest(40) As Double
Global fzmmtest As Integer Global bestscore(3)
Global bestcode(3)

Global threshold1 As Single

Global xo2() As Double
Global yo2() As Double
Global zo2() As Double
Global bestmutcode As String Global bestsscore As Double
Global bestsslope As Double Global bestmscore As Double
Global bestmslope As Double
Global bestmaxcomb(10) As Double
Global bestsumcomb(10) As Double
Global multiscore As Double Global depth As Integer
Global rwidth As Integer
Global rlength As Integer
Global cnum As Integer
Global bscore As Double
Global best As Single

```
Global pscore As Double
Global zmat() As Integer
Global z3mat() As Integer
Global xo() As Integer
Global yo() As Integer
Global zo() As Integer
Global ox(25) As Integer
Global oy(25) As Integer
Global oz(25) As Integer
Global codearray(40) As String
Global dipsum As Double
Global randarray(3000) As Single
Global testnumber As Integer
Global codenumber As Integer
Global proxsense As Single
Global prox As Integer
Global tarj() As Integer
Global tark() As Integer
Global tarz() As Double
Global tarcount As Integer Global centerx As Integer
Global centery As Integer
Global cenx As Integer
Global ceny As Integer
Global cl As Integer
Global clneg As Integer
Global xcz() As Integer
Global ycz() As Integer
Global zcz() As Integer
Global xczneg() As Integer
Global yczneg() As Integer
Global zczneg() As Integer Global pi As Double
Global pi2 As Double
Global mindiff As Double
Global zmm As Double Global flnm As String
Global fz As Integer
Global xs(40) As Single
Global ys(40) As Single
Global zs(40) As Single
Global A(24) As Integer
Global B(24) As Integer
Global C(24) As Integer
Global D(24) As Integer
Global E(24) As Integer
Global F(24) As Integer
```

```
Global G(24) As Integer
Global h As String

Global transscore As Double
Global bmscore As Double
Global muth As String
Global mutg As String
Global mutk As String
Global zs2 As String
Global v1 As Integer
Global v2 As Integer
Global v3 As Integer
Global v4 As Integer
Global v5 As Integer
Global ltot As Integer
Global t As String
Global v6 As Integer
Global v7 As Integer
Global v8 As Integer
Global v9 As Integer
Global x1 As Integer
Global x2 As Integer
Global y1 As Integer
Global y2 As Integer
Global x As Integer
Global y As Integer
Global z As Integer
Global z1 As Integer
Global z2 As Integer
Global scalar As Integer
Global sw As Integer
Global matrx(100, 100) As Integer
Global mtx(100, 100, 100) As Integer
Global mtrx(100, 100) As Integer Global hk As Integer
Global lm1 As Integer
Global pm1 As Integer
Global lm2 As Integer
Global pm2 As Integer
Global vs As Integer
Global mtxs() As Double
Global xmeans As Double
Global ymeans As Double
Global mnx As Double
Global mny As Double
Global dx As Integer
Global dy As Integer Global ytsmx As Integer
Global xtsmx As Integer
Global ytsmn As Integer
Global xtsmn As Integer
Global minx As Integer
```

```
Global maxx As Integer
Global miny As Integer
Global maxy As Integer
Global minz As Integer
Global maxz As Integer
Global radius(40) As Double
Global dipm(40) As Double
Global cradius(40) As Double
Global rcolor(40) As Integer
Global radius1(10, 40) As Double
Global dipm1(10, 40) As Double
Global cradius1(10, 40) As Double
Global colrm(10, 40) As Integer
Global colrmtest(40) As Integer
Global randcount As Integer
Global target(10) As Single
Global target1 As Single
Global mutnum As Integer Global counttarget As Integer Global mutsumcomb(10) As Double
Global mutmaxcomb(10) As Double Global xm(40) As Double
Global ym(40) As Double
Global zm(40) As Double Global xom(10, 40) As Double
Global yom(10, 40) As Double
Global zom(10, 40) As Double Global maxcombiscore As Double
Global sumcombi As Double
Global pmscore(40) As Double
Global sslope3(40) As Double
Global srxy3(40) As Double
Global mslope3(40) As Double
Global mrxy3(40) As Double
Global popsize As Integer Global maxcomb3(10, 40) As Double
Global maxcomb2() As Double
Global maxcomb1(10) As Double
Global sumcomb3(10, 40) As Double
Global sumcomb2() As Double
Global sumcomb1(10) As Double
Global slopes As Double Global fzmm(10) As Integer
Global fzmt As Integer
```

2. Control Object Specifications

```
VERSION 2.00
Begin Form Form1
   AutoRedraw      =  -1  'True
   BackColor       =  &H00808080&
   Caption         =  "ROBOMITE DEMO vers.31.0"
   ClientHeight    =  6825
   ClientLeft      =  540
   ClientTop       =  165
   ClientWidth     =  9600
   FontBold        =  0   'False
   FontItalic      =  0   'False
   FontName        =  "MS Sans Serif"
   FontSize        =  8.25
   FontStrikethru  =  0   'False
   FontUnderline   =  0   'False
   Height          =  7230
   Left            =  480
   LinkTopic       =  "Form1"
   ScaleHeight     =  6825
   ScaleWidth      =  9600
   Top             =  -180
   Width           =  9720
   WindowState     =  2   'Maximized
   Begin TextBox Text51
      Height    =  285
      Left      =  2520
      TabIndex  =  126
      Text      =  ""
      Top       =  5760
      Width     =  615
   End
   Begin TextBox Text50
      Height    =  285
      Left      =  1800
      TabIndex  =  125
      Text      =  ""
      Top       =  5760
      Width     =  615
   End
   Begin CommandButton Command10
      Caption        =  "HIGH AFFINITY"
      FontBold       =  0   'False
      FontItalic     =  0   'False
      FontName       =  "MS Sans Serif"
      FontSize       =  8.25
      FontStrikethru =  0   'False
      FontUnderline  =  0   'False
      Height         =  375
      Left           =  7440
      TabIndex       =  124
      Top            =  6360
```

```
      Width       = 2055
   End
   Begin TextBox Text49
      Height      = 285
      Left        = 6480
      TabIndex    = 123
      Text        = " "
      Top         = 6480
      Width       = 855
   End
   Begin TextBox Text48
      Height      = 285
      Left        = 5880
      TabIndex    = 122
      Text        = "0"
      Top         = 6480
      Width       = 495
   End
   Begin TextBox Text47
      Height      = 285
      Left        = 5280
      TabIndex    = 121
      Text        = "0"
      Top         = 6480
      Width       = 495
   End
   Begin TextBox Text46
      Height      = 285
      Left        = 6240
      TabIndex    = 119
      Text        = "3"
      Top         = 4200
      Width       = 495
   End
   Begin CommandButton Command9
      Caption     = "4"
      Height      = 255
      Left        = 5760
      TabIndex    = 118
      Top         = 4200
      Width       = 375
   End
   Begin CommandButton Command2
      Caption     = "3"
      Height      = 255
      Left        = 5280
      TabIndex    = 117
      Top         = 4200
      Width       = 375
   End
   Begin HScrollBar HScroll19
      Height      = 255
      LargeChange = 10
      Left        = 5280
```

8

```
   Max         =  500
   Min         =  1
   TabIndex    =  114
   Top         =  1320
   Value       =  60
   Width       =  855
End
Begin TextBox Text45
   Height      =  285
   Left        =  6840
   TabIndex    =  113
   Text        =  "#"
   Top         =  1320
   Width       =  495
End
Begin TextBox Text5
   Height      =  285
   Left        =  6840
   TabIndex    =  1
   Text        =  "#"
   Top         =  840
   Width       =  495
End
Begin CommandButton Command7
   Caption     =  "READ"
   Height      =  375
   Left        =  4320
   TabIndex    =  112
   Top         =  2400
   Width       =  855
End
Begin CommandButton Command5
   Caption     =  "FILE"
   Height      =  375
   Left        =  3240
   TabIndex    =  111
   Top         =  2400
   Width       =  855
End
Begin HScrollBar HScroll18
   Height      =  255
   Left        =  5280
   Max         =  10
   TabIndex    =  109
   Top         =  3720
   Width       =  1455
End
Begin TextBox Text44
   Height      =  285
   Left        =  6840
   TabIndex    =  108
   Text        =  "0"
   Top         =  3720
   Width       =  495
```

```
   End
Begin TextBox Text43
   Height      =  375
   Left        =  7440
   TabIndex    =  106
   Top         =  6000
   Width       =  1455
End
Begin TextBox Text42
   Height      =  285
   Left        =  2520
   TabIndex    =  105
   Text        =  " "
   Top         =  6480
   Width       =  615
End
Begin TextBox Text41
   BackColor   =  &H00FFFFFF&
   ForeColor   =  &H00000000&
   Height      =  285
   Left        =  1800
   TabIndex    =  104
   Text        =  " "
   Top         =  6480
   Width       =  615
End
Begin CommandButton Command4
   Caption        =  "TEST"
   FontBold       =  0  'False
   FontItalic     =  0  'False
   FontName       =  "MS Sans Serif"
   FontSize       =  8.25
   FontStrikethru =  0  'False
   FontUnderline  =  0  'False
   Height         =  375
   Left           =  8880
   TabIndex       =  103
   Top            =  6000
   Width          =  615
End
Begin TextBox Text40
   Height      =  285
   Left        =  6840
   TabIndex    =  102
   Text        =  "10"
   Top         =  5640
   Width       =  495
End
Begin HScrollBar HScroll17
   Height      =  255
   Left        =  5280
   Max         =  20
   Min         =  5
   TabIndex    =  101
```

```
         Top         =  5640
         Value       =  5
         Width       =  1455
      End
      Begin TextBox Text39
         Height      =  285
         Left        =  840
         TabIndex    =  99
         Text        =  " "
         Top         =  6480
         Width       =  615
      End
      Begin TextBox Text38
         Height      =  285
         Left        =  2520
         TabIndex    =  97
         Text        =  " "
         Top         =  6120
         Width       =  615
      End
      Begin CommandButton Command6
         Caption     =  "RECOMBINATION"
         FontBold    =  0  'False
         FontItalic  =  0  'False
         FontName    =  "MS Sans Serif"
         FontSize    =  8.25
         FontStrikethru = 0  'False
         FontUnderline  = 0  'False
         Height      =  375
         Left        =  7440
         TabIndex    =  96
         Top         =  5280
         Width       =  2055
      End
      Begin TextBox Text37
         Height      =  285
         Left        =  1800
         TabIndex    =  95
         Text        =  " "
         Top         =  6120
         Width       =  615
      End
      Begin TextBox Text34
         Height      =  285
         Left        =  840
         TabIndex    =  94
         Text        =  " "
         Top         =  6120
         Width       =  615
      End
      Begin TextBox Text21
         Height      =  285
         Left        =  120
         TabIndex    =  93
```

```
         Text        = " "
         Top         = 6120
         Width       = 615
      End
      Begin HScrollBar HScroll16
         Height      = 255
         Left        = 120
         Max         = 10
         Min         = 1
         TabIndex    = 92
         Top         = 3000
         Value       = 1
         Width       = 3015
      End
      Begin CommandButton Command3
         Caption     = "MUTATION"
         FontBold    = 0  'False
         FontItalic  = 0  'False
         FontName    = "MS Sans Serif"
         FontSize    = 8.25
         FontStrikethru = 0  'False
         FontUnderline  = 0  'False
         Height      = 375
         Left        = 7440
         TabIndex    = 91
         Top         = 4920
         Width       = 2055
      End
      Begin PictureBox Picture1
         Height      = 2895
         Left        = 120
         ScaleHeight = 2865
         ScaleWidth  = 2985
         TabIndex    = 89
         Top         = 120
         Width       = 3015
      End
      Begin CommandButton Command1
         Caption     = "MATURATION"
         FontBold    = 0  'False
         FontItalic  = 0  'False
         FontName    = "MS Sans Serif"
         FontSize    = 8.25
         FontStrikethru = 0  'False
         FontUnderline  = 0  'False
         Height      = 375
         Left        = 7440
         TabIndex    = 88
         Top         = 5640
         Width       = 2055
      End
      Begin TextBox Text20
         Height      = 285
         Left        = 2520
```

12

```
    TabIndex      =   86
    Text          =   " "
    Top           =   3600
    Width         =   615
End
Begin CommandButton Command13
    Caption       =   "INITIATION"
    FontBold      =   0  'False
    FontItalic    =   0  'False
    FontName      =   "MS Sans Serif"
    FontSize      =   8.25
    FontStrikethru =  0  'False
    FontUnderline =   0  'False
    Height        =   375
    Left          =   7440
    TabIndex      =   82
    Top           =   4560
    Width         =   2055
End
Begin GRAPH Graph2
    AsciiFFamily  =   "1~0~1"
    AsciiFSize    =   "80~150~60~100"
    AsciiFStyle   =   "0"
    AsciiSymbol   =   "7"
    GraphTitle    =   "Max Affinity"
    GraphType     =   9  'Scatter
    Height        =   1815
    Left          =   3240
    LineStats     =   8  'BestFit
    RandomData    =   0  'Off
    TabIndex      =   81
    Top           =   4920
    Width         =   1935
End
Begin TextBox Text33
    Height        =   285
    Left          =   6840
    TabIndex      =   74
    Text          =   "1"
    Top           =   6120
    Width         =   495
End
Begin HScrollBar HScroll10
    Height        =   255
    Left          =   5280
    Max           =   200
    Min           =   1
    TabIndex      =   72
    Top           =   6120
    Value         =   1
    Width         =   1455
End
Begin TextBox Text31
    Height        =   285
```

```
        Left            =   2520
        TabIndex        =   71
        Text            =   " "
        Top             =   5400
        Width           =   615
     End
     Begin TextBox Text30
        Height          =   285
        Left            =   1800
        TabIndex        =   70
        Text            =   " "
        Top             =   5400
        Width           =   615
     End
     Begin TextBox Text29
        Height          =   285
        Left            =   2520
        TabIndex        =   69
        Text            =   " "
        Top             =   4560
        Width           =   615
     End
     Begin TextBox Text28
        Height          =   285
        Left            =   1800
        TabIndex        =   68
        Text            =   " "
        Top             =   4560
        Width           =   615
     End
     Begin TextBox Text27
        Height          =   285
        Left            =   6840
        TabIndex        =   67
        Text            =   "7"
        Top             =   2640
        Width           =   495
     End
     Begin HScrollBar HScroll9
        Height          =   255
        Left            =   5280
        Max             =   20
        Min             =   1
        TabIndex        =   66
        Top             =   2640
        Value           =   7
        Width           =   1455
     End
     Begin TextBox Text9
        BackColor       =   &H00808080&
        BorderStyle     =   0  'None
        Height          =   285
        Left            =   3240
        TabIndex        =   6
```

```
         Text        = "4"
         Top         = 1320
         Width       = 255
      End
      Begin TextBox Text6
         BackColor   = &H00808080&
         BorderStyle = 0  'None
         Height      = 225
         Left        = 3240
         TabIndex    = 3
         Text        = "1"
         Top         = 600
         Width       = 255
      End
      Begin CommandButton Command8
         Caption     = "Reset"
         FontBold    = 0  'False
         FontItalic  = 0  'False
         FontName    = "MS Sans Serif"
         FontSize    = 8.25
         FontStrikethru = 0  'False
         FontUnderline  = 0  'False
         Height      = 375
         Left        = 8880
         TabIndex    = 65
         Top         = 1080
         Width       = 615
      End
      Begin ListBox List1
         FontBold    = 0  'False
         FontItalic  = 0  'False
         FontName    = "Small Fonts"
         FontSize    = 6
         FontStrikethru = 0  'False
         FontUnderline  = 0  'False
         Height      = 780
         Left        = 7440
         TabIndex    = 64
         Top         = 3720
         Width       = 2055
      End
      Begin TextBox Text26
         Height      = 285
         Left        = 120
         TabIndex    = 61
         Text        = ""
         Top         = 5400
         Width       = 615
      End
      Begin TextBox Text25
         Height      = 285
         Left        = 840
         TabIndex    = 62
         Text        = ""
```

```
    Top         = 5400
    Width       = 615
End
Begin CommonDialog CMDialog1
    Left        = 2160
    Top         = 1440
End
Begin TextBox Text18
    Height      = 285
    Left        = 6840
    TabIndex    = 60
    Text        = "7"
    Top         = 2280
    Width       = 495
End
Begin HScrollBar HScroll15
    Height      = 255
    Left        = 5280
    Max         = 20
    Min         = 1
    TabIndex    = 59
    Top         = 2280
    Value       = 7
    Width       = 1455
End
Begin TextBox Text24
    Height      = 285
    Left        = 120
    TabIndex    = 49
    Text        = " "
    Top         = 4560
    Width       = 615
End
Begin GRAPH Graph1
    AsciiFFamily = "1~0~1"
    AsciiFSize   = "80~150~60~100"
    AsciiFStyle  = "0"
    AsciiSymbol  = "7"
    GraphTitle   = "Sum Affinity"
    GraphType    = 9 'Scatter
    Height       = 1935
    Left         = 3240
    LineStats    = 8 'BestFit
    NumPoints    = 4
    RandomData   = 0 'Off
    TabIndex     = 53
    Top          = 2880
    Width        = 1935
End
Begin TextBox Text23
    Height      = 285
    Left        = 1800
    TabIndex    = 57
    Text        = " "
```

```
              Top         =  3600
              Width       =  615
           End
           Begin TextBox Text22
              Height      =  285
              Left        =  840
              TabIndex    =  55
              Text        =  ""
              Top         =  4560
              Width       =  615
           End
           Begin HScrollBar HScroll14
              Height      =  255
              Left        =  5280
              Max         =  10
              Min         =  1
              TabIndex    =  51
              Top         =  3240
              Value       =  6
              Width       =  1455
           End
           Begin TextBox Text17
              Height      =  285
              Left        =  6840
              TabIndex    =  50
              Text        =  "3"
              Top         =  3240
              Width       =  495
           End
           Begin TextBox Text16
              Height      =  285
              Left        =  840
              TabIndex    =  35
              Text        =  ""
              Top         =  3600
              Width       =  615
           End
           Begin TextBox Text10
              BackColor   =  &H00FFFFFF&
              Height      =  285
              Left        =  120
              TabIndex    =  46
              Text        =  ""
              Top         =  3600
              Width       =  615
           End
           Begin TextBox Text2
              Height      =  285
              Left        =  6840
              TabIndex    =  45
              Text        =  "25"
              Top         =  1920
              Width       =  495
           End
```

```
Begin HScrollBar HScroll13
   Height      =   255
   Left        =   5280
   Max         =   25
   TabIndex    =   44
   Top         =   1920
   Value       =   25
   Width       =   1455
End
Begin HScrollBar HScroll12
   Height      =   255
   LargeChange =   10
   Left        =   5280
   Max         =   100
   Min         =   1
   TabIndex    =   16
   Top         =   5160
   Value       =   1
   Width       =   1455
End
Begin HScrollBar HScroll11
   Height      =   255
   Left        =   5280
   Max         =   100
   TabIndex    =   43
   Top         =   4680
   Value       =   80
   Width       =   1455
End
Begin TextBox Text36
   Height      =   285
   Left        =   6840
   TabIndex    =   13
   Text        =   "1"
   Top         =   5160
   Width       =   495
End
Begin TextBox Text35
   Height      =   285
   Left        =   6840
   TabIndex    =   14
   Text        =   "80"
   Top         =   4680
   Width       =   495
End
Begin TextBox Text32
   Height      =   285
   Left        =   8880
   TabIndex    =   38
   Text        =   "0"
   Top         =   720
   Width       =   615
End
Begin HScrollBar HScroll8
```

```
        Height          =   285
        Left            =   7440
        Max             =   100
        TabIndex        =   37
        Top             =   720
        Width           =   1335
     End
     Begin TextBox Text4
        FontBold        =   0   'False
        FontItalic      =   0   'False
        FontName        =   "Arial"
        FontSize        =   8.25
        FontStrikethru  =   0   'False
        FontUnderline   =   0   'False
        Height          =   615
        Left            =   3240
        MultiLine       =   -1  'True
        ScrollBars      =   2   'Vertical
        TabIndex        =   0
        Text            =   "Code View"
        Top             =   1680
        Width           =   1935
     End
     Begin CommandButton Command12
        Caption         =   "Acquire Target"
        FontBold        =   0   'False
        FontItalic      =   0   'False
        FontName        =   "MS Sans Serif"
        FontSize        =   8.25
        FontStrikethru  =   0   'False
        FontUnderline   =   0   'False
        Height          =   375
        Left            =   7440
        TabIndex        =   36
        Top             =   1080
        Width           =   1335
     End
     Begin HScrollBar HScroll2
        Height          =   255
        Left            =   3480
        Max             =   10
        TabIndex        =   8
        Top             =   600
        Value           =   5
        Width           =   855
     End
     Begin PictureBox Picture2
        Height          =   2055
        Left            =   7440
        ScaleHeight     =   2025
        ScaleWidth      =   2025
        TabIndex        =   34
        Top             =   1560
        Width           =   2055
```

19

```
        End
        Begin TextBox Text19
           Height    = 285
           Left      = 7440
           TabIndex  = 33
           Top       = 360
           Width     = 2055
        End
        Begin PictureBox Picture3
           Height      = 2895
           Left        = 120
           ScaleHeight = 74.902
           ScaleMode   = 0 'User
           ScaleWidth  = 69.338
           TabIndex    = 32
           Top         = 120
           Width       = 3015
        End
        Begin TextBox Text3
           FontBold       = 0 'False
           FontItalic     = 0 'False
           FontName       = "MS Sans Serif"
           FontSize       = 8.25
           FontStrikethru = 0 'False
           FontUnderline  = 0 'False
           Height         = 285
           Left           = 6840
           TabIndex       = 31
           Top            = 360
           Width          = 495
        End
        Begin HScrollBar HScroll7
           Height      = 255
           LargeChange = 10
           Left        = 5280
           Max         = 40
           Min         = 1
           TabIndex    = 22
           Top         = 360
           Value       = 12
           Width       = 855
        End
        Begin TextBox Text15
           Height    = 285
           Left      = 4800
           TabIndex  = 21
           Text      = "%"
           Top       = 1320
           Width     = 375
        End
        Begin TextBox Text14
           Height    = 285
           Left      = 4800
           TabIndex  = 20
```

```
       Text       = "%"
       Top        = 1080
       Width      = 375
    End
    Begin TextBox Text13
       Height     = 285
       Left       = 4800
       TabIndex   = 19
       Text       = "%"
       Top        = 840
       Width      = 375
    End
    Begin TextBox Text12
       Height     = 285
       Left       = 4800
       TabIndex   = 18
       Text       = "%"
       Top        = 600
       Width      = 375
    End
    Begin TextBox Text11
       Height     = 285
       Left       = 4800
       TabIndex   = 17
       Text       = "%"
       Top        = 360
       Width      = 375
    End
    Begin HScrollBar HScroll6
       Height      = 255
       LargeChange = 10
       Left        = 5280
       Max         = 500
       Min         = 1
       TabIndex    = 12
       Top         = 840
       Value       = 60
       Width       = 855
    End
    Begin HScrollBar HScroll5
       Height     = 255
       Left       = 3480
       Max        = 10
       TabIndex   = 11
       Top        = 1320
       Value      = 5
       Width      = 855
    End
    Begin HScrollBar HScroll4
       Height     = 255
       Left       = 3480
       Max        = 10
       TabIndex   = 10
       Top        = 1080
```

```
        Value       = 5
        Width       = 855
     End
     Begin HScrollBar HScroll3
        Height      = 255
        Left        = 3480
        Max         = 10
        TabIndex    = 9
        Top         = 840
        Value       = 5
        Width       = 855
     End
     Begin HScrollBar HScroll1
        Height      = 255
        Left        = 3480
        Max         = 10
        TabIndex    = 7
        Top         = 360
        Value       = 5
        Width       = 855
     End
     Begin TextBox Text8
        BackColor   = &H00808080&
        BorderStyle = 0  'None
        Height      = 285
        Left        = 3240
        TabIndex    = 5
        Text        = "3"
        Top         = 1080
        Width       = 255
     End
     Begin TextBox Text7
        BackColor   = &H00808080&
        BorderStyle = 0  'None
        Height      = 285
        Left        = 3240
        TabIndex    = 4
        Text        = "2"
        Top         = 840
        Width       = 255
     End
     Begin TextBox Text1
        BackColor   = &H00808080&
        BorderStyle = 0  'None
        Height      = 285
        Left        = 3240
        TabIndex    = 2
        Text        = "0"
        Top         = 360
        Width       = 255
     End
     Begin Label Label39
        BackColor   = &H00808080&
        Caption     = "Coefficient"
```

```
      FontBold        = 0  'False
      FontItalic      = 0  'False
      FontName        = "Times New Roman"
      FontSize        = 9
      FontStrikethru  = 0  'False
      FontUnderline   = 0  'False
      Height          = 255
      Left            = 5280
      TabIndex        = 120
      Top             = 3960
      Width           = 975
   End
   Begin Label Label38
      Alignment       = 2  'Center
      BorderStyle     = 1  'Fixed Single
      Caption         = "1.67"
      Height          = 255
      Left            = 6240
      TabIndex        = 116
      Top             = 1320
      Width           = 495
   End
   Begin Label Label37
      BackColor       = &H00808080&
      Caption         = "- Charge Sites  (%)"
      FontBold        = 0  'False
      FontItalic      = 0  'False
      FontName        = "Times New Roman"
      FontSize        = 8.25
      FontStrikethru  = 0  'False
      FontUnderline   = 0  'False
      Height          = 255
      Left            = 5280
      TabIndex        = 115
      Top             = 1080
      Width           = 1455
   End
   Begin Label Label36
      BackColor       = &H00808080&
      Caption         = "Translation"
      FontBold        = 0  'False
      FontItalic      = 0  'False
      FontName        = "Times New Roman"
      FontSize        = 9
      FontStrikethru  = 0  'False
      FontUnderline   = 0  'False
      Height          = 255
      Left            = 5280
      TabIndex        = 110
      Top             = 3480
      Width           = 1335
   End
   Begin Label Label35
      BackColor       = &H00808080&
```

23

```
   Caption      =  "Population Size"
   FontBold     =  0  'False
   FontItalic   =  0  'False
   FontName     =  "Times New Roman"
   FontSize     =  8.25
   FontStrikethru = 0  'False
   FontUnderline = 0  'False
   Height       =  255
   Left         =  5280
   TabIndex     =  107
   Top          =  5400
   Width        =  1335
End
Begin Label Label34
   BackColor    =  &H00808080&
   Caption      =  "MEAN"
   Height       =  255
   Left         =  120
   TabIndex     =  100
   Top          =  6480
   Width        =  615
End
Begin Label Label33
   BackColor    =  &H00808080&
   Caption      =  "Parental Scores"
   Height       =  255
   Left         =  120
   TabIndex     =  98
   Top          =  5880
   Width        =  1455
End
Begin Label Label32
   BackColor    =  &H00808080&
   Caption      =  "Mutation Result"
   Height       =  255
   Left         =  1800
   TabIndex     =  90
   Top          =  4920
   Width        =  1455
End
Begin Label Label31
   BackColor    =  &H00808080&
   Caption      =  "Score"
   Height       =  255
   Left         =  2520
   TabIndex     =  87
   Top          =  3360
   Width        =  495
End
Begin Label Label30
   BackColor    =  &H00808080&
   Caption      =  "Mutation"
   Height       =  255
   Left         =  1800
```

```
         TabIndex       =   85
         Top            =   4080
         Width          =   1215
      End
      Begin Label Label29
         BackColor      =   &H00808080&
         Caption        =   "Max Affinity"
         Height         =   255
         Left           =   120
         TabIndex       =   84
         Top            =   4920
         Width          =   1095
      End
      Begin Label Label20
         BackColor      =   &H00808080&
         Caption        =   "Sum Affinity"
         Height         =   255
         Left           =   120
         TabIndex       =   83
         Top            =   4080
         Width          =   1215
      End
      Begin Label Label28
         BackColor      =   &H00808080&
         Caption        =   "Current"
         FontBold       =   0   'False
         FontItalic     =   0   'False
         FontName       =   "Times New Roman"
         FontSize       =   8.25
         FontStrikethru =   0   'False
         FontUnderline  =   0   'False
         Height         =   255
         Left           =   2520
         TabIndex       =   80
         Top            =   5160
         Width          =   495
      End
      Begin Label Label27
         BackColor      =   &H00808080&
         Caption        =   "MAX"
         FontBold       =   0   'False
         FontItalic     =   0   'False
         FontName       =   "Times New Roman"
         FontSize       =   8.25
         FontStrikethru =   0   'False
         FontUnderline  =   0   'False
         Height         =   255
         Left           =   1800
         TabIndex       =   79
         Top            =   5160
         Width          =   495
      End
      Begin Label Label26
         BackColor      =   &H00808080&
```

25

```
   Caption       = "M-Value"
   FontBold      = 0  'False
   FontItalic    = 0  'False
   FontName      = "Times New Roman"
   FontSize      = 8.25
   FontStrikethru = 0  'False
   FontUnderline = 0  'False
   Height        = 255
   Left          = 2520
   TabIndex      = 78
   Top           = 4320
   Width         = 615
End
Begin Label Label24
   BackColor     = &H00808080&
   Caption       = "M-Site"
   FontBold      = 0  'False
   FontItalic    = 0  'False
   FontName      = "Times New Roman"
   FontSize      = 8.25
   FontStrikethru = 0  'False
   FontUnderline = 0  'False
   Height        = 255
   Left          = 1800
   TabIndex      = 77
   Top           = 4320
   Width         = 495
End
Begin Label Label22
   BackColor     = &H00808080&
   Caption       = "slope"
   FontBold      = 0  'False
   FontItalic    = 0  'False
   FontName      = "Times New Roman"
   FontSize      = 8.25
   FontStrikethru = 0  'False
   FontUnderline = 0  'False
   Height        = 255
   Left          = 120
   TabIndex      = 76
   Top           = 5160
   Width         = 495
End
Begin Label Label21
   BackColor     = &H00808080&
   Caption       = "r-square"
   FontBold      = 0  'False
   FontItalic    = 0  'False
   FontName      = "Times New Roman"
   FontSize      = 8.25
   FontStrikethru = 0  'False
   FontUnderline = 0  'False
   Height        = 255
   Left          = 840
```

26

```
    TabIndex    = 75
    Top         = 5160
    Width       = 615
End
Begin Label Label19
    BackColor    = &H00808080&
    Caption      = "Maturation Cycles"
    FontBold     = 0  'False
    FontItalic   = 0  'False
    FontName     = "Times New Roman"
    FontSize     = 8.25
    FontStrikethru = 0  'False
    FontUnderline  = 0  'False
    Height      = 255
    Left        = 5280
    TabIndex    = 73
    Top         = 5880
    Width       = 1455
End
Begin Label Label17
    BackColor    = &H00808080&
    Caption      = "Target"
    FontBold     = 0  'False
    FontItalic   = 0  'False
    FontName     = "Times New Roman"
    FontSize     = 8.25
    FontStrikethru = 0  'False
    FontUnderline  = 0  'False
    Height      = 255
    Left        = 7440
    TabIndex    = 63
    Top         = 120
    Width       = 495
End
Begin Label Label15
    BackColor    = &H00808080&
    Caption      = "Target"
    FontBold     = 0  'False
    FontItalic   = 0  'False
    FontName     = "Times New Roman"
    FontSize     = 8.25
    FontStrikethru = 0  'False
    FontUnderline  = 0  'False
    Height      = 255
    Left        = 1800
    TabIndex    = 58
    Top         = 3360
    Width       = 495
End
Begin Label Label25
    BackColor    = &H00808080&
    Caption      = "slope"
    FontBold     = 0  'False
    FontItalic   = 0  'False
```

```
        FontName       = "Times New Roman"
        FontSize       = 8.25
        FontStrikethru = 0  'False
        FontUnderline  = 0  'False
        Height         = 255
        Left           = 120
        TabIndex       = 54
        Top            = 4320
        Width          = 615
     End
     Begin Label Label18
        BackColor      = &H00808080&
        Caption        = "r-square"
        FontBold       = 0  'False
        FontItalic     = 0  'False
        FontName       = "Times New Roman"
        FontSize       = 8.25
        FontStrikethru = 0  'False
        FontUnderline  = 0  'False
        Height         = 255
        Left           = 840
        TabIndex       = 56
        Top            = 4320
        Width          = 615
     End
     Begin Label Label6
        BackColor      = &H00808080&
        Caption        = "Proximity Sensitivity"
        FontBold       = 0  'False
        FontItalic     = 0  'False
        FontName       = "Times New Roman"
        FontSize       = 8.25
        FontStrikethru = 0  'False
        FontUnderline  = 0  'False
        Height         = 255
        Left           = 5280
        TabIndex       = 52
        Top            = 3000
        Width          = 1695
     End
     Begin Label Label23
        BackColor      = &H00808080&
        Caption        = "Test"
        FontBold       = 0  'False
        FontItalic     = 0  'False
        FontName       = "Times New Roman"
        FontSize       = 8.25
        FontStrikethru = 0  'False
        FontUnderline  = 0  'False
        Height         = 255
        Left           = 840
        TabIndex       = 48
        Top            = 3360
        Width          = 615
```

```
                                                28

End
       Begin Label Label5
         BackColor    = &H00808080&
         Caption      = "Code"
         FontBold     = 0  'False
         FontItalic   = 0  'False
         FontName     = "Times New Roman"
         FontSize     = 8.25
         FontStrikethru = 0  'False
         FontUnderline = 0  'False
         Height       = 255
         Left         = 120
         TabIndex     = 47
         Top          = 3360
         Width        = 495
       End
       Begin Label Label4
         BackColor    = &H00808080&
         Caption      = "Width/Depth Factors"
         FontBold     = 0  'False
         FontItalic   = 0  'False
         FontName     = "Times New Roman"
         FontSize     = 8.25
         FontStrikethru = 0  'False
         FontUnderline = 0  'False
         Height       = 255
         Left         = 5280
         TabIndex     = 42
         Top          = 1680
         Width        = 1575
       End
       Begin Label Label3
         BackColor    = &H00808080&
         Caption      = "Test Number"
         FontBold     = 0  'False
         FontItalic   = 0  'False
         FontName     = "Times New Roman"
         FontSize     = 8.25
         FontStrikethru = 0  'False
         FontUnderline = 0  'False
         Height       = 255
         Left         = 5280
         TabIndex     = 41
         Top          = 4920
         Width        = 1215
       End
       Begin Label Label2
         BackColor    = &H00808080&
         Caption      = "Threshold"
         FontBold     = 0  'False
         FontItalic   = 0  'False
         FontName     = "Times New Roman"
         FontSize     = 8.25
         FontStrikethru = 0  'False
```

```
      FontUnderline = 0  'False
      Height     = 255
      Left       = 5280
      TabIndex   = 40
      Top        = 4440
      Width      = 1215
   End
   Begin Label Label1
      BackColor   = &H00808080&
      Caption     = "Code Frequency"
      FontBold    = 0  'False
      FontItalic  = 0  'False
      FontName    = "Times New Roman"
      FontSize    = 8.25
      FontStrikethru = 0  'False
      FontUnderline  = 0  'False
      Height      = 255
      Left        = 3240
      TabIndex    = 39
      Top         = 120
      Width       = 1215
   End
   Begin Label Label16
      BackColor   = &H00808080&
      Caption     = "- Charge Sites (%)"
      FontBold    = 0  'False
      FontItalic  = 0  'False
      FontName    = "Times New Roman"
      FontSize    = 8.25
      FontStrikethru = 0  'False
      FontUnderline  = 0  'False
      Height      = 255
      Left        = 5280
      TabIndex    = 15
      Top         = 600
      Width       = 1455
   End
   Begin Label Label14
      BackColor   = &H00808080&
      Caption     = "Code Length"
      FontBold    = 0  'False
      FontItalic  = 0  'False
      FontName    = "Times New Roman"
      FontSize    = 8.25
      FontStrikethru = 0  'False
      FontUnderline  = 0  'False
      Height      = 255
      Left        = 5280
      TabIndex    = 30
      Top         = 120
      Width       = 1215
   End
   Begin Label Label13
      Alignment   = 2  'Center
```

```
         BorderStyle  = 1  'Fixed Single
         Caption      = "1.67"
         Height       = 255
         Left         = 6240
         TabIndex     = 29
         Top          = 840
         Width        = 495
      End
      Begin Label Label12
         Alignment    = 2  'Center
         BorderStyle  = 1  'Fixed Single
         Caption      = "20"
         Height       = 255
         Left         = 4320
         TabIndex     = 28
         Top          = 1320
         Width        = 375
      End
      Begin Label Label11
         Alignment    = 2  'Center
         BorderStyle  = 1  'Fixed Single
         Caption      = "20"
         Height       = 255
         Left         = 4320
         TabIndex     = 27
         Top          = 1080
         Width        = 375
      End
      Begin Label Label10
         Alignment    = 2  'Center
         BorderStyle  = 1  'Fixed Single
         Caption      = "20"
         Height       = 255
         Left         = 4320
         TabIndex     = 26
         Top          = 840
         Width        = 375
      End
      Begin Label Label9
         Alignment    = 2  'Center
         BorderStyle  = 1  'Fixed Single
         Caption      = "20"
         Height       = 255
         Left         = 4320
         TabIndex     = 25
         Top          = 600
         Width        = 375
      End
      Begin Label Label8
         Alignment    = 2  'Center
         BorderStyle  = 1  'Fixed Single
         Caption      = "20"
         Height       = 255
         Left         = 4320
```

```
      TabIndex      =  24
      Top           =  360
      Width         =  375
   End
   Begin Label Label7
      Alignment     =  2  'Center
      BorderStyle   =  1  'Fixed Single
      Caption       =  "180"
      FontBold      =  0  'False
      FontItalic    =  0  'False
      FontName      =  "MS Sans Serif"
      FontSize      =  8.25
      FontStrikethru =  0  'False
      FontUnderline =  0  'False
      Height        =  255
      Left          =  6240
      TabIndex      =  23
      Top           =  360
      Width         =  495
   End
End
```

31

3. Program Code

FUNCTION at1 (ratio As Double) As Double

'ARCTAN FOR Quadrant I at1 = Atn(Abs(ratio))

END FUNCTION

FUNCTION at2 (ratio As Double) As Double

'ARCTAN FOR II at2 = pi - Atn(Abs(ratio))

END FUNCTION

FUNCTION at3 (ratio As Double) As Double

'ARCTAN FOR III at3 = pi2 - Atn(Abs(ratio))

END FUNCTION

FUNCTION at4 (ratio As Double) As Double

'ARCTAN FOR IV at4 = pi + Atn(Abs(ratio))

END FUNCTION

*SUB* codecreate ()
'CODE CREATION SUBPROGRAM codei = codei + 1 text10.Text = codei

'initialise variables for calculating frequencies j1 = 0
J2 = 0
j3 = 0
j4 = 0
j5 = 0

'initialise string for storing code h = ""

'set charge site counters to zero

```
c1 = 0
c1neg = 0

'calculate probability values from selection panel values
'note v7 is the length of the string (number of elements)

tot = v1 + v2 + v3 + v4 + v5 t1 = 1 + v1
t2 = v1 + v2
t3 = t2 + 1
t4 = t2 + v3
t5 = t4 + 1
t6 = t4 + v4
t7 = t6 + 1
t8 = t6 + v5

'Assignment of string values

'start of primary code generating loop

For i = 1 To v7

'generation of random number

Rn = 1 + Int(tot * (Rnd(1)))

'generation of code sequence

Select Case Rn

Case 1 To v1
    'ALTERNATIVE CODING LINES
    zs2 = "0"
    'zs2 = "01211232234334 14"
    j1 = j1 + 1

Case t1 To t2
    zs2 = "1"
    J2 = J2 + 1

Case t3 To t4
    zs2 = "2"
    j3 = j3 + 1

Case t5 To t6
    zs2 = "3"
    j4 = j4 + 1

Case t7 To t8
    zs2 = "4"
    j5 = j5 + 1
```

34

```
End Select

'add charge sites
'note that if charge site is added. previous value for zs2 is overwritten
'this is necessary to keep string length a multiple of 15

If Int(v6 / 2) = 1 + Int(v6 * (Rnd(1))) Then zs2 = "5"

'increment charge site counter c1 = c1 + 1

End If
'add negative charge sites
'note that if charge site is added. previous value for zs2 is overwritten
'this is necessary to keep string length a multiple of 15

If Int(v9 / 2) = 1 + Int(v9 * (Rnd(1))) Then zs2 = "6"

'increment charge site counter c1neg = c1neg + 1

End If

'concatenate result to the string h = h + zs2

Next i

'display of report values

'report charge site counter value text5.Text = c1
text45.Text = c1neg

'length of code string ltot = Len(h)

text3.Text = ltot

'calculation of frequency distributions text11.Text = Int(100 * j1 / ltot)
text12.Text = Int(100 * j2 / ltot)
text13.Text = Int(100 * j3 / ltot)
text14.Text = Int(100 * j4 / ltot)
``` text15.Text = Int(100 * j5 / ltot)

*END SUB*

*SUB* Command1_Click ()

hscroll16.Visible = False
'Adaptive Routine 1
text39.Text = ""
text28.Text = ""
text29.Text = ""
text30.Text = ""
text31.Text = ""
text21.Text = ""
text34.Text = ""
text37.Text = ""
text38.Text = ""
text24.Text = ""
text22.Text = ""
text26.Text = ""
text25.Text = ""
text4.Text = ""

bh = h bscore = transscore
text20.Text = bscore

'Random mutation subroutine

For cycle = 1 To mutnum text10.Text = cycle h = bh locus = 1 + Int(Len(h) * Rnd)

text28.Text = locus allele = Int(5 * Rnd)

Do Until Mid$(h, locus, 1) <> Trim$(Str$(allele))

allele = Int(5 * Rnd)

Loop

If Int(v6 / 2) = 1 + Int((v6 * (Rnd(1))) Then allele = 5

36

```
End If text29.Text = allele

Mid$(h, locus, 1) = Trim$(Str$(allele))

'******* CREATE 3-D REPRESENTATION OF CODE *******

'Read in codes from code storage array
'Code index is codei

'report current code number text10.Text = cycle

'load next code into h for processing

'Code is stored in h

'run decoder to create receptor decodes

'***START TESTS ON TARGETS ****
For iy = 1 To counttarget text23.Text = iy

'reinitialize random number counter and target coordinates for each test series randcount = 0

'Start target in original position for each test series
'get number of atoms and store in fzmt (also used in tester1)

fzmt = fzmm(iy)

For ti = 1 To fzmt

'read in original target coordinates preserved in xom, yom and zom xm(ti) = xom(iy, ti)
ym(ti) = yom(iy, ti)
zm(ti) = zom(iy, ti)
radius(ti) = radius1(iy, ti)
cradius(ti) = cradius1(iy, ti)
dipm(ti) = dipm1(iy, ti)
```

37

```
Next ti

'start loop for test series

For testi = 1 To testnumber text16.Text = testi

'run test tester1

Next testi

'record maximum score for this code and clear maxscore for next cycle sumcomb1(iy) = sumcombi
maxcomb1(iy) = maxcombiscore maxcombiscore = 0
sumcombi = 0

Next iy

'end of test loop

'display results for sum affinity as graph graph1.DataReset = 1

For iy = 1 To counttarget graph1.GraphData = sumcomb1(iy)

Next iy graph1.GraphData = 0

For iy = 1 To counttarget graph1.XPosData = target(iy)

Next iy graph1.XPosData = 0 graph1.DrawMode = 2

'display results for maximum affinity as graph
```

38

```
graph2.DataReset = 1

For iy = 1 To counttarget graph2.GraphData = maxcomb1(iy)

Next iy graph2.GraphData = 0

For iy = 1 To counttarget graph2.XPosData = target(iy)

Next iy graph2.XPosData = 0 graph2.DrawMode = 2

'calculation of regression, correlation and primary scores
'includes 0.0 as point 'Calculation 1: Sum Affinity sumx = 0
sumx2 = 0
sumy = 0
sumy2 = 0
sumxy = 0

For iy = 1 To counttarget
sumx = sumx + target(iy)
sumx2 = sumx2 + target(iy) ^ 2
Next iy ssx = sumx2 - (((sumx) ^ 2) / (counttarget - 1))

For iy = 1 To counttarget
sumy = sumy + sumcomb1(iy)
sumy2 = sumy2 + sumcomb1(iy) ^ 2
Next iy ssy = sumy2 - (((sumy) ^ 2) / (counttarget + 1))

For iy = 1 To counttarget
sumxy = sumxy + (target(iy) * sumcomb1(iy))

Next iy ssxy = sumxy - ((sumx * sumy) / (counttarget - 1))
srxy2 = ((ssxy * ssxy) / (ssx * ssy))
```

```
sslope = ssxy / ssx sscore = Sgn(sslope) * srxy2 text22.Text = (Int(1000 * srxy2)) / 1000
text24.Text = (Int(1000 * sslope)) / 1000

'Calculation 2. MAX Affinity sumx = 0
sumx2 = 0
sumy = 0
sumy2 = 0
sumxy = 0

For iy = 1 To counttarget
sumx = sumx + target(iy)
sumx2 = sumx2 + target(iy) ^ 2
Next iy ssx = sumx2 - (((sumx) ^ 2) / (counttarget + 1))

For iy = 1 To counttarget
sumy = sumy + maxcomb1(iy)
sumy2 = sumy2 + maxcomb1(iy) ^ 2
Next iy ssy = sumy2 - (((sumy) ^ 2) / (counttarget + 1))

For iy = 1 To counttarget
sumxy = sumxy + (target(iy) * maxcomb1(iy))

Next iy ssxy = sumxy - ((sumx * sumy) / (counttarget + 1))
mrxy2 = ((ssxy * ssxy) / (ssx * ssy))
mslope = ssxy / ssx mscore = Sgn(mslope) * mrxy2 text25.Text = (Int(1000 * mrxy2)) / 1000
text26.Text = (Int(1000 * mslope)) / 1000 multiscore = Sgn(mslope) * Sqr(mrxy2 * srxy2)

text20.Text = multiscore

'keep track of best example text30.Text = bscore
text31.Text = multiscore

If bscore <= multiscore Then
```

```
bscore = multiscore
bmscore = bscore

'store results for best mutation result
'store results for best mutation result bestmutcode = h
bestsscore = sscore
bestsslope = sslope
bestmscore = mscore
bestmslope = mslope For iy = 1 To counttarget
bestmaxcomb(iy) = maxcomb1(iy)
bestsumcomb(iy) = sumcomb1(iy)
Next iy text30.Text = bscore bh = h End If Next cycle 'Display best mutation text28.Text = ""
text29.Text = ""
text30.Text = ""
text31.Text = ""
text21.Text = ""
text34.Text = ""
text37.Text = ""
text38.Text = ""
text4.Text = ""

text10.Text = ""
text16.Text = ""
text23.Text = ""

text24.Text = bestsslope
text22.Text = bestsscore
text26.Text = bestmslope
text25.Text = bestmscore text28.Text = ""
text29.Text = ""
text20.Text = bscore
text31.Text = ""
```

```
'DECODE BEST CODE

'Read in codes from code storage array h = bestmutcode
transscore = bscore

'print code hg = ""
For l = 0 To 14
For k = 1 To alen
hg = hg & Mid$(h, (l * alen) + k, 1)
Next k
hg = hg + " "
Next l text4.Text = hg decodes

'GRAPHING SUBROUTINE

'display affinity result as graph graph1.DataReset = 1

For iy = 1 To counttarget graph1.GraphData = bestsumcomb(iy)

Next iy graph1.GraphData = 0

For iy = 1 To counttarget graph1.XPosData = target(iy)

Next iy graph1.XPosData = 0 graph1.DrawMode = 2

'display results for maximum affinity as graph
```

```
graph2.DataReset = 1

For iy = 1 To counttarget graph2.GraphData = bestmaxcomb(iy)

Next iy graph2.GraphData = 0

For iy = 1 To counttarget graph2.XPosData = target(iy)

Next iy graph2.XPosData = 0 graph2.DrawMode = 2
```
END SUB

SUB Command10_Click ()
```
maximals = 0
maximalm = 0 text49.Text = 0
hscroll16.Visible = False
'find and display high affinity code
text39.Text = ""
text28.Text = ""
text29.Text = ""
text30.Text = ""
text31.Text = ""
text21.Text = ""
text34.Text = ""
text37.Text = ""
text38.Text = ""
text24.Text = ""
text22.Text = ""
text26.Text = ""
text25.Text = ""
text4.Text = ""

bscore = transscore
text20.Text = bscore
```

43

'***** CREATE 3-D REPRESENTATION OF CODE *****

'Read in codes from code storage array
'Code index is codei

'load next code into h for processing

'Code is stored in h

'run decoder to create receptor decodes

'*START TESTS ON TARGETS **** highaffinity = 0

For iy = 1 To counttarget text23.Text = iy

'reinitialize random number counter and target coordinates for each test series randcount = 0

'Start target in original position for each test series
'get number of atoms and store in fzmt (also used in tester1)

fzmt = fzmm(iy)

For ti = 1 To fzmt

'read in original target coordinates preserved in xom, yom and zom

```
xm(ti) = xom(iy, ti)
ym(ti) = yom(iy, ti)
zm(ti) = zom(iy, ti)
radius(ti) = radius1(iy, ti)
cradius(ti) = cradius1(iy, ti)
dipm(ti) = dipm1(iy, ti)
rcolor(ti) = colrm(iy, ti)
Next ti
```

'start loop for test series

For testi = 1 To testnumber text16.Text = testi

'run test tester2

44

Next testi

'record maximum score for this code and clear maxscore for next cycle sumcomb1(iy) = sumcombi
maxcomb1(iy) = maxcombiscore maxcombiscore = 0
sumcombi = 0

Next iy

'end of test loop

'display results for sum affinity as graph graph1.DataReset = 1

For iy = 1 To counttarget graph1.GraphData = sumcomb1(iy)

Next iy graph1.GraphData = 0

For iy = 1 To counttarget graph1.XPosData = target(iy)

Next iy graph1.XPosData = 0 graph1.DrawMode = 2

'display results for maximum affinity as graph graph2.DataReset = 1

For iy = 1 To counttarget graph2.GraphData = maxcomb1(iy)

Next iy graph2.GraphData = 0

For iy = 1 To counttarget

```
graph2.XPosData = target(iy)

Next iy graph2.XPosData = 0 graph2.DrawMode = 2

'calculation of regression, correlation and primary scores
'includes 0.0 as point 'Calculation 1: Sum Affinity sumx = 0
sumx2 = 0
sumy = 0
sumy2 = 0
sumxy = 0

For iy = 1 To counttarget
sumx = sumx + target(iy)
sumx2 = sumx2 + target(iy) ^ 2
Next iy ssx = sumx2 - (((sumx) ^ 2) / (counttarget + 1))

For iy = 1 To counttarget
sumy = sumy + sumcomb1(iy)
sumy2 = sumy2 + sumcomb1(iy) ^ 2
Next iy ssy = sumy2 - (((sumy) ^ 2) / (counttarget + 1))

For iy = 1 To counttarget
sumxy = sumxy + (target(iy) * sumcomb1(iy))

Next iy ssxy = sumxy - ((sumx * sumy) / (counttarget + 1))
srxy2 = ((ssxy * ssxy) / (ssx * ssy))
sslope = ssxy / ssx sscore = Sgn(sslope) * srxy2 text22.Text = (Int(1000 * srxy2)) / 1000
text24.Text = (Int(1000 * sslope)) / 1000

'Calculation 2: MAX Affinity sumx = 0
sumx2 = 0
sumy = 0
```

```
sumy2 = 0
sumxy = 0

For iy = 1 To counttarget
sumx = sumx + target(iy)
sumx2 = sumx2 + target(iy) ^ 2
Next iy ssx = sumx2 - (((sumx) ^ 2) / (counttarget + 1))

For iy = 1 To counttarget
sumy = sumy + maxcomb1(iy)
sumy2 = sumy2 + maxcomb1(iy) ^ 2
Next iy ssy = sumy2 - (((sumy) ^ 2) / (counttarget + 1))

For iy = 1 To counttarget
sumxy = sumxy + (target(iy) * maxcomb1(iy))

Next iy ssxy = sumxy - ((sumx * sumy) / (counttarget + 1))
mrxy2 = ((ssxy * ssxy) / (ssx * ssy))
mslope = ssxy / ssx mscore = Sgn(mslope) * mrxy2 text25.Text = (Int(1000 * mrxy2)) / 1000
text26.Text = (Int(1000 * mslope)) / 1000 multiscore = Sgn(mslope) * Sqr(mrxy2 * srxy2)

text20.Text = multiscore text50.Text = maximals
text51.Text = maximalm
```

*END SUB*

***SUB* Command12_Click ()**

'Increment target counter counttarget = counttarget + 1

'change graph graph1.NumPoints = counttarget - 1
graph2.NumPoints = counttarget - 1

```
'load target value target(counttarget) = target1

'FILE READING ROUTINE FOR TARGET ACQUISITION

'loading target

'test for filename: if present continue, if not, exit

If text19.Text <> "" Then

'prepare for display picture2.Cls
picture2.Scale (-7, 7)-(7, -7)

'compose filename string fname = "c:\vb3\mites\" & text19.Text & "s.txt"

list1.AddItem Str$(counttarget) & " " & text19.Text & " " & Str$(target(counttarget))

'open file

Open fname For Input As 1

'read in atom count(fzmm) as first item in file

Input #1, fzmm(counttarget)

'start loop to read in values from file for each atom

For i = 1 To fzmm(counttarget)

'store in arrays
'xx=x-center
'yy=y-center
'zz=z-center
'radius =atomic radius
'cradius=collision radius
'dipm=dipole moment Input #1, xx, yy, zz, radius1(counttarget, i), cvradm, cradius1(counttarget, i), dipm1(counttarget, i), colrm(counttarget, i)

'divide positional coordinates by 100 and store xom(counttarget, i) = xx / 100
yom(counttarget, i) = yy / 100
zom(counttarget, i) = zz / 100

Next i
```

48

```
'close file

Close 1

End If

'store grey color code gcol = RGB(50, 50, 50)

'start loop to calculate collision matrix values

For i = 1 To fzmm(counttarget)

zp = zom(counttarget, i)
xp = xom(counttarget, i)
yp = yom(counttarget, i)
rp = radius1(counttarget, i)
sp = cradius1(counttarget, i)
colm = colrm(counttarget, i)
'draw atoms using radius and collision radius picture2.Circle (xp, yp), rp, QBColor(colm)
'picture2.Circle (xp, yp), rp, gcol 'calculation of collision matrix sp = sp + .05

'start loop to calculate collision points

For j = Int(xp - sp) To Int(xp + sp + 1)
For k = Int(yp - sp) To Int(yp + sp + 1)

'calculate distance from atom center dist = Sqr((xp - j) ^ 2 + (yp - k) ^ 2)

'if distance is less than radius, then set collision
'height matrix component to radius If dist <= rp Then 'draw collision point picture2.Circle (j, k), 2

Else

'if distance is less than collision radius (but greater than radius)
'set collision matrix component to radius/2

If dist <= sp Then
```

```
'draw point picture2.PSet (j, k)

End If

End If

Next k

Next j

Next i

Close 1

'draw grid on target frame picture2.Line (0, 20)-(0, -20)
picture2.Line (20, 0)-(-20, 0)

END SUB

SUB Command13_Click ()

hscroll16.Visible = False
'reset counter and multiscore values multiscore = 0
codei = 0 text39.Text = ""
text28.Text = ""
text29.Text = ""
text30.Text = ""
text31.Text = ""
text21.Text = ""
text34.Text = ""
text37.Text = ""
text38.Text = ""
text20.Text = ""
text24.Text = ""
text22.Text = ""
text26.Text = ""
text25.Text = ""
text4.Text = ""

bscore = 0

Do Until multiscore > threshold1
```

'Set maximum target orientation number to 0
'Clear maxtarget mxtest = 0
mxtarget = 0
mxscore = 0 text47.Text = ""
text48.Text = ""
text49.Text = ""
codecreate

'MULTI TEST PRIMARY ROUTINE

'initialise best score

'***** CREATE 3-D REPRESENTATION OF CODE *****

'Read in code

'Code is stored in h

'run decoder to create receptor decodes

'***START TESTS ON TARGETS ****

For iy = 1 To counttarget

'report current target text23.Text = iy

'reinitialize random number counter and target coordinates for each test series randcount = 0

'Start target in original position for each test series
'get number of atoms and store in fzmt (also used in tester1)

fzmt = fzmm(iy)

For ti = 1 To fzmt

'read in original target coordinates preserved in xom, yom and zom xm(ti) = xom(iy, ti)
ym(ti) = yom(iy, ti)
zm(ti) = zom(iy, ti)
radius(ti) = radius1(iy, ti)
cradius(ti) = cradius1(iy, ti)

```
dipm(ti) = dipm1(iy, ti)

Next ti

'start loop for test series

For testi = 1 To testnumber text16.Text = testi

'run test transtest = testi
transtarget = iy tester1

Next testi

'record maximum score for this code and clear maxscore for next cycle sumcomb1(iy) = sumcombi
maxcomb1(iy) = maxcombiscore maxcombiscore = 0
sumcombi = 0

Next iy

'end of test loop

'display results for sum affinity as graph graph1.DataReset = 1

For iy = 1 To counttarget graph1.GraphData = sumcomb1(iy)

Next iy graph1.GraphData = 0

For iy = 1 To counttarget graph1.XPosData = target(iy)

Next iy graph1.XPosData = 0 graph1.DrawMode = 2

'display results for maximum affinity as graph
```

52

```
graph2.DataReset = 1

For iy = 1 To counttarget graph2.GraphData = maxcomb1(iy)

Next iy graph2.GraphData = 0

For iy = 1 To counttarget graph2.XPosData = target(iy)

Next iy graph2.XPosData = 0 graph2.DrawMode = 2

'calculation of regression, correlation and primary scores
'includes 0,0 as point 'Calculation 1: Sum Affinity sumx = 0
sumx2 = 0
sumy = 0
sumy2 = 0
sumxy = 0

For iy = 1 To counttarget
sumx = sumx + target(iy)
sumx2 = sumx2 + target(iy) ^ 2
Next iy ssx = sumx2 - (((sumx) ^ 2) / (counttarget + 1))

For iy = 1 To counttarget
sumy = sumy + sumcomb1(iy)
sumy2 = sumy2 + sumcomb1(iy) ^ 2
Next iy ssy = sumy2 - (((sumy) ^ 2) / (counttarget + 1))

For iy = 1 To counttarget
sumxy = sumxy + (target(iy) * sumcomb1(iy))

Next iy ssxy = sumxy - ((sumx * sumy) / (counttarget + 1))
```

```
srxy2 = ((ssxy * ssxy) / (ssx * ssy))
sslope = ssxy / ssx sscore = Sgn(sslope) * srxy2 text22.Text = (Int(1000 * srxy2)) / 1000
text24.Text = (Int(1000 * sslope)) / 1000

'Calculation 2: MAX Affinity sumx = 0
sumx2 = 0
sumy = 0
sumy2 = 0
sumxy = 0

For iy = 1 To counttarget
sumx = sumx + target(iy)
sumx2 = sumx2 + target(iy) ^ 2
Next iy ssx = sumx2 - (((sumx) ^ 2) / (counttarget + 1))

For iy = 1 To counttarget
sumy = sumy + maxcomb1(iy)
sumy2 = sumy2 + maxcomb1(iy) ^ 2
Next iy ssy = sumy2 - (((sumy) ^ 2) / (counttarget + 1))

For iy = 1 To counttarget
sumxy = sumxy + (target(iy) * maxcomb1(iy))

Next iy ssxy = sumxy - ((sumx * sumy) / (counttarget + 1))
mrxy2 = ((ssxy * ssxy) / (ssx * ssy))
mslope = ssxy / ssx mscore = Sgn(mslope) * mrxy2 text25.Text = (Int(1000 * mrxy2)) / 1000
text26.Text = (Int(1000 * mslope)) / 1000 multiscore = Sgn(mslope) * Sqr(mrxy2 * srxy2)

text20.Text = multiscore

'track best score

If bscore < multiscore Then
bscore = multiscore
text30.Text = bscore
```

54

```
End If

'track mean of codes generated sumcycle = sumcycle + multiscore text39.Text = sumcycle / codei maxcombiscore = 0
sumcombi = 0

Loop transscore = multiscore

'display code hg = ""
For l = 0 To 14
For k = 1 To alen
hg = hg & Mid$(h, (l * alen) + k, 1)
Next k
hg = hg + " "
Next l text4.Text = hg Beep

END SUB

SUB Command2_Click ()
coeff = 3
text46.Text = coeff
END SUB

SUB Command3_Click ()

hscroll16.Visible = True text24.Text = ""
text22.Text = ""
text26.Text = ""
text25.Text = ""

'RANDOMIZED POPULATION GENERATOR

For i = 1 To popsize text10.Text = i
```

```
hm = h

For j = 1 To Int(Len(h) / 40)

text16.Text = j locus = 1 + Int(Len(h) * Rnd)

text28.Text = locus allele = Int(5 * Rnd)

Do Until Mid$(hm, locus, 1) <> Trim$(Str$(allele))

allele = Int(5 * Rnd)

Loop

If Int(v6 / 2) = 1 + Int(v6 * (Rnd(1))) Then allele = 5

End If text29.Text = allele

Mid$(hm, locus, 1) = Trim$(Str$(allele))

Next j codearray(i) = hm

Next i codearray(0) = h multitester

END SUB

SUB Command4_Click ()

'FILE READING ROUTINE FOR TARGET ACQUISITION

'loading target

'test for filename: if present continue, if not, exit

If text43.Text <> "" Then

'prepare for display
```

```
picture2.Cls
picture2.Scale (-7, 7)-(7, -7)

'compose filename string fname = "c:\vb3\mites\" & text43.Text & "s.txt"

'open file

Open fname For Input As 1

'read in atom count(fzmm) as first item in file

Input #1, fzmmtest

'start loop to read in values from file for each atom

For i = 1 To fzmmtest

'store in arrays
'xx=x-center
'yy=y-center
'zz=z-center
'radius =atomic radius
'cradius=collision radius
'dipm=dipole moment Input #1, xx, yy, zz, radius1test(i), cvradm, cradius1test(i), dipm1test(i), colrmtest(i)

'divide positional coordinates by 100 and store xomtest(i) = xx / 100
yomtest(i) = yy / 100
zomtest(i) = zz / 100

Next i

'close file

Close 1

End If

'store grey color code gcol = RGB(50, 50, 50)

'start loop to calculate collision matrix values

For i = 1 To fzmmtest zp = zomtest(i)
```

```
xp = xomtest(i)
yp = yomtest(i)
rp = radius1test(i)
sp = cradius1test(i)
```

'draw atoms using radius and collision radius

```
picture2.Circle (xp, yp), rp, QBColor(colrmtest(i))
```

'calculation of collision matrix

```
sp = sp + .05
```

'start loop to calculate collision points

```
For j = Int(xp - sp) To Int(xp + sp + 1)
For k = Int(yp - sp) To Int(yp + sp + 1)
```

'calculate distance from atom center

```
dist = Sqr((xp - j) ^ 2 + (yp - k) ^ 2)
```

'if distance is less than radius, then set collision
'height matrix component to radius

```
If dist <= rp Then
```

'draw collision point

```
picture2.Circle (j, k), .2
```

```
Else
```

'if distance is less than collision radius (but greater than radius)
'set collision matrix component to radius/2

```
If dist <= sp Then
```

'draw point

```
picture2.PSet (j, k)

End If

End If

Next k

Next j

Next i

Close 1
```

58

```
'draw grid on target frame picture2.Line (0, 20)-(0, -20)
picture2.Line (20, 0)-(-20, 0)

'TEST PRIMARY ROUTINE maxcombiscore = 0
sumcombi = 0

'initialise best score, bestscore and bestcode text10.Text = "TEST"

text28.Text = ""
text29.Text = ""
text39.Text = ""

text21.Text = ""
text34.Text = ""
text37.Text = ""
text38.Text = ""

text4.Text = ""

'******* CREATE 3-D REPRESENTATION OF CODE *******

'Read in codes from code storage array
'Code index is codei

'load next code into h for processing

'Code is stored in h

'run decoder to create receptor decodes

'***START TESTS ON TARGETS ****

'report current target text23.Text = text43.Text

'reinitialize random number counter and target coordinates for each test series randcount = 0
```

59

```
'Start target in original position for each test series
'get number of atoms and store in fzmt (also used in tester1)

fzmt = fzmmtest

For ti = 1 To fzmt

'read in original target coordinates preserved in xom, yom and zom xm(ti) = xomtest(ti)
ym(ti) = yomtest(ti)
zm(ti) = zomtest(ti)
radius(ti) = radius1test(ti)
cradius(ti) = cradius1test(ti)
dipm(ti) = dipm1test(ti)

Next ti

'start loop for test series

For testi = 1 To testnumber text16.Text = testi

'run test tester1

Next testi

'record maximum score for this code and clear maxscore for next cycle text41.Text = sumcombi
text42.Text = maxcombiscore maxcombiscore = 0
sumcombi = 0

'display best code hg = ""
For l = 0 To 14
For k = 1 To alen
hg = hg & Mid$(h, (l * alen) + k, 1)
Next k
hg = hg + " "
Next l text4.Text = hg
```

*END SUB*

*SUB* Command5_Click ()
'ROUTINE FOR SAVING CODES IN FILE

'set file extension default cmdialog1.DefaultExt = ".cod"
cmdialog1.Filter = "code (*.cod)|*.cod"

'activate common dialog box for file input cmdialog1.Action = 2

'store filename codefilename = cmdialog1.Filetitle

Open codefilename For Output As 1

'write number of codes as first item in file

Write #1, h

Write #1, v7

Write #1, depth

Write #1, rwidth

Write #1, rlength

Write #1, proxsense

Write #1, testnumber

Write #1, popsize

Write #1, transval

Write #1, maximals

Write #1, maximalm

Close 1

*END SUB*

*SUB* Command6_Click ()
hscroll16.Visible = True
'ExchangeSort: The ExchangeSort compares each element--starting with
'the first--with every following element. If any of the following
'elements is smaller than the current element, it is exchanged with

61

```
'the current element and the process is repeated for the next element.

text24.Text = ""
text22.Text = ""
text26.Text = ""
text25.Text = ""
text39.Text = ""

'choose partners for recombination

For I = 1 To (popsize / 2)

text23.Text = I agene = Int(4 * Rnd)
Do
bgene = Int(4 * Rnd)
Loop Until bgene <> agene text10.Text = agene & " X " & bgene aacode = bestcode(agene)
bbcode = bestcode(bgene)

'selection of a crossover site genenumber = Int(Rnd * 15)

sitenumber = 1 + Int(alen * Rnd)

alleleposition = (alen * genenumber) + sitenumber text28.Text = alleleposition xlength = (alen - sitenumber) + 1 text29.Text = xlength

'extraction of code fragments xacode = Mid$(aacode, alleleposition, xlength)
xbcode = Mid$(bbcode, alleleposition, xlength)

'replacement of code fragments atcode = aacode
btcode = bbcode

Mid$(atcode, alleleposition, xlength) = xbcode
Mid$(btcode, alleleposition, xlength) = xacode
```

62

```
codearray(I) = atcode
codearray(I + (popsize / 2)) = btcode

Next I

'RANDOMIZED POPULATION GENERATOR

For i = 1 To Int(.5 * popsize)

codeselect = 1 + Int(Rnd * popsize)

text10.Text = codeselect hm = codearray(codeselect)

For j = 1 To 5
text16.Text = j
locus = 1 + Int(Len(h) * Rnd)

text28.Text = locus allele = Int(5 * Rnd)

Do Until Mid$(hm, locus, 1) <> Trim$(Str$(allele))

allele = Int(5 * Rnd)

Loop

If Int(v6 / 2) = 1 + Int(v6 * (Rnd(1))) Then allele = 5

End If text29.Text = allele

Mid$(hm, locus, 1) = Trim$(Str$(allele))

Next j codearray(codeselect) = hm

Next i

'include example of bestcode from last generation
For i = 1 To Int(.5 * popsize)

codeselect = 1 + Int(Rnd * popsize)
```

63

```
text10.Text = codeselect hm = codearray(codeselect)

For j = 1 To 1
text16.Text = j
locus = 1 + Int(Len(h) * Rnd)

text28.Text = locus allele = Int(5 * Rnd)

Do Until Mid$(hm, locus, 1) <> Trim$(Str$(allele))

allele = Int(5 * Rnd)

Loop

If Int(v6 / 2) = 1 + Int(v6 * (Rnd(1))) Then allele = 5

End If text29.Text = allele

Mid$(hm, locus, 1) = Trim$(Str$(allele))

Next j codearray(codeselect) = hm

Next i codearray(0) = bestcode(1)

multitester

END SUB

SUB Command7_Click ()
'ROUTINE FOR READING CODES FROM FILE

'Setting for default extension cmdialog1.DefaultExt = ".cod"

cmdialog1.Filter = "code (*.cod)|*.cod"
```

64

```
'activate file common dialog box cmdialog1.Action = 1

'store filename in codefilename codefilename = cmdialog1.Filetitle

Open codefilename For Input As 1

'get codenumber stored as first item in file

Input #1, h

Input #1, v7
hscroll7 = v7 / 15
label7.Caption = v7

Input #1, depth
hscroll13.Value = depth
text2.Text = depth

Input #1, rwidth
hscroll15.Value = rwidth
text8.Text = rwidth

Input #1, rlength
hscroll9.Value = rlength
text27.Text = rlength

Input #1, proxsense
hscroll14.Value = 2 * proxsense
text17.Text = proxsense

Input #1, testnumber
hscroll12.Value = testnumber
text36.Text = testnumber

Input #1, popsize
hscroll17.Value = popsize / 2
text40.Text = popsize

Input #1, transval
hscroll18.Value = transval
text44.Text = transval

Input #1, maximals

Input #1, maximalm

'close file
```

```
Close 1
'display code decodes hg = ""
For l = 0 To 14
For k = 1 To alen
hg = hg & Mid$(h, (l * alen) + k, 1)
Next k
hg = hg - " "
Next l text4.Text = hg Beep

END SUB

SUB Command8_Click ()
text19.Text = ""

picture2.Cls counttarget = 0
list1.Clear

END SUB

SUB Command9_Click ()
coeff = 4
text46.Text = coeff

END SUB

SUB decodes ()

'DECODER FOR CREATION OF RECEPTOR

'Clear vectors for storing x,y and z coordinates

Erase xo
Erase yo
Erase zo

'Redimension vector coordinates to length of code

ReDim xo(Len(h)) As Integer
ReDim yo(Len(h)) As Integer
ReDim zo(Len(h)) As Integer
```

66

```
'initialize min and max values maxx = -10000
maxy = -10000
maxz = -10000
minx = 10000
miny = 10000
minz = 10000

'set initial position in movement array. This determines the starting orientation n = 20

'initialise counters of charge sites c1 = 0
c1neg = 0

'calculate allele lengths (code length/15): store in alen alen = Len(h) / 15

'start loop for decoding
'one cycle per allele

For ni = 0 To 14

'load starting coordinates for each successive allele
'Coordinates stored in ox, oy and oz x = ox(ni)
y = oy(ni)
z = oz(ni)

'set initial position in movement array. This determines the starting orientation n = 20

'start loop to decode each allele

For i = 1 To alen

'read character from code zs2 = Mid$(h, (ni * alen) + i, 1)

'if character is 5 set as charge site

If zs2 = "5" Then

'move 1 unit in current direction
```

67

```
x = x + a(n): y = y + B(n): z = z + C(n)
```

'add one to charge site counter

```
c1 = c1 + 1
```

'redimension charge site storage vectors

```
ReDim Preserve xcz(c1)
ReDim Preserve ycz(c1)
ReDim Preserve zcz(c1)
```

'store charge site coordinates, using charge site counter as index

```
xcz(c1) = x
ycz(c1) = y
zcz(c1) = z
```

End If

'if character is 6 set as charge site

If zs2 = "6" Then

'move 1 unit in current direction

```
x = x + a(n): y = y + B(n): z = z + C(n)
```

'add one to charge site counter

```
c1neg = c1neg + 1
```

'redimension charge site storage vectors

```
ReDim Preserve xczneg(c1neg)
ReDim Preserve yczneg(c1neg)
ReDim Preserve zczneg(c1neg)
```

'store charge site coordinates, using charge site counter as index

```
xczneg(c1neg) = x
yczneg(c1neg) = y
zczneg(c1neg) = z
```

End If

'if character is not 5 or 6 start decoding
'select case according to character

Select Case Val(zs2)

68

'calculate new values for coordinates

```
Case 0
    x = x + a(n): y = y + B(n): z = z + C(n)
Case 1
    n = d(n): x = x + a(n): y = y - B(n): z = z + C(n)
Case 2
    n = e(n): x = x + a(n): y = y + B(n): z = z + C(n)
Case 3
    n = F(n): x = x + a(n): y = y + B(n): z = z + C(n)
Case 4
    n = g(n): x = x + a(n): y = y - B(n): z = z + C(n)
Case 5
Case 6

End Select
```

'*************
'write data to the file, use code index position as vector index xo((ni * alen) + i) = x
yo((ni * alen) + i) = y
zo((ni * alen) + i) = z 'find min and max values

```
    If x < minx Then
    minx = x
    End If

If x > maxx Then
    maxx = x
    End If

If y < miny Then
    miny = y
    End If

If y > maxy Then
    maxy = y
    End If

If z < minz Then
    minz = z
    End If

If z > maxz Then
    maxz = z
    End If
```

69

```
'LOOP

Next i

Next ni

'display of report values

'charge site counter values text5.Text = cl
text45.Text = clneg

'confirm length of current string ltot = Len(h)

'length of code string text3.Text = ltot

'Calculate center of matrix centerx = Int((maxx + minx) / 2)
centery = Int((maxy + miny) / 2)

'creates z matrix without drawing result
'Clear previous matrix of heights

Erase zmat
Erase z3mat

'Redim height matrix to minimum and maximum values

ReDim zmat(minx - centerx To maxx - centerx, miny - centery To maxy - centery) As Integer
ReDim z3mat(minx - centerx To maxx - centerx, miny - centery To maxy - centery, 1 To maxz + 1 - minz) As Integer 'Create new height matrix
'Get values from coordinate vector For i = 1 To Len(h)

'Calculate values for height normalized for minimum zi = zo(i) + 1 - minz

'Get x and y values for z coordinate to use as indices for height matrix xi = xo(i) - centerx
yi = yo(i) - centery
```

```
z3mat(xi, yi, zi) = 1

'Set values for height matrix
'Check to see whether matrix component has already been set
'If yes then check if new value is greater than old value
'set value to greater value If zmat(xi, yi) = 0 Then
    zmat(xi, yi) = zi
Else
    If zmat(xi, yi) < zi Then
        zmat(xi, yi) = zi End If End If Next i 'Set up picture for drawing result picture3.Cls
picture3.BackColor = RGB(0, 0, 0)
picture3.Scale (-20, 20)-(20, -20)

'Draw frame on picture picture3.Line (-20, 0)-(20, 0), RGB(255, 255, 255)
picture3.Line (0, -20)-(0, 20), RGB(255, 255, 255)
picture3.Line (10, 10)-(-10, -10), RGB(100, 0, 0), B 'Set color factor scale cfac = 255 / (maxz - minz)

'Draw height matrix

For i = maxy - centery To miny - centery Step -1
For j = minx - centerx To maxx - centerx ac = cfac * zmat(j, i)

If ac <> 0 Then colr = RGB(120, ac, ac)

picture3.Line (j + .25, i + .25)-(j - .25, i - .25), colr, BF

End If
```

```
Next j

Next i

'Set up to draw charge sites oldstyle = picture3.FillStyle
oldcolor = picture3.FillColor picture3.FillStyle = 0
picture3.FillColor = RGB(0, 0, 0)

'Draw charge sites

For ii = 1 To cl xcz(ii) = xcz(ii) - centerx
ycz(ii) = ycz(ii) - centery
zcz(ii) = zcz(ii) + 1 - minz If zmat(xcz(ii), ycz(ii)) = zcz(ii) Then
colz = QBColor(10)
Else
colz = QBColor(2)
End If picture3.Circle (xcz(ii), ycz(ii)), 1, colz Next ii For ii = 1 To clneg xczneg(ii) = xczneg(ii) - centerx
yczneg(ii) = yczneg(ii) - centery
zczneg(ii) = zczneg(ii) + 1 - minz If zmat(xczneg(ii), yczneg(ii)) = zczneg(ii) Then
colz = QBColor(12)
Else
colz = QBColor(4)
End If picture3.Circle (xczneg(ii), yczneg(ii)), 1, colz Next ii picture3.FillStyle = oldstyle
picture3.FillColor = oldcolor
```

*END SUB*

*FUNCTION* dist3d (x1, y1, z1, x2, y2, z2) As Double

72

```
'THREE DIMENSIONAL DISTANCE CALCULATION dist3d = Sqr((x1 - x2) ^ 2 + (y1 - y2) ^ 2 + (z1 - z2) ^ 2)

END FUNCTION

SUB Form_Load ()
hscroll16.Visible = False
'Set up picture for drawing result
picture1.Visible = False
picture3.Cls
picture3.BackColor = RGB(0, 0, 100)
picture3.Scale (-20, 20)-(20, -20)

'Draw frame on picture picture3.Line (-20, 0)-(20, 0), RGB(255, 255, 255)
picture3.Line (0, -20)-(0, 20), RGB(255, 255, 255)
picture3.Line (7, 7)-(-7, -7), RGB(100, 0, 0), B depth = 25
rwidth = 7
rlength = 7
cnum = 1
threshold1 = .8
popsize = 10
transval = 0
coeff = 3

'Set numerical constants pi = 3.14159265
pi2 = pi * 2

'test and code numbers testnumber = 1
codenumber = 1
proxsense = 3 counttarget = 0

'initialise target file entry boxes text19.Text = ""
text43.Text = ""

'initialises string frequencies
vs = 1
v1 = 5
```

```
v2 = 5
v3 = 5
v4 = 5
v5 = 5
v6 = 60
v7 = 180
v9 = 60
'set maxz=0 as default value
maxz = 0

'this routine loads the matrix required for code conversion

Open "c:\vb3\mites\robodat.bas" For Input As 1
Input #1, junk
Input #1, junk

For i = 1 To 24
Input #1, a(i)

Next i

For i = 1 To 24
Input #1, B(i)

Next i

For i = 1 To 24
Input #1, C(i)

Next i
For i = 1 To 24
Input #1, d(i)

Next i

For i = 1 To 24
Input #1, e(i)

Next i

For i = 1 To 24
Input #1, F(i)

Next i
For i = 1 To 24
Input #1, g(i)
```

74

```
Next i
Close fragorig

'set up random numbers

For i = 0 To 3000 randarray(i) = CSng(Rnd)

Next i

END SUB

SUB fragorig ()

'LOADS INITIAL RECEPTOR ORIGIN COORDINATES

'origins for fragments ox(0) = -7
ox(1) = 0
ox(2) = 7
ox(3) = -7
ox(4) = 0
ox(5) = 7
ox(6) = -7
ox(7) = 0
ox(8) = 7
ox(9) = -7
ox(10) = 0
ox(11) = 7
ox(12) = -7
ox(13) = 0
ox(14) = 7
oy(0) = 7
oy(1) = 7
oy(2) = 7
oy(3) = 7
oy(4) = 7
oy(5) = 7
oy(6) = 0
oy(7) = 0
oy(8) = 0
oy(9) = -7
oy(10) = -7
oy(11) = -7
oy(12) = -7
oy(13) = -7
```

```
oy(14) = -7
oz(0) = 0
oz(1) = 0
oz(2) = 0
oz(3) = -14
oz(4) = -14
oz(5) = -14
oz(6) = -28
oz(7) = -28
oz(8) = -28
oz(9) = -14
oz(10) = -14
oz(11) = -14
oz(12) = 0
oz(13) = 0
oz(14) = 0
```

*END SUB*

*SUB* HScroll1_Change ()

'CODE FREQUENCY CONTROL

'control for controlling code frequency for 0

'load value into v1 v1 = hscroll1.Value

'update total for frequency calculations tc = v1 + v2 + v3 + v4 + v5

'update frequency labels

```
label8.Caption = Int(100 * v1 / tc)
label9.Caption = Int(100 * v2 / tc)
label10.Caption = Int(100 * v3 / tc)
label11.Caption = Int(100 * v4 / tc)
label12.Caption = Int(100 * v5 / tc)
```

*END SUB*

```
SUB HScroll10_Change ()
mutnum = hscroll10.Value
text33.Text = mutnum
```
*END SUB*

```
SUB HScroll10_Scroll ()
mutnum = hscroll10.Value
text33.Text = mutnum
```

*END SUB*

76

```
SUB HScroll11_Change ()

'CODE NUMBER CONTROL

'load new number of codes into codenumber AND DISPLAY text35.Text = hscroll11.Value threshold1 = Val(hscroll11.Value) / 100

END SUB

SUB HScroll11_Scroll ()
'load number of codes into variable AND DISPLAY text35.Text = hscroll11.Value
codenumber = Val(hscroll11.Value)

END SUB

SUB HScroll12_Change ()

'TEST NUMBER CONTROL

'load number of tests into testnumber AND DISPLAY text36.Text = hscroll12.Value testnumber = Val(hscroll12.Value)

transscore = 0

END SUB

SUB HScroll12_Scroll ()
'load number of codes into variable AND DISPLAY text36.Text = hscroll12.Value
testnumber = Val(hscroll12.Value)

END SUB

SUB HScroll13_Change ()

'RECEPTOR DEPTH CONTROL

'get new value for receptor depth and display depth = hscroll13.Value
text2.Text = depth 'store new value in code origin vector
```

```
oz(6) = -1 * depth
oz(7) = -1 * depth
oz(8) = -1 * depth oz(3) = -1 * Int(depth / 2)
oz(4) = -1 * Int(depth / 2)
oz(5) = -1 * Int(depth / 2)

oz(9) = -1 * Int(depth / 2)
oz(10) = -1 * Int(depth / 2)
oz(11) = -1 * Int(depth / 2)
```

*END SUB*

*SUB* HScroll13_Scroll ()
'RECEPTOR DEPTH CONTROL

'get new value for receptor depth and display

```
depth = hscroll13.Value
text2.Text = depth
```

'store new value in code origin vector

```
oz(6) = -1 * depth
oz(7) = -1 * depth
oz(8) = -1 * depth oz(3) = -1 * Int(depth / 2)
oz(4) = -1 * Int(depth / 2)
oz(5) = -1 * Int(depth / 2)

oz(9) = -1 * Int(depth / 2)
oz(10) = -1 * Int(depth / 2)
oz(11) = -1 * Int(depth / 2)
```

*END SUB*

*SUB* HScroll14_Change ()

'PROXIMITY CONTROL

'get new proximity value and store in proxsense
'divide by two to allow intermediate values text17.Text = hscroll14.Value / 2 proxsense = hscroll14.Value / 2

*END SUB*

*SUB* HScroll14_Scroll ()

```
text17.Text = hscroll14.Value / 2
proxsense = hscroll14.Value / 2

END SUB

SUB HScroll15_Change ()

'RECEPTOR WIDTH CONTROL

'get new width value from scroll bar and display rwidth = hscroll15.Value
text18.Text = rwidth 'update width coordinates in code origin matrix oy(0) = rwidth
oy(1) = rwidth
oy(2) = rwidth
oy(3) = rwidth
oy(4) = rwidth
oy(5) = rwidth
oy(9) = -1 * rwidth
oy(10) = -1 * rwidth
oy(11) = -1 * rwidth
oy(12) = -1 * rwidth
oy(13) = -1 * rwidth
oy(14) = -1 * rwidth 'draw new receptor frame on screen picture3.Cls
picture3.Line ((-1 * rlength), (-1 * rwidth))-(rlength, rwidth), RGB(255, 0, 255), B

END SUB

SUB HScroll15_Scroll ()
'RECEPTOR WIDTH CONTROL

'get new width value from scroll bar and display rwidth = hscroll15.Value
text18.Text = rwidth 'update width coordinates in code origin matrix oy(0) = rwidth
oy(1) = rwidth
oy(2) = rwidth
oy(3) = rwidth
oy(4) = rwidth
oy(5) = rwidth
```

78

```
oy(9) = -1 * rwidth
oy(10) = -1 * rwidth
oy(11) = -1 * rwidth
oy(12) = -1 * rwidth
oy(13) = -1 * rwidth
oy(14) = -1 * rwidth 'draw new receptor frame on screen picture3.Cls
picture3.Line ((-1 * rlength), (-1 * rwidth))-(rlength, rwidth), RGB(255, 0, 255), B

END SUB

SUB HScroll16_Change ()

'SCAN RESULTS cnum = hscroll16.Value text22.Text = srxy3(cnum)
text24.Text = sslope3(cnum)
text25.Text = mrxy3(cnum)
text26.Text = mslope3(cnum)
text20.Text = pmscore(cnum)
text31.Text = pmscore(cnum)
text30.Text = bscore
transscore = pmscore(cnum)

text10.Text = cnum

'DECODE BEST CODE

'Read in codes from code storage array
'Code index is cnum
'prior to testing, cnum=0 h = codearray(cnum)

'Code is stored in h hg = ""
For l = 0 To 14
For k = 1 To alen
hg = hg & Mid$(h, (l * alen) + k, 1)
Next k
hg = hg + " "
Next l text4.Text = hg decodes
```

80

```
'GRAPHING SUBROUTINE

'display results for sum affinity as graph graph1.DataReset = 1

For iy = 1 To counttarget graph1.GraphData = sumcomb3(iy, cnum)

Next iy graph1.GraphData = 0

For iy = 1 To counttarget graph1.XPosData = target(iy)

Next iy graph1.XPosData = 0 graph1.DrawMode = 2

'display results for maximum affinity as graph graph2.DataReset = 1

For iy = 1 To counttarget graph2.GraphData = maxcomb3(iy, cnum)

Next iy graph2.GraphData = 0

For iy = 1 To counttarget graph2.XPosData = target(iy)

Next iy graph2.XPosData = 0 graph2.DrawMode = 2

END SUB

SUB HScroll17_Change ()

popsize = 2 * hscroll17.Value
```

```
text40.Text = popsize
hscroll16.max = popsize
END SUB

SUB HScroll17_Scroll ()

popsize = 2 * hscroll17.Value
text40.Text = popsize

END SUB

SUB HScroll18_Change ()
text44 = hscroll18.Value
transval = hscroll18.Value
END SUB SUB HScroll18_Scroll ()
text44 = hscroll18.Value
END SUB SUB HScroll19_Change ()
'CHARGE SITE FREQUENCY CONTROL 'get new value for charge site percentage from
'scroll bar and store in v6 v9 = hscroll19.Value

'update label with new charge site probability label38.Caption = (Int(10000 / v9)) / 100

END SUB

SUB HScroll2_Change ()

'CODE FREQUENCY CONTROL

'control for controlling code frequency for 1

'load value into v2 v2 = hscroll2.Value

'update total for frequency calculations tc = v1 + v2 + v3 + v4 + v5

'update frequency labels label8.Caption = Int(100 * v1 / tc)
label9.Caption = Int(100 * v2 / tc)
label10.Caption = Int(100 * v3 / tc)
label11.Caption = Int(100 * v4 / tc)
```

```
label12.Caption = Int(100 * v5 / tc)
```

END SUB

SUB HScroll3_Change ()

'CODE FREQUENCY CONTROL

'control for controlling code frequency for 4

'load value into v3

```
v3 = hscroll3.Value
```

'update total for frequency calculations

```
tc = v1 + v2 + v3 + v4 + v5
```

'update frequency labels

```
label8.Caption = Int(100 * v1 / tc)
label9.Caption = Int(100 * v2 / tc)
label10.Caption = Int(100 * v3 / tc)
label11.Caption = Int(100 * v4 / tc)
label12.Caption = Int(100 * v5 / tc)
```

END SUB

SUB HScroll4_Change ()

'CODE FREQUENCY CONTROL

'control for controlling code frequency for 3

'load value into v4

```
v4 = hscroll4.Value
```

'update total for frequency calculations

```
tc = v1 + v2 + v3 + v4 + v5
```

'update frequency labels

```
label8.Caption = Int(100 * v1 / tc)
label9.Caption = Int(100 * v2 / tc)
label10.Caption = Int(100 * v3 / tc)
label11.Caption = Int(100 * v4 / tc)
label12.Caption = Int(100 * v5 / tc)
```

END SUB

SUB HScroll5_Change ()

```
'CODE FREQUENCY CONTROL

'control for controlling code frequency for 4

'load value into v5 v5 = hscroll5.Value

'update total for frequency calculations tc = v1 + v2 + v3 + v4 + v5

'update frequency labels label8.Caption = Int(100 * v1 / tc)
label9.Caption = Int(100 * v2 / tc)
label10.Caption = Int(100 * v3 / tc)
label11.Caption = Int(100 * v4 / tc)
label12.Caption = Int(100 * v5 / tc)

END SUB

SUB HScroll6_Change ()

'CHARGE SITE FREQUENCY CONTROL

'get new value for charge site percentage from
'scroll bar and store in v6 v6 = hscroll6.Value

'update label with new charge site probability label13.Caption = (Int(10000 / v6)) / 100
END SUB SUB HScroll7_Change ()

'CODE LENGTH ADJUSTMENT CONTROL

'get new setting for code length from scroll bar
'and store in v7

'MULTIPLY by 15 to ensure codes are ALL multiples of 15 v7 = 15 * hscroll7.Value

'Update label label7.Caption = v7

END SUB

SUB HScroll7_Scroll ()
```

84

```
v7 = 15 * hscroll7.Value
label7.Caption = v7

END SUB

SUB HScroll8_Change ()

'TARGET VALUE CONTROL

'get new value, store in target1 and display target1 = hscroll8.Value / 10
text32.Text = hscroll8.Value / 10

END SUB

SUB HScroll8_Scroll ()
'TARGET VALUE CONTROL

'get new value, store in target1 and display target1 = hscroll8.Value / 10
text32.Text = hscroll8.Value / 10

END SUB

SUB HScroll9_Change ()
'RECEPTOR LENGTH CONTROL

'get new width value from scroll bar and display rlength = hscroll9.Value
text27.Text = rlength 'update width coordinates in code origin matrix ox(2) = rlength
ox(5) = rlength
ox(8) = rlength
ox(11) = rlength
ox(14) = rlength ox(0) = -1 * rlength
ox(3) = -1 * rlength
ox(6) = -1 * rlength
ox(9) = -1 * rlength
ox(12) = -1 * rlength 'draw new receptor frame on screen picture3.Cls
picture3.Line ((-1 * rlength), (-1 * rwidth))-(rlength, rwidth), RGB(255, 0, 255), B
```

85

*END SUB*

*SUB* HScroll9_Scroll ()
'RECEPTOR LENGTH CONTROL

'get new width value from scroll bar and display rlength = hscroll9.Value
text27.Text = rlength 'update width coordinates in code origin matrix ox(2) = rlength
ox(5) = rlength
ox(8) = rlength
ox(11) = rlength
ox(14) = rlength ox(0) = -1 * rlength
ox(3) = -1 * rlength
ox(6) = -1 * rlength
ox(9) = -1 * rlength
ox(12) = -1 * rlength 'draw new receptor frame on screen picture3.Cls
picture3.Line ((-1 * rlength), (-1 * rwidth))-(rlength, rwidth), RGB(255, 0, 255), B

*END SUB*

*FUNCTION* length (xl As Double, yl As Double) As Double

'LENGTH CALCULATION (Pythagorean)

length = Sqr(xl ^ 2 + yl ^ 2)

*END FUNCTION*

*FUNCTION* max (var1, var2)

If var1 > var2 Then
max = var1
Else
max = var2
End If

*END FUNCTION*

86

FUNCTION min (var1, var2)

If var1 < var2 Then
min = var1
Else
min = var2
End If

END FUNCTION

SUB multitester ()
'MULTI TEST PRIMARY ROUTINE

'initialise best score, bestscore and bestcode

Erase bestcode
Erase bestscore text28.Text = ""
text29.Text = ""
text39.Text = ""

text21.Text = ""
text34.Text = ""
text37.Text = ""
text38.Text = ""

text4.Text = ""

bscore = 0

'***** CREATE 3-D REPRESENTATION OF CODE *****

'Read in codes from code storage array
'Code index is codei

For codei = 0 To popsize

'report current code number text10.Text = codei

'load next code into h for processing h = codearray(codei)

'Code is stored in h

'run decoder to create receptor decodes

87

```
'*****START TESTS ON TARGETS ******
For iy = 1 To counttarget

'report current target text23.Text = iy

'reinitialize random number counter and target coordinates for each test series randcount = 0

'Start target in original position for each test series
'get number of atoms and store in fzmt (also used in tester1)

fzmt = fzmm(iy)

For ti = 1 To fzmt

'read in original target coordinates preserved in xom, yom and zom xm(ti) = xom(iy, ti)
ym(ti) = yom(iy, ti)
zm(ti) = zom(iy, ti)
radius(ti) = radius1(iy, ti)
cradius(ti) = cradius1(iy, ti)
dipm(ti) = dipm1(iy, ti)

Next ti

'start loop for test series

For testi = 1 To testnumber text16.Text = testi

'run test tester1

Next testi

'record maximum score for this code and clear maxscore for next cycle sumcomb3(iy, codei) = sumcombi
maxcomb3(iy, codei) = maxcombiscore
```

88

```
maxcombiscore = 0
sumcombi = 0

Next iy

'end of test loop

'display results for sum affinity as graph graph1.DataReset = 1

For iy = 1 To counttarget graph1.GraphData = sumcomb3(iy, codei)

Next iy graph1.GraphData = 0

For iy = 1 To counttarget graph1.XPosData = target(iy)

Next iy graph1.XPosData = 0 graph1.DrawMode = 2

'display results for maximum affinity as graph graph2.DataReset = 1

For iy = 1 To counttarget graph2.GraphData = maxcomb3(iy, codei)

Next iy graph2.GraphData = 0

For iy = 1 To counttarget graph2.XPosData = target(iy)

Next iy graph2.XPosData = 0 graph2.DrawMode = 2
```

'calculation of regression, correlation and primary scores
'includes 0,0 as point 'Calculation 1: Sum Affinity sumx = 0
sumx2 = 0
sumy = 0
sumy2 = 0
sumxy = 0

For iy = 1 To counttarget
sumx = sumx + target(iy)
sumx2 = sumx2 + target(iy) ^ 2
Next iy ssx = sumx2 - (((sumx) ^ 2) / (counttarget + 1))

For iy = 1 To counttarget
sumy = sumy + sumcomb3(iy, codei)
sumy2 = sumy2 + sumcomb3(iy, codei) ^ 2
Next iy ssy = sumy2 - (((sumy) ^ 2) / (counttarget + 1))

For iy = 1 To counttarget
sumxy = sumxy + (target(iy) * sumcomb3(iy, codei))

Next iy ssxy = sumxy - ((sumx * sumy) / (counttarget + 1))
srxy2 = ((ssxy * ssxy) / (ssx * ssy))
sslope = ssxy / ssx sscore = Sgn(sslope) * srxy2 text22.Text = (Int(1000 * srxy2)) / 1000
text24.Text = (Int(1000 * sslope)) / 1000

'Calculation 2: MAX Affinity sumx = 0
sumx2 = 0
sumy = 0
sumy2 = 0
sumxy = 0

For iy = 1 To counttarget
sumx = sumx + target(iy)
sumx2 = sumx2 + target(iy) ^ 2

```
Next iy ssx = sumx2 - (((sumx) ^ 2) / (counttarget + 1))

For iy = 1 To counttarget
sumy = sumy + maxcomb3(iy, codei)
sumy2 = sumy2 + maxcomb3(iy, codei) ^ 2
Next iy ssy = sumy2 - (((sumy) ^ 2) / (counttarget + 1))

For iy = 1 To counttarget
sumxy = sumxy + (target(iy) * maxcomb3(iy, codei))

Next iy ssxy = sumxy - ((sumx * sumy) / (counttarget - 1))
mrxy2 = ((ssxy * ssxy) / (ssx * ssy))
mslope = ssxy / ssx mscore = Sgn(mslope) * mrxy2 text25.Text = (Int(1000 * mrxy2)) / 1000
text26.Text = (Int(1000 * mslope)) / 1000

'calculate multiscore and assign sign multiscore = Sgn(mslope) * Sqr(mrxy2 * srxy2)
text20.Text = multiscore 'store output in vectors sslope3(codei) = sslope
srxy3(codei) = srxy2
mslope3(codei) = mslope
mrxy3(codei) = mrxy2
pmscore(codei) = multiscore 'keep track of 3 best examples If bscore < pmscore(codei) Then
bscore = pmscore(codei)
bcode = codei
End If text31.Text = bcode
text30.Text = bscore If pmscore(codei) > bestscore(3) Then
bestscore(3) = pmscore(codei)
bestcode(3) = h
End If
```

90

```
If pmscore(codei) > bestscore(2) Then
bestscore(3) = bestscore(2)
bestscore(2) = pmscore(codei)
bestcode(3) = bestcode(3)
bestcode(2) = h
End If If pmscore(codei) > bestscore(1) Then
bestscore(2) = bestscore(1)
bestscore(1) = pmscore(codei)
bestcode(2) = bestcode(1)
bestcode(1) = h
End If text21.Text = bestscore(1)
text34.Text = bestscore(2)
text37.Text = bestscore(3)

'variables reset for next cycle maxcombiscore = 0
sumcombi = 0

Next codei

'random selection of additional parent extra = Int(Rnd * (popsize + 1))
bestcode(0) = codearray(extra)
bestscore(0) = pmscore(extra)
text38.Text = bestscore(0)

'calculation of mean score sums = 0
For k = 0 To popsize
sums = sums + pmscore(k)
Next k 'calculate mean text39.Text = sums / (popsize + 1)

'transmit best code and best score h = bestcode(1)
transscore = bestscore(1)

'display best code hg = ""
For l = 0 To 14
```

```
For k = 1 To alen
hg = hg & Mid$(h, (l * alen) + k, 1)
Next k
hg = hg + " "
Next l text4.Text = hg

END SUB

SUB Picture1_Click ()
'Routine for restoring topographical view of receptor picture1.Visible = False
picture3.Visible = True
decodes

END SUB

SUB Picture3_Click ()
'LANDSCAPE PLOTTING ROUTINE 1 picture3.Visible = False
picture1.Visible = True
'Clear screen for drawing, set scale picture1.Cls
picture1.BackColor = RGB(0, 0, 0)
picture1.Scale (-25, 25)-(25, -25)

colr = RGB(255, 255, 255)

'read height values from matrix zmat

For i = miny - centery To maxy - centery
For j = minx - centerx To maxx - centerx - 1

'calculate line points yz1 = i + .2 * ((zmat(j, i)) + j)
yz2 = i + .2 * ((zmat(j + 1, i)) + (j + 1))

'plot lines picture1.Line (j, yz1)-(j + 1, yz2), colr

Next j

Next i

END SUB
```

93

```
SUB proxim ()

t0 = Timer prox = 0
For j = 1 To fzmt
dipc = dipm(j)
If Abs(dipc) < .7 Then radc = radius(j)
margin = Int(radc + proxsense + .5)

x2c = xm(j)
y2c = ym(j)
z2c = ((zm(j) - zmm) + 1000) - mindiff

'bounds calculation xupper = min(maxx - centerx, Int(x2c + margin))
xlower = max(minx - centerx, Int(x2c - margin))
yupper = min(maxy - centery, Int(y2c + margin))
ylower = max(miny - centery, Int(y2c - margin))
zupper = min(maxz + 1 - minz, Int(z2c + margin))
zlower = max(1, Int(z2c - margin))

For xmg = xlower To xupper
For ymg = ylower To yupper

If zmat(xmg, ymg) <> 0 Then

For zmg = zlower To zupper

If z3mat(xmg, ymg, zmg) <> 0 Then distc = dist3d(xmg, ymg, zmg, x2c, y2c, z2c)

If distc <= radc + proxsense Then prox = prox + 1

End If

End If

Next zmg
```

End If

Next ymg
Next xmg

End If
Next j

*END SUB*

*SUB* tester1 ()
'Erase target coordinate vectors to start cycle
'these vectors store updated target locations Erase tarj
Erase tark
Erase tarz 'Set target count to zero for start of each cycle tarcount = 0

'Set up picture to display target picture3.Cls
picture3.BackColor = RGB(0, 0, 0)
picture3.Scale (-20, 20)-(20, -20)

'Draw frame picture3.Line (-20, 0)-(20, 0), RGB(255, 255, 255)
picture3.Line (0, -20)-(0, 20), RGB(255, 255, 255)

'Set color scale cfac = 255 / (maxz - minz)

'Draw height matrix

For i = maxy - centery To miny - centery Step -1
   For j = minx - centerx To maxx - centerx ac = cfac * zmat(j, i)

If ac <> 0 Then colr = RGB(120, ac, ac)

picture3.Line (j + .25, i + .25)-(j - .25, i - .25), colr, BF

End If

```
            Next j

Next i

'Save picture properties oldstyle = picture3.FillStyle
        oldcolor = picture3.FillColor 'set picture values to draw charge sites picture3.FillStyle = 0

'Draw charge sites

For ii = 1 To c1

If zmat(xcz(ii), ycz(ii)) = zcz(ii) Then picture3.FillColor = QBColor(10)
        colz = QBColor(10)

Else picture3.FillColor = QBColor(2)
        colz = QBColor(2)

End If picture3.Circle (xcz(ii), ycz(ii)), 1, colz

Next ii

For ii = 1 To c1neg
        gtx = zmat(xczneg(ii), yczneg(ii))
        If gtx = zczneg(ii) Then picture3.FillColor = QBColor(12)
        colz = QBColor(12)

Else picture3.FillColor = QBColor(4)
        colz = QBColor(4)

End If picture3.Circle (xczneg(ii), yczneg(ii)), 1, colz

Next ii
```

96

```
'reset picture values picture3.FillStyle = oldstyle
picture3.FillColor = oldcolor 'Set random numbers for angle changes: Note-series stored in randarray
'Same series used for each test series 'Get random change for z rz = 6 * Int(randarray(randcount) * 60)

'advance counter randcount randcount = randcount + 1

'Calculate angle rrz = (rz / 6) * pi / 30

'Get random change for y ry = 6 * Int(randarray(randcount) * 60)

'advance counter randcount = randcount + 1

'Calculate angle rry = (ry / 6) * pi / 30

'Get random value for x rx = 6 * Int(randarray(randcount) * 60)

'Advance counter randcount = randcount + 1

'calculate angle rrx = (rx / 6) * pi / 30

'Random y translation xtrans = transval - Int(randarray(randcount) * (transval * 2 + 1))

randcount = randcount + 1

'set z rotation
```

```
'loop to calculate transformed coordinates of centers

For i = 1 To fzmt

'Calculate length to centers w = length(xm(i), ym(i))

'Transformation logic for 3-d rotations

'Set z rotation

Select Case xm(i)
   Case 0
      If ym(i) > 0 Then
      theta = pi / 2
      Else
      theta = 3 * pi / 2
      End If
   Case Is > 0
      If ym(i) >= 0 Then
      theta = at1(ym(i) / xm(i))
      Else theta = at3(ym(i) / xm(i))
      End If
   Case Is < 0
      If ym(i) >= 0 Then
      theta = at2(ym(i) / xm(i))
      Else theta = at4(ym(i) / xm(i))
      End If End Select ym(i) = w * Sin(theta + rrz)
xm(i) = w * Cos(theta + rrz)

Next i

'Set y rotation

For i = 1 To fzmt
w = length(xm(i), zm(i))

Select Case xm(i)
   Case 0
      If zm(i) > 0 Then
      theta = pi / 2
      Else
      theta = 3 * pi / 2
      End If
   Case Is > 0
```

98

```
       If zm(i) >= 0 Then
       theta = at1(zm(i) / xm(i))
       Else theta = at3(zm(i) / xm(i))
       End If
     Case Is < 0
       If zm(i) >= 0 Then
       theta = at2(zm(i) / xm(i))
       Else theta = at4(zm(i) / xm(i))
       End If End Select zm(i) = w * Sin(theta + rry)
xm(i) = w * Cos(theta + rry)

Next i

'Set x rotation

For i = 1 To fzmt w = length(ym(i), zm(i))

Select Case ym(i)
   Case 0
     If zm(i) > 0 Then
     theta = pi / 2
     Else
     theta = 3 * pi / 2
     End If
   Case Is > 0
     If zm(i) >= 0 Then
     theta = at1(zm(i) / ym(i))
     Else theta = at3(zm(i) / ym(i))
     End If
   Case Is < 0
     If zm(i) >= 0 Then
     theta = at2(zm(i) / ym(i))
     Else theta = at4(zm(i) / ym(i))
     End If End Select zm(i) = w * Sin(theta + rrx)
ym(i) = w * Cos(theta + rrx)

Next i gcol = RGB(150, 150, 150)
``` picture2.Cls

'load target coordinates and data

For i = 1 To fzmt zp = zm(i)
xp = xm(i) + xtrans
yp = ym(i)
rp = radius(i)
sp = cradius(i)

'draw transformed target

'picture2.Circle (xp, yp), sp, gcol
picture2.Circle (xp, yp), rp, gcol

'Set spacing value sp = sp + .05

'Create target surface matrix
'These calculations center the target
'use int() to round values to nearest coordinate point For j = Int(xp - sp) To Int(xp + sp + 1)
For k = Int(yp - sp) To Int(yp + sp + 1)

'Calculate height of target surface dist = Sqr((xp - j) ^ 2 + (yp - k) ^ 2)

'Simplify target surface

If dist <= rp Then

'if point is within 1 radius of center set height to z value minus radius

'Draw target surface picture2.Circle (j, k), .2

'Load target surface into storage vectors
'Increment counter for storage vector tarcount = tarcount + 1

'Redimension storage vectors, preserving current data

ReDim Preserve tarj(tarcount) As Integer
tarj(tarcount) = j
ReDim Preserve tark(tarcount) As Integer
tark(tarcount) = k

```
ReDim Preserve tarz(tarcount) As Double
tarz(tarcount) = zp - rp

Else

If dist <= sp Then

'if point is within 1 radius + 1 set height to z value - one half radius

'draw target surface picture2.PSet (j, k)

'Store data in vectors tarcount = tarcount + 1

ReDim Preserve tarj(tarcount) As Integer
tarj(tarcount) = j
ReDim Preserve tark(tarcount) As Integer
tark(tarcount) = k
ReDim Preserve tarz(tarcount) As Double
tarz(tarcount) = zp - (rp / 2)

End If

End If

Next k

Next j

Next i

'Start contact calculations
'Part 1:
'Determine point of minimum separation zmm = 100000

'Set initial minimum separation mindiff = 100000

'Load target height values

For ti = 1 To tarcount xtxt = tarj(ti)
ytxt = tark(ti)
ztxt = tarz(ti)

'get target surface minimum to normalise target surface
```

101

```
If zmm > ztxt Then

'find minimum value of z for substrate and store in zmm zmm = ztxt

End If

Next ti

'Load target height vectors

For ti = 1 To tarcount xtxt = tarj(ti)
ytxt = tark(ti)
ztxt = tarz(ti)

'Calculate target height matrix
'Draw target surface
'check that points are within receptor matrix If (xtxt <= (maxx - centerx)) And (ytxt <= (maxy - centery)) Then
If (xtxt >= (minx - centerx)) And (ytxt >= (miny - centery)) Then picture3.Circle (xtxt, ytxt), .5, RGB(255, 255, 0)

'Get height value of receptor surface at position xtxt, ytxt from zmat zrec = zmat(xtxt, ytxt)

'check that there is a receptor under the substrate
'if not, skip calculation

If zrec <> 0 Then

'Calculate difference in receptor and target heights
'get the height of the substrate at xtxt,ytxt '(ztxt-zmm) is the normalized value of the substrate
'(maxz+1-minz) is the maximum value of the zmat matrix (all of it!)
'adding these values ensures that all the values of the substrate are above the receptor 'ALTERNATIVE LINE
diff = (ztxt - zmm) + (1000) - zrec 'transx = (ztxt - zmm) + maxz + 1 - minz 'diff = the separation between the substrate and the receptor 'diff = transx - zrec
```

102

```
'Track minimal difference

If mindiff > diff Then
mindiff = diff
xlow = xtxt
ylow = ytxt
End If
End If
End If
End If Next ti 'Loop 'if the mindiff value has not changed then the substrate
'has missed the receptor, in which case don't continue
'calculations If mindiff <> 100000 Then picture3.Circle (xlow, ylow), 1, RGB(125, 255, 0)

'Calculate score
'the following section calculates the separation between the receptor and substrate charge sites score = 0 sumdist = 0 ncnt = 0

'calculation for positive charge sites

For i = 1 To c1

For j = 1 To fzmt

'Multiply by -1 to make negative dipoles attracted to positive charge sites dipc = -1 * dipm(j)

'only do calculation if there is a dipole moment

If dipc <> 0 Then

'get receptor charge coordinates x1c = xcz(i)
y1c = ycz(i)
z1c = zcz(i) - .5
```

```
'get substrate site locations x2c = xm(j)
y2c = ym(j)

'calculate the collision height of the substrate
'Alternative z2c = ((zm(j) - zmm) + 1000) - mindiff 'z2c = ((zm(j) - zmm) + maxz + 1 - minz) - mindiff 'calculate distance between charge sites distc = dist3d(x1c, y1c, z1c, x2c, y2c, z2c)

'calculate approximate value of electrostatic energy scorec = dipc / (distc ^ coeff)

'sum to obtain updated score score = score + scorec sumdist = sumdist + distc ncnt = ncnt + 1

End If

Next j
Next i

'calculation for positive charge sites

For i = 1 To clneg

For j = 1 To fzmt

'Multiply by +1 to make negative dipoles repelled by positive charge sites dipc = dipm(j)

'only do calculation if there is a dipole moment

If dipc <> 0 Then

'get receptor charge coordinates x1c = xczneg(i)
y1c = yczneg(i)
z1c = zczneg(i) - .5
```

104

```
'get substrate site locations x2c = xm(j)
y2c = ym(j)

'calculate the collision height of the substrate
'Alternative z2c = ((zm(j) - zmm) + 1000) - mindiff 'z2c = ((zm(j) - zmm) + maxz + 1 - minz) - mindiff 'calculate distance between charge sites distc = dist3d(x1c, y1c, z1c, x2c, y2c, z2c)

'calculate approximate value of electrostatic energy scorec = dipc / (distc ^ coeff)

'sum to obtain updated score score = score + scorec sumdist = sumdist + distc ncnt = ncnt + 1

End If

Next j
Next i

'********* A sophisticated (and very fast!!!!!) proximity detector proxim

'*********

'Display results

'Calculate proximity score as proportion of receptor points
'within proximity margin proxscore = prox / Len(h)

'calculate combined score as product combiscore = Int(proxscore * ((prox / 10000) + score) * 1000000) / 1000

'Accumulate combiscores for this test series
```

```
sumcombi = sumcombi + combiscore
text41.Text = sumcombi

'Track maximum affinity scores

If combiscore > maxcombiscore Then maxcombiscore = combiscore
text42.Text = maxcombiscore If maxcombiscore > mxscore Then
mxscore = maxcombiscore text49.Text = mxscore mxtest = transtest
mxtarget = transtarget
text47.Text = mxtarget
text48.Text = mxtest
End If End If End If

END SUB

SUB tester2 ()
'Erase target coordinate vectors to start cycle
'these vectors store updated target locations Erase tarj
Erase tark
Erase tarz 'Set target count to zero for start of each cycle tarcount = 0

'Set random numbers for angle changes. Note-series stored in randarray
'Same series used for each test series 'Get random change for z rz = 6 * Int(randarray(randcount) * 60)

'advance counter randcount randcount = randcount + 1
```

```
'Calculate angle rrz = (rz / 6) * pi / 30

'Get random change for y ry = 6 * Int(randarray(randcount) * 60)

'advance counter randcount = randcount + 1

'Calculate angle rry = (ry / 6) * pi / 30

'Get random value for x rx = 6 * Int(randarray(randcount) * 60)

'Advance counter randcount = randcount + 1

'calculate angle rrx = (rx / 6) * pi / 30

'Random y translation xtrans = transval - Int(randarray(randcount) * (transval * 2 + 1))

randcount = randcount + 1

'set z rotation

'loop to calculate transformed coordinates of centers

For i = 1 To fzmt

'Calculate length to centers w = length(xm(i), ym(i))

'Transformation logic for 3-d rotations

'Set z rotation

Select Case xm(i)
    Case 0
        If ym(i) > 0 Then
```

107

```
        theta = pi / 2
      Else
        theta = 3 * pi / 2
      End If
    Case Is > 0
      If ym(i) >= 0 Then
        theta = at1(ym(i) / xm(i))
        Else theta = at3(ym(i) / xm(i))
      End If
    Case Is < 0
      If ym(i) >= 0 Then
        theta = at2(ym(i) / xm(i))
        Else theta = at4(ym(i) / xm(i))
      End If End Select ym(i) = w * Sin(theta + rrz)
xm(i) = w * Cos(theta + rrz)

Next i

'Set y rotation

For i = 1 To fzmt
w = length(xm(i), zm(i))

Select Case xm(i)
    Case 0
      If zm(i) > 0 Then
        theta = pi / 2
      Else
        theta = 3 * pi / 2
      End If
    Case Is > 0
      If zm(i) >= 0 Then
        theta = at1(zm(i) / xm(i))
        Else theta = at3(zm(i) / xm(i))
      End If
    Case Is < 0
      If zm(i) >= 0 Then
        theta = at2(zm(i) / xm(i))
        Else theta = at4(zm(i) / xm(i))
      End If End Select zm(i) = w * Sin(theta + rry)
xm(i) = w * Cos(theta + rry)
```

108

```
Next i

'Set x rotation

For i = 1 To fzmt w = length(ym(i), zm(i))

Select Case ym(i)
   Case 0
      If zm(i) > 0 Then
      theta = pi / 2
      Else
      theta = 3 * pi / 2
      End If
   Case Is > 0
      If zm(i) >= 0 Then
      theta = at1(zm(i) / ym(i))
      Else theta = at3(zm(i) / ym(i))
      End If
   Case Is < 0
      If zm(i) >= 0 Then
      theta = at2(zm(i) / ym(i))
      Else theta = at4(zm(i) / ym(i))
      End If End Select zm(i) = w * Sin(theta + rrx)
ym(i) = w * Cos(theta + rrx)

Next i gcol = RGB(150, 150, 150)

'load target coordinates and data

For i = 1 To fzmt zp = zm(i)
xp = xm(i) + xtrans
yp = ym(i)
rp = radius(i)
sp = cradius(i)

'draw transformed target

'Set spacing value
```

```
sp = sp + .05

'Create target surface matrix
'These calculations center the target
'use int() to round values to nearest coordinate point For j = Int(xp - sp) To Int(xp + sp + 1)
For k = Int(yp - sp) To Int(yp + sp + 1)

'Calculate height of target surface dist = Sqr((xp - j) ^ 2 + (yp - k) ^ 2)

'Simplify target surface

If dist <= rp Then

'if point is within 1 radius of center set height to z value minus radius

'Draw target surface

'Load target surface into storage vectors
'Increment counter for storage vector tarcount = tarcount + 1

'Redimension storage vectors, preserving current data

ReDim Preserve tarj(tarcount) As Integer
tarj(tarcount) = j
ReDim Preserve tark(tarcount) As Integer
tark(tarcount) = k
ReDim Preserve tarz(tarcount) As Double
tarz(tarcount) = zp - rp Else If dist <= sp Then 'if point is within 1 radius + 1 set height to z value - one half radius 'Store data in vectors tarcount = tarcount + 1

ReDim Preserve tarj(tarcount) As Integer
tarj(tarcount) = j
ReDim Preserve tark(tarcount) As Integer
tark(tarcount) = k
ReDim Preserve tarz(tarcount) As Double
tarz(tarcount) = zp - (rp / 2)
```

```
        End If

End If

Next k

Next j

Next i

'Start contact calculations
'Part 1:
'Determine point of minimum separation zmm = 100000

'Set initial minimum separation mindiff = 100000

'Load target height values

For ti = 1 To tarcount xtxt = tarj(ti)
ytxt = tark(ti)
ztxt = tarz(ti)

'get target surface minimum to normalise target surface

If zmm > ztxt Then

'find minimum value of z for substrate and store in zmm zmm = ztxt

End If

Next ti

'Load target height vectors

For ti = 1 To tarcount xtxt = tarj(ti)
ytxt = tark(ti)
ztxt = tarz(ti)

'Calculate target height matrix
'Draw target surface
'check that points are within receptor matrix
```

110

111

```
If (xtxt <= (maxx - centerx)) And (ytxt <= (maxy - centery)) Then
If (xtxt >= (minx - centerx)) And (ytxt >= (miny - centery)) Then 'Get height value of receptor surface at position xtxt, ytxt from zmat zrec = zmat(xtxt, ytxt)

'check that there is a receptor under the substrate
'if not, skip calculation

If zrec <> 0 Then

'Calculate difference in receptor and target heights.
'get the height of the substrate at xtxt,ytxt '(ztxt-zmm) is the normalized value of the substrate
'(maxz+1-minz) is the maximum value of the zmat matrix (all of it!)
'adding these values ensures that all the values of the substrate are above the receptor 'ALTERNATIVE LINE
diff = (ztxt - zmm) + (1000) - zrec 'transx = (ztxt - zmm) + maxz + 1 - minz 'diff = the separation between the substrate and the receptor 'diff = transx - zrec 'Track minimal difference If mindiff > diff Then
mindiff = diff
xlow = xtxt
ylow = ytxt
End If
End If
End If
End If Next ti 'Loop 'if the mindiff value has not changed then the substrate
'has missed the receptor, in which case don't continue
'calculations If mindiff <> 100000 Then 'Calculate score
'the following section calculates the separation between the receptor and substrate charge sites
```

112

```
score = 0 sumdist = 0 ncnt = 0

'calculation for positive charge sites

For i = 1 To c1

For j = 1 To fzmt

'Multiply by -1 to make negative dipoles attracted to positive charge sites dipc = -1 * dipm(j)

'only do calculation if there is a dipole moment

If dipc <> 0 Then

'get receptor charge coordinates x1c = xcz(i)
y1c = ycz(i)
z1c = zcz(i) - .5

'get substrate site locations x2c = xm(j)
y2c = ym(j)

'calculate the collision height of the substrate
'Alternative z2c = ((zm(j) - zmm) + 1000) - mindiff 'z2c = ((zm(j) - zmm) + maxz - 1 - minz) - mindiff 'calculate distance between charge sites distc = dist3d(x1c, y1c, z1c, x2c, y2c, z2c)

'calculate approximate value of electrostatic energy scorec = dipc / (distc ^ coeff)

'sum to obtain updated score score = score + scorec sumdist = sumdist + distc ncnt = ncnt + 1
```

```
End If

Next j
Next i

'calculation for positive charge sites

For i = 1 To clneg

For j = 1 To fzmt

'Multiply by +1 to make negative dipoles repelled by positive charge sites dipc = dipm(j)

'only do calculation if there is a dipole moment

If dipc <> 0 Then

'get receptor charge coordinates x1c = xczneg(i)
y1c = yczneg(i)
z1c = zczneg(i) - .5

'get substrate site locations x2c = xm(j)
y2c = ym(j)

'calculate the collision height of the substrate
'Alternative z2c = ((zm(j) - zmm) + 1000) - mindiff 'z2c = ((zm(j) - zmm) + maxz + 1 - minz) - mindiff 'calculate distance between charge sites distc = dist3d(x1c, y1c, z1c, x2c, y2c, z2c)

'calculate approximate value of electrostatic energy scorec = dipc / (distc ^ coeff)

'sum to obtain updated score score = score + scorec sumdist = sumdist + distc ncnt = ncnt + 1
```

114

End If

Next j
Next i

'********* A sophisticated (and very fast!!!!!) proximity detector proxim

'*********

'Display results

'Calculate proximity score as proportion of receptor points
'within proximity margin proxscore = prox / Len(h)

'calculate combined score as product combiscore = Int(proxscore * ((prox / 10000) + score) * 1000000) / 1000

'Accumulate combiscores for this test series sumcombi = sumcombi + combiscore
text41.Text = sumcombi 'Track maximum affinity scores If combiscore > maxcombiscore Then maxcombiscore = combiscore
text42.Text = maxcombiscore 'Track maximum affinity for this target and draw current configuration If maxcombiscore > highaffinity Then
highaffinity = maxcombiscore
text49.Text = highaffinity 'Set up picture to display target picture3.Cls
picture3.BackColor = RGB(0, 0, 0)
picture3.Scale (-20, 20)-(20, -20)

'Draw frame

```
picture3.Line (-20, 0)-(20, 0), RGB(255, 255, 255)
picture3.Line (0, -20)-(0, 20), RGB(255, 255, 255)

'Set color scale cfac = 255 / (maxz - minz)

'Draw height matrix

For i = maxy - centery To miny - centery Step -1
    For j = minx - centerx To maxx - centerx ac = cfac * zmat(j, i)

If ac <> 0 Then colr = RGB(120, ac, ac)

picture3.Line (j + .25, i + .25)-(j - .25, i - .25), colr, BF

End If

Next j

Next i

'Save picture properties oldstyle = picture3.FillStyle
oldcolor = picture3.FillColor 'set picture values to draw charge sites picture3.FillStyle = 0

'Draw charge sites

For ii = 1 To c1

If zmat(xcz(ii), ycz(ii)) = zcz(ii) Then picture3.FillColor = QBColor(10)
colz = QBColor(10)

Else picture3.FillColor = QBColor(2)
colz = QBColor(2)

End If picture3.Circle (xcz(ii), ycz(ii)), 1, colz

Next ii
```

116

```
For ii = 1 To c1neg
gtx = zmat(xczneg(ii), yczneg(ii))
If gtx = zczneg(ii) Then picture3.FillColor = QBColor(12)
colz = QBColor(12)

Else picture3.FillColor = QBColor(4)
colz = QBColor(4)

End If picture3.Circle (xczneg(ii), yczneg(ii)), 1, colz

Next ii

'reset picture values picture3.FillStyle = oldstyle
picture3.FillColor = oldcolor
'End draw routine
'Draw target surface
picture2.Cls
For ij = 1 To fzmt zp = zm(ij)
xp = xm(ij) + xtrans
yp = ym(ij)
rp = radius(ij)
sp = cradius(ij)
colm = rcolor(ij)
'draw transformed target picture2.Circle (xp, yp), rp, QBColor(colm)
Next ij 'Load target height vectors For ti = 1 To tarcount xtxt = tarj(ti)
ytxt = tark(ti)
ztxt = tarz(ti)

If (xtxt <= (maxx - centerx)) And (ytxt <= (maxy - centery)) Then
If (xtxt >= (minx - centerx)) And (ytxt >= (miny - centery)) Then
``` picture3.Circle (xtxt, ytxt), .5, RGB(255, 255, 0)

End If
End If

Next ti

End If

End If

End If

If maximals < sumcombi Then
maximals = sumcombi
End If

If maximalm < maxcombiscore Then
maximalm = maxcombiscore
End If

*END SUB*

*SUB* Text19_Click ()

text19.Text = ""

*END SUB*

*SUB* Text36_Click ()
text36.Text = ""
*END SUB*

*SUB* Text43_Click ()
text43.Text = ""
*END SUB*

APPENDIX B

Molecular Assembly Program

Code: Microsoft Visual Basic 3.0

1. Globally Defined Variables

```
Global codefrag1 As String
Global codefrag2 As String
Global codefrag3 As String
Global startfrag As Integer
Global lenfrag As Integer
Global maximals As Double
Global maximalm As Double
Global mainscore As Double
Global maxtarget As Double
Global sumtarget As Double Global ppoint As Single
Global pseq As Single
Global pins As Single
Global pdel As Single
Global pdup As Single
Global pinv As Single
Global code As String
Global oldcode As String
Global codet As String
Global oldcodet As String
Global codeq As String
Global oldcodeq As String
Global codea As String
Global oldcodea As String
Global coded As String
Global ik As Integer
Global subscount(16) As Integer
Global chemform As String Global sscale(16) As Double
Global scolor(16) As Integer
Global stype(16) As Integer Global pring As Integer
Global s As String
Global g As String
Global q As String
Global ringcount As Integer
Global hetero As Single
Global methyl As Integer
Global methcount As Integer Global v1 As Integer
Global v2 As Integer
Global v3 As Integer
Global v4 As Integer
Global v5 As Integer
Global v6 As Integer
Global v7 As Integer
Global v8 As Integer
Global v9 As Integer
```

```
Global v10 As Integer
Global v11 As Integer
Global v12 As Integer
Global v13 As Integer
Global v14 As Integer
Global v15 As Integer Global ng As Integer
Global pg As Integer
Global og As Integer
Global sg As Integer
Global wg As Integer Global ic As Integer
Global id As Integer Global mtations As Integer
Global state As Integer
Global scount As Integer Global xc As Single
Global yc As Single
Global zc As Single Global codelength As Integer
Global atomcount As Integer
Global hnumber As Integer 'real coordinates
Global x(500) As Double
Global y(500) As Double
Global z(500) As Double
Global r(500) As Single Global subsx(1200, 2) As Double
Global subsy(1200, 2) As Double
Global subsz(1200, 2) As Double
Global subsr(1200) As Double
Global subsc(1200) As Integer Global pi As Double
Global pi2 As Double 'rectangular coordinates
Global xr(500) As Integer
Global yr(500) As Integer
Global zr(500) As Integer Global atoms(-20 To 20, -20 To 20, -20 To 20) As Integer
Global atomx(-20 To 20, -20 To 20, -20 To 20) As Single
```

```
Global atomy(-20 To 20, -20 To 20, -20 To 20) As Single
Global atomz(-20 To 20, -20 To 20, -20 To 20) As Single
Global atomstate(-20 To 20, -20 To 20, -20 To 20) As Integer
Global subn(-20 To 20, -20 To 20, -20 To 20, 4) As Integer
Global occupy(-20 To 20, -20 To 20, -20 To 20) As Integer
Global bond1(-20 To 20, -20 To 20, -20 To 20) As Integer
Global bond2(-20 To 20, -20 To 20, -20 To 20) As Integer
Global bond3(-20 To 20, -20 To 20, -20 To 20) As Integer
Global bond4(-20 To 20, -20 To 20, -20 To 20) As Integer Global molecule(500, 14) As Single
Global skelcol(500) As Integer
Global rcx(500) As Integer
Global rcy(500) As Integer
Global rcz(500) As Integer
Global subt(500) As Integer Global xa As Integer
Global ya As Integer
Global za As Integer Global subst As Single
Global sf As Single Global delx As Single
Global dely As Single
Global delz As Single
Global del2y As Single
Global rcarb As Single Global j1 As Integer
Global j2 As Integer
Global j3 As Integer
Global j4 As Integer
Global j5 As Integer
Global j6 As Integer
Global j7 As Integer
Global j8 As Integer
Global j9 As Integer
Global j10 As Integer
Global j11 As Integer
Global j12 As Integer
Global j13 As Integer
Global j14 As Integer
Global j15 As Integer
Global ws As Integer Global xaa As Integer
Global yaa As Integer
Global zaa As Integer
Global xab As Integer
Global yab As Integer
Global zab As Integer
Global xac As Integer
```

```
Global yac As Integer
Global zac As Integer

'variables for testing

Global h As String
Global clength As Integer
Global depth As Integer
Global rwidth As Integer
Global rlength As Integer
Global proxsense As Integer
Global testnumber As Integer
Global popsize As Integer
Global transval As Integer Global ph(10) As String
Global pclength(10) As Integer
Global pdepth(10) As Integer
Global prwidth(10) As Integer
Global prlength(10) As Integer
Global pproxsense(10) As Integer
Global ptestnumber(10) As Integer
Global ppopsize(10) As Integer
Global ptransval(10) As Integer
Global pmaximals(10) As Double
Global pmaximalm(10) As Double
Global targetp As Integer
Global codenum As Integer
Global codev As integer
Global transcore As Single
Global alen As Integer Global coeff As Integer
Global zs2 As String
Global xo() As Integer
Global yo() As Integer
Global zo() As Integer
Global zmat() As Integer
Global z3mat() As Integer
Global centerx As Integer
Global centery As Integer
Global randarray(3000) As Single
Global Aq(24) As Integer
Global Bq(24) As Integer
Global Cq(24) As Integer
Global Dq(24) As Integer
Global Eq(24) As Integer
Global Fq(24) As Integer
Global Gq(24) As Integer
Global c1 As Integer
Global c1neg As Integer
Global xcz() As Integer
Global ycz() As Integer
Global zcz() As Integer
```

6

```
Global xczneg() As Integer
Global yczneg() As Integer
Global zczneg() As Integer
Global minx As Integer
Global maxx As Integer
Global miny As Integer
Global maxy As Integer
Global minz As Integer
Global maxz As Integer
Global xq As Integer
Global yq As Integer
Global zq As Integer
Global ox(25) As Integer
Global oy(25) As Integer
Global oz(25) As Integer
Global dradius(21) As Single
Global clradius(21) As Single
Global colord(21) As Integer
Global dipoles(21) As Single Global xom(500) As Single
Global yom(500) As Single
Global zom(500) As Single
Global radius1(500) As Single
Global cradius1(500) As Single
Global dipm1(500) As Single
Global colrm(500) As Integer
Global xomtest(500) As Single
Global yomtest(500) As Single
Global zomtest(500) As Single
Global radius1test(500) As Single
Global cradius1test(500) As Single
Global dipm1test(500) As Single
Global colrmtest(500) As Integer
Global xm(500) As Double
Global ym(500) As Double
Global zm(500) As Double
Global radius(500) As Single
Global cradius(500) As Single
Global dipm(500) As Single
Global tarj() As Integer
Global tark() As Integer
Global tarz() As Double
Global fzmt As Integer
Global sumcombi As Double
Global maxcombiscore As Double
Global prox As Integer
Global mindiff As Double
Global zmm As Double
Global tarcount As Integer
Global threshold As Single
Global maxaffinity As Single
Global testno As Integer
```

2. Control Object Specifications

```
VERSION 2.00
Begin Form Form1
   BackColor       =   &H00FF0000&
   Caption         =   "ASSEMBLER 7.1"
   ClientHeight    =   6915
   ClientLeft      =   210
   ClientTop       =   1515
   ClientWidth     =   9600
   FontBold        =   -1  'True
   FontItalic      =   0   'False
   FontName        =   "Small Fonts"
   FontSize        =   6.75
   FontStrikethru  =   0   'False
   FontUnderline   =   0   'False
   Height          =   7320
   Left            =   150
   LinkTopic       =   "Form1"
   ScaleHeight     =   6915
   ScaleWidth      =   9600
   Top             =   1170
   Width           =   9720
   WindowState     =   2   'Maximized
   Begin CommandButton Command4
      Caption         =   "EVOLVE3"
      FontBold        =   0   'False
      FontItalic      =   0   'False
      FontName        =   "MS Sans Serif"
      FontSize        =   8.25
      FontStrikethru  =   0   'False
      FontUnderline   =   0   'False
      Height          =   375
      Left            =   6600
      TabIndex        =   177
      Top             =   1920
      Width           =   855
   End
   Begin ListBox List2
      Height          =   615
      Left            =   7560
      TabIndex        =   176
      Top             =   4680
      Width           =   1815
   End
   Begin CommandButton Command3
      Caption         =   "EVOLVE2"
      FontBold        =   0   'False
      FontItalic      =   0   'False
      FontName        =   "MS Sans Serif"
      FontSize        =   8.25
      FontStrikethru  =   0   'False
      FontUnderline   =   0   'False
      Height          =   375
```

9

```
      Left        =   5640
      TabIndex    =   175
      Top         =   1920
      Width       =   855
   End
   Begin TextBox Text78
      Height      =   285
      Left        =   7560
      TabIndex    =   174
      Text        =   ""
      Top         =   3840
      Width       =   1815
   End
   Begin TextBox Text77
      Height      =   285
      Left        =   7560
      TabIndex    =   173
      Text        =   ""
      Top         =   3480
      Width       =   855
   End
   Begin ListBox List1
      FontBold        =   0   'False
      FontItalic      =   0   'False
      FontName        =   "MS Sans Serif"
      FontSize        =   8.25
      FontStrikethru  =   0   'False
      FontUnderline   =   0   'False
      Height      =   420
      Left        =   3960
      TabIndex    =   172
      Top         =   5280
      Width       =   1575
   End
   Begin CommandButton Command1
      Caption     =   "CLS"
      Height      =   375
      Left        =   3360
      TabIndex    =   171
      Top         =   5280
      Width       =   495
   End
   Begin TextBox Text76
      Height      =   285
      Left        =   4560
      TabIndex    =   169
      Text        =   ""
      Top         =   6600
      Width       =   495
   End
   Begin TextBox Text75
      FontBold    =   0   'False
      FontItalic  =   0   'False
      FontName    =   "MS Sans Serif"
```

```
                           10
      FontSize        =   8.25
      FontStrikethru  =   0   'False
      FontUnderline   =   0   'False
      Height          =   285
      Left            =   1680
      TabIndex        =   168
      Text            =   "0"
      Top             =   2640
      Width           =   375
   End
   Begin TextBox Text74
      FontBold        =   0   'False
      FontItalic      =   0   'False
      FontName        =   "MS Sans Serif"
      FontSize        =   8.25
      FontStrikethru  =   0   'False
      FontUnderline   =   0   'False
      Height          =   285
      Left            =   1200
      TabIndex        =   167
      Text            =   " 0"
      Top             =   2640
      Width           =   375
   End
   Begin HScrollBar HScroll30
      Height          =   255
      Left            =   120
      Max             =   100
      TabIndex        =   165
      Top             =   2640
      Width           =   495
   End
   Begin TextBox Text73
      Height          =   285
      Left            =   8520
      TabIndex        =   164
      Text            =   " "
      Top             =   3480
      Width           =   855
   End
   Begin TextBox Text72
      Height          =   285
      Left            =   8880
      TabIndex        =   163
      Text            =   "100"
      Top             =   5640
      Width           =   495
   End
   Begin HScrollBar HScroll29
      Height          =   255
      Left            =   7560
      Max             =   200
      TabIndex        =   161
      Top             =   5640
```

```
   Value      = 100
   Width      = 1215
End
Begin TextBox Text71
   FontBold      = 0  'False
   FontItalic    = 0  'False
   FontName      = "MS Sans Serif"
   FontSize      = 8.25
   FontStrikethru = 0  'False
   FontUnderline  = 0  'False
   Height     = 285
   Left       = 7560
   TabIndex   = 158
   Text       = ""
   Top        = 1920
   Width      = 615
End
Begin TextBox Text70
   FontBold      = 0  'False
   FontItalic    = 0  'False
   FontName      = "MS Sans Serif"
   FontSize      = 8.25
   FontStrikethru = 0  'False
   FontUnderline  = 0  'False
   Height     = 285
   Left       = 7560
   TabIndex   = 157
   Text       = ""
   Top        = 2760
   Width      = 615
End
Begin TextBox Text69
   FontBold      = 0  'False
   FontItalic    = 0  'False
   FontName      = "MS Sans Serif"
   FontSize      = 8.25
   FontStrikethru = 0  'False
   FontUnderline  = 0  'False
   Height     = 285
   Left       = 5640
   TabIndex   = 154
   Text       = ""
   Top        = 6600
   Width      = 975
End
Begin TextBox Text68
   FontBold      = 0  'False
   FontItalic    = 0  'False
   FontName      = "MS Sans Serif"
   FontSize      = 8.25
   FontStrikethru = 0  'False
   FontUnderline  = 0  'False
   Height     = 285
   Left       = 5640
```

12

```
      TabIndex    =  153
      Text        =  ""
      Top         =  6240
      Width       =  975
   End
   Begin TextBox Text67
      Height      =  375
      Left        =  2160
      TabIndex    =  152
      Text        =  ""
      Top         =  3240
      Width       =  495
   End
   Begin TextBox Text66
      FontBold    =  0  'False
      FontItalic  =  0  'False
      FontName    =  "MS Sans Serif"
      FontSize    =  8.25
      FontStrikethru = 0  'False
      FontUnderline =  0  'False
      Height      =  375
      Left        =  2760
      TabIndex    =  151
      Text        =  ""
      Top         =  3240
      Width       =  1335
   End
   Begin HScrollBar HScroll28
      Height      =  255
      Left        =  5640
      Max         =  100
      TabIndex    =  147
      Top         =  5880
      Value       =  50
      Width       =  1215
   End
   Begin HScrollBar HScroll27
      Height      =  255
      Left        =  5640
      Max         =  100
      TabIndex    =  146
      Top         =  5400
      Value       =  50
      Width       =  1215
   End
   Begin HScrollBar HScroll26
      Height      =  255
      Left        =  5640
      Max         =  100
      TabIndex    =  145
      Top         =  4920
      Value       =  50
      Width       =  1215
   End
```

```
Begin TextBox Text65
    Height    = 285
    Left      = 6960
    TabIndex  = 144
    Text      = ".5"
    Top       = 5880
    Width     = 495
End
Begin TextBox Text64
    Height    = 285
    Left      = 6960
    TabIndex  = 143
    Text      = ".5"
    Top       = 5400
    Width     = 495
End
Begin TextBox Text54
    Height    = 285
    Left      = 6960
    TabIndex  = 142
    Text      = ".5"
    Top       = 4920
    Width     = 495
End
Begin HScrollBar HScroll25
    Height    = 255
    Left      = 5640
    Max       = 100
    TabIndex  = 138
    Top       = 4440
    Value     = 50
    Width     = 1215
End
Begin HScrollBar HScroll24
    Height    = 255
    Left      = 5640
    Max       = 100
    TabIndex  = 137
    Top       = 3960
    Value     = 50
    Width     = 1215
End
Begin HScrollBar HScroll23
    Height    = 255
    Left      = 5640
    Max       = 100
    TabIndex  = 136
    Top       = 3480
    Value     = 50
    Width     = 1215
End
Begin HScrollBar HScroll22
    Height    = 255
    Left      = 7560
```

```
   Max          = 10
   TabIndex     = 114
   Top          = 6600
   Width        = 1215
End
Begin TextBox Text63
   FontBold     = 0  'False
   FontItalic   = 0  'False
   FontName     = "Small Fonts"
   FontSize     = 6.75
   FontStrikethru = 0  'False
   FontUnderline  = 0  'False
   Height       = 375
   Left         = 4200
   MultiLine    = -1  'True
   TabIndex     = 135
   Text         = " "
   Top          = 3240
   Width        = 1335
End
Begin CommandButton Command10
   Caption      = "EVOLVE"
   FontBold     = 0  'False
   FontItalic   = 0  'False
   FontName     = "MS Sans Serif"
   FontSize     = 8.25
   FontStrikethru = 0  'False
   FontUnderline  = 0  'False
   Height       = 375
   Left         = 4800
   TabIndex     = 131
   Top          = 1440
   Width        = 735
End
Begin TextBox Text62
   FontBold     = 0  'False
   FontItalic   = 0  'False
   FontName     = "MS Sans Serif"
   FontSize     = 8.25
   FontStrikethru = 0  'False
   FontUnderline  = 0  'False
   Height       = 315
   Left         = 8520
   TabIndex     = 130
   Text         = "0"
   Top          = 4200
   Width        = 855
End
Begin TextBox Text61
   FontBold     = 0  'False
   FontItalic   = 0  'False
   FontName     = "MS Sans Serif"
   FontSize     = 8.25
   FontStrikethru = 0  'False
```

```
         FontUnderline = 0  'False
         Height    = 315
         Left      = 2160
         TabIndex  = 129
         Text      = "0"
         Top       = 2400
         Width     = 615
      End
      Begin TextBox Text60
         Height    = 285
         Left      = 6960
         TabIndex  = 126
         Text      = "0"
         Top       = 2520
         Width     = 495
      End
      Begin TextBox Text59
         Height    = 285
         Left      = 6960
         TabIndex  = 125
         Text      = "0"
         Top       = 3000
         Width     = 495
      End
      Begin HScrollBar HScroll21
         Height    = 255
         Left      = 5640
         Max       = 100
         TabIndex  = 124
         Top       = 2520
         Width     = 1215
      End
      Begin HScrollBar HScroll20
         Height    = 255
         Left      = 5640
         Max       = 100
         TabIndex  = 123
         Top       = 3000
         Width     = 1215
      End
      Begin HScrollBar HScroll19
         Height    = 255
         Left      = 7560
         Max       = 100
         TabIndex  = 122
         Top       = 6120
         Width     = 1215
      End
      Begin TextBox Text58
         FontBold      = 0  'False
         FontItalic    = 0  'False
         FontName      = "MS Sans Serif"
         FontSize      = 8.25
         FontStrikethru = 0  'False
```

```
      FontUnderline =  0  'False
      Height      =  285
      Left        =  3720
      TabIndex    =  119
      Text        =  ""
      Top         =  2400
      Width       =  615
   End
   Begin TextBox Text57
      FontBold       =  0  'False
      FontItalic     =  0  'False
      FontName       =  "MS Sans Serif"
      FontSize       =  8.25
      FontStrikethru =  0  'False
      FontUnderline  =  0  'False
      Height      =  285
      Left        =  7560
      TabIndex    =  118
      Text        =  ""
      Top         =  3120
      Width       =  615
   End
   Begin TextBox Text42
      FontBold       =  0  'False
      FontItalic     =  0  'False
      FontName       =  "MS Sans Serif"
      FontSize       =  8.25
      FontStrikethru =  0  'False
      FontUnderline  =  0  'False
      Height      =  285
      Left        =  7560
      TabIndex    =  117
      Text        =  ""
      Top         =  2280
      Width       =  615
   End
   Begin PictureBox Picture4
      Height      =  1695
      Left        =  7560
      ScaleHeight =  1665
      ScaleWidth  =  1785
      TabIndex    =  116
      Top         =  120
      Width       =  1815
   End
   Begin PictureBox Picture3
      Height      =  1695
      Left        =  5640
      ScaleHeight =  1665
      ScaleWidth  =  1785
      TabIndex    =  115
      Top         =  120
      Width       =  1815
   End
```

```
Begin TextBox Text56
   Height      =   375
   Left        =   2160
   MultiLine   =   -1  'True
   ScrollBars  =   2   'Vertical
   TabIndex    =   106
   Text        =   ""
   Top         =   5760
   Width       =   3375
End
Begin TextBox Text55
   FontBold       =   0   'False
   FontItalic     =   0   'False
   FontName       =   "MS Sans Serif"
   FontSize       =   8.25
   FontStrikethru =   0   'False
   FontUnderline  =   0   'False
   Height         =   285
   Left           =   8880
   TabIndex       =   105
   Text           =   ""
   Top            =   6600
   Width          =   495
End
Begin TextBox Text53
   FontBold       =   0   'False
   FontItalic     =   0   'False
   FontName       =   "MS Sans Serif"
   FontSize       =   8.25
   FontStrikethru =   0   'False
   FontUnderline  =   0   'False
   Height         =   285
   Left           =   8880
   TabIndex       =   104
   Text           =   ""
   Top            =   6120
   Width          =   495
End
Begin TextBox Text52
   FontBold       =   0   'False
   FontItalic     =   0   'False
   FontName       =   "MS Sans Serif"
   FontSize       =   8.25
   FontStrikethru =   0   'False
   FontUnderline  =   0   'False
   Height         =   285
   Left           =   4560
   TabIndex       =   103
   Text           =   ""
   Top            =   6240
   Width          =   495
End
Begin TextBox Text51
   FontBold       =   0   'False
```

```
        FontItalic     = 0  'False
        FontName       = "MS Sans Serif"
        FontSize       = 8.25
        FontStrikethru = 0  'False
        FontUnderline  = 0  'False
        Height     = 285
        Left       = 3360
        TabIndex   = 102
        Text       = ""
        Top        = 6600
        Width      = 495
     End
     Begin TextBox Text50
        FontBold       = 0  'False
        FontItalic     = 0  'False
        FontName       = "MS Sans Serif"
        FontSize       = 8.25
        FontStrikethru = 0  'False
        FontUnderline  = 0  'False
        Height     = 285
        Left       = 3360
        TabIndex   = 101
        Text       = ""
        Top        = 6240
        Width      = 495
     End
     Begin TextBox Text49
        FontBold       = 0  'False
        FontItalic     = 0  'False
        FontName       = "MS Sans Serif"
        FontSize       = 8.25
        FontStrikethru = 0  'False
        FontUnderline  = 0  'False
        Height     = 285
        Left       = 2160
        TabIndex   = 100
        Text       = ""
        Top        = 6600
        Width      = 495
     End
     Begin TextBox Text48
        FontBold       = 0  'False
        FontItalic     = 0  'False
        FontName       = "MS Sans Serif"
        FontSize       = 8.25
        FontStrikethru = 0  'False
        FontUnderline  = 0  'False
        Height     = 285
        Left       = 2160
        TabIndex   = 99
        Text       = ""
        Top        = 6240
        Width      = 495
     End
```

```
Begin CommonDialog CMDialog1
   Left      =  2520
   Top       =  5640
End
Begin CommandButton Command2
   Caption   =  "File Read"
   Height    =  375
   Left      =  2160
   TabIndex  =  98
   Top       =  5280
   Width     =  1095
End
Begin TextBox Text47
   FontBold      =  0  'False
   FontItalic    =  0  'False
   FontName      =  "MS Sans Serif"
   FontSize      =  8.25
   FontStrikethru =  0  'False
   FontUnderline =  0  'False
   Height        =  285
   Left          =  1680
   TabIndex      =  96
   Text          =  "0"
   Top           =  2280
   Width         =  375
End
Begin TextBox Text46
   FontBold      =  0  'False
   FontItalic    =  0  'False
   FontName      =  "MS Sans Serif"
   FontSize      =  8.25
   FontStrikethru =  0  'False
   FontUnderline =  0  'False
   Height        =  285
   Left          =  1200
   TabIndex      =  95
   Text          =  "0"
   Top           =  2280
   Width         =  375
End
Begin HScrollBar HScroll18
   Height    =  255
   Left      =  120
   Max       =  50
   TabIndex  =  94
   Top       =  2280
   Width     =  495
End
Begin TextBox Text45
   FontBold      =  0  'False
   FontItalic    =  0  'False
   FontName      =  "MS Sans Serif"
   FontSize      =  8.25
   FontStrikethru =  0  'False
```

```
         FontUnderline  =  0  'False
         Height      =   375
         Left       =   3720
         TabIndex     =   93
         Text       =   " "
         Top        =   2760
         Width      =   1815
      End
      Begin HScrollBar HScroll17
         Height      =   255
         Left       =   120
         Max        =   10
         TabIndex     =   91
         Top        =   4440
         Width      =   495
      End
      Begin TextBox Text44
         FontBold     =   0  'False
         FontItalic    =   0  'False
         FontName     =   "MS Sans Serif"
         FontSize     =   8.25
         FontStrikethru  =   0  'False
         FontUnderline   =   0  'False
         Height      =   285
         Left       =   1200
         TabIndex     =   90
         Text       =   "0"
         Top        =   4440
         Width      =   375
      End
      Begin TextBox Text43
         FontBold     =   0  'False
         FontItalic    =   0  'False
         FontName     =   "MS Sans Serif"
         FontSize     =   8.25
         FontStrikethru  =   0  'False
         FontUnderline   =   0  'False
         Height      =   285
         Left       =   1680
         TabIndex     =   89
         Text       =   "0"
         Top        =   4440
         Width      =   375
      End
      Begin HScrollBar HScroll16
         Height      =   255
         Left       =   120
         Max        =   40
         TabIndex     =   87
         Top        =   6600
         Width      =   495
      End
      Begin TextBox Text41
         FontBold     =   0  'False
```

```
        FontItalic     = 0  'False
        FontName       = "MS Sans Serif"
        FontSize       = 8.25
        FontStrikethru = 0  'False
        FontUnderline  = 0  'False
        Height         = 285
        Left           = 1680
        TabIndex       = 86
        Text           = "0"
        Top            = 6600
        Width          = 375
    End
    Begin TextBox Text38
        FontBold       = 0  'False
        FontItalic     = 0  'False
        FontName       = "MS Sans Serif"
        FontSize       = 8.25
        FontStrikethru = 0  'False
        FontUnderline  = 0  'False
        Height         = 285
        Left           = 1200
        TabIndex       = 85
        Text           = "0"
        Top            = 6600
        Width          = 375
    End
    Begin TextBox Text35
        FontBold       = 0  'False
        FontItalic     = 0  'False
        FontName       = "MS Sans Serif"
        FontSize       = 8.25
        FontStrikethru = 0  'False
        FontUnderline  = 0  'False
        Height         = 285
        Left           = 1200
        TabIndex       = 84
        Text           = "0"
        Top            = 6360
        Width          = 375
    End
    Begin TextBox Text40
        FontBold       = 0  'False
        FontItalic     = 0  'False
        FontName       = "MS Sans Serif"
        FontSize       = 8.25
        FontStrikethru = 0  'False
        FontUnderline  = 0  'False
        Height         = 285
        Left           = 1200
        TabIndex       = 83
        Text           = "0"
        Top            = 6120
        Width          = 375
    End
```

22

```
Begin HScrollBar HScroll15
   Height      =  255
   Left        =  120
   Max         =  40
   TabIndex    =  81
   Top         =  6120
   Width       =  495
End
Begin TextBox Text39
   FontBold      =  0   'False
   FontItalic    =  0   'False
   FontName      =  "MS Sans Serif"
   FontSize      =  8.25
   FontStrikethru =  0   'False
   FontUnderline  =  0   'False
   Height        =  285
   Left          =  1680
   TabIndex      =  80
   Text          =  "0"
   Top           =  6120
   Width         =  375
End
Begin TextBox Text37
   FontBold      =  0   'False
   FontItalic    =  0   'False
   FontName      =  "MS Sans Serif"
   FontSize      =  8.25
   FontStrikethru =  0   'False
   FontUnderline  =  0   'False
   Height        =  285
   Left          =  1200
   TabIndex      =  78
   Text          =  "0"
   Top           =  5160
   Width         =  375
End
Begin TextBox Text36
   FontBold      =  0   'False
   FontItalic    =  0   'False
   FontName      =  "MS Sans Serif"
   FontSize      =  8.25
   FontStrikethru =  0   'False
   FontUnderline  =  0   'False
   Height        =  285
   Left          =  1680
   TabIndex      =  77
   Text          =  "0"
   Top           =  5160
   Width         =  375
End
Begin HScrollBar HScroll14
   Height      =  255
   Left        =  120
   Max         =  10
```

```
      TabIndex    = 76
      Top         = 5160
      Width       = 495
   End
   Begin TextBox Text34
      FontBold     = 0  'False
      FontItalic   = 0  'False
      FontName     = "MS Sans Serif"
      FontSize     = 8.25
      FontStrikethru = 0  'False
      FontUnderline  = 0  'False
      Height      = 285
      Left        = 1680
      TabIndex    = 74
      Text        = "0"
      Top         = 6360
      Width       = 375
   End
   Begin HScrollBar HScroll13
      Height      = 255
      Left        = 120
      Max         = 40
      TabIndex    = 73
      Top         = 6360
      Width       = 495
   End
   Begin TextBox Text33
      FontBold     = 0  'False
      FontItalic   = 0  'False
      FontName     = "MS Sans Serif"
      FontSize     = 8.25
      FontStrikethru = 0  'False
      FontUnderline  = 0  'False
      Height      = 285
      Left        = 1200
      TabIndex    = 71
      Text        = "0"
      Top         = 5640
      Width       = 375
   End
   Begin TextBox Text32
      FontBold     = 0  'False
      FontItalic   = 0  'False
      FontName     = "MS Sans Serif"
      FontSize     = 8.25
      FontStrikethru = 0  'False
      FontUnderline  = 0  'False
      Height      = 285
      Left        = 1680
      TabIndex    = 70
      Text        = "0"
      Top         = 5640
      Width       = 375
   End
```

```
Begin HScrollBar HScroll12
   Height      = 255
   Left        = 120
   Max         = 10
   TabIndex    = 69
   Top         = 5640
   Width       = 495
End
Begin TextBox Text31
   FontBold      = 0  'False
   FontItalic    = 0  'False
   FontName      = "MS Sans Serif"
   FontSize      = 8.25
   FontStrikethru = 0  'False
   FontUnderline = 0  'False
   Height      = 285
   Left        = 1200
   TabIndex    = 67
   Text        = "0"
   Top         = 5880
   Width       = 375
End
Begin TextBox Text30
   FontBold      = 0  'False
   FontItalic    = 0  'False
   FontName      = "MS Sans Serif"
   FontSize      = 8.25
   FontStrikethru = 0  'False
   FontUnderline = 0  'False
   Height      = 285
   Left        = 1680
   TabIndex    = 66
   Text        = "0"
   Top         = 5880
   Width       = 375
End
Begin HScrollBar HScroll11
   Height      = 255
   Left        = 120
   Max         = 40
   TabIndex    = 65
   Top         = 5880
   Width       = 495
End
Begin TextBox Text29
   FontBold      = 0  'False
   FontItalic    = 0  'False
   FontName      = "Small Fonts"
   FontSize      = 6.75
   FontStrikethru = 0  'False
   FontUnderline = 0  'False
   Height      = 375
   Left        = 2160
   MultiLine   = -1  'True
```

25

```
      TabIndex       = 64
      Text           = " "
      Top            = 1920
      Width          = 3375
   End
   Begin HScrollBar HScroll1
      Height         = 240
      Left           = 120
      Max            = 50
      Min            = 1
      TabIndex       = 2
      Top            = 3000
      Value          = 5
      Width          = 495
   End
   Begin HScrollBar HScroll10
      Height         = 255
      Left           = 120
      Max            = 10
      TabIndex       = 63
      Top            = 5400
      Width          = 495
   End
   Begin TextBox Text28
      FontBold       = 0  'False
      FontItalic     = 0  'False
      FontName       = "MS Sans Serif"
      FontSize       = 8.25
      FontStrikethru = 0  'False
      FontUnderline  = 0  'False
      Height         = 285
      Left           = 1680
      TabIndex       = 61
      Text           = "0"
      Top            = 5400
      Width          = 375
   End
   Begin TextBox Text11
      FontBold       = 0  'False
      FontItalic     = 0  'False
      FontName       = "MS Sans Serif"
      FontSize       = 8.25
      FontStrikethru = 0  'False
      FontUnderline  = 0  'False
      Height         = 285
      Left           = 1200
      TabIndex       = 60
      Text           = "0"
      Top            = 5400
      Width          = 375
   End
   Begin PictureBox Picture2
      AutoRedraw     = -1 'True
      FontBold       = -1 'True
```

```
      FontItalic      =  0  'False
      FontName        =  "Times New Roman"
      FontSize        =  9
      FontStrikethru  =  0  'False
      FontUnderline   =  0  'False
      Height          =  1695
      Left            =  2160
      ScaleHeight     =  1665
      ScaleWidth      =  1785
      TabIndex        =  59
      Top             =  120
      Width           =  1815
   End
   Begin TextBox Text27
      FontBold        =  0  'False
      FontItalic      =  0  'False
      FontName        =  "MS Sans Serif"
      FontSize        =  8.25
      FontStrikethru  =  0  'False
      FontUnderline   =  0  'False
      Height          =  285
      Left            =  1200
      TabIndex        =  57
      Text            =  "0"
      Top             =  1920
      Width           =  375
   End
   Begin HScrollBar HScroll2
      Height          =  255
      Left            =  120
      Max             =  100
      TabIndex        =  56
      Top             =  1920
      Width           =  495
   End
   Begin ListBox List3
      FontBold        =  0  'False
      FontItalic      =  0  'False
      FontName        =  "Arial"
      FontSize        =  8.25
      FontStrikethru  =  0  'False
      FontUnderline   =  0  'False
      Height          =  450
      Left            =  2160
      TabIndex        =  55
      Top             =  4560
      Width           =  3375
   End
   Begin TextBox Text26
      FontBold        =  0  'False
      FontItalic      =  0  'False
      FontName        =  "MS Sans Serif"
      FontSize        =  8.25
      FontStrikethru  =  0  'False
```

27

```
      FontUnderline = 0  'False
      Height     = 285
      Left       = 1680
      TabIndex    = 53
      Text       = "0"
      Top        = 1920
      Width      = 375
   End
   Begin HScrollBar HScroll9
      Height     = 255
      Left       = 120
      Max        = 100
      Min        = 1
      TabIndex    = 52
      Top        = 3240
      Value      = 50
      Width      = 495
   End
   Begin TextBox Text25
      FontBold    = 0  'False
      FontItalic   = 0  'False
      FontName    = "MS Sans Serif"
      FontSize    = 8.25
      FontStrikethru = 0  'False
      FontUnderline = 0  'False
      Height     = 285
      Left       = 1680
      TabIndex    = 50
      Text       = "0"
      Top        = 3240
      Width      = 375
   End
   Begin TextBox Text24
      FontBold    = 0  'False
      FontItalic   = 0  'False
      FontName    = "MS Sans Serif"
      FontSize    = 8.25
      FontStrikethru = 0  'False
      FontUnderline = 0  'False
      Height     = 285
      Left       = 1200
      TabIndex    = 49
      Text       = "50"
      Top        = 3240
      Width      = 375
   End
   Begin TextBox Text23
      FontBold    = 0  'False
      FontItalic   = 0  'False
      FontName    = "MS Sans Serif"
      FontSize    = 8.25
      FontStrikethru = 0  'False
      FontUnderline = 0  'False
      Height     = 285
```

```
      Left       = 1680
      TabIndex   = 48
      Text       = "0"
      Top        = 3480
      Width      = 375
   End
   Begin TextBox Text22
      FontBold      = 0  'False
      FontItalic    = 0  'False
      FontName      = "MS Sans Serif"
      FontSize      = 8.25
      FontStrikethru = 0  'False
      FontUnderline = 0  'False
      Height     = 285
      Left       = 1680
      TabIndex   = 47
      Text       = "0"
      Top        = 3720
      Width      = 375
   End
   Begin TextBox Text21
      FontBold      = 0  'False
      FontItalic    = 0  'False
      FontName      = "MS Sans Serif"
      FontSize      = 8.25
      FontStrikethru = 0  'False
      FontUnderline = 0  'False
      Height     = 285
      Left       = 1680
      TabIndex   = 46
      Text       = "0"
      Top        = 3960
      Width      = 375
   End
   Begin TextBox Text20
      FontBold      = 0  'False
      FontItalic    = 0  'False
      FontName      = "MS Sans Serif"
      FontSize      = 8.25
      FontStrikethru = 0  'False
      FontUnderline = 0  'False
      Height     = 285
      Left       = 1680
      TabIndex   = 45
      Text       = "0"
      Top        = 4200
      Width      = 375
   End
   Begin TextBox Text19
      FontBold      = 0  'False
      FontItalic    = 0  'False
      FontName      = "MS Sans Serif"
      FontSize      = 8.25
      FontStrikethru = 0  'False
```

```
      FontUnderline = 0  'False
      Height     = 285
      Left       = 1680
      TabIndex   = 44
      Text       = "0"
      Top        = 4680
      Width      = 375
   End
   Begin TextBox Text18
      FontBold    = 0  'False
      FontItalic  = 0  'False
      FontName    = "MS Sans Serif"
      FontSize    = 8.25
      FontStrikethru = 0  'False
      FontUnderline = 0  'False
      Height     = 285
      Left       = 1680
      TabIndex   = 43
      Text       = "0"
      Top        = 4920
      Width      = 375
   End
   Begin TextBox Text17
      FontBold    = 0  'False
      FontItalic  = 0  'False
      FontName    = "MS Sans Serif"
      FontSize    = 8.25
      FontStrikethru = 0  'False
      FontUnderline = 0  'False
      Height     = 285
      Left       = 1200
      TabIndex   = 36
      Text       = "0"
      Top        = 4920
      Width      = 375
   End
   Begin TextBox Text16
      FontBold    = 0  'False
      FontItalic  = 0  'False
      FontName    = "MS Sans Serif"
      FontSize    = 8.25
      FontStrikethru = 0  'False
      FontUnderline = 0  'False
      Height     = 285
      Left       = 1200
      TabIndex   = 35
      Text       = "0"
      Top        = 4680
      Width      = 375
   End
   Begin TextBox Text15
      FontBold    = 0  'False
      FontItalic  = 0  'False
      FontName    = "MS Sans Serif"
```

```
                FontSize         = 8.25
                FontStrikethru   = 0   'False
                FontUnderline    = 0   'False
                Height           = 285
                Left             = 1200
                TabIndex         = 34
                Text             = "0"
                Top              = 4200
                Width            = 375
             End
             Begin TextBox Text14
                FontBold         = 0   'False
                FontItalic       = 0   'False
                FontName         = "MS Sans Serif"
                FontSize         = 8.25
                FontStrikethru   = 0   'False
                FontUnderline    = 0   'False
                Height           = 285
                Left             = 1200
                TabIndex         = 33
                Text             = "0"
                Top              = 3960
                Width            = 375
             End
             Begin TextBox Text13
                FontBold         = 0   'False
                FontItalic       = 0   'False
                FontName         = "MS Sans Serif"
                FontSize         = 8.25
                FontStrikethru   = 0   'False
                FontUnderline    = 0   'False
                Height           = 285
                Left             = 1200
                TabIndex         = 32
                Text             = "0"
                Top              = 3720
                Width            = 375
             End
             Begin TextBox Text12
                FontBold         = 0   'False
                FontItalic       = 0   'False
                FontName         = "MS Sans Serif"
                FontSize         = 8.25
                FontStrikethru   = 0   'False
                FontUnderline    = 0   'False
                Height           = 285
                Left             = 1200
                TabIndex         = 31
                Text             = "0"
                Top              = 3480
                Width            = 375
             End
             Begin HScrollBar HScroll8
                Height           = 255
```

```
      Left          =   120
      Max           =   10
      TabIndex      =   30
      Top           =   4920
      Width         =   495
   End
   Begin HScrollBar HScroll7
      Height        =   255
      Left          =   120
      Max           =   10
      TabIndex      =   29
      Top           =   4680
      Width         =   495
   End
   Begin HScrollBar HScroll6
      Height        =   255
      Left          =   120
      Max           =   10
      TabIndex      =   28
      Top           =   4200
      Width         =   495
   End
   Begin HScrollBar HScroll5
      Height        =   255
      Left          =   120
      Max           =   10
      TabIndex      =   27
      Top           =   3960
      Width         =   495
   End
   Begin HScrollBar HScroll4
      Height        =   255
      Left          =   120
      Max           =   10
      TabIndex      =   26
      Top           =   3720
      Width         =   495
   End
   Begin HScrollBar HScroll3
      Height        =   255
      Left          =   120
      Max           =   10
      TabIndex      =   25
      Top           =   3480
      Width         =   495
   End
   Begin CommandButton Command6
      Caption       =   "CODE"
      FontBold      =   0  'False
      FontItalic    =   0  'False
      FontName      =   "MS Sans Serif"
      FontSize      =   8.25
      FontStrikethru =  0  'False
      FontUnderline =   0  'False
```

```
       Height      =  375
       Left        =  4080
       TabIndex    =  24
       Top         =  1440
       Width       =  735
    End
    Begin CommandButton Command23
       Caption     =  "-z"
       Height      =  255
       Left        =  5040
       TabIndex    =  23
       Top         =  360
       Width       =  495
    End
    Begin CommandButton Command22
       Caption     =  "+90x"
       Height      =  255
       Left        =  4560
       TabIndex    =  22
       Top         =  840
       Width       =  495
    End
    Begin CommandButton Command21
       Caption     =  "+90y"
       Height      =  255
       Left        =  4080
       TabIndex    =  21
       Top         =  840
       Width       =  495
    End
    Begin CommandButton Command20
       Caption     =  "-x"
       Height      =  255
       Left        =  4560
       TabIndex    =  20
       Top         =  600
       Width       =  495
    End
    Begin CommandButton Command19
       Caption     =  "+x"
       Height      =  255
       Left        =  4560
       TabIndex    =  19
       Top         =  360
       Width       =  495
    End
    Begin CommandButton Command18
       Caption     =  "-y"
       Height      =  255
       Left        =  4080
       TabIndex    =  18
       Top         =  600
       Width       =  495
    End
```

```
Begin CommandButton Command17
    Caption     =   "+y"
    Height      =   255
    Left        =   4080
    TabIndex    =   17
    Top         =   360
    Width       =   495
End
Begin TextBox Text10
    Height      =   285
    Left        =   5040
    TabIndex    =   16
    Text        =   "0"
    Top         =   120
    Width       =   495
End
Begin CommandButton Command16
    Caption     =   "Z"
    Height      =   255
    Left        =   5040
    TabIndex    =   15
    Top         =   1080
    Width       =   495
End
Begin CommandButton Command14
    Caption     =   "-z"
    Height      =   255
    Left        =   5040
    TabIndex    =   14
    Top         =   600
    Width       =   495
End
Begin TextBox Text9
    Height      =   285
    Left        =   1680
    TabIndex    =   13
    Text        =   " "
    Top         =   3000
    Width       =   375
End
Begin CommandButton Command12
    Caption     =   "-90z"
    Height      =   255
    Left        =   5040
    TabIndex    =   12
    Top         =   840
    Width       =   495
End
Begin TextBox Text8
    Height      =   375
    Left        =   2160
    TabIndex    =   11
    Text        =   " "
    Top         =   2760
```

```
         Width       = 1455
      End
      Begin TextBox Text7
         Height      = 285
         Left        = 6960
         TabIndex    = 10
         Text        = ".5"
         Top         = 3480
         Width       = 495
      End
      Begin TextBox Text6
         Height      = 285
         Left        = 6960
         TabIndex    = 9
         Text        = ".5"
         Top         = 3960
         Width       = 495
      End
      Begin TextBox Text5
         Height      = 285
         Left        = 6960
         TabIndex    = 8
         Text        = ".5"
         Top         = 4440
         Width       = 495
      End
      Begin CommandButton Command8
         Caption     = "X"
         Height      = 255
         Left        = 4560
         TabIndex    = 7
         Top         = 1080
         Width       = 495
      End
      Begin CommandButton Command7
         Caption     = "Y"
         Height      = 255
         Left        = 4080
         TabIndex    = 6
         Top         = 1080
         Width       = 495
      End
      Begin TextBox Text4
         Height      = 285
         Left        = 4560
         TabIndex    = 5
         Text        = "0"
         Top         = 120
         Width       = 495
      End
      Begin TextBox Text3
         Height      = 285
         Left        = 4080
         TabIndex    = 4
```

```
    Text        = "0"
    Top         = 120
    Width       = 495
End
Begin TextBox Text2
    FontBold      = 0  'False
    FontItalic    = 0  'False
    FontName      = "MS Sans Serif"
    FontSize      = 8.25
    FontStrikethru = 0  'False
    FontUnderline  = 0  'False
    Height        = 285
    Left          = 1200
    TabIndex      = 3
    Text          = "5"
    Top           = 3000
    Width         = 375
End
Begin TextBox Text1
    FontBold      = 0  'False
    FontItalic    = 0  'False
    FontName      = "Arial"
    FontSize      = 9
    FontStrikethru = 0  'False
    FontUnderline  = 0  'False
    Height        = 735
    Left          = 2160
    MultiLine     = -1  'True
    ScrollBars    = 2  'Vertical
    TabIndex      = 1
    Text          = " "
    Top           = 3720
    Width         = 3375
End
Begin PictureBox Picture1
    AutoRedraw    = -1  'True
    BackColor     = &H00FFFFFF&
    FontBold      = 0  'False
    FontItalic    = 0  'False
    FontName      = "Small Fonts"
    FontSize      = 6
    FontStrikethru = 0  'False
    FontTransparent = 0  'False
    FontUnderline  = 0  'False
    ForeColor     = &H00000000&
    Height        = 1695
    Left          = 120
    ScaleHeight   = 1665
    ScaleWidth    = 1785
    TabIndex      = 0
    Top           = 120
    Width         = 1815
End
Begin Label Label45
```

```
   BackColor     =  &H00FF0000&
   Caption       =  "#"
   ForeColor     =  &H0000FFFF&
   Height        =  255
   Left          =  5160
   TabIndex      =  170
   Top           =  6600
   Width         =  375
End
Begin Label Label44
   BackColor     =  &H00FF0000&
   Caption       =  "CH4"
   ForeColor     =  &H0000FFFF&
   Height        =  255
   Left          =  720
   TabIndex      =  166
   Top           =  2640
   Width         =  615
End
Begin Label Label43
   BackColor     =  &H00FF0000&
   Caption       =  "TARGET LEVEL"
   FontBold      =  0  'False
   FontItalic    =  0  'False
   FontName      =  "MS Sans Serif"
   FontSize      =  8.25
   FontStrikethru =  0  'False
   FontUnderline =  0  'False
   ForeColor     =  &H00FFFFFF&
   Height        =  255
   Left          =  7560
   TabIndex      =  162
   Top           =  5400
   Width         =  1335
End
Begin Label Label42
   BackColor     =  &H00FF0000&
   Caption       =  "Target Sum"
   FontBold      =  0  'False
   FontItalic    =  0  'False
   FontName      =  "MS Sans Serif"
   FontSize      =  8.25
   FontStrikethru =  0  'False
   FontUnderline =  0  'False
   ForeColor     =  &H00FFFFFF&
   Height        =  255
   Left          =  8280
   TabIndex      =  160
   Top           =  1920
   Width         =  1215
End
Begin Label Label41
   BackColor     =  &H00FF0000&
   Caption       =  "Target Max"
```

37

```
   FontBold      = 0  'False
   FontItalic    = 0  'False
   FontName      = "MS Sans Serif"
   FontSize      = 8.25
   FontStrikethru = 0  'False
   FontUnderline = 0  'False
   ForeColor     = &H00FFFFFF&
   Height        = 255
   Left          = 8280
   TabIndex      = 159
   Top           = 2760
   Width         = 1095
End
Begin Label Label40
   BackColor     = &H00FF0000&
   Caption       = "Max Max"
   FontBold      = 0  'False
   FontItalic    = 0  'False
   FontName      = "MS Sans Serif"
   FontSize      = 8.25
   FontStrikethru = 0  'False
   FontUnderline = 0  'False
   ForeColor     = &H00FFFFFF&
   Height        = 255
   Left          = 6720
   TabIndex      = 156
   Top           = 6600
   Width         = 735
End
Begin Label Label39
   BackColor     = &H00FF0000&
   Caption       = "Max Sum"
   FontBold      = 0  'False
   FontItalic    = 0  'False
   FontName      = "MS Sans Serif"
   FontSize      = 8.25
   FontStrikethru = 0  'False
   FontUnderline = 0  'False
   ForeColor     = &H00FFFFFF&
   Height        = 255
   Left          = 6720
   TabIndex      = 155
   Top           = 6240
   Width         = 735
End
Begin Label Label38
   BackColor     = &H00FF0000&
   Caption       = "Insertion - M"
   FontBold      = 0  'False
   FontItalic    = 0  'False
   FontName      = "MS Sans Serif"
   FontSize      = 8.25
   FontStrikethru = 0  'False
   FontUnderline = 0  'False
```

```
      ForeColor       =   &H00FFFFFF&
      Height          =   255
      Left            =   5640
      TabIndex        =   150
      Top             =   5640
      Width           =   1215
   End
   Begin Label Label37
      BackColor       =   &H00FF0000&
      Caption         =   "Inversion - M"
      FontBold        =   0  'False
      FontItalic      =   0  'False
      FontName        =   "MS Sans Serif"
      FontSize        =   8.25
      FontStrikethru  =   0  'False
      FontUnderline   =   0  'False
      ForeColor       =   &H00FFFFFF&
      Height          =   255
      Left            =   5640
      TabIndex        =   149
      Top             =   5160
      Width           =   1215
   End
   Begin Label Label36
      BackColor       =   &H00FF0000&
      Caption         =   "Duplication - M"
      FontBold        =   0  'False
      FontItalic      =   0  'False
      FontName        =   "MS Sans Serif"
      FontSize        =   8.25
      FontStrikethru  =   0  'False
      FontUnderline   =   0  'False
      ForeColor       =   &H00FFFFFF&
      Height          =   255
      Left            =   5640
      TabIndex        =   148
      Top             =   4680
      Width           =   1215
   End
   Begin Label Label35
      BackColor       =   &H00FF0000&
      Caption         =   "Deletion - M"
      FontBold        =   0  'False
      FontItalic      =   0  'False
      FontName        =   "MS Sans Serif"
      FontSize        =   8.25
      FontStrikethru  =   0  'False
      FontUnderline   =   0  'False
      ForeColor       =   &H00FFFFFF&
      Height          =   255
      Left            =   5640
      TabIndex        =   141
      Top             =   4200
      Width           =   1215
```

39

```
            End
            Begin Label Label34
               BackColor     =   &H00FF0000&
               Caption       =   "Sequence - M"
               FontBold      =   0   'False
               FontItalic    =   0   'False
               FontName      =   "MS Sans Serif"
               FontSize      =   8.25
               FontStrikethru =  0   'False
               FontUnderline =   0   'False
               ForeColor     =   &H00FFFFFF&
               Height        =   255
               Left          =   5640
               TabIndex      =   140
               Top           =   3720
               Width         =   1215
            End
            Begin Label Label26
               BackColor     =   &H00FF0000&
               Caption       =   "Point - M"
               FontBold      =   0   'False
               FontItalic    =   0   'False
               FontName      =   "MS Sans Serif"
               FontSize      =   8.25
               FontStrikethru =  0   'False
               FontUnderline =   0   'False
               ForeColor     =   &H00FFFFFF&
               Height        =   255
               Left          =   5640
               TabIndex      =   139
               Top           =   3240
               Width         =   1215
            End
            Begin Label Label33
               BackColor     =   &H00FF0000&
               Caption       =   "Orientation"
               FontBold      =   0   'False
               FontItalic    =   0   'False
               FontName      =   "MS Sans Serif"
               FontSize      =   8.25
               FontStrikethru =  0   'False
               FontUnderline =   0   'False
               ForeColor     =   &H00FFFFFF&
               Height        =   255
               Left          =   4440
               TabIndex      =   134
               Top           =   2400
               Width         =   855
            End
            Begin Label Label32
               BackColor     =   &H00FF0000&
               Caption       =   "Mutation"
               FontBold      =   0   'False
               FontItalic    =   0   'False
```

```
            FontName      = "MS Sans Serif"
            FontSize      = 8.25
            FontStrikethru = 0  'False
            FontUnderline = 0  'False
            ForeColor     = &H00FFFFFF&
            Height        = 255
            Left          = 2880
            TabIndex      = 133
            Top           = 2400
            Width         = 735
         End
         Begin Label Label31
            BackColor     = &H00FF0000&
            Caption       = "Best Score"
            FontBold      = 0  'False
            FontItalic    = 0  'False
            FontName      = "MS Sans Serif"
            FontSize      = 8.25
            FontStrikethru = 0  'False
            FontUnderline = 0  'False
            ForeColor     = &H00FFFFFF&
            Height        = 255
            Left          = 7560
            TabIndex      = 132
            Top           = 4200
            Width         = 855
         End
         Begin Label Label30
            BackColor     = &H00FF0000&
            Caption       = "Threshold"
            FontBold      = 0  'False
            FontItalic    = 0  'False
            FontName      = "MS Sans Serif"
            FontSize      = 8.25
            FontStrikethru = 0  'False
            FontUnderline = 0  'False
            ForeColor     = &H00FFFFFF&
            Height        = 255
            Left          = 5640
            TabIndex      = 128
            Top           = 2280
            Width         = 1335
         End
         Begin Label Label27
            BackColor     = &H00FF0000&
            Caption       = "Maturation Cycles"
            FontBold      = 0  'False
            FontItalic    = 0  'False
            FontName      = "MS Sans Serif"
            FontSize      = 8.25
            FontStrikethru = 0  'False
            FontUnderline = 0  'False
            ForeColor     = &H00FFFFFF&
            Height        = 255
```

```
      Left            =   5640
      TabIndex        =   127
      Top             =   2760
      Width           =   1335
   End
   Begin Label Label29
      BackColor       =   &H00FF0000&
      Caption         =   "Sample Affinity"
      FontBold        =   0  'False
      FontItalic      =   0  'False
      FontName        =   "MS Sans Serif"
      FontSize        =   8.25
      FontStrikethru  =   0  'False
      FontUnderline   =   0  'False
      ForeColor       =   &H00FFFFFF&
      Height          =   255
      Left            =   8280
      TabIndex        =   120
      Top             =   3120
      Width           =   1215
   End
   Begin Label Label28
      BackColor       =   &H00FF0000&
      Caption         =   "Sum Affinity"
      FontBold        =   0  'False
      FontItalic      =   0  'False
      FontName        =   "MS Sans Serif"
      FontSize        =   8.25
      FontStrikethru  =   0  'False
      FontUnderline   =   0  'False
      ForeColor       =   &H00FFFFFF&
      Height          =   255
      Left            =   8280
      TabIndex        =   121
      Top             =   2280
      Width           =   1215
   End
   Begin Label Label25
      BackColor       =   &H00FF0000&
      Caption         =   "Trans"
      FontBold        =   0  'False
      FontItalic      =   0  'False
      FontName        =   "MS Sans Serif"
      FontSize        =   8.25
      FontStrikethru  =   0  'False
      FontUnderline   =   0  'False
      ForeColor       =   &H00FFFFFF&
      Height          =   255
      Left            =   7560
      TabIndex        =   113
      Top             =   6360
      Width           =   615
   End
   Begin Label Label24
```

42

```
   BackColor       =   &H00FF0000&
   Caption         =   "Test No"
   FontBold        =   0   'False
   FontItalic      =   0   'False
   FontName        =   "MS Sans Serif"
   FontSize        =   8.25
   FontStrikethru  =   0   'False
   FontUnderline   =   0   'False
   ForeColor       =   &H00FFFFFF&
   Height          =   255
   Left            =   7560
   TabIndex        =   112
   Top             =   5880
   Width           =   615
End
Begin Label Label23
   BackColor       =   &H00FF0000&
   Caption         =   "Prox"
   FontBold        =   0   'False
   FontItalic      =   0   'False
   FontName        =   "MS Sans Serif"
   FontSize        =   8.25
   FontStrikethru  =   0   'False
   FontUnderline   =   0   'False
   ForeColor       =   &H00FFFFFF&
   Height          =   255
   Left            =   5160
   TabIndex        =   111
   Top             =   6240
   Width           =   375
End
Begin Label Label22
   BackColor       =   &H00FF0000&
   Caption         =   "Height"
   FontBold        =   0   'False
   FontItalic      =   0   'False
   FontName        =   "MS Sans Serif"
   FontSize        =   8.25
   FontStrikethru  =   0   'False
   FontUnderline   =   0   'False
   ForeColor       =   &H00FFFFFF&
   Height          =   255
   Left            =   3960
   TabIndex        =   110
   Top             =   6600
   Width           =   615
End
Begin Label Label21
   BackColor       =   &H00FF0000&
   Caption         =   "Width"
   FontBold        =   0   'False
   FontItalic      =   0   'False
   FontName        =   "MS Sans Serif"
   FontSize        =   8.25
```

```
         FontStrikethru = 0 'False
         FontUnderline = 0 'False
         ForeColor     = &H00FFFFFF&
         Height    = 255
         Left      = 3960
         TabIndex  = 109
         Top       = 6240
         Width     = 615
      End
      Begin Label Label20
         BackColor     = &H00FF0000&
         Caption       = "Depth"
         FontBold      = 0 'False
         FontItalic    = 0 'False
         FontName      = "MS Sans Serif"
         FontSize      = 8.25
         FontStrikethru = 0 'False
         FontUnderline = 0 'False
         ForeColor     = &H00FFFFFF&
         Height    = 255
         Left      = 2760
         TabIndex  = 108
         Top       = 6600
         Width     = 615
      End
      Begin Label Label19
         BackColor     = &H00FF0000&
         Caption       = "Length"
         FontBold      = 0 'False
         FontItalic    = 0 'False
         FontName      = "MS Sans Serif"
         FontSize      = 8.25
         FontStrikethru = 0 'False
         FontUnderline = 0 'False
         ForeColor     = &H00FFFFFF&
         Height    = 255
         Left      = 2760
         TabIndex  = 107
         Top       = 6240
         Width     = 615
      End
      Begin Label Label18
         BackColor     = &H00FF0000&
         Caption       = "Desat"
         FontBold      = 0 'False
         FontItalic    = 0 'False
         FontName      = "MS Sans Serif"
         FontSize      = 8.25
         FontStrikethru = 0 'False
         FontUnderline = 0 'False
         ForeColor     = &H0000FFFF&
         Height    = 255
         Left      = 720
         TabIndex  = 97
```

```
   Top            = 2280
   Width          = 495
End
Begin Label Label17
   Alignment      = 1  'Right Justify
   BackColor      = &H00FF0000&
   Caption        = "-SH"
   ForeColor      = &H00FFFFFF&
   Height         = 255
   Left           = 720
   TabIndex       = 92
   Top            = 4440
   Width          = 375
End
Begin Label Label16
   Alignment      = 1  'Right Justify
   BackColor      = &H00FF0000&
   Caption        = "-S-"
   ForeColor      = &H00FFFFFF&
   Height         = 255
   Left           = 600
   TabIndex       = 88
   Top            = 6600
   Width          = 495
End
Begin Label Label15
   Alignment      = 1  'Right Justify
   BackColor      = &H00FF0000&
   Caption        = "-N-"
   ForeColor      = &H00FFFFFF&
   Height         = 255
   Left           = 600
   TabIndex       = 82
   Top            = 6120
   Width          = 495
End
Begin Label Label14
   Alignment      = 1  'Right Justify
   BackColor      = &H00FF0000&
   Caption        = "-NO2"
   ForeColor      = &H00FFFFFF&
   Height         = 255
   Left           = 600
   TabIndex       = 79
   Top            = 5160
   Width          = 495
End
Begin Label Label13
   Alignment      = 1  'Right Justify
   BackColor      = &H00FF0000&
   Caption        = "-O-"
   ForeColor      = &H00FFFFFF&
   Height         = 255
   Left           = 600
```

```
         TabIndex    = 75
         Top         = 6360
         Width       = 495
      End
      Begin Label Label12
         Alignment   = 1 'Right Justify
         BackColor   = &H00FF0000&
         Caption     = "=S"
         ForeColor   = &H00FFFFFF&
         Height      = 255
         Left        = 600
         TabIndex    = 72
         Top         = 5640
         Width       = 495
      End
      Begin Label Label11
         Alignment   = 1 'Right Justify
         BackColor   = &H00FF0000&
         Caption     = "-N="
         ForeColor   = &H00FFFFFF&
         Height      = 255
         Left        = 600
         TabIndex    = 68
         Top         = 5880
         Width       = 495
      End
      Begin Label Label10
         Alignment   = 1 'Right Justify
         BackColor   = &H00FF0000&
         Caption     = "=O"
         ForeColor   = &H00FFFFFF&
         Height      = 255
         Left        = 600
         TabIndex    = 62
         Top         = 5400
         Width       = 495
      End
      Begin Label Label9
         Alignment   = 2 'Center
         BackColor   = &H00FF0000&
         Caption     = "Rings"
         FontBold    = 0 'False
         FontItalic  = 0 'False
         FontName    = "MS Sans Serif"
         FontSize    = 8.25
         FontStrikethru = 0 'False
         FontUnderline = 0 'False
         ForeColor   = &H0000FFFF&
         Height      = 255
         Left        = 600
         TabIndex    = 58
         Top         = 1920
         Width       = 615
      End
```

46

```
Begin Label Label8
    Alignment   =  1  'Right Justify
    BackColor   =  &H00FF0000&
    Caption     =  "-C-"
    ForeColor   =  &H00FFFFFF&
    Height      =  255
    Left        =  720
    TabIndex    =  54
    Top         =  3000
    Width       =  375
End
Begin Label Label7
    Alignment   =  1  'Right Justify
    BackColor   =  &H00FF0000&
    Caption     =  "-H"
    ForeColor   =  &H00FFFFFF&
    Height      =  255
    Left        =  720
    TabIndex    =  51
    Top         =  3240
    Width       =  375
End
Begin Label Label6
    Alignment   =  1  'Right Justify
    BackColor   =  &H00FF0000&
    Caption     =  "-CN"
    ForeColor   =  &H00FFFFFF&
    Height      =  255
    Left        =  720
    TabIndex    =  42
    Top         =  4920
    Width       =  375
End
Begin Label Label5
    Alignment   =  1  'Right Justify
    BackColor   =  &H00FF0000&
    Caption     =  "-NH2"
    ForeColor   =  &H00FFFFFF&
    Height      =  255
    Left        =  600
    TabIndex    =  41
    Top         =  4680
    Width       =  495
End
Begin Label Label4
    Alignment   =  1  'Right Justify
    BackColor   =  &H00FF0000&
    Caption     =  "-OH"
    ForeColor   =  &H00FFFFFF&
    Height      =  255
    Left        =  720
    TabIndex    =  40
    Top         =  4200
    Width       =  375
```

```
      End
      Begin Label Label3
         Alignment   =  1  'Right Justify
         BackColor   =  &H00FF0000&
         Caption     =  "-Br"
         ForeColor   =  &H00FFFFFF&
         Height      =  255
         Left        =  720
         TabIndex    =  39
         Top         =  3960
         Width       =  375
      End
      Begin Label Label2
         Alignment   =  1  'Right Justify
         BackColor   =  &H00FF0000&
         Caption     =  "-Cl"
         ForeColor   =  &H00FFFFFF&
         Height      =  255
         Left        =  720
         TabIndex    =  38
         Top         =  3720
         Width       =  375
      End
      Begin Label Label1
         Alignment   =  1  'Right Justify
         BackColor   =  &H00FF0000&
         Caption     =  "-F"
         ForeColor   =  &H00FFFFFF&
         Height      =  255
         Left        =  720
         TabIndex    =  37
         Top         =  3480
         Width       =  375
      End
End
```

48

3. Program Code

*SUB* ami1 ()

'Subroutine for amine construction

```
scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
    subsz(scount, 1) = subsz(scount - 1, 1) - .34
    subsx(scount, 1) = subsx(scount - 1, 1) + .3
    subsy(scount, 1) = subsy(scount - 1, 1) + .51
    subsz(scount + 1, 1) = subsz(scount - 1, 1) - .34
    subsx(scount + 1, 1) = subsx(scount - 1, 1) - .3
    subsy(scount + 1, 1) = subsy(scount - 1, 1) - .51

Case 2
    subsz(scount, 1) = subsz(scount - 1, 1) + .34
    subsx(scount, 1) = subsx(scount - 1, 1) + .3
    subsy(scount, 1) = subsy(scount - 1, 1) + .51
    subsz(scount + 1, 1) = subsz(scount - 1, 1) + .34
    subsx(scount + 1, 1) = subsx(scount - 1, 1) - .3
    subsy(scount + 1, 1) = subsy(scount - 1, 1) - .51

Case 3
    subsz(scount, 1) = subsz(scount - 1, 1) + .34
    subsx(scount, 1) = subsx(scount - 1, 1) + .3
    subsy(scount, 1) = subsy(scount - 1, 1) + .51
    subsz(scount + 1, 1) = subsz(scount - 1, 1) + .34
    subsx(scount + 1, 1) = subsx(scount - 1, 1) - .3
    subsy(scount + 1, 1) = subsy(scount - 1, 1) - .51

Case 4
    subsz(scount, 1) = subsz(scount - 1, 1) - .34
    subsx(scount, 1) = subsx(scount - 1, 1) - .3
    subsy(scount, 1) = subsy(scount - 1, 1) - .51
    subsz(scount + 1, 1) = subsz(scount - 1, 1) - .34
    subsx(scount + 1, 1) = subsx(scount - 1, 1) + .3
    subsy(scount + 1, 1) = subsy(scount - 1, 1) + .51

End Select subsr(scount) = .4206
```

```
subsc(scount) = 12
subsr(scount + 1) = .4206
subsc(scount + 1) = 12 subt(scount) = 4
subt(scount + 1) = 4 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)
picture1.Line (subsx(scount + 1, 1), subsy(scount + 1, 1))-(subsx(scount + 1, 2), subsy(scount + 1, 2)),
QBColor(13)
picture1.Circle (subsx(scount + 1, 1), subsy(scount + 1, 1)), subsr(scount + 1), QBColor(12)

scount = scount + 1

END SUB

SUB am2 ()

'Subroutine for amine construction scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
    subsz(scount, 1) = subsz(scount - 1, 1) - .34
    subsx(scount, 1) = subsx(scount - 1, 1) + .3
    subsy(scount, 1) = subsy(scount - 1, 1) - .51
    subsz(scount + 1, 1) = subsz(scount - 1, 1) - .34
    subsx(scount + 1, 1) = subsx(scount - 1, 1) - .3
    subsy(scount + 1, 1) = subsy(scount - 1, 1) + .51

Case 2
    subsz(scount, 1) = subsz(scount - 1, 1) + .34
    subsx(scount, 1) = subsx(scount - 1, 1) - .3
    subsy(scount, 1) = subsy(scount - 1, 1) + .51
    subsz(scount + 1, 1) = subsz(scount - 1, 1) + .34
    subsx(scount + 1, 1) = subsx(scount - 1, 1) + .3
    subsy(scount + 1, 1) = subsy(scount - 1, 1) - .51

Case 3
    subsz(scount, 1) = subsz(scount - 1, 1) + .34
    subsx(scount, 1) = subsx(scount - 1, 1) + .3
    subsy(scount, 1) = subsy(scount - 1, 1) - .51
    subsz(scount + 1, 1) = subsz(scount - 1, 1) + .34
```

```
        subsx(scount + 1, 1) = subsx(scount - 1, 1) - .3
        subsy(scount + 1, 1) = subsy(scount - 1, 1) + .51

Case 4
        subsz(scount, 1) = subsz(scount - 1, 1) - .34
        subsx(scount, 1) = subsx(scount - 1, 1) - .3
        subsy(scount, 1) = subsy(scount - 1, 1) + .51
        subsz(scount + 1, 1) = subsz(scount - 1, 1) - .34
        subsx(scount + 1, 1) = subsx(scount - 1, 1) + .3
        subsy(scount + 1, 1) = subsy(scount - 1, 1) - .51

End Select subsr(scount) = .4206
subsc(scount) = 12
subsr(scount + 1) = .4206
subsc(scount + 1) = 12 subt(scount) = 4
subt(scount + 1) = 4 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)
picture1.Line (subsx(scount + 1, 1), subsy(scount + 1, 1))-(subsx(scount + 1, 2), subsy(scount + 1, 2)),
QBColor(13)
picture1.Circle (subsx(scount + 1, 1), subsy(scount + 1, 1)), subsr(scount + 1), QBColor(12)

scount = scount + 1

END SUB

SUB ami3 ()

'Subroutine for amine construction scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
        subsz(scount, 1) = subsz(scount - 1, 1) - .34
        subsx(scount, 1) = subsx(scount - 1, 1) + .59
        subsy(scount, 1) = subsy(scount - 1, 1)
```

```
    subsz(scount + 1, 1) = subsz(scount - 1, 1) - .34
    subsx(scount + 1, 1) = subsx(scount - 1, 1) - .59
    subsy(scount + 1, 1) = subsy(scount - 1, 1)

Case 2
    subsz(scount, 1) = subsz(scount - 1, 1) + .34
    subsx(scount, 1) = subsx(scount - 1, 1) - .59
    subsy(scount, 1) = subsy(scount - 1, 1)
    subsz(scount + 1, 1) = subsz(scount - 1, 1) + .34
    subsx(scount + 1, 1) = subsx(scount - 1, 1) + .59
    subsy(scount + 1, 1) = subsy(scount - 1, 1)

Case 3
    subsz(scount, 1) = subsz(scount - 1, 1) + .34
    subsx(scount, 1) = subsx(scount - 1, 1) + .59
    subsy(scount, 1) = subsy(scount - 1, 1)
    subsz(scount + 1, 1) = subsz(scount - 1, 1) + .34
    subsx(scount + 1, 1) = subsx(scount - 1, 1) - .59
    subsy(scount + 1, 1) = subsy(scount - 1, 1)

Case 4
    subsz(scount, 1) = subsz(scount - 1, 1) - .34
    subsx(scount, 1) = subsx(scount - 1, 1) - .59
    subsy(scount, 1) = subsy(scount - 1, 1)
    subsz(scount + 1, 1) = subsz(scount - 1, 1) - .34
    subsx(scount + 1, 1) = subsx(scount - 1, 1) + .59
    subsy(scount + 1, 1) = subsy(scount - 1, 1)

End Select subsr(scount) = .4206
subsc(scount) = 12
subsr(scount + 1) = .4206
subsc(scount + 1) = 12 subt(scount) = 4
subt(scount + 1) = 4 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)
picture1.Line (subsx(scount + 1, 1), subsy(scount + 1, 1))-(subsx(scount + 1, 2), subsy(scount + 1, 2)), QBColor(13)
picture1.Circle (subsx(scount + 1, 1), subsy(scount + 1, 1)), subsr(scount + 1), QBColor(12)

scount = scount + 1

END SUB

SUB ami4 ()
```

52

```
'Subroutine for amine construction scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
    subsz(scount, 1) = subsz(scount - 1, 1) + .34
    subsx(scount, 1) = subsx(scount - 1, 1) + .51
    subsy(scount, 1) = subsy(scount - 1, 1) - .3
    subsz(scount + 1, 1) = subsz(scount - 1, 1) + .34
    subsx(scount + 1, 1) = subsx(scount - 1, 1) - .51
    subsy(scount + 1, 1) = subsy(scount - 1, 1) - .3

Case 2
    subsz(scount, 1) = subsz(scount - 1, 1) - .34
    subsx(scount, 1) = subsx(scount - 1, 1) + .51
    subsy(scount, 1) = subsy(scount - 1, 1) + .3
    subsz(scount + 1, 1) = subsz(scount - 1, 1) - .34
    subsx(scount + 1, 1) = subsx(scount - 1, 1) - .51
    subsy(scount + 1, 1) = subsy(scount - 1, 1) + .3

Case 3
    subsz(scount, 1) = subsz(scount - 1, 1) - .34
    subsx(scount, 1) = subsx(scount - 1, 1) + .51
    subsy(scount, 1) = subsy(scount - 1, 1) - .3
    subsz(scount + 1, 1) = subsz(scount - 1, 1) - .34
    subsx(scount + 1, 1) = subsx(scount - 1, 1) - .51
    subsy(scount + 1, 1) = subsy(scount - 1, 1) - .3

Case 4
    subsz(scount, 1) = subsz(scount - 1, 1) + .34
    subsx(scount, 1) = subsx(scount - 1, 1) - .51
    subsy(scount, 1) = subsy(scount - 1, 1) + .3
    subsz(scount + 1, 1) = subsz(scount - 1, 1) + .34
    subsx(scount + 1, 1) = subsx(scount - 1, 1) + .51
    subsy(scount + 1, 1) = subsy(scount - 1, 1) - .3

End Select subsr(scount) = .4206
subsc(scount) = 12
subsr(scount + 1) = .4206
subsc(scount + 1) = 12
```

```
subt(scount) = 4
subt(scount + 1) = 4 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)
picture1.Line (subsx(scount + 1, 1), subsy(scount + 1, 1))-(subsx(scount + 1, 2), subsy(scount + 1, 2)), QBColor(13)
picture1.Circle (subsx(scount + 1, 1), subsy(scount + 1, 1)), subsr(scount + 1), QBColor(12)

scount = scount + 1

END SUB

SUB assemble1 ()

'LIGAND BACKBONE CONSTRUCTION ROUTINE
'PART 1 of ligand code translation
'builds unsubstituted carbon skeleton and labels atom substituent types codelength = Len(code)

Erase atoms
Erase bond1
Erase bond2
Erase bond3
Erase bond4
Erase atomx
Erase atomy
Erase atomz Erase atomstate
Erase subn
Erase occupy picture1.Cls
picture2.Cls text3.Text = 0
text4.Text = 0 state = 1
xc = 0
yc = 0
zc = 0 xa = 0
ya = 0
za = 0
```

54

```
delx = .75
dely = .433 picture1.Circle (0, 0), .6
picture2.Circle (0, 0), .6 x(0) = 0
y(0) = 0
z(0) = 0 atomx(0, 0, 0) = 0
    atomy(0, 0, 0) = 0
    atomz(0, 0, 0) = 0
    atomstate(0, 0, 0) = 1
    subn(0, 0, 0, 1) = 1
    subn(0, 0, 0, 2) = 1
    subn(0, 0, 0, 3) = 1
    subn(0, 0, 0, 4) = 1
    occupy(0, 0, 0) = 8
For i = 1 To codelength oxc = xc
oyc = yc rule = Mid$(code, i, 1)

snum = Mid$(codeq, i, 1)

substd = Mid$(codet, i, 1)

Select Case substd

Case "a"
    'hydrogen
    kind = 1
    skind = 0
Case "b"
    'flourine
    kind = 2
    skind = 1
Case "c"
    'chlorine
    kind = 3
    skind = 1
Case "d"
    'bromine
    kind = 4
    skind = 1
Case "e"
    'hydroxy
    kind = 5
    skind = 1
Case "f"
    'amine
```

```
            kind = 6
            skind = 1
        Case "g"
            'cyano
            kind = 7
            skind = 1
        Case "h"
            'nitro
            kind = 8
            skind = 1
        Case "k"
            'thiol
            kind = 9
            skind = 1
        Case "i"
            'ketone
            kind = 10
            skind = 1
        Case "j"
            'thione
            kind = 11
            skind = 1
        Case "n"
            'pyrrole
            kind = 12
            skind = 1
        Case "p"
            'pyridine
            kind = 13
            skind = 1
        Case "o"
            'ether/pyran
            kind = 14
            skind = 1
        Case "s"
            'sulfide/thiophene
            kind = 15
            skind = 1
        Case "w"
            'desaturate
            kind = 16
            skind = 1

End Select

Select Case rule

Case 1 bond1(xa, ya, za) = 1
    atoms(xa, ya, za) = bond1(xa, ya, za) + bond2(xa, ya, za) + bond3(xa, ya, za) + bond4(xa, ya, za)
```

```
Select Case state

Case 1 xc = xc - delx
xa = xa - 1 yc = yc + dely
ya = ya zc = zc - .5
za = za state = 2

Case 2 xc = xc + delx
xa = xa + 1 yc = yc - dely
ya = ya zc = zc + .5
za = za state = 1

Case 3 xc = xc - delx
xa = xa - 1 yc = yc + dely
ya = ya zc = zc + .5
za = za state = 4

Case 4 xc = xc + delx
xa = xa + 1 yc = yc - dely
ya = ya zc = zc - .5
za = za
```

```
            state = 3

End Select atomx(xa, ya, za) = xc
        atomy(xa, ya, za) = yc
        atomz(xa, ya, za) = zc
        occupy(xa, ya, za) = 8
        atomstate(xa, ya, za) = state subn(xa, ya, za, snum) = kind
        bond1(xa, ya, za) = 1
        atoms(xa, ya, za) = bond1(xa, ya, za) + bond2(xa, ya, za) + bond3(xa, ya, za) + bond4(xa, ya, za)

Case 2 bond2(xa, ya, za) = 1
        atoms(xa, ya, za) = bond1(xa, ya, za) + bond2(xa, ya, za) + bond3(xa, ya, za) + bond4(xa, ya, za)

Select Case state

Case 1 xc = xc + delx
            xa = xa + 1 yc = yc + dely
            ya = ya zc = zc - .5
            za = za state = 2

Case 2 xc = xc - delx
            xa = xa - 1 yc = yc - dely
            ya = ya zc = zc + .5
            za = za state = 1

Case 3 xc = xc + delx
            xa = xa - 1
```

```
yc = yc + dely
ya = ya zc = zc + .5
za = za state = 4

Case 4 xc = xc - delx
xa = xa - 1 yc = yc - dely
ya = ya zc = zc - .5
za = za state = 3

End Select atomx(xa, ya, za) = xc
atomy(xa, ya, za) = yc
atomz(xa, ya, za) = zc
occupy(xa, ya, za) = 8
atomstate(xa, ya, za) = state
subn(xa, ya, za, snum) = kind
bond2(xa, ya, za) = 1
atoms(xa, ya, za) = bond1(xa, ya, za) + bond2(xa, ya, za) + bond3(xa, ya, za) + bond4(xa, ya, za)

Case 3 bond3(xa, ya, za) = 1
atoms(xa, ya, za) = bond1(xa, ya, za) + bond2(xa, ya, za) + bond3(xa, ya, za) + bond4(xa, ya, za)

Select Case state

Case 1 xc = xc
xa = xa yc = yc - .864
ya = ya - 1 zc = zc - .5
```

```
                                                                    59 za = za state = 2

Case 2 xc = xc
xa = xa yc = yc + .864
ya = ya + 1 zc = zc + .5
za = za state = 1

Case 3 xc = xc
xa = xa yc = yc - .864
ya = ya - 1 zc = zc + .5
za = za state = 4

Case 4 xc = xc
xa = xa yc = yc + .864
ya = ya + 1 zc = zc - .5
za = za state = 3

End Select atomx(xa, ya, za) = xc
atomy(xa, ya, za) = yc
atomz(xa, ya, za) = zc
occupy(xa, ya, za) = 8
``` atomstate(xa, ya, za) = state
subn(xa, ya, za, snum) = kind
bond3(xa, ya, za) = 1
atoms(xa, ya, za) = bond1(xa, ya, za) + bond2(xa, ya, za) + bond3(xa, ya, za) + bond4(xa, ya, za)

Case 4 bond4(xa, ya, za) = 1
atoms(xa, ya, za) = bond1(xa, ya, za) + bond2(xa, ya, za) + bond3(xa, ya, za) + bond4(xa, ya, za)

Select Case state

Case 1

$xc = xc$
$xa = xa$ $yc = yc$
$ya = ya$ $zc = zc + 1$
$za = za + 1$ state = 3

Case 2

$xc = xc$
$xa = xa$ $yc = yc$
$ya = ya$ $zc = zc - 1$
$za = za - 1$ state = 4

Case 3

$xc = xc$
$xa = xa$ $yc = yc$
$ya = ya$ $zc = zc - 1$
$za = za - 1$

61

```
        state = 1

Case 4 xc = xc
        xa = xa yc = yc
        ya = ya zc = zc + 1
        za = za + 1 state = 2

End Select atomx(xa, ya, za) = xc
        atomy(xa, ya, za) = yc
        atomz(xa, ya, za) = zc
        occupy(xa, ya, za) = 8
        atomstate(xa, ya, za) = state
        subn(xa, ya, za, snum) = kind
        bond4(xa, ya, za) = 1
        atoms(xa, ya, za) = bond1(xa, ya, za) + bond2(xa, ya, za) + bond3(xa, ya, za) + bond4(xa, ya, za)

End Select x(i) = xc
    y(i) = yc
    z(i) = zc
    r(i) = .6 xr(i) = xa
    yr(i) = ya
    zr(i) = za picture1.Line (oxc, oyc)-(xc, yc)
    picture1.Circle (xc, yc), .6 picture2.Line (oxc, oyc)-(xc, yc)
    picture2.Circle (xc, yc), .6

Next i

END SUB
```

62

```
FUNCTION at1 (ratio As Double) As Double

'Arctan calculation
'First quadrant at1 = Atn(Abs(ratio))

END FUNCTION

FUNCTION at2 (ratio As Double) As Double

'Arctan calculation
'Second quadrant at2 = pi - Atn(Abs(ratio))
END FUNCTION

FUNCTION at3 (ratio As Double) As Double

'Arctan calculation
'Third quadrant at3 = pi2 - Atn(Abs(ratio))
END FUNCTION

FUNCTION at4 (ratio As Double) As Double

'Arctan calculation
'Fourth quadrant at4 = pi + Atn(Abs(ratio))
END FUNCTION

SUB changer ()

'Subroutine for swapping virtual receptor parameters in
'evolution programs using more than one receptor for
'ligand testing h = ph(codev)

text56.Text = h clength = pclength(codev)
    text48.Text = clength depth = pdepth(codev)
    text49.Text = depth rwidth = prwidth(codev)
    text50.Text = rwidth
```

63

```
rlength = prlength(codev)
   text51.Text = rlength proxsense = pproxsense(codev)
   text52.Text = proxsense testnumber = ptestnumber(codev)
   text53.Text = testnumber
   hscroll19.Value = testnumber popsize = 0
'  text54.Text = popsize transval = ptransval(codev)
   text55.Text = transval
   hscroll22.Value = transval maximals = pmaximals(codev)
   text68.Text = maximals
   sumtarget = maximals
   text71.Text = sumtarget maximalm = pmaximalm(codev)
   text69.Text = maximalm
   maxtarget = maximalm
   text70.Text = maxtarget maxtarget = maximalm * (targetp / 100)
sumtarget = maximals * (targetp / 100)
text70.Text = maxtarget
text71.Text = sumtarget
```

*END SUB*

*SUB* codecreate ()

'Routine for the generation of ligand codes
'Calls ring and methy for insertion of
'cyclohexyl rings and methyl groups codelength = hscroll1.Value ringcount = 0
methcount = 0 text26.Text = "0"

```
code = ""
codet = ""
codeq = ""

ws = 0
j1 = 0
j2 = 0
j3 = 0
j4 = 0
j5 = 0
j6 = 0
j7 = 0
j8 = 0
j9 = 0
j10 = 0
j11 = 0
j12 = 0
j13 = 0
j14 = 0

'calculate probability values from selection panel values tot = v1 + v2 + v3 + v4 + v5 + v6 + v7 + v8 + v9 + v10 t1 = 1 + v1
t2 = v1 + v2
t3 = t2 + 1
t4 = t2 + v3
t5 = t4 + 1
t6 = t4 + v4
t7 = t6 + 1
t8 = t6 + v5
t9 = t8 + 1
t10 = t8 + v6
t11 = t10 + 1
t12 = t10 + v7
t13 = t12 + 1
t14 = t12 + v8
t15 = t14 + 1
t16 = t14 + v9
t17 = t16 + 1
t18 = t16 + v10

'Iterative character creation/selection for primary, secondary
'and tertiary code construction.
'Repeat as specified by codelength.

For i = 1 To codelength

If pring > 1 + Int(Rnd * 100) Then

'Call ring generation subroutine
``` rings

Else

If methyl > 1 + Int(Rnd * 100) Then

'Call methyl group generation subroutine methy

Else

'Generate primary code character s = Trim$(Str$(Int(1 + 4 * Rnd)))

'Check for functional group availability and add hydrogens
'if no functional groups are available for substitution If tc + td = 0 Then
hyd = 1
Else
hyd = (hscroll9.Value / 100)
End If If Rnd <= hyd Then ' This section adds characters to secondary code that instruct
'the molecular assebler to replace carbon atom in skeleton
' with oxygen, nitrogen or sulfur If Rnd > (wg / 100) Then g = "a"
q = Trim$(Str$(Int(1 + 4 * Rnd)))

Else g = "w"
q = Trim$(Str$(Int(1 + 4 * Rnd)))
ws = ws + 1
End If jhyd = jhyd + 1

Else

If (Rnd) < ng / 100 Then
g = "n"
j12 = j12 + 1

Else
If (Rnd) < pg / 100 Then
g = "p"

```
j13 = j13 + 1

Else
If (Rnd) < og / 100 Then
g = "o"
j14 = j14 + 1

Else

If (Rnd) < sg / 100 Then
g = "s"
j15 = j15 + 1

Else

'Assignment of string values for substituents

'start of main secondary code generating loop.
'Characters instruct assembler to add substituents
'to primary skeleton.

'Begins with generation of random number

Rn = 1 + Int(tot * (Rnd(1)))

'generation of code sequence

Select Case Rn

Case 1 To v1 g = "b"

j1 = j1 + 1

Case t1 To t2
    g = "c"
    j2 = j2 + 1

Case t3 To t4
    g = "d"
    j3 = j3 + 1

Case t5 To t6
    g = "e"
    j4 = j4 + 1

Case t7 To t8
    g = "f"
    j5 = j5 + 1

Case t9 To t10
    g = "g"
    j6 = j6 + 1
```

```
        Case t11 To t12
            g = "h"
            j7 = j7 + 1

Case t13 To t14
            g = "i"
            j8 = j8 + 1

Case t15 To t16
            g = "j"
            j9 = j9 + 1

Case t17 To t18
            g = "k"
            j10 = j10 + 1

End Select

End If
End If
End If
End If

'Generation of character for tertiary code vector.

q = Trim$(Str$(Int((Rnd * 4) + 1)))

End If

End If
End If

'Assemble primary, secondary and tertiary code vectors
'by concatenation of new characters with the vectors code = code & s
codet = codet & g
codeq = codeq & q Next i 'Set codelngth variable to length of code generated by
'preceding steps. Note: new codelength may differ from
'old codelength due to the introduction of rings and methyl groups.

codelength = Len(code)

coded = ""

'Display resulting code as string.
```

```
For j = 1 To codelength coded = coded & Mid$(codet, j, 1) & "(" & Mid$(codeq, j, 1) & ")" & Mid$(code, j, 1) & " " & Chr$(126)

Next j text1.Text = coded oldcode = code
oldcodet = codet
oldcodeq = codeq

'calculation of frequency distributions of substituents ltot = j1 + j2 + j3 + j4 + j5 + j6 + j7 + j8 + j9 + j10

If ltot <> 0 Then text23.Text = Int(100 * j1 / ltot)
text22.Text = Int(100 * j2 / ltot)
text21.Text = Int(100 * j3 / ltot)
text20.Text = Int(100 * j4 / ltot)
text19.Text = Int(100 * j5 / ltot)
text18.Text = Int(100 * j6 / ltot)
text36.Text = Int(100 * j7 / ltot)
text28.Text = Int(100 * j8 / ltot)
text32.Text = Int(100 * j9 / ltot)
text43.Text = Int(100 * j10 / ltot)
text30.Text = j12
text39.Text = j13
text34.Text = j14
text41.Text = j15

End If text30.Text = j12
text39.Text = j13
text34.Text = j14
text41.Text = j15 text47.Text = ws
text25.Text = jhyd
```

*END SUB*

*SUB* codemaker ()

```
'Code generation subroutine
'(DIAGNOSTIC)

text29.Text = ""
codecreate
assemble1
``` list substitutes

*END SUB*

*SUB* Command1_Click ()

codenum = 0
text76.Text = codenum

Erase ph
Erase pclength
Erase pdepth
Erase prwidth
Erase prlength
Erase pproxsense
Erase ptestnumber
Erase ppopsize
Erase ptransval
Erase pmaximals
Erase pmaximalm list1.Clear h = ""
text56.Text = ""

clength = 0
    text48.Text = clength depth = 0
    text49.Text = depth rwidth = 0
    text50.Text = rwidth rlength = 0
    text51.Text = rlength proxsense = 0
    text52.Text = proxsense testnumber = 0
    text53.Text = testnumber
    hscroll19.Value = testnumber popsize = 0

```
'   text54.Text = popsize transval = 0
   text55.Text = transval
   hscroll22.Value = transval maximals = 0
   text68.Text = maximals
   sumtarget = maximals
   text71.Text = sumtarget maximalm = 0
   text69.Text = maximalm
   maxtarget = maximalm
   text70.Text = maxtarget

END SUB

SUB Command10_Click ()

'EVOLUTION 1 PROGRAM
'Evolution of ligands against a single virtual receptor picture1.Cls
picture2.Cls picture1.AutoRedraw = False
picture2.AutoRedraw = False 'Initial variable settings maxaffinity = 0
bestscore = 100
mainscore = 100

'Ligand Counter initialised
im = 0

'Generation and testing of random ligands until a ligand
'of sufficient affinity for the virtual receptor is produced Do Until mainscore < threshold im = im + 1
text61.Text = im codemaker
singtest 'testing of new ligand score against best previous score
```

```
If bestscore > mainscore Then
bestscore = mainscore
text62.Text = Int(bestscore * 1000) / 1000

End If

Loop text62.Text = Int(bestscore * 1000) / 1000

'one-way evolution of ligand by mutation and selection
'process continues for preset number (=testno) of cycles For i = 1 To testno text61.Text = i 'mutation
mainmutate 'evaluation
singtest 'comparison of new ligand with best previous best score
'and selection of ligand with best score If bestscore > mainscore Then
bestscore = mainscore
text62.Text = Int(bestscore * 1000) / 1000 oldcode = code
oldcodet = codet
oldcodeq = codeq

End If

Next i text61.Text = "Final"

'display of best ligand generated by procedure code = oldcode
codet = oldcodet
codeq = oldcodeq assemble1
list
substitutes singtest
```

72

```
text62.Text = Int(bestscore * 1000) / 1000 picture1.AutoRedraw = True
picture2.AutoRedraw = True
```

*END SUB*

*SUB* Command12_Click ()

```
' Control for positive rotation around z-axis;
' uses 90 degree increments text10.Text = (text10.Text + 90) Mod 360
For i = 1 To codelength
w = length(x(i), y(i))

Select Case x(i)
   Case 0
      If y(i) > 0 Then
      theta = pi / 2
      Else
      theta = 3 * pi / 2
      End If
   Case Is > 0
      If y(i) >= 0 Then
      theta = at1(y(i) / x(i))
      Else theta = at3(y(i) / x(i))
      End If
   Case Is < 0
      If y(i) >= 0 Then
      theta = at2(y(i) / x(i))
      Else theta = at4(y(i) / x(i))
      End If End Select y(i) = w * Sin(theta + (pi / 2))
x(i) = w * Cos(theta + (pi / 2))

Next i picture1.Cls
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
```

73

```
picture2.Line (x(i + 1), y(i + 1))-(x(i), y(i))

Next i picture1.Circle (x(codelength), y(codelength)), .6
picture2.Circle (x(codelength), y(codelength)), .6

For i = 1 To hnumber
w = length(subsx(i, 1), subsy(i, 1))

Select Case subsx(i, 1)
   Case 0
      If subsy(i, 1) > 0 Then
      theta2 = pi / 2
      Else
      theta2 = 3 * pi / 2
      End If
   Case Is > 0
      If subsy(i, 1) >= 0 Then
      theta2 = at1(subsy(i, 1) / subsx(i, 1))
      Else theta2 = at3(subsy(i, 1) / subsx(i, 1))
      End If
   Case Is < 0
      If subsy(i, 1) >= 0 Then
      theta2 = at2(subsy(i, 1) / subsx(i, 1))
      Else theta2 = at4(subsy(i, 1) / subsx(i, 1))
      End If End Select subsy(i, 1) = w * Sin(theta2 + (pi / 2))
subsx(i, 1) = w * Cos(theta2 + (pi / 2))

Next i

For i = 1 To hnumber
w = length(subsx(i, 2), subsy(i, 2))

Select Case subsx(i, 2)
   Case 0
      If subsy(i, 2) > 0 Then
      theta2 = pi / 2
      Else
      theta2 = 3 * pi / 2
      End If
   Case Is > 0
      If subsy(i, 2) >= 0 Then
      theta2 = at1(subsy(i, 2) / subsx(i, 2))
```

```
            Else theta2 = at3(subsy(i, 2) / subsx(i, 2))
            End If
        Case Is < 0
            If subsy(i, 2) >= 0 Then
            theta2 = at2(subsy(i, 2) / subsx(i, 2))
            Else theta2 = at4(subsy(i, 2) / subsx(i, 2))
            End If End Select subsy(i, 2) = w * Sin(theta2 + (pi / 2))
subsx(i, 2) = w * Cos(theta2 + (pi / 2))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))
Next i picture1.ForeColor = QBColor(0)

END SUB

SUB Command14_Click ()

' Control for negative rotation around z-axis:
' uses 6 degree increments text10.Text = (text10.Text - 6) Mod 360
For i = 1 To codelength
w = length(x(i), y(i))

Select Case x(i)
    Case 0
        If y(i) > 0 Then
        theta = pi / 2
        Else
        theta = 3 * pi / 2
        End If
    Case Is > 0
        If y(i) >= 0 Then
        theta = at1(y(i) / x(i))
        Else theta = at3(y(i) / x(i))
        End If
```

```
      Case Is < 0
        If y(i) >= 0 Then
        theta = at2(y(i) / x(i))
        Else theta = at4(y(i) / x(i))
        End If End Select y(i) = w * Sin(theta - (pi / 30))
x(i) = w * Cos(theta - (pi / 30))

Next i picture1.Cls
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
picture2.Line (x(i + 1), y(i + 1))-(x(i),    )

Next i picture1.Circle (x(codelength), y(codelength)), .6
picture2.Circle (x(codelength), y(codelength)), .6

For i = 1 To hnumber
w = length(subsx(i, 1), subsy(i, 1))

Select Case subsx(i, 1)
   Case 0
     If subsy(i, 1) > 0 Then
     theta2 = pi / 2
     Else
     theta2 = 3 * pi / 2
     End If
   Case Is > 0
     If subsy(i, 1) >= 0 Then
     theta2 = at1(subsy(i, 1) / subsx(i, 1))
     Else theta2 = at3(subsy(i, 1) / subsx(i, 1))
     End If
   Case Is < 0
     If subsy(i, 1) >= 0 Then
     theta2 = at2(subsy(i, 1) / subsx(i, 1))
     Else theta2 = at4(subsy(i, 1) / subsx(i, 1))
     End If
```

End Select

```
subsy(i, 1) = w * Sin(theta2 - (pi / 30))
subsx(i, 1) = w * Cos(theta2 - (pi / 30))

Next i

For i = 1 To hnumber
w = length(subsx(i, 2), subsy(i, 2))

Select Case subsx(i, 2)
   Case 0
      If subsy(i, 2) > 0 Then
      theta2 = pi / 2
      Else
      theta2 = 3 * pi / 2
      End If
   Case Is > 0
      If subsy(i, 2) >= 0 Then
      theta2 = at1(subsy(i, 2) / subsx(i, 2))
      Else theta2 = at3(subsy(i, 2) / subsx(i, 2))
      End If
   Case Is < 0
      If subsy(i, 2) >= 0 Then
      theta2 = at2(subsy(i, 2) / subsx(i, 2))
      Else theta2 = at4(subsy(i, 2) / subsx(i, 2))
      End If End Select subsy(i, 2) = w * Sin(theta2 - (pi / 30))
subsx(i, 2) = w * Cos(theta2 - (pi / 30))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))
Next i picture1.ForeColor = QBColor(0)
```

*END SUB*

*SUB* Command16_Click ()

' Control for positive rotation around z-axis;
' continuous movement through 360 degrees picture1.Cls
picture1.AutoRedraw = False For j = 1 To 60 text10.Text = (text10.Text + 6) Mod 360
For i = 1 To codelength
w = length(x(i), y(i))

Select Case x(i)
   Case 0
      If y(i) > 0 Then
      theta = pi / 2
      Else
      theta = 3 * pi / 2
      End If
   Case Is > 0
      If y(i) >= 0 Then
      theta = at1(y(i) / x(i))
      Else theta = at3(y(i) / x(i))
      End If
   Case Is < 0
      If y(i) >= 0 Then
      theta = at2(y(i) / x(i))
      Else theta = at4(y(i) / x(i))
      End If End Select y(i) = w * Sin(theta + (pi / 30))
x(i) = w * Cos(theta + (pi / 30))

Next i picture1.Cls

For i = 0 To codelength - 1 picture1.Circle (x(i), y(i)), .6
picture1.Line (x(i + 1), y(i + 1))-(x(i), y(i))

```
Next i picture1.Circle (x(codelength), y(codelength)), .6

For i = 1 To hnumber
w = length(subsx(i, 1), subsy(i, 1))

Select Case subsx(i, 1)
   Case 0
      If subsy(i, 1) > 0 Then
      theta2 = pi / 2
      Else
      theta2 = 3 * pi / 2
      End If
   Case Is > 0
      If subsy(i, 1) >= 0 Then
      theta2 = at1(subsy(i, 1) / subsx(i, 1))
      Else theta2 = at3(subsy(i, 1) / subsx(i, 1))
      End If
   Case Is < 0
      If subsy(i, 1) >= 0 Then
      theta2 = at2(subsy(i, 1) / subsx(i, 1))
      Else theta2 = at4(subsy(i, 1) / subsx(i, 1))
      End If End Select subsy(i, 1) = w * Sin(theta2 + (pi / 30))
subsx(i, 1) = w * Cos(theta2 + (pi / 30))

Next i

For i = 1 To hnumber
w = length(subsx(i, 2), subsy(i, 2))

Select Case subsx(i, 2)
   Case 0
      If subsy(i, 2) > 0 Then
      theta2 = pi / 2
      Else
      theta2 = 3 * pi / 2
      End If
   Case Is > 0
      If subsy(i, 2) >= 0 Then
      theta2 = at1(subsy(i, 2) / subsx(i, 2))
      Else theta2 = at3(subsy(i, 2) / subsx(i, 2))
      End If
   Case Is < 0
```

```
            If subsy(i, 2) >= 0 Then
            theta2 = at2(subsy(i, 2) / subsx(i, 2))
            Else theta2 = at4(subsy(i, 2) / subsx(i, 2))
            End If End Select subsy(i, 2) = w * Sin(theta2 + (pi / 30))
    subsx(i, 2) = w * Cos(theta2 + (pi / 30))

Next i picture1.ForeColor = QBColor(9)

For i = 1 To hnumber picture1.Circle (subsx(i, 1), subsy(i, 1)), subsr(i), QBColor(subsc(i))
    picture1.Line (subsx(i, 1), subsy(i, 1))-(subsx(i, 2), subsy(i, 2))
    Next i picture1.ForeColor = QBColor(0)

Next j picture1.AutoRedraw = True
END SUB

SUB Command17_Click ()

' Control for positive rotation around y-axis:
' uses 6 degree increments text3.Text = (text3.Text + 6) Mod 360
For i = 1 To codelength
w = length(x(i), z(i))

Select Case x(i)
    Case 0
        If z(i) > 0 Then
        theta = pi / 2
        Else
        theta = 3 * pi / 2
        End If
    Case Is > 0
        If z(i) >= 0 Then
        theta = at1(z(i) / x(i))
        Else theta = at3(z(i) / x(i))
        End If
```

```
    Case Is < 0
      If z(i) >= 0 Then
      theta = at2(z(i) / x(i))
      Else theta = at4(z(i) / x(i))
      End If End Select z(i) = w * Sin(theta + (pi / 30))
x(i) = w * Cos(theta + (pi / 30))

Next i picture1.Cls
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
picture2.Line (x(i + 1), y(i + 1))-(x(i), y(i))

Next i picture1.Circle (x(codelength), y(codelength)), .6
picture2.Circle (x(codelength), y(codelength)), .6

For i = 1 To hnumber
w = length(subsx(i, 1), subsz(i, 1))

Select Case subsx(i, 1)
   Case 0
      If subsz(i, 1) > 0 Then
      theta2 = pi / 2
      Else
      theta2 = 3 * pi / 2
      End If
   Case Is > 0
      If subsz(i, 1) >= 0 Then
      theta2 = at1(subsz(i, 1) / subsx(i, 1))
      Else theta2 = at3(subsz(i, 1) / subsx(i, 1))
      End If
   Case Is < 0
      If subsz(i, 1) >= 0 Then
      theta2 = at2(subsz(i, 1) / subsx(i, 1))
      Else theta2 = at4(subsz(i, 1) / subsx(i, 1))
      End If
```

81

End Select subsz(i, 1) = w * Sin(theta2 + (pi / 30))
subsx(i, 1) = w * Cos(theta2 + (pi / 30))

Next i

For i = 1 To hnumber
w = length(subsx(i, 2), subsz(i, 2))

Select Case subsx(i, 2)
　　Case 0
　　　　If subsz(i, 2) > 0 Then
　　　　theta2 = pi / 2
　　　　Else
　　　　theta2 = 3 * pi / 2
　　　　End If
　　Case Is > 0
　　　　If subsz(i, 2) >= 0 Then
　　　　theta2 = at1(subsz(i, 2) / subsx(i, 2))
　　　　Else theta2 = at3(subsz(i, 2) / subsx(i, 2))
　　　　End If
　　Case Is < 0
　　　　If subsz(i, 2) >= 0 Then
　　　　theta2 = at2(subsz(i, 2) / subsx(i, 2))
　　　　Else theta2 = at4(subsz(i, 2) / subsx(i, 2))
　　　　End If End Select subsz(i, 2) = w * Sin(theta2 + (pi / 30))
subsx(i, 2) = w * Cos(theta2 + (pi / 30))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))
Next i picture1.ForeColor = QBColor(0)

*END SUB*

*SUB* Command18_Click ()

' Control for negative rotation around y-axis;
' uses 6 degree increments

```
text3.Text = (text3.Text - 6) Mod 360
For i = 1 To codelength
w = length(x(i), z(i))

Select Case x(i)
   Case 0
      If z(i) > 0 Then
      theta = pi / 2
      Else
      theta = 3 * pi / 2
      End If
   Case Is > 0
      If z(i) >= 0 Then
      theta = at1(z(i) / x(i))
      Else theta = at3(z(i) / x(i))
      End If
   Case Is < 0
      If z(i) >= 0 Then
      theta = at2(z(i) / x(i))
      Else theta = at4(z(i) / x(i))
      End If End Select z(i) = w * Sin(theta - (pi / 30))
x(i) = w * Cos(theta - (pi / 30))

Next i picture1.Cls
picture2.Cls
For i = 0 To codelength - 1 picture1.Circle (x(i), y(i)), .6, QBColor(skelcol(i))
picture1.Line (x(i + 1), y(i + 1))-(x(i), y(i))
picture2.Circle (x(i), y(i)), .6, QBColor(skelcol(i))
picture2.Line (x(i + 1), y(i + 1))-(x(i), y(i))

Next i picture1.Circle (x(codelength), y(codelength)), .6
picture2.Circle (x(codelength), y(codelength)), .6
```

82

83

```
For i = 1 To hnumber
w = length(subsx(i, 1), subsz(i, 1))

Select Case subsx(i, 1)
   Case 0
      If subsz(i, 1) > 0 Then
      theta2 = pi / 2
      Else
      theta2 = 3 * pi / 2
      End If
   Case Is > 0
      If subsz(i, 1) >= 0 Then
      theta2 = at1(subsz(i, 1) / subsx(i, 1))
      Else theta2 = at3(subsz(i, 1) / subsx(i, 1))
      End If
   Case Is < 0
      If subsz(i, 1) >= 0 Then
      theta2 = at2(subsz(i, 1) / subsx(i, 1))
      Else theta2 = at4(subsz(i, 1) / subsx(i, 1))
      End If End Select subsz(i, 1) = w * Sin(theta2 - (pi / 30))
subsx(i, 1) = w * Cos(theta2 - (pi / 30))

Next i

For i = 1 To hnumber
w = length(subsx(i, 2), subsz(i, 2))

Select Case subsx(i, 2)
   Case 0
      If subsz(i, 2) > 0 Then
      theta2 = pi / 2
      Else
      theta2 = 3 * pi / 2
      End If
   Case Is > 0
      If subsz(i, 2) >= 0 Then
      theta2 = at1(subsz(i, 2) / subsx(i, 2))
      Else theta2 = at3(subsz(i, 2) / subsx(i, 2))
      End If
   Case Is < 0
      If subsz(i, 2) >= 0 Then
      theta2 = at2(subsz(i, 2) / subsx(i, 2))
      Else theta2 = at4(subsz(i, 2) / subsx(i, 2))
```

84

End If

End Select subsz(i, 2) = w * Sin(theta2 - (pi / 30))
subsx(i, 2) = w * Cos(theta2 - (pi / 30))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 2), subsy(i, 2))-(subsx(i, 1), subsy(i, 1))

Next i picture1.ForeColor = QBColor(0)

*END SUB*

*SUB* Command19_Click ()

' Control for positive rotation around x-axis:
' uses 6 degree increments text4.Text = (text4.Text + 6) Mod 360
For i = 1 To codelength
w = length(y(i), z(i))

Select Case y(i)
    Case 0
        If z(i) > 0 Then
        theta = pi / 2
        Else
        theta = 3 * pi / 2
        End If
    Case Is > 0
        If z(i) >= 0 Then
        theta = at1(z(i) / y(i))
        Else theta = at3(z(i) / y(i))
        End If
    Case Is < 0
        If z(i) >= 0 Then
        theta = at2(z(i) / y(i))
        Else theta = at4(z(i) / y(i))

```
      End If

End Select z(i) = w * Sin(theta + (pi / 30))
   y(i) = w * Cos(theta + (pi / 30))

Next i picture1.Cls
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
picture2.Line (x(i + 1), y(i + 1))-(x(i), y(i))

Next i picture1.Circle (x(codelength), y(codelength)), .6
picture2.Circle (x(codelength), y(codelength)), .6

For i = 1 To hnumber
w = length(subsy(i, 1), subsz(i, 1))

Select Case subsy(i, 1)
   Case 0
      If subsz(i, 1) > 0 Then
      theta2 = pi / 2
      Else
      theta2 = 3 * pi / 2
      End If
   Case Is > 0
      If subsz(i, 1) >= 0 Then
      theta2 = at1(subsz(i, 1) / subsy(i, 1))
      Else theta2 = at3(subsz(i, 1) / subsy(i, 1))
      End If
   Case Is < 0
      If subsz(i, 1) >= 0 Then
      theta2 = at2(subsz(i, 1) / subsy(i, 1))
      Else theta2 = at4(subsz(i, 1) / subsy(i, 1))
      End If End Select subsz(i, 1) = w * Sin(theta2 - (pi / 30))
```

86

```
subsy(i, 1) = w * Cos(theta2 + (pi / 30))

Next i

For i = 1 To hnumber
w = length(subsy(i, 2), subsz(i, 2))

Select Case subsy(i, 2)
   Case 0
      If subsz(i, 2) > 0 Then
      theta2 = pi / 2
      Else
      theta2 = 3 * pi / 2
      End If
   Case Is > 0
      If subsz(i, 2) >= 0 Then
      theta2 = at1(subsz(i, 2) / subsy(i, 2))
      Else theta2 = at3(subsz(i, 2) / subsy(i, 2))
      End If
   Case Is < 0
      If subsz(i, 2) >= 0 Then
      theta2 = at2(subsz(i, 2) / subsy(i, 2))
      Else theta2 = at4(subsz(i, 2) / subsy(i, 2))
      End If End Select subsz(i, 2) = w * Sin(theta2 + (pi / 30))
subsy(i, 2) = w * Cos(theta2 + (pi / 30))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))

Next i picture1.ForeColor = QBColor(0)

END SUB
```

87

```
SUB Command2_Click ()
'ROUTINE FOR READING VIRTUAL RECEPTOR CODES FROM FILE

'Setting for default extension cmdialog1.DefaultExt = ".cod"

cmdialog1.Filter = "code (*.cod)|*.cod"

'activate file common dialog box cmdialog1.Action = 1

'store filename in codefilename codefilename = cmdialog1.Filetitle

Open codefilename For Input As 1

'set codenum to count number of virtual receptors entered codenum = codenum + 1 text76.Text = codenum list1.AddItem codefilename

Input #1, h
   ph(codenum) = h
' h=code string for virtual receptor

Input #1, clength
   text48.Text = clength
   pclength(codenum) = clength
' clength=number of chartacters in virtual receptor code string Input #1, depth
   text49.Text = depth
   pdepth(codenum) = depth
' depth=depth setting for the virtual receptor Input #1, rwidth
   text50.Text = rwidth
   prwidth(codenum) = rwidth
' width=width setting for the virtual receptor Input #1, rlength
   text51.Text = rlength
   prlength(codenum) = rlength
' length=length setting for virtual receptor
' length, width and depth are used to set the starting points for the
' virtual receptor polymers and are used by the fragorig routine
```

```
Input #1, proxsense
   text52.Text = proxsense
   pproxsense(codenum) = proxsense
' proxsense=the proximity threshold used in the affinity calculation Input #1, testnumber
   text53.Text = testnumber
   hscroll19.Value = testnumber
   ptestnumber(codenum) = testnumber
' testnumber= the number of ligand orientations tested for each ligand Input #1, popsize
   ppopsize(codenum) = popsize
'  (not used by EVOLVE)

Input #1, transval
   text55.Text = transval
   hscroll22.Value = transval
   ptransval(codenum) = transval
' transval=the distance the ligand is shifted laterally during testing Input #1, maximals
   text68.Text = maximals
   sumtarget = maximals
   text71.Text = sumtarget
   pmaximals(codenum) = maximals
' maximals=the maximum sum affinity value obtained for the current virtual receptor Input #1, maximalm
   text69.Text = maximalm
   maxtarget = maximalm
   text70.Text = maxtarget
   pmaximalm(codenum) = maximalm
' maximalm=the maximum max affinity value obtained for the current virtual receptor 'close file Close 1

'display code fragorig decodes alen = Len(h) / 15 hg = ""
For l = 0 To 14
For k = 1 To alen
hg = hg & Mid$(h, (l * alen) + k, 1)
Next k
hg = hg + " "
Next l
``` text56.Text = hg

Beep

*END SUB*

*SUB* Command20_Click ()

' Control for negative rotation around x-axis;
' uses 6 degree increments text4.Text = (text4.Text - 6) Mod 360
For i = 1 To codelength
w = length(y(i), z(i))

Select Case y(i)
   Case 0
     If z(i) > 0 Then
     theta = pi / 2
     Else
     theta = 3 * pi / 2
     End If
   Case Is > 0
     If z(i) >= 0 Then
     theta = at1(z(i) / y(i))
     Else theta = at3(z(i) / y(i))
     End If
   Case Is < 0
     If z(i) >= 0 Then
     theta = at2(z(i) / y(i))
     Else theta = at4(z(i) / y(i))
     End If End Select z(i) = w * Sin(theta - (pi / 30))
y(i) = w * Cos(theta - (pi / 30))

Next i picture1.Cls
picture2.Cls

For i = 0 To codelength - 1 picture1.Circle (x(i), y(i)), .6

90

```
picture1.Line (x(i + 1), y(i + 1))-(x(i), y(i))
picture2.Circle (x(i), y(i)), .6
picture2.Line (x(i + 1), y(i + 1))-(x(i), y(i))

Next i picture1.Circle (x(codelength), y(codelength)), 6
picture2.Circle (x(codelength), y(codelength)), 6

For i = 1 To hnumber
w = length(subsy(i, 1), subsz(i, 1))

Select Case subsy(i, 1)
   Case 0
      If subsz(i, 1) > 0 Then
      theta2 = pi / 2
      Else
      theta2 = 3 * pi / 2
      End If
   Case Is > 0
      If subsz(i, 1) >= 0 Then
      theta2 = at1(subsz(i, 1) / subsy(i, 1))
      Else theta2 = at3(subsz(i, 1) / subsy(i, 1))
      End If
   Case Is < 0
      If subsz(i, 1) >= 0 Then
      theta2 = at2(subsz(i, 1) / subsy(i, 1))
      Else theta2 = at4(subsz(i, 1) / subsy(i, 1))
      End If End Select subsz(i, 1) = w * Sin(theta2 - (pi / 30))
subsy(i, 1) = w * Cos(theta2 - (pi / 30))

Next i

For i = 1 To hnumber
w = length(subsy(i, 2), subsz(i, 2))

Select Case subsy(i, 2)
   Case 0
      If subsz(i, 2) > 0 Then
      theta2 = pi / 2
      Else
      theta2 = 3 * pi / 2
      End If
   Case Is > 0
```

```
        If subsz(i, 2) >= 0 Then
        theta2 = at1(subsz(i, 2) / subsy(i, 2))
        Else theta2 = at3(subsz(i, 2) / subsy(i, 2))
        End If
     Case Is < 0
        If subsz(i, 2) >= 0 Then
        theta2 = at2(subsz(i, 2) / subsy(i, 2))
        Else theta2 = at4(subsz(i, 2) / subsy(i, 2))
        End If End Select subsz(i, 2) = w * Sin(theta2 - (pi / 30))
subsy(i, 2) = w * Cos(theta2 - (pi / 30))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 2), subsy(i, 2))-(subsx(i, 1), subsy(i, 1))

Next i picture1.ForeColor = QBColor(0)
```

END SUB

*SUB* Command21_Click ()

' Control for positive rotation around y-axis:
' uses 90 degree increments

```
text3.Text = (text3.Text + 90) Mod 360
For i = 1 To codelength
w = length(x(i), z(i))

Select Case x(i)
    Case 0
       If z(i) > 0 Then
       theta = pi / 2
       Else
       theta = 3 * pi / 2
       End If
    Case Is > 0
       If z(i) >= 0 Then
       theta = at1(z(i) / x(i))
```

```
        Else theta = at3(z(i) / x(i))
        End If
      Case Is < 0
        If z(i) >= 0 Then
        theta = at2(z(i) / x(i))
        Else theta = at4(z(i) / x(i))
        End If End Select z(i) = w * Sin(theta + (pi / 2))
x(i) = w * Cos(theta + (pi / 2))

Next i picture1.Cls
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
picture2.Line (x(i + 1), y(i + 1))-(x(i), y(i))

Next i picture1.Circle (x(codelength), y(codelength)), .6
picture2.Circle (x(codelength), y(codelength)), .6

For i = 1 To hnumber
w = length(subsx(i, 1), subsz(i, 1))

Select Case subsx(i, 1)
   Case 0
      If subsz(i, 1) > 0 Then
      theta2 = pi / 2
      Else
      theta2 = 3 * pi / 2
      End If
   Case Is > 0
      If subsz(i, 1) >= 0 Then
      theta2 = at1(subsz(i, 1) / subsx(i, 1))
      Else theta2 = at3(subsz(i, 1) / subsx(i, 1))
      End If
   Case Is < 0
      If subsz(i, 1) >= 0 Then
      theta2 = at2(subsz(i, 1) / subsx(i, 1))
      Else theta2 = at4(subsz(i, 1) / subsx(i, 1))
```

```
            End If

End Select subsz(i, 1) = w * Sin(theta2 + (pi / 2))
    subsx(i, 1) = w * Cos(theta2 + (pi / 2))

Next i

For i = 1 To hnumber
w = length(subsx(i, 2), subsz(i, 2))

Select Case subsx(i, 2)
    Case 0
        If subsz(i, 2) > 0 Then
        theta3 = pi / 2
        Else
        theta3 = 3 * pi / 2
        End If
    Case Is > 0
        If subsz(i, 2) >= 0 Then
        theta3 = at1(subsz(i, 2) / subsx(i, 2))
        Else theta3 = at3(subsz(i, 2) / subsx(i, 2))
        End If
    Case Is < 0
        If subsz(i, 2) >= 0 Then
        theta3 = at2(subsz(i, 2) / subsx(i, 2))
        Else theta3 = at4(subsz(i, 2) / subsx(i, 2))
        End If End Select subsz(i, 2) = w * Sin(theta3 + (pi / 2))
subsx(i, 2) = w * Cos(theta3 + (pi / 2))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 2), subsy(i, 2))-(subsx(i, 1), subsy(i, 1))
Next i
```

94

```
picture1.ForeColor = QBColor(0)

END SUB

SUB Command22_Click ()

' Control for positive rotation around x-axis;
' uses 90 degree increments text4.Text = (text4.Text + 90) Mod 360
For i = 1 To codelength
w = length(y(i), z(i))

Select Case y(i)
   Case 0
      If z(i) > 0 Then
      theta = pi / 2
      Else
      theta = 3 * pi / 2
      End If
   Case Is > 0
      If z(i) >= 0 Then
      theta = at1(z(i) / y(i))
      Else theta = at3(z(i) / y(i))
      End If
   Case Is < 0
      If z(i) >= 0 Then
      theta = at2(z(i) / y(i))
      Else theta = at4(z(i) / y(i))
      End If End Select z(i) = w * Sin(theta + (pi / 2))
y(i) = w * Cos(theta + (pi / 2))

Next i picture1.Cls
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
picture2.Line (x(i + 1), y(i + 1))-(x(i), y(i))
```

95

```
Next i picture1.Circle (x(codelength), y(codelength)), .6
picture2.Circle (x(codelength), y(codelength)), .6

For i = 1 To hnumber
w = length(subsy(i, 1), subsz(i, 1))

Select Case subsy(i, 1)
   Case 0
      If subsz(i, 1) > 0 Then
      theta2 = pi / 2
      Else
      theta2 = 3 * pi / 2
      End If
   Case Is > 0
      If subsz(i, 1) >= 0 Then
      theta2 = at1(subsz(i, 1) / subsy(i, 1))
      Else theta2 = at3(subsz(i, 1) / subsy(i, 1))
      End If
   Case Is < 0
      If subsz(i, 1) >= 0 Then
      theta2 = at2(subsz(i, 1) / subsy(i, 1))
      Else theta2 = at4(subsz(i, 1) / subsy(i, 1))
      End If End Select subsz(i, 1) = w * Sin(theta2 + (pi / 2))
subsy(i, 1) = w * Cos(theta2 + (pi / 2))

Next i

For i = 1 To hnumber
w = length(subsy(i, 2), subsz(i, 2))

Select Case subsy(i, 2)
   Case 0
      If subsz(i, 2) > 0 Then
      theta2 = pi / 2
      Else
      theta2 = 3 * pi / 2
      End If
   Case Is > 0
      If subsz(i, 2) >= 0 Then
      theta2 = at1(subsz(i, 2) / subsy(i, 2))
      Else theta2 = at3(subsz(i, 2) / subsy(i, 2))
      End If
```

```
    Case Is < 0
       If subsz(i, 2) >= 0 Then
         theta2 = at2(subsz(i, 2) / subsy(i, 2))
         Else theta2 = at4(subsz(i, 2) / subsy(i, 2))
       End If End Select subsz(i, 2) = w * Sin(theta2 + (pi / 2))
subsy(i, 2) = w * Cos(theta2 + (pi / 2))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))

Next i picture1.ForeColor = QBColor(0)

END SUB

SUB Command23_Click ()

' Control for positive rotation around z-axis:
' uses 6 degree increments text10.Text = (text10.Text + 6) Mod 360
For i = 1 To codelength
w = length(x(i), y(i))

Select Case x(i)
   Case 0
      If y(i) > 0 Then
      theta = pi / 2
      Else
      theta = 3 * pi / 2
      End If
   Case Is > 0
      If y(i) >= 0 Then
      theta = at1(y(i) / x(i))
      Else theta = at3(y(i) / x(i))
      End If
```

```
    Case Is < 0
       If y(i) >= 0 Then
          theta = at2(y(i) / x(i))
          Else theta = at4(y(i) / x(i))
       End If End Select y(i) = w * Sin(theta + (pi / 30))
x(i) = w * Cos(theta + (pi / 30))

Next i picture1.Cls
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
picture2.Line (x(i + 1), y(i + 1))-(x(i), y(i))

Next i picture1.Circle (x(codelength), y(codelength)), .6
picture2.Circle (x(codelength), y(codelength)), .6

For i = 1 To hnumber
w = length(subsx(i, 1), subsy(i, 1))

Select Case subsx(i, 1)
   Case 0
      If subsy(i, 1) > 0 Then
      theta2 = pi / 2
      Else
      theta2 = 3 * pi / 2
      End If
   Case Is > 0
      If subsy(i, 1) >= 0 Then
      theta2 = at1(subsy(i, 1) / subsx(i, 1))
      Else theta2 = at3(subsy(i, 1) / subsx(i, 1))
      End If
   Case Is < 0
      If subsy(i, 1) >= 0 Then
      theta2 = at2(subsy(i, 1) / subsx(i, 1))
      Else theta2 = at4(subsy(i, 1) / subsx(i, 1))
      End If
```

98

End Select subsy(i, 1) = w * Sin(theta2 + (pi / 30))
subsx(i, 1) = w * Cos(theta2 + (pi / 30))

Next i

For i = 1 To hnumber
w = length(subsx(i, 2), subsy(i, 2))

Select Case subsx(i, 2)
   Case 0
      If subsy(i, 2) > 0 Then
      theta2 = pi / 2
      Else
      theta2 = 3 * pi / 2
      End If
   Case Is > 0
      If subsy(i, 2) >= 0 Then
      theta2 = at1(subsy(i, 2) / subsx(i, 2))
      Else theta2 = at3(subsy(i, 2) / subsx(i, 2))
      End If
   Case Is < 0
      If subsy(i, 2) >= 0 Then
      theta2 = at2(subsy(i, 2) / subsx(i, 2))
      Else theta2 = at4(subsy(i, 2) / subsx(i, 2))
      End If End Select subsy(i, 2) = w * Sin(theta2 + (pi / 30))
subsx(i, 2) = w * Cos(theta2 + (pi / 30))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))
Next i picture1.ForeColor = QBColor(0)

*END SUB*

*SUB* Command3_Click ()

'EVOLUTION 2 PROGRAM
'Evolution of ligands against multiple virtual receptors
'Fixed number of selection and mutation cycles picture1.Cls
picture2.Cls 'Initial variable settings picture1.AutoRedraw = False
picture2.AutoRedraw = False
maxaffinity = 0
bestscore = 100
mainscore = 100

'Ligand Counter initialised
im = 0

'Generation and testing of random ligands until a ligand
'of sufficient affinity for the virtual receptor is produced Do Until mainscore < threshold im = im + 1
text61.Text = im codemaker
manytest 'testing of new ligand score against best previous score If bestscore > mainscore Then
bestscore = mainscore
text62.Text = Int(bestscore * 1000) / 1000

End If

Loop text62.Text = Int(bestscore * 1000) / 1000

'one-way evolution of ligand by mutation and selection
'process continues for preset number (=testno) of cycles For i = 1 To testno text61.Text = i 'mutation
mainmutate

```
'evaluation
manytest

'comparison of new ligand with best previous best score
'and selection of ligand with best score If bestscore > mainscore Then
bestscore = mainscore
text62.Text = Int(bestscore * 1000) / 1000 oldcode = code
oldcodet = codet
oldcodeq = codeq

End If

Next i text61.Text = "Final"

'display of best ligand generated by procedure code = oldcode
codet = oldcodet
codeq = oldcodeq assemble1
list
substitutes manytest text62.Text = Int(bestscore * 1000) / 1000 picture1.AutoRedraw = True
picture2.AutoRedraw = True

END SUB

SUB Command4_Click ()

'EVOLUTION 3 PROGRAM
'Evolution of ligands against multiple virtual receptors
'Two-step model:
'Step 1. Ligand is evolved for high affinity for one member of
'virtual receptor population
'Step 2. Partially optimized ligand is optimized using all other
'virtual receptors in population 'STEP 1
'Partial optimization of ligand using
```

```
'first virtual receptor in test panel picture1.Cls
picture2.Cls picture1.AutoRedraw = False
picture2.AutoRedraw = False
maxaffinity = 0
bestscore = 100
mainscore = 100

'Ligand Counter initialised
im = 0

'Generation and testing of random ligands until a ligand
'of sufficient affinity for the virtual receptor is produced Do Until mainscore < threshold im = im + 1
text61.Text = im codemaker
singtest 'testing of new ligand score against best previous score If bestscore > mainscore Then
bestscore = mainscore
text62.Text = Int(bestscore * 1000) / 1000

End If

Loop text62.Text = Int(bestscore * 1000) / 1000 im = 0

'one-way evolution of ligand by mutation and selection
'process continues until score threshold is achieved Do Until mainscore < (threshold * .25)

im = im + 1
text61.Text = im mainmutate
singtest

If bestscore > mainscore Then
bestscore = mainscore
text62.Text = Int(bestscore * 1000) / 1000

102

```
oldcode = code
oldcodet = codet
oldcodeq = codeq

End If

Loop text61.Text = "Final"

code = oldcode
codet = oldcodet
codeq = oldcodeq assemble1
list
substitutes singtest text62.Text = Int(bestscore * 1000) / 1000

'STEP 2
'Complete optimization of ligand using
'all virtual receptors in test panel text61.Text = 0 manytest bestscore = mainscore text62.Text = Int(bestscore * 1000) / 1000

'one-way evolution of ligand by mutation and selection
'process continues for preset number (=testno) of cycles For i = 1 To testno text61.Text = i mainmutate
manytest If bestscore > mainscore Then
bestscore = mainscore
text62.Text = Int(bestscore * 1000) / 1000 oldcode = code
oldcodet = codet
oldcodeq = codeq
```

103

```
End If

Next i text61.Text = "Final"

'Display best ligand code = oldcode
codet = oldcodet
codeq = oldcodeq assemble1
list
substitutes manytest text62.Text = Int(bestscore * 1000) / 1000 picture1.AutoRedraw = True
picture2.AutoRedraw = True

END SUB

SUB Command6_Click ()

'Code creation and display (DIAGNOSTIC)

text29.Text = ""
codecreate
assemble1
list substitutes
'Increment target counter counttarget = 1

'load target value

'prepare for display picture4.Cls
picture4.Scale (-7, 7)-(7, -7)

fzmm = atomcount + hnumber

'start loop to read in values from file for each atom
```

```
For i = 1 To atomcount xom(i) = 1.54 * molecule(i, 2)
yom(i) = 1.54 * molecule(i, 3)
zom(i) = 1.54 * molecule(i, 4)

radius1(i) = dradius(molecule(i, 9))
cradius1(i) = clradius(molecule(i, 9))
dipm1(i) = dipoles(molecule(i, 9))

colrm(i) = colord(molecule(i, 9))

'divide positional coordinates by 100 and store

Next i
For i = 1 To hnumber xom(i + atomcount) = 1.54 * subsx(i, 1)
yom(i + atomcount) = 1.54 * subsy(i, 1)
zom(i + atomcount) = 1.54 * subsz(i, 1)

radius1(i + atomcount) = dradius(subt(i))
cradius1(i + atomcount) = clradius(subt(i))
dipm1(i + atomcount) = dipoles(subt(i))

colrm(i + atomcount) = colord(subt(i))

'divide positional coordinates by 100 and store

Next i

'store grey color code gcol = RGB(50, 50, 50)

'start loop to calculate collision matrix values

For i = 1 To fzmm zp = zom(i)
xp = xom(i)
yp = yom(i)
rp = radius1(i)
sp = cradius1(i)
colm = colrm(i)
'draw atoms using radius and collision radius picture4.Circle (xp, yp), rp, QBColor(colm)
'picture2.Circle (xp, yp), rp, gcol 'calculation of collision matrix
```

```
sp = sp + .05

'start loop to calculate collision points

For j = Int(xp - sp) To Int(xp + sp + 1)
For k = Int(yp - sp) To Int(yp + sp + 1)

'calculate distance from atom center dist = Sqr((xp - j) ^ 2 + (yp - k) ^ 2)

'if distance is less than radius, then set collision
'height matrix component to radius If dist <= rp Then 'draw collision point picture4.Circle (j, k), .2

Else

'if distance is less than collision radius (but greater than radius)
'set collision matrix component to radius/2

If dist <= sp Then

'draw point picture4.PSet (j, k)

End If

End If

Next k

Next j

Next i

Close 1

'draw grid on target frame picture4.Line (0, 20)-(0, -20)
picture4.Line (20, 0)-(-20, 0)

END SUB

SUB Command7_Click ()
```

106

```
' Control for positive rotation around y-axis:
' continuous movement through 360 degrees picture1.Cls
picture1.AutoRedraw = False
For j = 1 To 60
text3.Text = (text3.Text + 6) Mod 360

For i = 1 To codelength
w = length(x(i), z(i))

Select Case x(i)
   Case 0
      If z(i) > 0 Then
      theta = pi / 2
      Else
      theta = 3 * pi / 2
      End If
   Case Is > 0
      If z(i) >= 0 Then
      theta = at1(z(i) / x(i))
      Else theta = at3(z(i) / x(i))
      End If
   Case Is < 0
      If z(i) >= 0 Then
      theta = at2(z(i) / x(i))
      Else theta = at4(z(i) / x(i))
      End If End Select z(i) = w * Sin(theta + (pi / 30))
x(i) = w * Cos(theta + (pi / 30))

Next i picture1.Cls

For i = 0 To codelength - 1 picture1.Circle (x(i), y(i)), .6
picture1.Line (x(i + 1), y(i + 1))-(x(i), y(i))

Next i picture1.Circle (x(codelength), y(codelength)), .6

For i = 1 To hnumber
w = length(subsx(i, 1), subsz(i, 1))
```

107

```
Select Case subsx(i, 1)
    Case 0
       If subsz(i, 1) > 0 Then
       theta2 = pi / 2
       Else
       theta2 = 3 * pi / 2
       End If
    Case Is > 0
       If subsz(i, 1) >= 0 Then
       theta2 = at1(subsz(i, 1) / subsx(i, 1))
       Else theta2 = at3(subsz(i, 1) / subsx(i, 1))
       End If
    Case Is < 0
       If subsz(i, 1) >= 0 Then
       theta2 = at2(subsz(i, 1) / subsx(i, 1))
       Else theta2 = at4(subsz(i, 1) / subsx(i, 1))
       End If End Select subsz(i, 1) = w * Sin(theta2 + (pi / 30))
subsx(i, 1) = w * Cos(theta2 + (pi / 30))

Next i

For i = 1 To hnumber
w = length(subsx(i, 2), subsz(i, 2))

Select Case subsx(i, 2)
    Case 0
       If subsz(i, 2) > 0 Then
       theta2 = pi / 2
       Else
       theta2 = 3 * pi / 2
       End If
    Case Is > 0
       If subsz(i, 2) >= 0 Then
       theta2 = at1(subsz(i, 2) / subsx(i, 2))
       Else theta2 = at3(subsz(i, 2) / subsx(i, 2))
       End If
    Case Is < 0
       If subsz(i, 2) >= 0 Then
       theta2 = at2(subsz(i, 2) / subsx(i, 2))
       Else theta2 = at4(subsz(i, 2) / subsx(i, 2))
       End If End Select
```

108

```
subsz(i, 2) = w * Sin(theta2 + (pi / 30))
subsx(i, 2) = w * Cos(theta2 + (pi / 30))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))
Next i picture1.ForeColor = QBColor(0)

Next j picture1.AutoRedraw = True
END SUB

SUB Command8_Click ()

' Control for positive rotation around x-axis;
' continuous movement through 360 degrees picture1.Cls
picture1.AutoRedraw = False For j = 1 To 120 text4.Text = (text4.Text + 6) Mod 360
For i = 1 To codelength
w = length(y(i), z(i))

Select Case y(i)
   Case 0
      If z(i) > 0 Then
      theta = pi / 2
      Else
      theta = 3 * pi / 2
      End If
   Case Is > 0
      If z(i) >= 0 Then
      theta = at1(z(i) / y(i))
      Else theta = at3(z(i) / y(i))
      End If
   Case Is < 0
```

```
            If z(i) >= 0 Then
            theta = at2(z(i) / y(i))
            Else theta = at4(z(i) / y(i))
            End If End Select z(i) = w * Sin(theta + (pi / 60))
     y(i) = w * Cos(theta + (pi / 60))

Next i picture1.Cls

For i = 0 To codelength - 1 picture1.Circle (x(i), y(i)), .6
picture1.Line (x(i + 1), y(i + 1))-(x(i), y(i))

Next i picture1.Circle (x(codelength), y(codelength)), .6

For i = 1 To hnumber
w = length(subsy(i, 1), subsz(i, 1))

Select Case subsy(i, 1)
    Case 0
        If subsz(i, 1) > 0 Then
        theta2 = pi / 2
        Else
        theta2 = 3 * pi / 2
        End If
    Case Is > 0
        If subsz(i, 1) >= 0 Then
        theta2 = at1(subsz(i, 1) / subsy(i, 1))
        Else theta2 = at3(subsz(i, 1) / subsy(i, 1))
        End If
    Case Is < 0
        If subsz(i, 1) >= 0 Then
        theta2 = at2(subsz(i, 1) / subsy(i, 1))
        Else theta2 = at4(subsz(i, 1) / subsy(i, 1))
        End If End Select subsz(i, 1) = w * Sin(theta2 + (pi / 60))
subsy(i, 1) = w * Cos(theta2 + (pi / 60))
```

```
Next i

For i = 1 To hnumber
w = length(subsy(i, 2), subsz(i, 2))

Select Case subsy(i, 2)
   Case 0
      If subsz(i, 2) > 0 Then
      theta2 = pi / 2
      Else
      theta2 = 3 * pi / 2
      End If
   Case Is > 0
      If subsz(i, 2) >= 0 Then
      theta2 = at1(subsz(i, 2) / subsy(i, 2))
      Else theta2 = at3(subsz(i, 2) / subsy(i, 2))
      End If
   Case Is < 0
      If subsz(i, 2) >= 0 Then
      theta2 = at2(subsz(i, 2) / subsy(i, 2))
      Else theta2 = at4(subsz(i, 2) / subsy(i, 2))
      End If End Select subsz(i, 2) = w * Sin(theta2 + (pi / 60))
subsy(i, 2) = w * Cos(theta2 + (pi / 60))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 1), subsy(i, 1))-(subsx(i, 2), subsy(i, 2))

Next i picture1.ForeColor = QBColor(0)

Next j picture1.AutoRedraw = True
```

111

*END SUB*

*SUB* cyan1 ()

'Subroutine for nitrile construction scount = scount + 1
subsx(scount, 2) = subsx(scount - 1, 1)
subsy(scount, 2) = subsy(scount - 1, 1)
subsz(scount, 2) = subsz(scount - 1, 1)

Select Case state

Case 1
   subsz(scount, 1) = subsz(scount - 1, 1) - .38
   subsx(scount, 1) = subsx(scount - 1, 1) - .57
   subsy(scount, 1) = subsy(scount - 1, 1) + .33
Case 2
   subsz(scount, 1) = subsz(scount - 1, 1) + .38
   subsx(scount, 1) = subsx(scount - 1, 1) + .57
   subsy(scount, 1) = subsy(scount - 1, 1) - .33

Case 3
   subsz(scount, 1) = subsz(scount - 1, 1) + .38
   subsx(scount, 1) = subsx(scount - 1, 1) - .57
   subsy(scount, 1) = subsy(scount - 1, 1) + .33

Case 4
   subsz(scount, 1) = subsz(scount - 1, 1) - .38
   subsx(scount, 1) = subsx(scount - 1, 1) + .57
   subsy(scount, 1) = subsy(scount - 1, 1) - .33

End Select subsr(scount) = .55
subsc(scount) = 9 subt(scount) = 15
subt(scount - 1) = 8 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(9)

*END SUB*

*SUB* cyan2 ()

'Subroutine for nitrile construction scount = scount + 1
subsx(scount, 2) = subsx(scount - 1, 1)

```
subsy(scount, 2) = subsy(scount - 1, 1)
subsz(scount, 2) = subsz(scount - 1, 1)

Select Case state

Case 1
    subsz(scount, 1) = subsz(scount - 1, 1) - .38
    subsx(scount, 1) = subsx(scount - 1, 1) + .57
    subsy(scount, 1) = subsy(scount - 1, 1) + .33
Case 2
    subsz(scount, 1) = subsz(scount - 1, 1) + .38
    subsx(scount, 1) = subsx(scount - 1, 1) - .57
    subsy(scount, 1) = subsy(scount - 1, 1) - .33

Case 3
    subsz(scount, 1) = subsz(scount - 1, 1) + .38
    subsx(scount, 1) = subsx(scount - 1, 1) + .57
    subsy(scount, 1) = subsy(scount - 1, 1) + .33

Case 4
    subsz(scount, 1) = subsz(scount - 1, 1) - .38
    subsx(scount, 1) = subsx(scount - 1, 1) - .57
    subsy(scount, 1) = subsy(scount - 1, 1) - .33

End Select subsr(scount) = .55
subsc(scount) = 9 subt(scount) = 15
subt(scount - 1) = 8 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(9)
```

*END SUB*

*SUB* cyan3 ()

'Subroutine for nitrile construction

```
scount = scount + 1
subsx(scount, 2) = subsx(scount - 1, 1)
subsy(scount, 2) = subsy(scount - 1, 1)
subsz(scount, 2) = subsz(scount - 1, 1)

subsx(scount, 1) = subsx(scount - 1, 1)
```

Select Case state

Case 1

113

```
        subsz(scount, 1) = subsz(scount - 1, 1) - .38 subsy(scount, 1) = subsy(scount - 1, 1) - .65
    Case 2
        subsz(scount, 1) = subsz(scount - 1, 1) + .38 subsy(scount, 1) = subsy(scount - 1, 1) + .65

Case 3
        subsz(scount, 1) = subsz(scount - 1, 1) + .38 subsy(scount, 1) = subsy(scount - 1, 1) - .65

Case 4
        subsz(scount, 1) = subsz(scount - 1, 1) - .38 subsy(scount, 1) = subsy(scount - 1, 1) + .65

End Select subsr(scount) = .55
subsc(scount) = 9 subt(scount) = 15
subt(scount - 1) = 8 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(9)

END SUB

SUB cyan4 ()

'Subroutine for nitrile construction scount = scount + 1
subsx(scount, 2) = subsx(scount - 1, 1)
subsy(scount, 2) = subsy(scount - 1, 1)
subsz(scount, 2) = subsz(scount - 1, 1)

subsx(scount, 1) = subsx(scount - 1, 1)
subsy(scount, 1) = subsy(scount - 1, 1)

Select Case state

Case 1
    subsz(scount, 1) = subsz(scount - 1, 1) + .75

Case 2
    subsz(scount, 1) = subsz(scount - 1, 1) - .75
```

114

```
Case 3
    subsz(scount, 1) = subsz(scount - 1, 1) - .75

Case 4
    subsz(scount, 1) = subsz(scount - 1, 1) + .75

End Select subsr(scount) = .55
subsc(scount) = 9 subt(scount) = 15
subt(scount - 1) = 8 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(9)
```

*END SUB*

*SUB* decodes ()

'DECODER FOR CREATION OF VIRTUAL RECEPTOR

'Clear vectors for storing x,y and z coordinates

```
Erase xo
Erase yo
Erase zo
```

'Redimension vector coordinates to length of code

```
ReDim xo(Len(h)) As Integer
ReDim yo(Len(h)) As Integer
ReDim zo(Len(h)) As Integer
```

'initialize min and max values

```
maxx = -10000
maxy = -10000
maxz = -10000
minx = 10000
miny = 10000
minz = 10000
```

'set initial position in movement array. This determines the starting orientation n = 20

'initialise counters of charge sites

```
c1 = 0
c1neg = 0
```

115

```
'calculate allele lengths (code length/15); store in alen alen = Len(h) / 15

'start loop for decoding
'one cycle per allele

For ni = 0 To 14

'load starting coordinates for each successive allele
'Coordinates stored in ox, oy and oz xq = ox(ni)
yq = oy(ni)
zq = oz(ni)

'set initial position in movement array. This determines the starting orientation n = 20

'start loop to decode each allele

For i = 1 To alen

'read character from code zs2 = Mid$(h, (ni * alen) + i, 1)

'if character is 5 set as charge site

If zs2 = "5" Then

'move 1 unit in current direction xq = xq + aq(n): yq = yq + Bq(n): zq = zq + Cq(n)

'add one to charge site counter c1 = c1 + 1

'redimension charge site storage vectors

ReDim Preserve xcz(c1)
ReDim Preserve ycz(c1)
ReDim Preserve zcz(c1)

'store charge site coordinates, using charge site counter as index xcz(c1) = xq
ycz(c1) = yq
zcz(c1) = zq
```

116

End If

'if character is 6 set as charge site

If zs2 = "6" Then

'move 1 unit in current direction xq = xq + aq(n): yq = yq + Bq(n): zq = zq + Cq(n)

'add one to charge site counter c1neg = c1neg + 1

'redimension charge site storage vectors

ReDim Preserve xczneg(c1neg)
ReDim Preserve yczneg(c1neg)
ReDim Preserve zczneg(c1neg)

'store charge site coordinates, using charge site counter as index xczneg(c1neg) = xq
yczneg(c1neg) = yq
zczneg(c1neg) = zq

End If

'if character is not 5 or 6 start decoding
'select case according to character

Select Case Val(zs2)

'calculate new values for coordinates

```
Case 0
    xq = xq + aq(n): yq = yq + Bq(n): zq = zq + Cq(n)
Case 1
    n = dq(n): xq = xq + aq(n): yq = yq + Bq(n): zq = zq + Cq(n)
Case 2
    n = eq(n): xq = xq + aq(n): yq = yq + Bq(n): zq = zq + Cq(n)
Case 3
    n = Fq(n): xq = xq + aq(n): yq = yq + Bq(n): zq = zq + Cq(n)
Case 4
    n = gq(n): xq = xq + aq(n): yq = yq + Bq(n): zq = zq + Cq(n)
Case 5
Case 6
```

End Select

```
'*************
'write data to the file, use code index position as vector index xo((ni * alen) + i) = xq
yo((ni * alen) + i) = yq
zo((ni * alen) + i) = zq 'find min and max values If xq < minx Then
    minx = xq
    End If If xq > maxx Then
    maxx = xq
    End If If yq < miny Then
    miny = yq
    End If If yq > maxy Then
    maxy = yq
    End If If zq < minz Then
    minz = zq
    End If If zq > maxz Then
    maxz = zq
    End If

'LOOP

Next i

Next ni

'confirm length of current string ltot = Len(h)

'length of code string text3.Text = ltot

'Calculate center of matrix centerx = Int((maxx + minx) / 2)
centery = Int((maxy + miny) / 2)
```

```
'creates z matrix without drawing result
'Clear previous matrix of heights

Erase zmat
Erase z3mat

'Redim height matrix to minimum and maximum values

ReDim zmat(minx - centerx To maxx - centerx, miny - centery To maxy - centery) As Integer
ReDim z3mat(minx - centerx To maxx - centerx, miny - centery To maxy - centery, 1 To maxz + 1 - minz) As Integer 'Create new height matrix
'Get values from coordinate vector For i = 1 To Len(h)

'Calculate values for height normalized for minimum zi = zo(i) + 1 - minz

'Get x and y values for z coordinate to use as indices for height matrix xi = xo(i) - centerx
yi = yo(i) - centery z3mat(xi, yi, zi) = 1

'Set values for height matrix
'Check to see whether matrix component has already been set
'If yes then check if new value is greater than old value
'set value to greater value If zmat(xi, yi) = 0 Then
    zmat(xi, yi) = zi
Else
    If zmat(xi, yi) < zi Then
        zmat(xi, yi) = zi End If End If Next i 'Set up picture for drawing result picture3.Cls
```

118

119

```
picture3.BackColor = RGB(0, 0, 0)
picture3.Scale (-15, 15)-(15, -15)

'Draw frame on picture picture3.Line (-15, 0)-(15, 0), RGB(255, 255, 255)
picture3.Line (0, -15)-(0, 15), RGB(255, 255, 255)
picture3.Line (10, 10)-(-10, -10), RGB(100, 0, 0), B 'Set color factor scale cfac = 255 / (maxz - minz)

'Draw height matrix

For i = maxy - centery To miny - centery Step -1
For j = minx - centerx To maxx - centerx ac = cfac * zmat(j, i)

If ac <> 0 Then colr = RGB(120, ac, ac)

picture3.Line (j + .25, i - .25)-(j - .25, i - .25), colr, BF

End If

Next j

Next i

'Set up to draw charge sites oldstyle = picture3.FillStyle
oldcolor = picture3.FillColor picture3.FillStyle = 0
picture3.FillColor = RGB(0, 0, 0)

'Draw charge sites

For ii = 1 To c1 xcz(ii) = xcz(ii) - centerx
ycz(ii) = ycz(ii) - centery
zcz(ii) = zcz(ii) + 1 - minz If zmat(xcz(ii), ycz(ii)) = zcz(ii) Then
colz = QBColor(10)
Else
colz = QBColor(2)
End If
```

```
picture3.Circle (xcz(ii), ycz(ii)), 1, colz

Next ii

For ii = 1 To clneg xczneg(ii) = xczneg(ii) - centerx
yczneg(ii) = yczneg(ii) - centery
zczneg(ii) = zczneg(ii) + 1 - minz If zmat(xczneg(ii), yczneg(ii)) = zczneg(ii) Then
colz = QBColor(12)
Else
colz = QBColor(4)
End If picture3.Circle (xczneg(ii), yczneg(ii)), 1, colz Next ii picture3.FillStyle = oldstyle
picture3.FillColor = oldcolor
```

*END SUB*

*FUNCTION* dist3d (x1, y1, z1, x2, y2, z2) As Double

'THREE DIMENSIONAL DISTANCE CALCULATION dist3d = Sqr((x1 - x2) ^ 2 + (y1 - y2) ^ 2 + (z1 - z2) ^ 2)

*END FUNCTION*

*SUB* fdelete ()

'Deletion Mutation subroutine

```
lb = startfrag - 1
rb = 1 + Len(code) - startfrag - lenfrag code = Left$(code, lb) & Right$(code, rb)
codet = Left$(codet, lb) & Right$(codet, rb)
codeq = Left$(codeq, lb) & Right$(codeq, rb)
```

*END SUB*

*SUB* fduplicate ()

'Duplication Mutation subroutine

```
codefrag1 = codefrag1 & codefrag1
codefrag2 = codefrag2 & codefrag2
codefrag3 = codefrag3 & codefrag3
```

*END SUB*

*SUB* finsert ()

'Insertion Mutation subroutine

```
insertp = Int(Rnd * Len(code))

code = Left$(code, insertp) & codefrag1 & Right$(code, Len(code) - insertp)
codeq = Left$(codeq, insertp) & codefrag2 & Right$(codeq, Len(codeq) - insertp)
codet = Left$(codet, insertp) & codefrag3 & Right$(codet, Len(codet) - insertp)
```

*END SUB*

*SUB* finvert ()

'inversion Mutation subroutine

```
codefrag1 = strinv(codefrag1)
codefrag2 = strinv(codefrag2)
codefrag3 = strinv(codefrag3)
```

*END SUB*

```
SUB Form_Load ()
v1 = 0
v2 = 0
v3 = 0
v4 = 0
v5 = 0
v6 = 0
v7 = 0
v8 = 0
v9 = 0
v10 = 0
v11 = 0
v12 = 0
v13 = 0
v14 = 0 tc = 0 pi = 3.14159265358979
pi2 = 2 * pi codenum = 0
codelength = 5
state = 1
mtations = 1
```

```
pdup = .5
pinv = .5
pins = .5
pdel = .5
ppoint = .5
pseq = .5
targetp = 100 picture1.Scale (-5, 5)-(5, -5)
picture2.Scale (-5, 5)-(5, -5)

'Needed for test routines

'Set up picture for drawing result picture3.Cls
picture3.BackColor = RGB(0, 0, 100)
picture3.Scale (-15, 15)-(15, -15)

'Draw frame on picture picture3.Line (-15, 0)-(15, 0), RGB(255, 255, 255)
picture3.Line (0, -15)-(0, 15), RGB(255, 255, 255)
picture3.Line (7, 7)-(-7, -7), RGB(100, 0, 0), B coeff = 3

'test and code numbers testnumber = 1
codenumber = 1
proxsense = 3 counttarget = 0

'set maxz=0 as default value
maxz = 0

'this routine loads the matrix required for code conversion

Open "c:\vb3\mites\robodat.bas" For Input As 1
Input #1, junk
Input #1, junk

For i = 1 To 24
Input #1, aq(i)

Next i

For i = 1 To 24
```

122

```
Input #1, Bq(i)

Next i

For i = 1 To 24
Input #1, Cq(i)

Next i
For i = 1 To 24
Input #1, dq(i)

Next i

For i = 1 To 24
Input #1, eq(i)

Next i

For i = 1 To 24
Input #1, Fq(i)

Next i
For i = 1 To 24
Input #1, gq(i)

Next i
Close

'set up random numbers

For i = 0 To 3000 randarray(i) = CSng(Rnd)

Next i dradius(1) = 1
dradius(2) = 1
dradius(3) = 1
dradius(4) = 1
dradius(5) = 1.28
dradius(6) = 1.64
dradius(7) = 1.72
```

```
dradius(8) = 1.54
dradius(9) = 1.54
dradius(10) = 1.36
dradius(11) = 1.36
dradius(12) = 1.36
dradius(13) = 1.36
dradius(14) = 1.36
dradius(15) = 1.36
dradius(16) = 1.36
dradius(17) = 1.36
dradius(18) = 1.36
dradius(19) = 1.64
dradius(20) = 1.64
dradius(21) = 1.64 clradius(1) = 1.5
clradius(2) = 1.5
clradius(3) = 1.5
clradius(4) = 1.5
clradius(5) = 1.78
clradius(6) = 2.14
clradius(7) = 2.22
clradius(8) = 2.04
clradius(9) = 2.04
clradius(10) = 1.86
clradius(11) = 1.86
clradius(12) = 1.86
clradius(13) = 1.86
clradius(14) = 1.86
clradius(15) = 1.86
clradius(16) = 1.86
clradius(17) = 1.86
clradius(18) = 1.86
clradius(19) = 2.14
clradius(20) = 2.14
clradius(21) = 2.14 colord(1) = 12
colord(2) = 12
colord(3) = 12
colord(4) = 12
colord(5) = 10
colord(6) = 2
colord(7) = 5
colord(8) = 0
colord(9) = 0
colord(10) = 11
colord(11) = 11
colord(12) = 11
colord(13) = 11
colord(14) = 9
colord(15) = 9
colord(16) = 9
colord(17) = 9
```

```
colord(18) = 9
colord(19) = 14
colord(20) = 14
colord(21) = 14 dipoles(1) = .35
dipoles(2) = 1.5
dipoles(3) = 1.1
dipoles(4) = 1.3
dipoles(5) = -1.8
dipoles(6) = -2
dipoles(7) = -2.1
dipoles(8) = 0
dipoles(9) = 0
dipoles(10) = -1.1
dipoles(11) = -2
dipoles(12) = -2.9
dipoles(13) = -.8
dipoles(14) = -1.3
dipoles(15) = -4
dipoles(16) = 3.8
dipoles(17) = -1.3
dipoles(18) = -1.3
dipoles(19) = -.83
dipoles(20) = 0
dipoles(21) = -.9
```

*END SUB*

*SUB* fragorig ()

'LOADS INITIAL RECEPTOR ORIGIN COORDINATES

'origins for fragments

```
ox(0) = -rlength
ox(1) = 0
ox(2) = rlength
ox(3) = -rlength
ox(4) = 0
ox(5) = rlength
ox(6) = -rlength
ox(7) = 0
ox(8) = rlength
ox(9) = -rlength
ox(10) = 0
ox(11) = rlength
ox(12) = -rlength
ox(13) = 0
ox(14) = rlength
oy(0) = rwidth
oy(1) = rwidth
oy(2) = rwidth
oy(3) = rwidth
```

```
oy(4) = rwidth
oy(5) = rwidth
oy(6) = 0
oy(7) = 0
oy(8) = 0
oy(9) = -rwidth
oy(10) = -rwidth
oy(11) = -rwidth
oy(12) = -rwidth
oy(13) = -rwidth
oy(14) = -rwidth
oz(0) = 0
oz(1) = 0
oz(2) = 0
oz(3) = -Int(depth / 2)
oz(4) = -Int(depth / 2)
oz(5) = -Int(depth / 2)
oz(6) = -depth
oz(7) = -depth
oz(8) = -depth
oz(9) = -Int(depth / 2)
oz(10) = -Int(depth / 2)
oz(11) = -Int(depth / 2)
oz(12) = 0
oz(13) = 0
oz(14) = 0
```

*END SUB*

*SUB* frplace ()

'Subroutine for replacing mutated sequences during sequence mutation process insertp = startfrag - 1 code = Left$(code, insertp) & codefrag1 & Right$(code, Len(code) - insertp - lenfrag)
codeq = Left$(codeq, insertp) & codefrag2 & Right$(codeq, Len(codeq) - insertp - lenfrag)
codet = Left$(codet, insertp) & codefrag3 & Right$(codet, Len(codet) - insertp - lenfrag)

*END SUB*

*SUB* HScroll1_Change ()

'Sets code length
'The number of carbon atoms in the resulting molecule wil be
'less than or equal to this number codelength = hscroll1.Value text2.Text = codelength

*END SUB*

127

```
SUB HScroll1_Scroll ()

codelength = hscroll1.Value
text2.Text = codelength

END SUB

SUB HScroll10_Change ()
'CODE FREQUENCY CONTROL
'Carbonyl oxygen substituents
'control for controlling code frequency for O 'load value into v1 v8 = hscroll10.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)
END SUB SUB HScroll11_Change ()

'Control for setting percentage (=ng)
'of carbon atoms replaced with sp2 nitrogen ng = hscroll11.Value
text31.Text = ng td = ng + pg + og + sg
END SUB SUB HScroll11_Scroll ()

ng = hscroll11.Value
text31.Text = ng
```

*END SUB*

*SUB* HScroll12_Change ()
'CODE FREQUENCY CONTROL
'Thione substituents
'control for controlling code frequency for O 'load value into v1 v9 = hscroll12.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)

*END SUB*

*SUB* HScroll13_Change ()

'Control for setting percentage (=og)
'of carbon atoms replaced with ether oxygen og = hscroll13.Value
text35.Text = og td = ng - pg + og + sg
*END SUB*

*SUB* HScroll13_Scroll ()

og = hscroll13.Value
text35.Text = og

*END SUB*

*SUB* HScroll14_Change ()

129

```
'CODE FREQUENCY CONTROL
'Nitro substituents
'control for controlling code frequency for 0

'load value into v1 v7 = hscroll14.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)

END SUB

SUB HScroll15_Change ()

'Control for setting percentage (=pg)
'of carbon atoms replaced with sp3 nitrogen pg = hscroll15.Value
text40.Text = pg td = ng + pg + og + sg
END SUB SUB HScroll15_Scroll ()

pg = hscroll15.Value
text40.Text = pg

END SUB

SUB HScroll16_Change ()

'Control for setting percentage (=sg)
'of carbon atoms replaced with sulphide sulphur
```

```
sg = hscroll16.Value
text38.Text = sg td = ng + pg + og + sg

END SUB

SUB HScroll16_Scroll ()

sg = hscroll16.Value
text38.Text = sg

END SUB

SUB HScroll17_Change ()
'CODE FREQUENCY CONTROL
'Thiol substituents
'control for controlling code frequency for 0

'load value into v1 v10 = hscroll17.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)

END SUB

SUB HScroll18_Change ()

'Control for setting the percentage likelihood (=wg) that
'a carbon atom will be sp3 (unsaturated)

wg = hscroll18.Value
text46.Text = wg
```

130

*END SUB*

*SUB* HScroll18_Scroll ()

wg = hscroll18.Value
text46.Text = wg

*END SUB*

*SUB* HScroll19_Change ()

'Control for setting the number of ligand orientations to be tested testnumber = hscroll19.Value
text53.Text = testnumber

*END SUB*

*SUB* HScroll19_Scroll ()
testnumber = hscroll19.Value
text53.Text = testnumber

*END SUB*

*SUB* HScroll2_Change ()

'Control for setting the percentage likelihood (stored as pring)
'that a carbon atom will be replaced by a cyclohexyl ring pring = hscroll2.Value text27.Text = pring

*END SUB*

*SUB* HScroll20_Change ()

'Control for setting the number of mutation cycles for the
'directed evolution of ligands testno = hscroll20.Value
text59.Text = testno

*END SUB*

*SUB* HScroll20_Scroll ()
testno = hscroll20.Value
text59.Text = testno

*END SUB*

*SUB* HScroll21_Change ()

'Control for setting the threshold value for the acceptance of

132

```
'of randomly generated ligands for directed evolution threshold = hscroll21.Value / 100
text60.Text = threshold

END SUB

SUB HScroll21_Scroll ()
threshold = hscroll21.Value
text60.Text = threshold

END SUB

SUB HScroll22_Change ()

'Control for setting the amount of lateral movement of the ligand
'during testing transval = hscroll22.Value
text55.Text = transval

END SUB

SUB HScroll22_Scroll ()

transval = hscroll22.Value
text55.Text = transval

END SUB

SUB HScroll23_Change ()

'Control for setting the likelihood of point mutations ppoint = hscroll23.Value / 100
text7.Text = ppoint
END SUB SUB HScroll23_Scroll ()
ppoint = hscroll23.Value / 100
text7.Text = ppoint

END SUB

SUB HScroll24_Change ()

'Control for setting the likelihood of sequence mutations pseq = hscroll24.Value / 100
text6.Text = pseq

END SUB

SUB HScroll24_Scroll ()
```

```
pseq = hscroll24.Value / 100
text6.Text = pseq

END SUB

SUB HScroll25_Change ()

'Control for setting the percentage of deletion mutations pdel = hscroll25.Value / 100
text5.Text = pdel

END SUB

SUB HScroll25_Scroll ()

pdel = hscroll25.Value / 100
text5.Text = pdel

END SUB

SUB HScroll26_Change ()

'Control for setting the percentage of duplication mutations pdup = hscroll26.Value / 100
text54.Text = pdup

END SUB

SUB HScroll26_Scroll ()
pdup = hscroll26.Value / 100
text54.Text = pdup

END SUB

SUB HScroll27_Change ()

'Control for setting the percentage of inversion mutations pinv = hscroll27.Value / 100
text64.Text = pinv

END SUB

SUB HScroll27_Scroll ()
pinv = hscroll27.Value / 100
text64.Text = pinv

END SUB

SUB HScroll28_Change ()
```

134

'Control for setting the percentage of insertion mutations

```
pins = hscroll28.Value / 100
text65.Text = pins
```

*END SUB*

*SUB* HScroll28_Scroll ()
```
pins = hscroll28.Value / 100
text65.Text = pins
```

*END SUB*

*SUB* HScroll29_Change ()

'Control for setting the target values sum and max affinity for ligand evolution

```
targetp = hscroll29.Value
text72.Text = targetp
maxtarget = maximalm * (targetp / 100)
sumtarget = maximals * (targetp / 100)
text70.Text = maxtarget
text71.Text = sumtarget
```
*END SUB*

*SUB* HScroll3_Change ()
'CODE FREQUENCY CONTROL
'Flourine sustituents
'control for controlling code frequency for 0

'load value into v1 v1 = hscroll3.Value

'update total for frequency calculations tc = v1 + v2 + v3 + v4 + v5 + v6 + v7 + v8 + v9 + v10

'update frequency labels

```
If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)
```

*END SUB*

*SUB* HScroll30_Change ()

'Control for setting the percentage likelihood (= methyl)
'that a code triplet will be repeated to generate a methyl group methyl = hscroll30.Value
text74.Text = methyl

*END SUB*

*SUB* HScroll4_Change ()
'CODE FREQUENCY CONTROL
'Chlorine substituents
'control for controlling code frequency for ()

'load value into v1 v2 = hscroll4.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)

*END SUB*

*SUB* HScroll5_Change ()
'CODE FREQUENCY CONTROL
'bromine substituents
'control for controlling code frequency for ()

'load value into v1 v3 = hscroll5.Value

136

```
'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)

END SUB

SUB HScroll6_Change ()
'CODE FREQUENCY CONTROL
'Hydroxyl substituents
'control for controlling code frequency for 0

'load value into v1 v4 = hscroll6.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)

END SUB
```

```
SUB HScroll7_Change ()
'CODE FREQUENCY CONTROL
'Amine substituents
'control for controlling code frequency for 0

'load value into v1 v5 = hscroll7.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)

END SUB

SUB HScroll8_Change ()
'CODE FREQUENCY CONTROL
'Nitrile substituents
'control for controlling code frequency for 0

'load value into v1 v6 = hscroll8.Value

'update total for frequency calculations tc = v1 + v2 + v3 + v4 + v5 + v6 + v7 + v8 + v9 + v10

'update frequency labels

If tc = 0 Then
tc = 1
End If text12.Text = Int(100 * v1 / tc)
text13.Text = Int(100 * v2 / tc)
```

```
text14.Text = Int(100 * v3 / tc)
text15.Text = Int(100 * v4 / tc)
text16.Text = Int(100 * v5 / tc)
text17.Text = Int(100 * v6 / tc)
text37.Text = Int(100 * v7 / tc)
text11.Text = Int(100 * v8 / tc)
text33.Text = Int(100 * v9 / tc)
text44.Text = Int(100 * v10 / tc)
```

*END SUB*

*SUB* HScroll9_Change ()

'Control for setting the percentage of substituents that will
'not be hydrogen atoms (=100-hscroll2.value)

```
text24.Text = hscroll9.Value
```

*END SUB*

*SUB* HScroll9_Scroll ()

```
text24.Text = hscroll9.Value
```

*END SUB*

*SUB* hyd1 ()

'Subroutine for hydroxyl group construction

```
scount = scount + 1
subsx(scount, 2) = subsx(scount - 1, 1)
subsy(scount, 2) = subsy(scount - 1, 1)
subsz(scount, 2) = subsz(scount - 1, 1)

subsx(scount, 1) = subsx(scount - 1, 1)
subsy(scount, 1) = subsy(scount - 1, 1)

Select Case state

Case 1
    subsz(scount, 1) = subsz(scount - 1, 1) - .63

Case 2
    subsz(scount, 1) = subsz(scount - 1, 1) + .63

Case 3
    subsz(scount, 1) = subsz(scount - 1, 1) + .63

Case 4
    subsz(scount, 1) = subsz(scount - 1, 1) - .63

End Select
```

139

```
subsr(scount) = .4206
subsc(scount) = 12 subt(scount) = 2 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)
```

*END SUB*

*SUB* hyd2 ()

```
'Subroutine for hydroxyl group construction scount = scount + 1
subsx(scount, 2) = subsx(scount - 1, 1)
subsy(scount, 2) = subsy(scount - 1, 1)
subsz(scount, 2) = subsz(scount - 1, 1)

subsx(scount, 1) = subsx(scount - 1, 1)

Select Case state

Case 1
    subsy(scount, 1) = subsy(scount - 1, 1) + .55
    subsz(scount, 1) = subsz(scount - 1, 1) + .31

Case 2
    subsy(scount, 1) = subsy(scount - 1, 1) - .55
    subsz(scount, 1) = subsz(scount - 1, 1) - .31

Case 3
    subsy(scount, 1) = subsy(scount - 1, 1) + .55
    subsz(scount, 1) = subsz(scount - 1, 1) - .31

Case 4
    subsy(scount, 1) = subsy(scount - 1, 1) - .55
    subsz(scount, 1) = subsz(scount - 1, 1) + .31

End Select subsr(scount) = .4206
subsc(scount) = 12 subt(scount) = 2 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)
```

140

*END SUB*

*SUB* keto1 ()

'Subroutine for addition of carbonyl oxygen

```
If molecule(ik, 6) = 0 Then
molecule(ik, 6) = 1
sub12
Else
If molecule(ik, 7) = 0 Then
molecule(ik, 7) = 1
sub13
Else
If molecule(ik, 8) = 0 Then
molecule(ik, 8) = 1
sub14
End If
End If
End If
```
*END SUB*

*SUB* keto2 ()

'Subroutine for addition of carbonyl oxygen

```
If molecule(ik, 7) = 0 Then
molecule(ik, 7) = 1
sub23
Else
If molecule(ik, 8) = 0 Then
molecule(ik, 8) = 1
sub24
Else
If molecule(ik, 5) = 0 Then
molecule(ik, 5) = 1
sub12
End If
End If
End If
```

*END SUB*

*SUB* keto3 ()

'Subroutine for addition of carbonyl oxygen

```
If molecule(ik, 6) = 0 Then
molecule(ik, 6) = 1
sub23
Else
If molecule(ik, 5) = 0 Then
molecule(ik, 5) = 1
sub13
```

```
Else
If molecule(ik, 8) = 0 Then
molecule(ik, 8) = 1
sub34
End If
End If
End If
```

*END SUB*

*SUB* keto4 ()

'Subroutine for addition of carbonyl oxygen

```
If molecule(ik, 6) = 0 Then
molecule(ik, 6) = 1
sub4
Else
If molecule(ik, 7) = 0 Then
molecule(ik, 7) = 1
sub4
Else
If molecule(ik, 5) = 0 Then
molecule(ik, 5) = 1
sub4
End If
End If
End If
```

*END SUB*

*FUNCTION* length (x1 As Double, y1 As Double) As Double

'Subroutine for 2-Dimensional length calculations length = Sqr(x1 ^ 2 - y1 ^ 2)

*END FUNCTION*

*SUB* list ()

'ROUTINE FOR THE GENERATION OF ATOM LIST
'Translates assemble1 arrays into molecular mapping matrix for
'substitutions atomcount = 0

For i = -15 To 15
For j = -15 To 15
For k = -15 To 15

If atoms(i, j, k) <> 0 Then
atomcount = atomcount + 1

```
molecule(atomcount, 11) = subn(i, j, k, 1)
molecule(atomcount, 12) = subn(i, j, k, 2)
molecule(atomcount, 13) = subn(i, j, k, 3)
molecule(atomcount, 14) = subn(i, j, k, 4)
rcx(atomcount) = i
rcy(atomcount) = j
rcz(atomcount) = k molecule(atomcount, 1) = atomstate(i, j, k)
molecule(atomcount, 2) = atomx(i, j, k)
molecule(atomcount, 3) = atomy(i, j, k)
molecule(atomcount, 4) = atomz(i, j, k)
molecule(atomcount, 5) = bond1(i, j, k)
molecule(atomcount, 6) = bond2(i, j, k)
molecule(atomcount, 7) = bond3(i, j, k)
molecule(atomcount, 8) = bond4(i, j, k)
molecule(atomcount, 9) = 8
molecule(atomcount, 10) = 4 - atoms(i, j, k)

skelcol(atomcount) = 1

End If

Next k
Next j
Next i text9.Text = atomcount

END SUB

SUB mammutate ()

'PRIMARY MUTATION ROUTINE
'Coordinates both point and sequence mutations text8.Text = ""
text67.Text = ""
text45.Text = ""
text66.Text = ""
text63.Text = ""

code = oldcode
codet = oldcodet
codeq = oldcodeq

'Point mutation control pp1 = Rnd
If pp1 <= ppoint Then
pointmut
```

143

End If

'Sequence mutation control pp2 = Rnd
If pp2 <= pseq Then
sequencemut
End If
codelength = Len(code)

coded = ""

For j = 1 To codelength coded = coded & Mid$(codet, j, 1) & "(" & Mid$(codeq, j, 1) & ")" & Mid$(code, j, 1) & " " & Chr$(126)

Next j text1.Text = coded assemble1
list
substitutes

*END SUB*

*SUB* manytest ()

'ROUTINE FOR TESTING LIGAND AGAINST MORE THAN
'ONE VIRTUAL RECEPTOR scorev = 0

For i = 1 To codenum codev = i
text77.Text = codev changer
singtest scorev = scorev + mainscore
text78.Text = scorev / codev Next i mainscore = scorev / codenum

*END SUB*

*FUNCTION* max (var1, var2)

'Subroutine for finding the largest of two numbers

```
If var1 > var2 Then
max = var1
Else
max = var2
End If
```

*END FUNCTION*

*SUB* methy ()

'Subroutine for Methyl group construction

```
methcount = methcount + 1
text75.Text = methcount ss = Trim$(Str$(Int(Rnd * 4) + 1))
mm = ss & ss
qq = ""
pp = ""

tot = v1 + v2 + v3 + v4 + v5 + v6 + v7 + v8 + v9 + v10 t1 = 1 + v1
t2 = v1 + v2
t3 = t2 + 1
t4 = t2 + v3
t5 = t4 + 1
t6 = t4 + v4
t7 = t6 + 1
t8 = t6 + v5
t9 = t8 + 1
t10 = t8 + v6
t11 = t10 + 1
t12 = t10 + v7
t13 = t12 + 1
t14 = t12 + v8
t15 = t14 + 1
t16 = t14 + v9
t17 = t16 + 1
t18 = t16 + v10

For k = 1 To 2

If tc + td = 0 Then
hyd = 1
Else
hyd = (hscroll9.Value / 100)
End If

If Rnd <= hyd Then

If Rnd > (wg / 100) Then
```

```
        g = "a"
        q = Trim$(Str$(Int(1 + 4 * Rnd)))

Else g = "w"
        q = Trim$(Str$(Int(1 + 4 * Rnd)))
        ws = ws + 1
      End If jhyd = jhyd + 1

Else

If (Rnd) < ng / 100 Then
        g = "n"
        j12 = j12 + 1

Else
      If (Rnd) < pg / 100 Then
        g = "p"
        j13 = j13 + 1

Else
      If (Rnd) < og / 100 Then
        g = "o"
        j14 = j14 + 1
      Else If (Rnd) < sg / 100 Then
        g = "s"
        j15 = j15 + 1

Else

'Assignment of string values for substituents

'start of primary code generating loop

'generation of random number

Rn = 1 + Int(tot * (Rnd(1)))

'generation of code sequence

Select Case Rn

Case 1 To v1 g = "b"

j1 = j1 + 1
```

145

```
Case t1 To t2
    g = "c"
    j2 = j2 + 1

Case t3 To t4
    g = "d"
    j3 = j3 + 1

Case t5 To t6
    g = "e"
    j4 = j4 + 1

Case t7 To t8
    g = "f"
    j5 = j5 + 1

Case t9 To t10
    g = "g"
    j6 = j6 + 1

Case t11 To t12
    g = "h"
    j7 = j7 + 1

Case t13 To t14
    g = "i"
    j8 = j8 + 1

Case t15 To t16
    g = "j"
    j9 = j9 + 1

Case t17 To t18
    g = "k"
    j10 = j10 + 1

End Select

End If
End If
End If
End If q = Trim$(Str$(Int(Rnd * 4) + 1))

End If gg = gg & g
qq = qq & q

Next k
```

147

```
s = mm
g = gg
q = qq
```

*END SUB*

*FUNCTION* min (var1, var2)

'Subroutine for finding the smallest of two numbers

```
If var1 < var2 Then
min = var1
Else
min = var2
End If
```

*END FUNCTION*

*SUB* nitro1 ()

'Subroutine for nitro group construction

```
scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
    subsz(scount, 1) = subsz(scount - 1, 1) - .815
    subsx(scount, 1) = subsx(scount - 1, 1)
    subsy(scount, 1) = subsy(scount - 1, 1)
    subsz(scount + 1, 1) = subsz(scount - 1, 1) + .407
    subsx(scount + 1, 1) = subsx(scount - 1, 1) - .61
    subsy(scount + 1, 1) = subsy(scount - 1, 1) + .35

Case 2
    subsz(scount, 1) = subsz(scount - 1, 1) + .815
    subsx(scount, 1) = subsx(scount - 1, 1)
    subsy(scount, 1) = subsy(scount - 1, 1)
    subsz(scount + 1, 1) = subsz(scount - 1, 1) - .407
    subsx(scount + 1, 1) = subsx(scount - 1, 1) + .61
    subsy(scount + 1, 1) = subsy(scount - 1, 1) - .35

Case 3
    subsz(scount, 1) = subsz(scount - 1, 1) + .815
```

```
    subsx(scount, 1) = subsx(scount - 1, 1)
    subsy(scount, 1) = subsy(scount - 1, 1)
    subsz(scount + 1, 1) = subsz(scount - 1, 1) - .407
    subsx(scount + 1, 1) = subsx(scount - 1, 1) - .61
    subsy(scount + 1, 1) = subsy(scount - 1, 1) + .35

Case 4
    subsz(scount, 1) = subsz(scount - 1, 1) - .815
    subsx(scount, 1) = subsx(scount - 1, 1)
    subsy(scount, 1) = subsy(scount - 1, 1)
    subsz(scount + 1, 1) = subsz(scount - 1, 1) + .407
    subsx(scount + 1, 1) = subsx(scount - 1, 1) + .61
    subsy(scount + 1, 1) = subsy(scount - 1, 1) - .35

End Select subsr(scount) = .55
subsc(scount) = 13
subsr(scount + 1) = .55
subsc(scount + 1) = 13 subt(scount) = 11
subt(scount + 1) = 11 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(13)
picture1.Line (subsx(scount + 1, 1), subsy(scount + 1, 1))-(subsx(scount + 1, 2), subsy(scount + 1, 2)),
QBColor(13)
picture1.Circle (subsx(scount + 1, 1), subsy(scount + 1, 1)), subsr(scount + 1), QBColor(13)

scount = scount + 1

END SUB

SUB nitro2 ()

'Subroutine for nitro group construction scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
    subsz(scount, 1) = subsz(scount - 1, 1) - .815
    subsx(scount, 1) = subsx(scount - 1, 1)
```

```
    subsy(scount, 1) = subsy(scount - 1, 1)
    subsz(scount + 1, 1) = subsz(scount - 1, 1) + .407
    subsx(scount + 1, 1) = subsx(scount - 1, 1) + .61
    subsy(scount + 1, 1) = subsy(scount - 1, 1) + .35
,
Case 2
    subsz(scount, 1) = subsz(scount - 1, 1) + .815
    subsx(scount, 1) = subsx(scount - 1, 1)
    subsy(scount, 1) = subsy(scount - 1, 1)
    subsz(scount + 1, 1) = subsz(scount - 1, 1) - .407
    subsx(scount + 1, 1) = subsx(scount - 1, 1) - .61
    subsy(scount + 1, 1) = subsy(scount - 1, 1) - .35
,
Case 3
    subsz(scount, 1) = subsz(scount - 1, 1) + .815
    subsx(scount, 1) = subsx(scount - 1, 1)
    subsy(scount, 1) = subsy(scount - 1, 1)
    subsz(scount + 1, 1) = subsz(scount - 1, 1) - .407
    subsx(scount + 1, 1) = subsx(scount - 1, 1) + .61
    subsy(scount + 1, 1) = subsy(scount - 1, 1) + .35
,
Case 4
    subsz(scount, 1) = subsz(scount - 1, 1) - .815
    subsx(scount, 1) = subsx(scount - 1, 1)
    subsy(scount, 1) = subsy(scount - 1, 1)
    subsz(scount + 1, 1) = subsz(scount - 1, 1) + .407
    subsx(scount + 1, 1) = subsx(scount - 1, 1) - .61
    subsy(scount + 1, 1) = subsy(scount - 1, 1) - .35
,
,
End Select
,
subsr(scount) = .55
subsc(scount) = 13
subsr(scount + 1) = .55
subsc(scount + 1) = 13 subt(scount) = 11
subt(scount + 1) = 11
,
picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(13)
picture1.Line (subsx(scount + 1, 1), subsy(scount + 1, 1))-(subsx(scount + 1, 2), subsy(scount + 1, 2)), QBColor(13)
picture1.Circle (subsx(scount + 1, 1), subsy(scount + 1, 1)), subsr(scount + 1), QBColor(13)

scount = scount + 1
,
END SUB

SUB nitro3 ()

'Subroutine for nitro group construction
```

150

```
scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
    subsz(scount, 1) = subsz(scount - 1, 1) - .815
    subsx(scount, 1) = subsx(scount - 1, 1)
    subsy(scount, 1) = subsy(scount - 1, 1)
    subsz(scount + 1, 1) = subsz(scount - 1, 1) + .407
    subsx(scount + 1, 1) = subsx(scount - 1, 1)
    subsy(scount + 1, 1) = subsy(scount - 1, 1) - .706
'
Case 2
    subsz(scount, 1) = subsz(scount - 1, 1) + .815
    subsx(scount, 1) = subsx(scount - 1, 1)
    subsy(scount, 1) = subsy(scount - 1, 1)
    subsz(scount + 1, 1) = subsz(scount - 1, 1) - .407
    subsx(scount + 1, 1) = subsx(scount - 1, 1)
    subsy(scount + 1, 1) = subsy(scount - 1, 1) + .706
    '
'
Case 3
    subsz(scount, 1) = subsz(scount - 1, 1) + .815
    subsx(scount, 1) = subsx(scount - 1, 1)
    subsy(scount, 1) = subsy(scount - 1, 1)
    subsz(scount + 1, 1) = subsz(scount - 1, 1) - .407
    subsx(scount + 1, 1) = subsx(scount - 1, 1)
    subsy(scount + 1, 1) = subsy(scount - 1, 1) - .706
'
Case 4
    subsz(scount, 1) = subsz(scount - 1, 1) - .815
    subsx(scount, 1) = subsx(scount - 1, 1)
    subsy(scount, 1) = subsy(scount - 1, 1)
    subsz(scount + 1, 1) = subsz(scount - 1, 1) + .407
    subsx(scount + 1, 1) = subsx(scount - 1, 1)
    subsy(scount + 1, 1) = subsy(scount - 1, 1) + .706
'
'
End Select
'
subsr(scount) = .55
subsc(scount) = 13
subsr(scount + 1) = .55
subsc(scount + 1) = 13 subt(scount) = 11
```

[51]

```
subt(scount + 1) = 11 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(13)
picture1.Line (subsx(scount + 1, 1), subsy(scount + 1, 1))-(subsx(scount + 1, 2), subsy(scount + 1, 2)),
QBColor(13)
picture1.Circle (subsx(scount + 1, 1), subsy(scount + 1, 1)), subsr(scount + 1), QBColor(13)

scount = scount + 1

END SUB

SUB nitro4 ()

'Subroutine for nitro group construction scount = scount + 1
subsx(scount, 2) = subsx(scount - 1, 1)
subsy(scount, 2) = subsy(scount - 1, 1)
subsz(scount, 2) = subsz(scount - 1, 1)
subsx(scount + 1, 2) = subsx(scount - 1, 1)
subsy(scount + 1, 2) = subsy(scount - 1, 1)
subsz(scount + 1, 2) = subsz(scount - 1, 1)

Select Case state

Case 1
    subsz(scount, 1) = subsz(scount - 1, 1) + .407
    subsx(scount, 1) = subsx(scount - 1, 1) + .706
    subsy(scount, 1) = subsy(scount - 1, 1)
    subsz(scount + 1, 1) = subsz(scount - 1, 1) + .407
    subsx(scount + 1, 1) = subsx(scount - 1, 1) - .706
    subsy(scount + 1, 1) = subsy(scount - 1, 1)

Case 2
    subsz(scount, 1) = subsz(scount - 1, 1) - .407
    subsx(scount, 1) = subsx(scount - 1, 1) + .706
    subsy(scount, 1) = subsy(scount - 1, 1)
    subsz(scount + 1, 1) = subsz(scount - 1, 1) - .407
    subsx(scount + 1, 1) = subsx(scount - 1, 1) - .706
    subsy(scount + 1, 1) = subsy(scount - 1, 1)

Case 3
    subsz(scount, 1) = subsz(scount - 1, 1) - .407
    subsx(scount, 1) = subsx(scount - 1, 1) - .706
    subsy(scount, 1) = subsy(scount - 1, 1)
    subsz(scount + 1, 1) = subsz(scount - 1, 1) - .407
    subsx(scount + 1, 1) = subsx(scount - 1, 1) + .706
    subsy(scount + 1, 1) = subsy(scount - 1, 1)

Case 4
    subsz(scount, 1) = subsz(scount - 1, 1) - .407
```

```
    subsx(scount, 1) = subsx(scount - 1, 1) + .706
    subsy(scount, 1) = subsy(scount - 1, 1)
    subsz(scount + 1, 1) = subsz(scount - 1, 1) + .407
    subsx(scount + 1, 1) = subsx(scount - 1, 1) - .706
    subsy(scount + 1, 1) = subsy(scount - 1, 1)
.
.
.
End Select subsr(scount) = .55
subsc(scount) = 13
subsr(scount + 1) = .55
subsc(scount + 1) = 13 subt(scount) = 11
subt(scount + 1) = 11 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(13)
picture1.Line (subsx(scount + 1, 1), subsy(scount + 1, 1))-(subsx(scount + 1, 2), subsy(scount + 1, 2)),
QBColor(13)
picture1.Circle (subsx(scount + 1, 1), subsy(scount + 1, 1)), subsr(scount + 1), QBColor(13)

scount = scount + 1

END SUB

SUB nreplace ()

'Subroutine for replacing carbon atom with nitrogen xc = molecule(ik, 2)
yc = molecule(ik, 3)
zc = molecule(ik, 4)
picture1.Circle (xc, yc), .6, RGB(0, 0, 255)
picture2.Circle (xc, yc), .6, RGB(0, 0, 255)

If subst = 12 Then
molecule(ik, 9) = 17
subscount(12) = subscount(12) + 1

Else
molecule(ik, 9) = 18
subscount(13) = subscount(13) + 1

End If skelcol(ik) = 9
END SUB

SUB oreplace ()

'Subroutine for replacing carbon atom with ether oxygen
```

153

```
xc = molecule(ik, 2)
yc = molecule(ik, 3)
zc = molecule(ik, 4)
picture1.Circle (xc, yc), .6, RGB(0, 255, 255)
picture2.Circle (xc, yc), .6, RGB(0, 255, 255)
subscount(14) = subscount(14) + 1
molecule(ik, 9) = 13
skelcol(ik) = 3
END SUB SUB oxy1 ()

'Subroutine for ether construction

If molecule(ik, 6) = 0 Then
molecule(ik, 6) = 1
oreplace

Else
If molecule(ik, 7) = 0 Then
molecule(ik, 7) = 1
oreplace

Else
If molecule(ik, 8) = 0 Then
molecule(ik, 8) = 1
oreplace

End If
End If
End If

END SUB

SUB oxy2 ()

'Subroutine for ether construction

If molecule(ik, 7) = 0 Then
molecule(ik, 7) = 1
oreplace

Else
If molecule(ik, 8) = 0 Then
molecule(ik, 8) = 1
oreplace

Else
If molecule(ik, 5) = 0 Then
molecule(ik, 5) = 1
oreplace
```

End If
End If
End If

*END SUB*

*SUB* oxy3 ()

'Subroutine for ether construction

If molecule(ik, 6) = 0 Then
molecule(ik, 6) = 1
oreplace

Else
If molecule(ik, 5) = 0 Then
molecule(ik, 5) = 1
oreplace

Else
If molecule(ik, 8) = 0 Then
molecule(ik, 8) = 1
oreplace

End If
End If
End If

*END SUB*

*SUB* oxy4 ()

'Subroutine for ether construction

If molecule(ik, 6) = 0 Then
molecule(ik, 6) = 1
oreplace

Else
If molecule(ik, 7) = 0 Then
molecule(ik, 7) = 1
oreplace

Else
If molecule(ik, 5) = 0 Then
molecule(ik, 5) = 1
oreplace

End If
End If
End If

155

*END SUB*

*SUB* Picture1_Click ()

'Routine for saving current structure diagram as a bitmap assemble1
list
substitutes picture1.CurrentX = -6
picture1.CurrentY = -5
picture1.Print code
picture1.CurrentY = -6
picture1.CurrentX = -6
picture1.Print chemform SavePicture picture1.Image, "c:\amol1.bmp"

text3.Text = (text3.Text + 90) Mod 360
For i = 1 To codelength
w = length(x(i), z(i))

Select Case x(i)
    Case 0
        If z(i) > 0 Then
        theta = pi / 2
        Else
        theta = 3 * pi / 2
        End If
    Case Is > 0
        If z(i) >= 0 Then
        theta = at1(z(i) / x(i))
        Else theta = at3(z(i) / x(i))
        End If
    Case Is < 0
        If z(i) >= 0 Then
        theta = at2(z(i) / x(i))
        Else theta = at4(z(i) / x(i))
        End If End Select z(i) = w * Sin(theta + (pi / 2))
x(i) = w * Cos(theta + (pi / 2))

Next i picture1.Cls
```

156

```
picture2.Cls

For i = 0 To codelength - 1 picture1.Circle (x(i), y(i)), .6
picture1.Line (x(i + 1), y(i + 1))-(x(i), y(i))
picture2.Circle (x(i), y(i)), .6
picture2.Line (x(i + 1), y(i + 1))-(x(i), y(i))

Next i picture1.Circle (x(codelength), y(codelength)), .6
picture2.Circle (x(codelength), y(codelength)), .6

For i = 1 To hnumber
w = length(subsx(i, 1), subsz(i, 1))

Select Case subsx(i, 1)
   Case 0
      If subsz(i, 1) > 0 Then
      theta2 = pi / 2
      Else
      theta2 = 3 * pi / 2
      End If
   Case Is > 0
      If subsz(i, 1) >= 0 Then
      theta2 = at1(subsz(i, 1) / subsx(i, 1))
      Else theta2 = at3(subsz(i, 1) / subsx(i, 1))
      End If
   Case Is < 0
      If subsz(i, 1) >= 0 Then
      theta2 = at2(subsz(i, 1) / subsx(i, 1))
      Else theta2 = at4(subsz(i, 1) / subsx(i, 1))
      End If End Select subsz(i, 1) = w * Sin(theta2 + (pi / 2))
subsx(i, 1) = w * Cos(theta2 + (pi / 2))

Next i

For i = 1 To hnumber
w = length(subsx(i, 2), subsz(i, 2))

Select Case subsx(i, 2)
   Case 0
      If subsz(i, 2) > 0 Then
```

```
        theta3 = pi / 2
      Else
        theta3 = 3 * pi / 2
      End If
  Case Is > 0
    If subsz(i, 2) >= 0 Then
      theta3 = at1(subsz(i, 2) / subsx(i, 2))
      Else theta3 = at3(subsz(i, 2) / subsx(i, 2))
    End If
  Case Is < 0
    If subsz(i, 2) >= 0 Then
      theta3 = at2(subsz(i, 2) / subsx(i, 2))
      Else theta3 = at4(subsz(i, 2) / subsx(i, 2))
    End If End Select subsz(i, 2) = w * Sin(theta3 + (pi / 2))
subsx(i, 2) = w * Cos(theta3 + (pi / 2))

Next i picture1.ForeColor = QBColor(9)

For i = 1 To hnumber picture1.Circle (subsx(i, 1), subsy(i, 1)), subsr(i), QBColor(subsc(i))
picture1.Line (subsx(i, 2), subsy(i, 2))-(subsx(i, 1), subsy(i, 1))
Next i picture1.ForeColor = QBColor(0)

picture1.CurrentX = -6
picture1.CurrentY = -5
picture1.Print code
picture1.CurrentY = -6
picture1.CurrentX = -6
picture1.Print chemform SavePicture picture1.Image, "c:\amol2.bmp"

END SUB

SUB pmut ()

'POINT MUTATION ROUTINE

'Set location of point mutation
```

158

```
position = Int(1 + codelength * Rnd)
text8.Text = Str$(position)

'Routine to mutate primary code mutation = Trim$(Str$(Int(1 + 4 * Rnd)))
Mid$(code, position, 1) = mutation 'Routine to mutate secondary code 'calculate probability values from selection panel values tot = v1 + v2 + v3 + v4 + v5 + v6 + v7 + v8 + v9 + v10 t1 = 1 + v1
t2 = v1 + v2
t3 = t2 + 1
t4 = t2 + v3
t5 = t4 + 1
t6 = t4 + v4
t7 = t6 + 1
t8 = t6 + v5
t9 = t8 + 1
t10 = t8 + v6
t11 = t10 + 1
t12 = t10 + v7
t13 = t12 + 1
t14 = t12 + v8
t15 = t14 + 1
t16 = t14 + v9
t17 = t16 + 1
t18 = t16 + v10

If pring > 1 + Int(Rnd * 100) Then rings

Else s = Trim$(Str$(Int(1 + 4 * Rnd)))

If tc + td = 0 Then
hyd = 1
Else
hyd = (hscroll9.Value / 100)
```

```
End If

If Rnd <= hyd Then g = "a"
q = Trim$(Str$(Int(1 + 4 * Rnd)))

jhyd = jhyd + 1

Else

If (Rnd) < ng / 100 Then
g = "n"
j12 = j12 + 1

Else
If (Rnd) < pg / 100 Then
g = "p"
j13 = j13 + 1

Else
If (Rnd) < og / 100 Then
g = "o"
j14 = j14 + 1

Else

If (Rnd) < sg / 100 Then
g = "s"
j15 = j15 + 1

Else

'Assignment of string values for substituents

'start of primary code generating loop

'generation of random number

Rn = 1 + Int(tot * (Rnd(1)))

'generation of code sequence

Select Case Rn

Case 1 To v1 g = "b"

j1 = j1 + 1

Case t1 To t2
   g = "c"
   j2 = j2 + 1
```

160

```
Case t3 To t4
   g = "d"
   j3 = j3 + 1

Case t5 To t6
   g = "e"
   j4 = j4 + 1

Case t7 To t8
   g = "f"
   j5 = j5 + 1

Case t9 To t10
   g = "g"
   j6 = j6 + 1

Case t11 To t12
   g = "h"
   j7 = j7 + 1

Case t13 To t14
   g = "i"
   j8 = j8 + 1

Case t15 To t16
   g = "j"
   j9 = j9 + 1

Case t17 To t18
   g = "k"
   j10 = j10 + 1

End Select

End If
End If
End If
End If q = Trim$(Str$(Int(Rnd * 4) + 1))

End If

End If text45.Text = Mid$(oldcodet, position, 1) & "(" & Mid$(oldcodeq, position, 1) & ")" & Mid$(oldcode,
position, 1) & " ->" & g & "(" & q & ")" & Mid$(code, position, 1)
Mid$(codet, position, 1) = g Mid$(codeq, position, 1) = q codelength = Len(code)
```

161

```
coded = ""

For j = 1 To codelength coded = coded & Mid$(codet, j, 1) & "(" & Mid$(codeq, j, 1) & ")" & Mid$(code, j, 1) & " " & Chr$(126)

Next j text1.Text = coded assemble1
list
substitutes
```

*END SUB*

*SUB* pointmut ()

'POINT MUTATION ROUTINE

```
codelength = Len(code)

mi1 = "0"
mi2 = "0"
mi3 = "0 "
```

'Set location of point mutation

```
position = Int(1 + codelength * Rnd)
text8.Text = Str$(position)
```

'Routine to mutate primary code

If Rnd <= .67 Then mi3 = "3 "

```
s = Trim$(Str$(Int(1 + 4 * Rnd)))
Mid$(code, position, 1) = s
```

End If

'Routine to mutate secondary code

If Rnd <= .67 Then mi1 = "1"

'calculate probability values from selection panel values

162

```
tot = v1 + v2 + v3 + v4 + v5 + v6 + v7 + v8 + v9 + v10 t1 = 1 + v1
t2 = v1 + v2
t3 = t2 + 1
t4 = t2 + v3
t5 = t4 + 1
t6 = t4 + v4
t7 = t6 + 1
t8 = t6 + v5
t9 = t8 + 1
t10 = t8 + v6
t11 = t10 + 1
t12 = t10 + v7
t13 = t12 + 1
t14 = t12 + v8
t15 = t14 + 1
t16 = t14 + v9
t17 = t16 + 1
t18 = t16 + v10

If tc + td = 0 Then
hyd = 1
Else
hyd = (hscroll9.Value / 100)
End If

If Rnd <= hyd Then g = "a"
q = Trim$(Str$(Int(1 + 4 * Rnd)))

jhyd = jhyd + 1

Else

If (Rnd) < ng / 100 Then
g = "n"
j12 = j12 + 1

Else
If (Rnd) < pg / 100 Then
g = "p"
j13 = j13 + 1

Else
If (Rnd) < og / 100 Then
g = "o"
j14 = j14 + 1

Else
```

163

```
If (Rnd) < sg / 100 Then
g = "s"
j15 = j15 + 1

Else

'Assignment of string values for substituents

'start of primary code generating loop

'generation of random number

Rn = 1 + Int(tot * (Rnd(1)))

'generation of code sequence

Select Case Rn

Case 1 To v1 g = "b"

j1 = j1 + 1

Case t1 To t2
    g = "c"
    j2 = j2 + 1

Case t3 To t4
    g = "d"
    j3 = j3 + 1

Case t5 To t6
    g = "e"
    j4 = j4 + 1

Case t7 To t8
    g = "f"
    j5 = j5 + 1

Case t9 To t10
    g = "g"
    j6 = j6 + 1

Case t11 To t12
    g = "h"
    j7 = j7 + 1

Case t13 To t14
    g = "i"
    j8 = j8 + 1

Case t15 To t16
    g = "j"
```

164

```
        j9 = j9 + 1

Case t17 To t18
    g = "k"
    j10 = j10 + 1

End Select

End If
End If
End If
End If
End If

Mid$(codet, position, 1) = g

End If
'Routine for tertiary code

If Rnd <= .67 Then mi2 = "2"

q = Trim$(Str$(Int(Rnd * 4) + 1))
Mid$(codeq, position, 1) = q

End If

'Assemble code codelength = Len(code)

text45.Text = mi1 & mi2 & mi3 & Mid$(oldcodet, position, 1) & "(" & Mid$(oldcodeq, position, 1) & ")"
    & Mid$(oldcode, position, 1) & " ->" & Mid$(codet, position, 1) & "(" & Mid$(codeq, position, 1) & ")"
    & Mid$(code, position, 1)
```

*END SUB*

*SUB* proxim ()

'Subroutine for calculating proximity between receptor and ligand

```
t0 = Timer prox = 0
For j = 1 To fzmt
dipc = dipm(j)
If Abs(dipc) < 7 Then radc = radius(j)
margin = Int(radc + proxsense + .5)

x2c = xm(j)
```

165

```
y2c = ym(j)
z2c = ((zm(j) - zmm) + 1000) - mindiff

'bounds calculation xupper = min(maxx - centerx, Int(x2c + margin))
xlower = max(minx - centerx, Int(x2c - margin))
yupper = min(maxy - centery, Int(y2c + margin))
ylower = max(miny - centery, Int(y2c - margin))
zupper = min(maxz + 1 - minz, Int(z2c + margin))
zlower = max(1, Int(z2c - margin))

For xmg = xlower To xupper
For ymg = ylower To yupper

If zmat(xmg, ymg) <> 0 Then

For zmg = zlower To zupper

If z3mat(xmg, ymg, zmg) <> 0 Then distc = dist3d(xmg, ymg, zmg, x2c, y2c, z2c)

If distc <= radc + proxsense Then prox = prox + 1

End If

End If

Next zmg

End If

Next ymg
Next xmg

End If
Next j

END SUB

SUB pur1 ()
```

166

'Subroutine for pyridine construction

If molecule(ik, 6) = 0 Then
molecule(ik, 6) = 1
nreplace

Else
If molecule(ik, 7) = 0 Then
molecule(ik, 7) = 1
nreplace

Else
If molecule(ik, 8) = 0 Then
molecule(ik, 8) = 1
nreplace

End If
End If
End If

*END SUB*

*SUB* pur2 ()

'Subroutine for pyridine construction

If molecule(ik, 7) = 0 Then
molecule(ik, 7) = 1
nreplace

Else
If molecule(ik, 8) = 0 Then
molecule(ik, 8) = 1
nreplace

Else
If molecule(ik, 5) = 0 Then
molecule(ik, 5) = 1
nreplace

End If
End If
End If

*END SUB*

*SUB* pur3 ()

'Subroutine for pyridine construction

If molecule(ik, 6) = 0 Then
molecule(ik, 6) = 1
nreplace

```
        Else
        If molecule(ik, 5) = 0 Then
        molecule(ik, 5) = 1
        nreplace Else
        If molecule(ik, 8) = 0 Then
        molecule(ik, 8) = 1
        nreplace End If
        End If
        End If
```

*END SUB*

*SUB* pur4 ()

'Subroutine for pyridine construction

```
If molecule(ik, 6) = 0 Then
molecule(ik, 6) = 1
nreplace

Else
If molecule(ik, 7) = 0 Then
molecule(ik, 7) = 1
nreplace

Else
If molecule(ik, 5) = 0 Then
molecule(ik, 5) = 1
nreplace

End If
End If
End If
```

*END SUB*

*SUB* rings ()

'Subroutine for adding ring sequences to ligand codes

```
ringcount = ringcount + 1
text26.Text = ringcount circ = Int(Rnd * 6)

qq = ""
pp = ""
```

168

```
tot = v1 + v2 + v3 + v4 + v5 + v6 + v7 + v8 + v9 + v10 t1 = 1 + v1
t2 = v1 + v2
t3 = t2 + 1
t4 = t2 + v3
t5 = t4 + 1
t6 = t4 + v4
t7 = t6 + 1
t8 = t6 + v5
t9 = t8 + 1
t10 = t8 + v6
t11 = t10 + 1
t12 = t10 + v7
t13 = t12 + 1
t14 = t12 + v8
t15 = t14 + 1
t16 = t14 + v9
t17 = t16 + 1
t18 = t16 + v10

For k = 1 To 6 + circ

If tc + td = 0 Then
hyd = 1
Else
hyd = (hscroll9.Value / 100)
End If

If Rnd <= hyd Then

If Rnd > (wg / 100) Then g = "a"
q = Trim$(Str$(Int(1 + 4 * Rnd)))

Else g = "w"
q = Trim$(Str$(Int(1 + 4 * Rnd)))
ws = ws + 1
End If jhyd = jhyd + 1

Else

If (Rnd) < ng / 100 Then
g = "n"
j12 = j12 + 1

Else
If (Rnd) < pg / 100 Then
g = "p"
```

169

```
j13 = j13 + 1

Else
If (Rnd) < og / 100 Then
g = "o"
j14 = j14 + 1
Else

If (Rnd) < sg / 100 Then
g = "s"
j15 = j15 + 1

Else

'Assignment of string values for substituents

'start of primary code generating loop

'generation of random number

Rn = 1 + Int(tot * (Rnd(1)))

'generation of code sequence

Select Case Rn

Case 1 To t1 g = "b"

j1 = j1 + 1

Case t1 To t2
    g = "c"
    j2 = j2 + 1

Case t3 To t4
    g = "d"
    j3 = j3 + 1

Case t5 To t6
    g = "e"
    j4 = j4 + 1

Case t7 To t8
    g = "f"
    j5 = j5 + 1

Case t9 To t10
    g = "g"
    j6 = j6 + 1
```

```
Case t11 To t12
    g = "h"
    j7 = j7 + 1

Case t13 To t14
    g = "i"
    j8 = j8 + 1

Case t15 To t16
    g = "j"
    j9 = j9 + 1

Case t17 To t18
    g = "k"
    j10 = j10 + 1

End Select

End If
End If
End If
End If q = Trim$(Str$(Int(Rnd * 4) + 1))

End If gg = gg & g
qq = qq & q

Next k randring = 1 + Int(Rnd * 8)
rring = 1 + Int(Rnd * 3)

Select Case randring

Case 1
    ring = Mid$("431413431413431", rring, 6 + circ)

Case 2
    ring = Mid$("413431413431413", rring, 6 + circ)

Case 3
    ring = Mid$("1321321321321321", rring, 6 + circ)

Case 4
    ring = Mid$("1231231231231231", rring, 6 + circ)

Case 5
    ring = Mid$("421412421412421", rring, 6 + circ)

Case 6
    ring = Mid$("412421412421412", rring, 6 + circ)
```

170

```
Case 7
    ring = Mid$("4324234324423432", rmg, 6 + circ)

Case 8
    ring = Mid$("4234324234432423", rmg, 6 + circ)

End Select s = ring
g = gg
q = qq
```

END SUB

*SUB* sequencemut ()

'SEQUENCE MUTATION ROUTINE

```
startfrag = 1 + Int(Rnd * Len(code))
lenfrag = 1 + Int(Rnd * (Len(code) - startfrag))
text67.Text = Str$(startfrag)

codefrag1 = Mid$(code, startfrag, lenfrag)
codefrag2 = Mid$(codeq, startfrag, lenfrag)
codefrag3 = Mid$(codet, startfrag, lenfrag)

text63.Text = codefrag1 & " " & codefrag2 & " " & codefrag3

If Rnd <= pinv Then
m1s = "inv "
finvert
End If

If Rnd <= pdup Then
m2s = "dup "
fduplicate
End If

If Rnd <= pdel Then
m3s = "del "
fdelete
Else
frplace
End If

If Rnd <= pins Then
m4s = "ins "
finsert
End If text66.Text = m1s & m2s & m3s & m4s
```

172

*END SUB*

*SUB* singtest ()

'ROUTINE FOR TESTING A LIGAND AGAINST A SINGLE VIRTUAL RECEPTOR

'loading target

'prepare for display picture4.Cls
picture4.Scale (-7, 7)-(7, -7)

fzmmtest = atomcount + hnumber

'start loop to read in values from file for each atom

For i = 1 To atomcount xomtest(i) = 1.54 * molecule(i, 2)
yomtest(i) = 1.54 * molecule(i, 3)
zomtest(i) = 1.54 * molecule(i, 4)

radius1test(i) = dradius(molecule(i, 9))
cradius1test(i) = clradius(molecule(i, 9))
dipm1test(i) = dipoles(molecule(i, 9))

colrmtest(i) = colord(molecule(i, 9))

'divide positional coordinates by 100 and store

Next i
For i = 1 To hnumber xomtest(i + atomcount) = 1.54 * subsx(i, 1)
yomtest(i + atomcount) = 1.54 * subsy(i, 1)
zomtest(i + atomcount) = 1.54 * subsz(i, 1)

radius1test(i + atomcount) = dradius(subt(i))
cradius1test(i + atomcount) = clradius(subt(i))
dipm1test(i + atomcount) = dipoles(subt(i))

colrmtest(i + atomcount) = colord(subt(i))

'divide positional coordinates by 100 and store

Next i

'store grey color code

173

```
gcol = RGB(50, 50, 50)

'start loop to calculate collision matrix values

For i = 1 To fzmmtest zp = zomtest(i)
xp = xomtest(i)
yp = yomtest(i)
rp = radius1test(i)
sp = cradius1test(i)
colm = colrmtest(i)
'draw atoms using radius and collision radius picture4.Circle (xp, yp), rp, QBColor(colm)
'picture2.Circle (xp, yp), rp, gcol 'calculation of collision matrix sp = sp + .05

'start loop to calculate collision points

For j = Int(xp - sp) To Int(xp + sp + 1) To Int(xp + sp + 1)
For k = Int(yp - sp) To Int(yp + sp + 1)

'calculate distance from atom center dist = Sqr((xp - j) ^ 2 + (yp - k) ^ 2)

'if distance is less than radius, then set collision
'height matrix component to radius If dist <= rp Then 'draw collision point picture4.Circle (j, k), .2

Else

'if distance is less than collision radius (but greater than radius)
'set collision matrix component to radius/2

If dist <= sp Then

'draw point picture4.PSet (j, k)

End If

End If
```

Next k

Next j

Next i

Close 1

'draw grid on target frame picture4.Line (0, 20)-(0, -20)
picture4.Line (20, 0)-(-20, 0)

'TEST PRIMARY ROUTINE maxcombiscore = 0
sumcombi = 0

'initialise best score, bestscore and bestcode

'***** CREATE 3-D REPRESENTATION OF CODE *****

'Read in codes from code storage array
'Code index is codei

'load next code into h for processing

'Code is stored in h

'run decoder to create receptor decodes

'***START TESTS ON TARGETS ***

'report current target

'reinitialize random number counter and target coordinates for each test series randcount = 0

'Start target in original position for each test series
'get number of atoms and store in fzmt (also used in tester1)

fzmt = fzmmtest

For ti = 1 To fzmmtest

175

```
'read in original target coordinates preserved in xom, yom and zom xm(ti) = xomtest(ti)
ym(ti) = yomtest(ti)
zm(ti) = zomtest(ti)
radius(ti) = radius1test(ti)
cradius(ti) = cradius1test(ti)
dipm(ti) = dipm1test(ti)

Next ti

'start loop for test series

For testi = 1 To testnumber text58.Text = testi

'run test tester1

Next testi

'record maximum score for this code and clear maxscore for next cycle text42.Text = sumcombi
text57.Text = maxcombiscore mainscore = (((Abs(maxcombiscore - maxtarget)) / maxtarget) + ((Abs(sumcombi - sumtarget)) / sumtarget)) / 2
text73.Text = mainscore
END SUB SUB sreplace ()

'Subroutine for replacing carbon atom with sulfur xc = molecule(ik, 2)
yc = molecule(ik, 3)
zc = molecule(ik, 4)
picture1.Circle (xc, yc), .6, RGB(255, 255, 0)
picture2.Circle (xc, yc), .6, RGB(255, 255, 0)
subscount(15) = subscount(15) + 1
molecule(ik, 9) = 21
skelcol(ik) = 14

END SUB

FUNCTION strinv (fs As String) As String

'Subroutine for inverting a character string
```

```
outs = ""
lfs = Len(fs)

For i = lfs To 1 Step -1
outs = outs & Mid$(fs, i, 1)
Next i
strinv = outs
```

*END FUNCTION*

*SUB* sub1 ()
   Select Case state

Case 1 xh = xc - delx * sf yh = yc + dely * sf zh = zc - delz * sf xab = xaa - 1
   yab = yaa
   zab = zaa Case 2 xh = xc + delx * sf yh = yc - dely * sf zh = zc - delz * sf xab = xaa + 1
   yab = yaa
   zab = zaa Case 3 xh = xc - delx * sf yh = yc + dely * sf zh = zc + delz * sf xab = xaa - 1
   yab = yaa
   zab = zaa Case 4 xh = xc + delx * sf yh = yc - dely * sf

```
            zh = zc - delz * sf xab = xaa + 1
        yab = yaa
        zab = zaa End Select If occupy(xab, yab, zab) = 0 Then scount = scount + 1
    subsx(scount, 1) = xh
    subsy(scount, 1) = yh
    subsz(scount, 1) = zh
    subsx(scount, 2) = xc
    subsy(scount, 2) = yc
    subsz(scount, 2) = zc occupy(xab, yab, zab) = stype(subst)
    subt(scount) = stype(subst)
    subsr(scount) = .6 * sf
    subsc(scount) = scolor(subst)
    subscount(subst) = subscount(subst) + 1
    picture1.Line (xc, yc)-(xh, yh)
    picture1.Circle (xh, yh), subsr(scount), QBColor(scolor(subst))

If subst = 5 Then hyd1

End If

If subst = 7 Then cyan1

End If

If subst = 9 Then thiol1

End If

If subst = 6 Then ami1

End If

If subst = 8 Then nitro1
```

178

```
End If
End If
```

*END SUB*

*SUB* sub12 ()
   Select Case state

Case 1 xh = xc yh = yc + dely * sf zh = zc - delz * sf

Case 2 xh = xc yh = yc - dely * sf zh = zc + delz * sf

Case 3 xh = xc yh = yc + dely * sf zh = zc + delz * sf

Case 4 xh = xc yh = yc - dely * sf zh = zc - delz * sf

End Select

```
scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc subt(scount) = stype(subst)
molecule(ik, 9) = 9
```

```
subsr(scount) = .6 * sf
subsc(scount) = scolor(subst)
subscount(subst) = subscount(subst) + 1
picture1.Line (xc, yc)-(xh, yh)
picture1.Circle (xh, yh), subsr(scount), QBColor(scolor(subst))

END SUB

SUB sub13 ()
   Select Case state

Case 1 xh = xc - delx * sf yh = yc - dely * sf zh = zc - delz * sf

Case 2 xh = xc + delx * sf yh = yc + dely * sf zh = zc + delz * sf

Case 3 xh = xc - delx * sf yh = yc - dely * sf zh = zc + delz * sf

Case 4 xh = xc + delx * sf yh = yc + dely * sf zh = zc - delz * sf

End Select scount = scount + 1
subsx(scount, 1) = xh
subsy(scount, 1) = yh
subsz(scount, 1) = zh
subsx(scount, 2) = xc
subsy(scount, 2) = yc
```

180

```
subsz(scount, 2) = zc subt(scount) = stype(subst)
molecule(ik, 9) = 9 subsr(scount) = .6 * sf
subsc(scount) = scolor(subst)
subscount(subst) = subscount(subst) + 1 picture1.Line (xc, yc)-(xh, yh)
picture1.Circle (xh, yh), subsr(scount), QBColor(scolor(subst))
```

*END SUB*

*SUB* sub14 ()
   Select Case state

Case 1 xh = xc - delx * sf yh = yc - dely * sf zh = zc + delz * sf

Case 2 xh = xc + delx * sf yh = yc - dely * sf zh = zc - delz * sf

Case 3 xh = xc - delx * sf yh = yc + dely * sf zh = zc - delz * sf

Case 4 xh = xc + delx * sf yh = yc - dely * sf zh = zc + delz * sf

End Select

```
scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc subt(scount) = stype(subst)
molecule(ik, 9) = 9 subsr(scount) = .6 * sf
subsc(scount) = scolor(subst)
subscount(subst) = subscount(subst) + 1 picture1.Line (xc, yc)-(xh, yh)
picture1.Circle (xh, yh), subsr(scount), QBColor(scolor(subst))
```

*END SUB*

*SUB* sub2 ()
   Select Case state

Case 1 xh = xc + delx * sf yh = yc + dely * sf zh = zc - delz * sf xab = xaa + 1
   yab = yaa
   zab = zaa Case 2 xh = xc - delx * sf yh = yc - dely * sf zh = zc + delz * sf xab = xaa - 1
   yab = yaa
   zab = zaa Case 3 xh = xc + delx * sf yh = yc + dely * sf

```
zh = zc + delz * sf xab = xaa + 1
yab = yaa
zab = zaa

Case 4 xh = xc - delx * sf yh = yc - dely * sf zh = zc - delz * sf xab = xaa - 1
yab = yaa
zab = zaa End Select If occupy(xab, yab, zab) = 0 Then scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc occupy(xab, yab, zab) = stype(subst)
subt(scount) = stype(subst)

subsr(scount) = .6 * sf
subsc(scount) = scolor(subst)
subscount(subst) = subscount(subst) + 1 picture1.Line (xc, yc)-(xh, yh)
picture1.Circle (xh, yh), subsr(scount), QBColor(scolor(subst))

If subst = 5 Then hyd1

End If

If subst = 7 Then cyan2

End If
```

182

183

```
If subst = 9 Then thiol1

End If

If subst = 6 Then ami2

End If

If subst = 8 Then nitro2

End If
End If
```

*END SUB*

*SUB* sub23 ()
```
    Select Case state

Case 1 xh = xc + delx * sf yh = yc - dely * sf zh = zc - delz * sf

Case 2 xh = xc - delx * sf yh = yc + dely * sf zh = zc + delz * sf

Case 3 xh = xc + delx * sf yh = yc - dely * sf zh = zc + delz * sf

Case 4 xh = xc - delx * sf yh = yc + dely * sf
```

184

```
            zh = zc - delz * sf

End Select scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc subt(scount) = stype(subst)
molecule(ik, 9) = 9 subsr(scount) = .6 * sf
subsc(scount) = scolor(subst)
subscount(subst) = subscount(subst) - 1 picture1.Line (xc, yc)-(xh, yh)
picture1.Circle (xh, yh), subsr(scount), QBColor(scolor(subst))
```

*END SUB*

*SUB* sub24 ()
   Select Case state

Case 1 xh = xc + delx * sf yh = yc + dely * sf zh = zc + delz * sf

Case 2 xh = xc - delx * sf yh = yc - dely * sf zh = zc - delz * sf

Case 3 xh = xc + delx * sf yh = yc + dely * sf

```
        zh = zc - delz * sf

Case 4 xh = xc - delx * sf yh = yc - dely * sf zh = zc + delz * sf

End Select scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc subt(scount) = stype(subst)
molecule(ik, 9) = 9 subsr(scount) = .6 * sf
subsc(scount) = scolor(subst)
subscount(subst) = subscount(subst) + 1 picture1.Line (xc, yc)-(xh, yh)
picture1.Circle (xh, yh), subsr(scount), QBColor(scolor(subst))

END SUB

SUB sub3 ()
    Select Case state

Case 1 xh = xc yh = yc - del2y * sf zh = zc - delz * sf xab = xaa
        yab = yaa - 1
        zab = zaa Case 2 xh = xc
```

185

186

```
yh = yc + del2y * sf zh = zc + delz * sf xab = xaa
yab = yaa + 1
zab = zaa

Case 3 xh = xc yh = yc - del2y * sf zh = zc + delz * sf xab = xaa
yab = yaa - 1
zab = zaa Case 4 xh = xc yh = yc + del2y * sf zh = zc - delz * sf xab = xaa
yab = yaa + 1
zab = zaa End Select If occupy(xab, yab, zab) = 0 Then scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc occupy(xab, yab, zab) = stype(subst)
subt(scount) = stype(subst)

subsr(scount) = .6 * sf
subsc(scount) = scolor(subst)
subscount(subst) = subscount(subst) + 1 picture1.Line (xc, yc)-(xh, yh)
picture1.Circle (xh, yh), subsr(scount), QBColor(scolor(subst))
```

```
If subst = 5 Then
hyd1
End If

If subst = 7 Then
cyan3
End If

If subst = 9 Then
thiol1
End If

If subst = 6 Then
ami3
End If

If subst = 8 Then
nitro3
End If
End If
```
*END SUB*

*SUB* sub34 ()
```
  Select Case state

Case 1 xh = xc yh = yc - del2y * sf zh = zc + delz * sf

Case 2 xh = xc yh = yc + del2y * sf zh = zc - delz * sf

Case 3
```

188

```
        xh = xc yh = yc - del2y * sf zh = zc - delz * sf

Case 4 xh = xc yh = yc + del2y * sf zh = zc + delz * sf

End Select scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc subt(scount) = stype(subst)
molecule(ik, 9) = 9 subsr(scount) = .6 * sf
subsc(scount) = scolor(subst)
subscount(subst) = subscount(subst) + 1 picture1.Line (xc, yc)-(xh, yh)
picture1.Circle (xh, yh), subsr(scount), QBColor(scolor(subst))
```

*END SUB*

***SUB* sub4 ()**
   Select Case state

Case 1 xh = xc yh = yc zh = zc + sf xab = xaa
   yab = yaa
   zab = zaa + 1

Case 2 xh = xc yh = yc zh = zc - sf xab = xaa
yab = yaa
zab = zaa - 1

Case 3 xh = xc yh = yc zh = zc - sf xab = xaa
yab = yaa
zab = zaa - 1

Case 4 xh = xc yh = yc zh = zc + sf xab = xaa
yab = yaa
zab = zaa + 1

End Select

If occupy(xab, yab, zab) = 0 Then scount = scount + 1
subsx(scount, 1) = xh
subsy(scount, 1) = yh
subsz(scount, 1) = zh
subsx(scount, 2) = xc
subsy(scount, 2) = yc
subsz(scount, 2) = zc occupy(xab, yab, zab) = stype(subst)
subt(scount) = stype(subst)

subsr(scount) = .6 * sf
subsc(scount) = scolor(subst)

190

```
subscount(subst) = subscount(subst) + 1 picture1.Line (xc, yc)-(xh, yh)
picture1.Circle (xh, yh), subsr(scount), QBColor(scolor(subst))

If subst = 5 Then hyd2

End If

If subst = 7 Then cyan4

End If

If subst = 9 Then thiol2

End If

If subst = 6 Then ami4

End If

If subst = 8 Then nitro4

End If

End If
```

*END SUB*

*SUB* substitutes ()

```
'LIGAND SUBSTITUTION CONSTRUCTION ROUTINE
'PART 2 of ligand code translation
'builds substituted carbon skeleton
'
'Values for the OCCUPY(i,j,k) matrix '0 = unoccupied
'1 = Alkyl Hydrogen
'2 = Hydroxy Hydrogen
'3 = Thiol Hydrogen
'4 = Amine Hydrogen
'5 = Flourine
```

191

```
'6 = Chlorine
'7 = Bromine
'8 = Alkyl Carbon
'9 = Alkenyl Carbon
'10 = Hydroxy Oxygen
'11 = Nitro Oxygen
'12 = Keto Oxygen
'13 = Ether / Pyran Oxygen
'14 = Amino Nitrogen
'15 = Cyano Nitrogen
'16 = Nitro Nitrogen
'17 = Pyrrole Nitrogen
'18 = Pyrido Nitrogen
'19 = Thiol Sulfur
'20 = Thione Sufur
'21 = Sulphide Sulfur 'Values for substituents
'a=1=hydrogen
'b=2=flourine
'c=3=chlorine
'd=4=bromine
'e=5=hydroxyl group
'f=6=amine
'g=7=cyano
'h=8=nitro
'k=9=thiol
'i=10=ketone
'j=11=thione
'n=12=pyrrole
'p=13=pyridine
'o=14=ether/pyran
's=15=sulfide/thiophene list3.Clear Erase subscount Erase subsx Erase subsy Erase subsz Erase subsr Erase subsc sscale(0) = .701
sscale(1) = .701
sscale(2) = .883
sscale(3) = 1.15
```

192

```
sscale(4) = 1.25
sscale(5) = .929
sscale(6) = .961
sscale(7) = .891
sscale(8) = .961
sscale(9) = 1.1
sscale(10) = .8
sscale(11) = .8
sscale(16) = .701 scolor(0) = 12
scolor(1) = 12
scolor(2) = 10
scolor(3) = 2
scolor(4) = 5
scolor(5) = 11
scolor(6) = 9
scolor(7) = 0
scolor(8) = 9
scolor(9) = 14
scolor(10) = 13
scolor(11) = 14
scolor(16) = 12 stype(0) = 1
stype(1) = 1
stype(2) = 5
stype(3) = 6
stype(4) = 7
stype(5) = 10
stype(6) = 14
stype(7) = 15
stype(8) = 16
stype(9) = 19
stype(10) = 12
stype(11) = 20
stype(12) = 17
stype(13) = 18
stype(14) = 13
stype(15) = 21
stype(16) = 1 delx = .75 dely = .43
delz = .5
del2y = .864
rcarb = 6 scount = 0
```

193

```
For i = 1 To atomcount
ik = i picture1.ForeColor = QBColor(9)

state = molecule(i, 1)

xc = molecule(i, 2)
yc = molecule(i, 3)
zc = molecule(i, 4)

atype = molecule(i, 9)

xaa = rcx(i)
yaa = rcy(i)
zaa = rcz(i)

'Routine for destauration (requires two empty valences)

If molecule(i, 5) = 0 Then subst = molecule(i, 11)
sf = sscale(subst)

If subst = 16 Then
keto1
End If

End If

If molecule(i, 6) = 0 Then subst = molecule(i, 12)
sf = sscale(subst)

If subst = 16 Then
keto2
End If

End If

If molecule(i, 7) = 0 Then subst = molecule(i, 13)
sf = sscale(subst)

If subst = 16 Then
keto3

End If

End If
```

194

```
If molecule(i, 8) = 0 Then subst = molecule(i, 14)
sf = sscale(subst)

If subst = 16 Then
keto4

End If

End If

'Routine for adding Osp3 oxygens to skeleton

If molecule(i, 5) = 0 Then subst = molecule(i, 11)
sf = sscale(subst)

If subst = 14 Then oxy1

End If

End If

If molecule(i, 6) = 0 Then subst = molecule(i, 12)
sf = sscale(subst)

If subst = 14 Then oxy2

End If

End If

If molecule(i, 7) = 0 Then subst = molecule(i, 13)
sf = sscale(subst)

If subst = 14 Then oxy3

End If

End If
```

195

```
If molecule(i, 8) = 0 Then subst = molecule(i, 14)
sf = sscale(subst)

If subst = 14 Then oxy4

End If

End If

'Routine for adding Nsp2 nitrogens to skeleton

If molecule(i, 5) = 0 Then subst = molecule(i, 11)
sf = sscale(subst)

If subst = 13 Then pur1

End If

End If

If molecule(i, 6) = 0 Then subst = molecule(i, 12)
sf = sscale(subst)

If subst = 13 Then pur2

End If

End If

If molecule(i, 7) = 0 Then subst = molecule(i, 13)
sf = sscale(subst)

If subst = 13 Then pur3

End If

End If
```

196

```
If molecule(i, 8) = 0 Then subst = molecule(i, 14)
sf = sscale(subst)

If subst = 13 Then pur4

End If

End If

'Routine for adding Ssp3 sulfurs to skeleton

If molecule(i, 5) = 0 Then subst = molecule(i, 11)
sf = sscale(subst)

If subst = 15 Then sul1

End If

End If

If molecule(i, 6) = 0 Then subst = molecule(i, 12)
sf = sscale(subst)

If subst = 15 Then sul2

End If

End If

If molecule(i, 7) = 0 Then subst = molecule(i, 13)
sf = sscale(subst)

If subst = 15 Then sul3

End If

End If
```

197

```
If molecule(i, 8) = 0 Then subst = molecule(i, 14)
sf = sscale(subst)

If subst = 15 Then sul4

End If

End If

'Routine for adding Nsp3 nitrogens to skeleton

If molecule(i, 5) = 0 Then subst = molecule(i, 11)
sf = sscale(subst)

If subst = 12 Then nreplace

End If

End If

If molecule(i, 6) = 0 Then subst = molecule(i, 12)
sf = sscale(subst)

If subst = 12 Then nreplace

End If

End If

If molecule(i, 7) = 0 Then subst = molecule(i, 13)
sf = sscale(subst)

If subst = 12 Then nreplace

End If
```

198

End If

If molecule(i, 8) = 0 Then subst = molecule(i, 14)
sf = sscale(subst)

If subst = 12 Then nreplace

End If

End If

'Routine for adding ketones (requires two empty valences)

If molecule(i, 5) = 0 Then subst = molecule(i, 11)
sf = sscale(subst)

If subst = 10 Then
keto1
End If

End If

If molecule(i, 6) = 0 Then subst = molecule(i, 12)
sf = sscale(subst)

If subst = 10 Then
keto2
End If

End If

If molecule(i, 7) = 0 Then subst = molecule(i, 13)
sf = sscale(subst)

If subst = 10 Then
keto3

End If

End If

If molecule(i, 8) = 0 Then

```
subst = molecule(i, 14)
sf = sscale(subst)

If subst = 10 Then
keto4

End If

End If

'Routine for adding thiones

If molecule(i, 5) = 0 Then subst = molecule(i, 11)
sf = sscale(subst)

If subst = 11 Then
thio1
End If

End If

If molecule(i, 6) = 0 Then subst = molecule(i, 12)
sf = sscale(subst)

If subst = 11 Then
thio2
End If

End If

If molecule(i, 7) = 0 Then subst = molecule(i, 13)
sf = sscale(subst)

If subst = 11 Then
thio3

End If

End If

If molecule(i, 8) = 0 Then subst = molecule(i, 14)
sf = sscale(subst)

If subst = 11 Then
```

```
                                                                        200 thio4

End If

End If

'Routine for adding single valence substituents

If molecule(i, 5) = 0 Then subst = molecule(i, 11)
sf = sscale(subst)

If subst < 10 Then
sub1
End If

End If

If molecule(i, 6) = 0 Then subst = molecule(i, 12)
sf = sscale(subst)

If subst < 10 Then
sub2
End If

End If

If molecule(i, 7) = 0 Then subst = molecule(i, 13)
sf = sscale(subst)

If subst < 10 Then
sub3
End If

End If

If molecule(i, 8) = 0 Then subst = molecule(i, 14)
sf = sscale(subst)

If subst < 10 Then
sub4
End If
End If

Next i
```

201

```
hnumber = scount picture1.ForeColor = QBColor(0)

For m = 1 To atomcount lstr = "C" & Trim$(Str$(m)) & " " & Str$(Int(154 * molecule(m, 2)) / 100) & " " & Str$(Int(154 *
molecule(m, 3)) / 100) & " " & Str$(Int(154 * molecule(m, 4)) / 100) & " " & Str$(molecule(m, 9))

list3.AddItem lstr

Next m

For m = 1 To hnumber list3.AddItem "S" & Trim$(Str$(m)) & " " & Str$(Int(154 * subsx(m, 1)) / 100) & " " & Str$(Int(154 *
subsy(m, 1)) / 100) & " " & Str$(Int(154 * subsz(m, 1)) / 100) & " " & Str$(subt(m))

Next m

'Formula builder htx = " H" & Str$(subscount(0) + subscount(1) + subscount(16))
If subscount(2) <> 0 Then
ftx = " F " & Trim$(Str$(subscount(2)))
End If
If subscount(3) <> 0 Then
ctx = " Cl " & Trim$(Str$(subscount(3)))
End If
If subscount(4) <> 0 Then
btx = " Br " & Trim$(Str$(subscount(4)))
End If
If subscount(5) <> 0 Then
otx = " OH " & Trim$(Str$(subscount(5)))
End If
If subscount(6) <> 0 Then
ntx = " NH2 " & Trim$(Str$(subscount(6)))
End If
If subscount(7) <> 0 Then
ytx = " CN " & Trim$(Str$(subscount(7)))
End If
If subscount(8) <> 0 Then
ttx = " NO2 " & Trim$(Str$(subscount(8)))
End If
If subscount(9) <> 0 Then
stx = " SH " & Trim$(Str$(subscount(9)))
End If
If subscount(10) <> 0 Then
ktx = " O= " & Trim$(Str$(subscount(10)))
End If
If subscount(11) <> 0 Then
ytx = " S= " & Trim$(Str$(subscount(11)))
```

```
End If
If subscount(12) <> 0 Then
    hn1 = " [N1= " & Trim$(Str$(subscount(12))) & "]"
End If
If subscount(13) <> 0 Then
    hn2 = " [N2= " & Trim$(Str$(subscount(13))) & "]"
End If
If subscount(14) <> 0 Then
    ho = " [O= " & Trim$(Str$(subscount(14))) & "]"
End If
If subscount(15) <> 0 Then
    hs = " [S= " & Trim$(Str$(subscount(15))) & "]"
End If heterocycle = subscount(12) + subscount(13) + subscount(14) + subscount(15)

'Formula display chemform = "C" & Str$(atomcount - heterocycle) & hn1 & hn2 & ho & hs & htx & ftx & ctx & btx & otx
& ntx & ytx & ttx & ktx & stx
text29.Text = chemform
END SUB SUB sul1 ()

'Subroutine for adding sulphide

If molecule(ik, 6) = 0 Then
    molecule(ik, 6) = 1
    sreplace

Else
If molecule(ik, 7) = 0 Then
    molecule(ik, 7) = 1
    sreplace

Else
If molecule(ik, 8) = 0 Then
    molecule(ik, 8) = 1
    sreplace

End If
End If
End If

END SUB

SUB sul2 ()

'Subroutine for adding sulphide
```

```
If molecule(ik, 7) = 0 Then
molecule(ik, 7) = 1
sreplace

Else
If molecule(ik, 8) = 0 Then
molecule(ik, 8) = 1
sreplace

Else
If molecule(ik, 5) = 0 Then
molecule(ik, 5) = 1
sreplace

End If
End If
End If
```

*END SUB*

*SUB* sul3 ()

'Subroutine for adding sulphide

```
If molecule(ik, 6) = 0 Then
molecule(ik, 6) = 1
sreplace

Else
If molecule(ik, 5) = 0 Then
molecule(ik, 5) = 1
sreplace

Else
If molecule(ik, 8) = 0 Then
molecule(ik, 8) = 1
sreplace

End If
End If
End If
```

*END SUB*

*SUB* sul4 ()

'Subroutine for adding sulphide

```
If molecule(ik, 6) = 0 Then
molecule(ik, 6) = 1
sreplace

Else
```

204

```
If molecule(ik, 7) = 0 Then
molecule(ik, 7) = 1
sreplace

Else
If molecule(ik, 5) = 0 Then
molecule(ik, 5) = 1
sreplace

End If
End If
End If
```

*END SUB*

*SUB* tester1 ()

'AFFINITY TESTING ROUTINE

'Erase target coordinate vectors to start cycle
'these vectors store updated target locations

```
Erase tarj
Erase tark
Erase tarz
```

'Set target count to zero for start of each cycle tarcount = 0

'Set up picture to display target picture4.Cls

```
picture3.Cls
picture3.BackColor = RGB(0, 0, 0)
picture3.Scale (-15, 15)-(15, -15)
```

'Draw frame

```
picture3.Line (-15, 0)-(15, 0), RGB(255, 255, 255)
picture3.Line (0, -15)-(0, 15), RGB(255, 255, 255)
```

'Set color scale cfac = 255 / (maxz - minz)

'Draw height matrix

```
For i = maxy - centery To miny - centery Step -1
    For j = minx - centerx To maxx - centerx
```

205

```
    ac = cfac * zmat(j, i)

If ac <> 0 Then colr = RGB(120, ac, ac)

picture3.Line (j + .25, i + .25)-(j - .25, i - .25), colr, BF

End If

Next j

Next i

'Save picture properties oldstyle = picture3.FillStyle
oldcolor = picture3.FillColor 'set picture values to draw charge sites picture3.FillStyle = 0

'Draw charge sites

For ii = 1 To c1

If zmat(xcz(ii), ycz(ii)) = zcz(ii) Then picture3.FillColor = QBColor(10)
colz = QBColor(10)

Else picture3.FillColor = QBColor(2)
colz = QBColor(2)

End If picture3.Circle (xcz(ii), ycz(ii)), 1, colz

Next ii

For ii = 1 To c1neg
gtx = zmat(xczneg(ii), yczneg(ii))
If gtx = zczneg(ii) Then picture3.FillColor = QBColor(12)
colz = QBColor(12)

Else
```

206

```
picture3.FillColor = QBColor(4)
colz = QBColor(4)

End If picture3.Circle (xczneg(ii), yczneg(ii)), 1, colz

Next ii

'reset picture values picture3.FillStyle = oldstyle
picture3.FillColor = oldcolor 'Set random numbers for angle changes: Note-series stored in randarray
'Same series used for each test series 'Get random change for z rz = 6 * Int(randarray(randcount) * 60)

'advance counter randcount randcount = randcount + 1

'Calculate angle rrz = (rz / 6) * pi / 30

'Get random change for y ry = 6 * Int(randarray(randcount) * 60)

'advance counter randcount = randcount + 1

'Calculate angle rry = (ry / 6) * pi / 30

'Get random value for x rx = 6 * Int(randarray(randcount) * 60)

'Advance counter randcount = randcount + 1

'calculate angle rrx = (rx / 6) * pi / 30
```

207

```
'Random y translation xtrans = transval - Int(randarray(randcount) * (transval * 2 + 1))

randcount = randcount + 1

'set z rotation

'loop to calculate transformed coordinates of centers

For i = 1 To fzmt

'Calculate length to centers w = length(xm(i), ym(i))

'Transformation logic for 3-d rotations

'Set z rotation

Select Case xm(i)
   Case 0
      If ym(i) > 0 Then
      theta = pi / 2
      Else
      theta = 3 * pi / 2
      End If
   Case Is > 0
      If ym(i) >= 0 Then
      theta = at1(ym(i) / xm(i))
      Else theta = at3(ym(i) / xm(i))
      End If
   Case Is < 0
      If ym(i) >= 0 Then
      theta = at2(ym(i) / xm(i))
      Else theta = at4(ym(i) / xm(i))
      End If End Select ym(i) = w * Sin(theta + rrz)
xm(i) = w * Cos(theta + rrz)

Next i

'Set y rotation

For i = 1 To fzmt
w = length(xm(i), zm(i))
```

208

```
Select Case xm(i)
   Case 0
      If zm(i) > 0 Then
      theta = pi / 2
      Else
      theta = 3 * pi / 2
      End If
   Case Is > 0
      If zm(i) >= 0 Then
      theta = at1(zm(i) / xm(i))
      Else theta = at3(zm(i) / xm(i))
      End If
   Case Is < 0
      If zm(i) >= 0 Then
      theta = at2(zm(i) / xm(i))
      Else theta = at4(zm(i) / xm(i))
      End If End Select zm(i) = w * Sin(theta + rry)
xm(i) = w * Cos(theta + rry)

Next i

'Set x rotation

For i = 1 To fzmt w = length(ym(i), zm(i))

Select Case ym(i)
   Case 0
      If zm(i) > 0 Then
      theta = pi / 2
      Else
      theta = 3 * pi / 2
      End If
   Case Is > 0
      If zm(i) >= 0 Then
      theta = at1(zm(i) / ym(i))
      Else theta = at3(zm(i) / ym(i))
      End If
   Case Is < 0
      If zm(i) >= 0 Then
      theta = at2(zm(i) / ym(i))
      Else theta = at4(zm(i) / ym(i))
      End If End Select
```

209

```
zm(i) = w * Sin(theta + rrx)
ym(i) = w * Cos(theta + rrx)

Next i gcol = RGB(150, 150, 150)

picture4.Cls

'load target coordinates and data

For i = 1 To fzmt zp = zm(i)
xp = xm(i) + xtrans
yp = ym(i)
rp = radius(i)
sp = cradius(i)

'draw transformed target

'picture4.Circle (xp, yp), sp, gcol
picture4.Circle (xp, yp), rp, gcol

'Set spacing value sp = sp + .05

'Create target surface matrix
'These calculations center the target
'use int() to round values to nearest coordinate point For j = Int(xp - sp) To Int(xp + sp + 1)
For k = Int(yp - sp) To Int(yp + sp + 1)

'Calculate height of target surface dist = Sqr((xp - j) ^ 2 + (yp - k) ^ 2)

'Simplify target surface

If dist <= rp Then

'if point is within 1 radius of center set height to z value minus radius

'Draw target surface picture4.Circle (j, k), .2

'Load target surface into storage vectors
'Increment counter for storage vector
```

```
tarcount = tarcount + 1

'Redimension storage vectors, preserving current data

ReDim Preserve tarj(tarcount) As Integer
tarj(tarcount) = j
ReDim Preserve tark(tarcount) As Integer
tark(tarcount) = k
ReDim Preserve tarz(tarcount) As Double
tarz(tarcount) = zp - rp Else If dist <= sp Then 'if point is within 1 radius + 1 set height to z value - one half radius 'draw target surface picture4.PSet (j, k)

'Store data in vectors tarcount = tarcount + 1

ReDim Preserve tarj(tarcount) As Integer
tarj(tarcount) = j
ReDim Preserve tark(tarcount) As Integer
tark(tarcount) = k
ReDim Preserve tarz(tarcount) As Double
tarz(tarcount) = zp - (rp / 2)

End If

End If

Next k

Next j

Next i

'Start contact calculations
'Part 1:
'Determine point of minimum separation zmm = 100000

'Set initial minimum separation mindiff = 100000

'Load target height values
```

211

```
For ti = 1 To tarcount xtxt = tarj(ti)
ytxt = tark(ti)
ztxt = tarz(ti)

'get target surface minimum to normalise target surface

If zmm > ztxt Then

'find minimum value of z for substrate and store in zmm zmm = ztxt

End If

Next ti

'Load target height vectors

For ti = 1 To tarcount xtxt = tarj(ti)
ytxt = tark(ti)
ztxt = tarz(ti)

'Calculate target height matrix
'Draw target surface
'check that points are within receptor matrix If (xtxt <= (maxx - centerx)) And (ytxt <= (maxy - centery)) Then
If (xtxt >= (minx - centerx)) And (ytxt >= (miny - centery)) Then picture3.Circle (xtxt, ytxt), 5, RGB(255, 255, 0)

'Get height value of receptor surface at position xtxt, ytxt from zmat zrec = zmat(xtxt, ytxt)

'check that there is a receptor under the substrate
'if not, skip calculation

If zrec <> 0 Then

'Calculate difference in receptor and target heights
'get the height of the substrate at xtxt,ytxt '(ztxt-zmm) is the normalized value of the substrate
'(maxz+1-minz) is the maximum value of the zmat matrix (all of it!)
'adding these values ensures that all the values of the substrate are above the receptor
```

212

```
'ALTERNATIVE LINE
diff = (ztxt - zmm) + (1000) - zrec

'transx = (ztxt - zmm) + maxz + 1 - minz

'diff = the separation between the substrate and the receptor

'diff = transx - zrec

'Track minimal difference

If mindiff > diff Then
mindiff = diff
xlow = xtxt
ylow = ytxt
End If
End If
End If
End If Next ti 'Loop 'if the mindiff value has not changed then the substrate
'has missed the receptor, in which case don't continue
'calculations If mindiff <> 100000 Then picture3.Circle (xlow, ylow), 1, RGB(125, 255, 0)

'Calculate score
'the following section calculates the separation between the receptor and substrate charge sites score = 0 sumdist = 0 ncnt = 0

'calculation for positive charge sites

For i = 1 To c1

For j = 1 To fzmt

'Multiply by -1 to make negative dipoles attracted to positive charge sites dipc = -1 * dipm(j)
```

213

```
'only do calculation if there is a dipole moment

If dipc <> 0 Then

'get receptor charge coordinates x1c = xcz(i)
y1c = ycz(i)
z1c = zcz(i) - .5

'get substrate site locations x2c = xm(j)
y2c = ym(j)

'calculate the collision height of the substrate
'Alternative z2c = ((zm(j) - zmm) + 1000) - mindiff 'z2c = ((zm(j) - zmm) + maxz + 1 - minz) - mindiff 'calculate distance between charge sites distc = dist3d(x1c, y1c, z1c, x2c, y2c, z2c)

'calculate approximate value of electrostatic energy scorec = dipc / (distc ^ coeff)

'sum to obtain updated score score = score + scorec sumdist = sumdist + distc ncnt = ncnt + 1

End If

Next j
Next i

'calculation for positive charge sites

For i = 1 To c1neg

For j = 1 To fzmt

'Multiply by +1 to make negative dipoles repelled by positive charge sites dipc = dipm(j)

'only do calculation if there is a dipole moment
```

214

```
If dipc <> 0 Then

'get receptor charge coordinates x1c = xczneg(i)
    y1c = yczneg(i)
    z1c = zczneg(i) - .5

'get substrate site locations x2c = xm(j)
    y2c = ym(j)

'calculate the collision height of the substrate
    'Alternative z2c = ((zm(j) - zmm) + 1000) - mindiff 'z2c = ((zm(j) - zmm) + maxz + 1 - minz) - mindiff 'calculate distance between charge sites distc = dist3d(x1c, y1c, z1c, x2c, y2c, z2c)

'calculate approximate value of electrostatic energy scorec = dipc / (distc ^ coeff)

'sum to obtain updated score score = score + scorec sumdist = sumdist + distc ncnt = ncnt + 1

End If

Next j
Next i

'********* A sophisticated (and very fast!!!!!) proximity detector proxim

'*********

'Display results

'Calculate proximity score as proportion of receptor points
```

215

```
'within proximity margin proxscore = prox / Len(h)

'calculate combined score as product combiscore = Int(proxscore * ((prox / 10000) + score) * 1000000) / 1000

'Accumulate combiscores for this test series sumcombi = sumcombi + combiscore

'Track maximum affinity scores

If combiscore > maxcombiscore Then maxcombiscore = combiscore
'text42.Text = maxcombiscore If maxcombiscore > mxscore Then
mxscore = maxcombiscore mxtest = transtest
mxtarget = transtarget End If End If End If

END SUB

SUB Text10_Change ()

'display of current z angle, updated by rotation control

END SUB

SUB Text3_Change ()

'display of current y angle, updated by rotation control

END SUB

SUB Text4_Change ()

'display of current x angle, updated by rotation
```

216

*END SUB*

*SUB* thio1 ()

'Subroutine for adding thiones

```
If molecule(ik, 6) = 0 Then
molecule(ik, 6) = 1
sub12
Else
If molecule(ik, 7) = 0 Then
molecule(ik, 7) = 1
sub13
Else
If molecule(ik, 8) = 0 Then
molecule(ik, 8) = 1
sub14
End If
End If
End If
```

*END SUB*

*SUB* thio2 ()

'Subroutine for adding thiones

```
If molecule(ik, 7) = 0 Then
molecule(ik, 7) = 1
sub23
Else
If molecule(ik, 8) = 0 Then
molecule(ik, 8) = 1
sub24
Else
If molecule(ik, 5) = 0 Then
molecule(ik, 5) = 1
sub12
End If
End If
End If
```

*END SUB*

*SUB* thio3 ()

'Subroutine for adding thiones

```
If molecule(ik, 6) = 0 Then
molecule(ik, 6) = 1
sub23
Else
If molecule(ik, 5) = 0 Then
```

217

```
molecule(ik, 5) = 1
sub13
Else
If molecule(ik, 8) = 0 Then
molecule(ik, 8) = 1
sub34
End If
End If
End If
```

*END SUB*

***SUB* thio4 ()**

'Subroutine for adding thiones

```
If molecule(ik, 6) = 0 Then
molecule(ik, 6) = 1
sub4
Else
If molecule(ik, 7) = 0 Then
molecule(ik, 7) = 1
sub4
Else
If molecule(ik, 5) = 0 Then
molecule(ik, 5) = 1
sub4
End If
End If
End If
```

*END SUB*

***SUB* thiol1 ()**

'Subroutine for adding thiol group

```
scount = scount + 1
subsx(scount, 2) = subsx(scount - 1, 1)
subsy(scount, 2) = subsy(scount - 1, 1)
subsz(scount, 2) = subsz(scount - 1, 1)

subsx(scount, 1) = subsx(scount - 1, 1)
subsy(scount, 1) = subsy(scount - 1, 1)

Select Case state

Case 1
    subsz(scount, 1) = subsz(scount - 1, 1) - .87

Case 2
    subsz(scount, 1) = subsz(scount - 1, 1) + .87
```

218

```
Case 3
    subsz(scount, 1) = subsz(scount - 1, 1) + .87

Case 4
    subsz(scount, 1) = subsz(scount - 1, 1) - .87

End Select subsr(scount) = .4206
subsc(scount) = 12 subt(scount) = 3 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)

END SUB

SUB thiol2 ()

'Subroutine for adding thiol group scount = scount + 1
subsx(scount, 2) = subsx(scount - 1, 1)
subsy(scount, 2) = subsy(scount - 1, 1)
subsz(scount, 2) = subsz(scount - 1, 1)

subsx(scount, 1) = subsx(scount - 1, 1)

Select Case state

Case 1
    subsy(scount, 1) = subsy(scount - 1, 1) + .76
    subsz(scount, 1) = subsz(scount - 1, 1) + .43

Case 2
    subsy(scount, 1) = subsy(scount - 1, 1) - .76
    subsz(scount, 1) = subsz(scount - 1, 1) - .43

Case 3
    subsy(scount, 1) = subsy(scount - 1, 1) + .76
    subsz(scount, 1) = subsz(scount - 1, 1) - .43

Case 4
    subsy(scount, 1) = subsy(scount - 1, 1) - .76
    subsz(scount, 1) = subsz(scount - 1, 1) + .43

End Select
``` subsr(scount) = .4206
subsc(scount) = 12 subt(scount) = 3 picture1.Line (subsx(scount, 1), subsy(scount, 1))-(subsx(scount, 2), subsy(scount, 2)), QBColor(13)
picture1.Circle (subsx(scount, 1), subsy(scount, 1)), subsr(scount), QBColor(12)

*END SUB*

APPENDIX C

Contents of file robodat.bas used by receptor generation and molecular assembly programs 0 ,-1 ,1 ,0 ,0 ,0 ,0 ,0 ,-1 ,0 ,0 ,-1 ,0 ,1 ,0 ,1 ,0 ,0 ,0 ,1 ,-1 ,0 ,0 ,0,1 ,0 ,0 ,0 ,0 ,0 ,0 ,-1 ,0 ,1 ,-1 ,0 ,1
,0 ,-1 ,0 ,0 ,0 ,1 ,0 ,0 ,0 ,-1 ,0 ,0 ,0 ,0 ,-1 ,1 ,-1 ,-1 ,0 ,0 ,0 ,0 ,0 ,0 ,0 ,0 ,-1 ,1 ,0 ,0 ,0 ,1 ,0 ,1 ,2
,15 ,1 ,12 ,9 ,11 ,13 ,7 ,17 ,6 ,22 ,18 ,24 ,4 ,3 ,5 ,16 ,14 ,20 ,23 ,19 ,10 ,21 ,8 ,4 ,6 ,7 ,23 ,1 ,20
,21 ,9 ,10 ,14 ,16 ,11 ,12 ,8 ,17 ,13 ,19 ,15 ,18 ,24 ,22 ,3 ,5 ,2 ,3 ,1 ,15 ,14 ,16 ,10 ,8 ,24 ,5 ,22 ,6
,4 ,7 ,18 ,2 ,17 ,9 ,12 ,21 ,19 ,23 ,11 ,20 ,13 ,5 ,24 ,22 ,1 ,23 ,2 ,3 ,14 ,8 ,9 ,12 ,13 ,16 ,10 ,18 ,11
,15 ,19 ,17 ,6 ,7 ,21 ,4 ,20

What is claimed is:

1. A computer-based method of designing chemical structures having a preselected functional characteristic, comprising the steps of:
   (a) producing a physical model of a simulated receptor phenotype encoded in a linear character sequence, and providing a set of target molecules sharing at least one quantifiable functional characteristic;
   (b) for each target molecule;
      (i) calculating an affinity between the receptor and the target molecule in each of a plurality of orientations using an effective affinity calculation;
      (ii) calculating a sum affinity by summing the calculated affinities;
      (iii) identifying a maximal affinity;
   (c) using the calculated sum and maximal affinities to:
      (i) calculate a maximal affinity correlation coefficient between the maximal affinities and the quantifiable functional characteristic;
      (ii) calculate a sum affinity correlation coefficient between the sum affinities and the quantifiable functional characteristic;
   (d) using the maximal correlation coefficient and sum correlation coefficient to calculate a fitness coefficient;
   (e) altering the structure of the receptor and repeating steps (b) through (d) until a population of receptors having a preselected fitness coefficient are obtained;
   (f) providing a physical model of a chemical structure encoded in a molecular linear character sequence, calculating an affinity between the chemical structure and each receptor in a plurality of orientations using said effective affinity calculation, using the calculated affinities to calculate an affinity fitness score;
   (g) altering the chemical structure to produce a variant of the chemical structure and repeating step (f); and
   (h) retaining and further altering those variants of the chemical structure whose affinity score approaches a preselected affinity score.

2. The method according to claim 1 wherein the linear character sequence encoding said receptor phenotype is produced by generating a receptor linear character sequence which codes for spatial occupancy and charge, and wherein the step of producing a physical model of a chemical structure comprises generating said molecular linear character sequence which codes for spatial occupancy and charge.

3. The method according to claim 2 wherein said effective affinity calculation comprises two measures, the first being a proximity measure wherein the proportion of uncharged portions on said simulated receptors being sufficiently close to non-polar regions on said molecular structure to generate effective London dispersion forces is estimated, and the second being the summed strengths of charge-dipole electrostatic force interactions generated between charged portions of said simulated receptor and dipoles present in said molecular structure.

4. The method according to claim 2 wherein said step of calculating the affinity fitness score includes calculating a sum and maximal affinity between the molecular structure and each receptor, the fitness score being calculated as:

$$\Sigma\{|\text{calculated maximal affinity}-\text{target maximal affinity}|/\text{target maximal affinity}\}$$

and wherein said preselected fitness score is substantially zero.

5. The method according to claim 2 wherein said step of calculating the affinity fitness score includes calculating a sum and maximal affinity between the molecular structure and each receptor, the fitness score being calculated as:

$$\Sigma\{(|\text{calculated maximal affinity}-\text{target maximal affinity}|/2\times\text{target maximal affinity})+(|\text{calculated sum affinity}-\text{target sum affinity}|/2\times\text{target sum affinity})\}$$

and wherein said preselected fitness score is substantially zero.

6. The method according to claim 2 wherein said sum affinity correlation coefficient is $r_{SA}^2$, said maximal affinity correlation coefficient is $r_{MA}^2$, and wherein said fitness coefficient is $F=(r_{MA}^2 \times r_{SA}^2)^{0.5}$, and wherein said preselected fitness coefficient is substantially unity.

7. The method according to claim 2 wherein said sum affinity correlation coefficient is $r_{SA_2MA}^2$, said maximal affinity correlation coefficient is $r_{MA}^2$, and wherein said fitness coefficient is $F=(r_{MA}^2 \times (1-r_{SA}^2))^{0.5}$, and wherein said preselected fitness coefficient is substantially unity.

8. The method according to claim 2 wherein said molecular linear character sequences comprise a plurality of sequential character triplets, a first character of said triplet being randomly selected from a first character set specifying position and identity of an occupying atom in a molecular skeleton of said molecular structure, a second character of said triplet being randomly selected from a second character set specifying the identity of a substituent group attached to said occupying atom, and a third character of said triplet being randomly selected from a third character set specifying the location of said substituent on the atom specified by said first character of the triplet.

9. The method according to claim 8 wherein the molecular linear character sequence is decoded using an effective molecular assembly algorithm which sequentially translates each triplet from said molecular linear sequence and thereafter fills unfilled positions on said molecular skeleton with hydrogen atoms.

10. The method according to claim 9 wherein the step of altering said molecular structure includes at least one of the following steps: i) mutating said molecular genotype by randomly interchanging at least one of said first, second and third characters of at least one triplet from the associated character sets, ii) deletion wherein a triplet from molecular genotype is deleted, iii) duplication wherein a triplet in the molecular genotype is duplicated, iv) inversion wherein the sequential order of one or more triplets in the molecular genotype is reversed, and v) insertion wherein a triplet from the molecular genotype is inserted at a different position in the molecular genotype.

11. The method according to claim 10 wherein the step of mutating said molecular genotypes includes recombining randomly selected pairs of said retained mutated molecular genotypes whereby corresponding characters in said molecular linear sequences are interchanged.

12. The method according to claim 2 wherein each character in the receptor linear character sequence specifies one of either a spatial turning instruction and a charged site with no turn.

13. The method according to claim 12 wherein said receptor phenotype comprises at least one linear polymer provided with a plurality of subunits, one of said subunits being a first subunit in said at least one linear polymer.

14. The method according to claim 13 wherein said receptor linear character sequence is decoded using an effective receptor assembly algorithm in which turning instructions applied to each subunit subsequent to said first subunit are made relative to an initial position of said first subunit.

15. The method according to claim 14 wherein said characters specifying spatial turning instructions code for no turn, right turn, left turn, up turn, down turn, and wherein characters specifying charge sites code for positively charged site with no turn, and negatively charged site with no turn.

16. The method according to claim 14 wherein said subunits are substantially spherical having a Van der Waals radii substantially equal to the Van der Waals radius of hydrogen.

17. The method according to claim 15 wherein the step of altering said receptor genotype includes at least one of the following steps: i) deletion wherein a character from the receptor genotype is deleted, ii) duplication wherein a character in the receptor genotype is duplicated, iii) inversion wherein the sequential order of one or more characters in the receptor genotype is reversed, and iv) insertion wherein a character from the receptor genotype is inserted at a different position in the genotype.

18. The method according to claim 17 wherein the step of mutating said receptor genotypes includes recombining randomly selected pairs of said retained mutated receptor genotypes whereby corresponding characters in said receptor linear sequences are interchanged.

19. A method of screening chemical structures for preselected functional characteristics, comprising:

a) producing a simulated receptor genotype by generating a receptor linear character sequence which codes for spatial occupancy and charge;

b) decoding the genotype to produce a receptor phenotype, providing at least one target molecule exhibiting a selected functional characteristic, calculating an affinity between the receptor and each target molecule in a plurality of orientations using an effective affinity calculation, calculating a sum and maximal affinity between each target molecule and receptor, calculating a sum affinity correlation coefficient for sum affinity versus said functional characteristic of the target molecule and a maximal affinity correlation coefficient for maximal affinity versus said functional characteristic, and calculating a fitness coefficient dependent on said sum and maximal affinity correlation coefficients;

c) mutating the receptor genotype and repeating step b) and retaining and mutating those receptors exhibiting increased fitness coefficients until a population of receptors with preselected fitness coefficients are obtained; thereafter d) calculating an affinity between a chemical structure being screened and each receptor in a plurality of orientations using said effective affinity calculation, calculating an affinity fitness score which includes calculating a sum and maximal affinity between the compound and each receptor and comparing at least one of said sum and maximal affinity to the sum and maximal affinities between said at least one target and said population of receptors whereby said comparison is indicative of the level of functional activity of said chemical structure relative to said at least one target molecule.

20. The method according to claim 19 wherein said effective affinity calculation comprises two measures, the first being a proximity measure wherein a proportion of uncharged portions on said simulated receptors being sufficiently close to non-polar regions on said molecular structure to generate effective London dispersion forces is estimated, and the second being the summed strengths of charge-dipole electrostatic force interactions generated between charged portions of said simulated receptor and dipoles present in said molecular structure.

21. The method according to claim 20 wherein the fitness score is calculated as $\Sigma\{|\text{calculated maximal affinity} - \text{target maximal affinity}|/\text{target maximal affinity}\}$.

22. The method according to claim 20 wherein the fitness score is calculated as:
$\Sigma\{(|\text{calculated maximal affinity} - \text{target maximal affinity}|/2 \times \text{target maximal affinity}) + (|\text{calculated sum affinity} - \text{target sum affinity}|/2 \times \text{target sum affinity})\}$.

23. The method according to claim 20 wherein said sum affinity correlation coefficient is $r_{SA}^2$, said maximal affinity correlation coefficient is $r_{MA}^2$, and wherein said fitness coefficient is $F=(r_{MA}^2 \times r_{SA}^2)^{0.5}$, and wherein said preselected fitness coefficient is substantially unity.

24. The method according to claim 20 wherein said sum affinity correlation coefficient is $r_{SA}^2$, said maximal affinity correlation coefficient is $r_{MA}^2$, and wherein said fitness coefficient is $F=(r_{MA}^2 \times (1-r_{SA-MA}^2))^{0.5}$, and wherein said preselected fitness coefficient is substantially unity.

25. The method according to claim 20 wherein each character in the receptor linear character sequence specifies one of either a spatial turning instruction and a charged site with no turn.

26. The method according to claim 25 wherein said receptor phenotype comprises at least one linear polymer provided with a plurality of subunits, one of said subunits being a first subunit in said at least one linear polymer.

27. The method according to claim 26 wherein said receptor linear character sequence is decoded using an effective receptor assembly algorithm in which turning instructions applied to each subunit subsequent to said first subunit are made relative to an initial position of said first subunit.

28. The method according to claim 27 wherein said characters specifying spatial turning instructions code for no turn, right turn, left turn, up turn, down turn, and wherein characters specifying charge sites code for positively charged site with no turn, and negatively charged site with no turn.

29. The method according to claim 28 wherein said subunits are substantially spherical having a Van der Waals radii substantially equal to the Van der Waals radius of hydrogen.

30. The method according to claim 27 wherein the step of mutating said receptor genotype includes at least one of the following steps: i) deletion wherein a character from the receptor genotype is deleted, ii) duplication wherein a character in the receptor genotype is duplicated, iii) inversion wherein the sequential order of one or more characters in the receptor genotype is reversed, and iv) insertion wherein a character from the receptor genotype is inserted at a different position in the genotype.

31. The method according to claim 30 wherein the step of mutating said receptor genotypes includes recombining randomly selected pairs of said retained mutated receptor genotypes whereby corresponding characters in said receptor linear sequences are interchanged.

32. A method of designing simulated receptors mimicking biological receptors exhibiting selective affinity for compounds with similar functional characteristics, comprising the steps of:

a) producing a simulated receptor genotype by generating a receptor linear character sequence which codes for spatial occupancy and charge;

b) decoding the genotype to produce a receptor phenotype, providing a set of target molecules sharing similar functional characteristics, calculating an affinity between the receptor and each target molecule in a plurality of orientations using an effective affinity calculation, calculating a sum and maximal affinity between each target molecule and receptor, calculating a sum affinity correlation coefficient for sum affinity versus a functional characteristic for each target molecule and a maximal affinity correlation coefficient for maximal affinity versus said functional characteristic for each target molecule, and calculating a fitness coefficient dependent on said sum and maximal affinity correlation coefficients for each target molecule; and c) mutating the genotype and repeating step b) and retaining and mutating those receptors exhibiting increased fitness coefficients until a population of receptors with preselected fitness coefficients are obtained.

33. The method according to claim 32 wherein each character in the receptor linear character sequence specifies one of either a spatial turning instruction and a charged site with no turn.

34. The method according to claim 33 wherein said receptor phenotype comprises a plurality of linear polymers provided with a plurality of subunits, each linear polymer being coded for by a corresponding linear character sequence, one of said subunits being a first subunit in said at least one linear polymer.

35. The method according to claim 34 wherein said receptor linear character sequence is decoded using an effective receptor assembly algorithm in which turning instructions applied to each subunit subsequent to said first subunit are made relative to an initial position of said first subunit.

36. The method according to claim 35 wherein said characters specifying spatial turning instructions code for no turn, right turn, left turn, up turn, down turn, and wherein characters specifying charge sites code for positively charged site with no turn, and negatively charged site with no turn.

37. The method according to claim 36 wherein said subunits are substantially spherical having a Van der Waals radii substantially equal to the Van der Waals radius of hydrogen.

38. The method according to claim 35 wherein the step of mutating said receptor genotype includes at least one of the following steps: i) deletion wherein a character from the receptor genotype is deleted, ii) duplication wherein a character in the receptor genotype is duplicated, iii) inversion wherein the sequential order of one or more characters in the receptor genotype is reversed, and iv) insertion wherein a character from the receptor genotype is inserted at a different position in the genotype.

39. The method according to claim 38 wherein the step of mutating said receptor genotypes includes recombining randomly selected pairs of said retained mutated receptor genotypes whereby corresponding characters in said receptor linear sequences are interchanged.

40. The method according to claim 33 wherein said effective affinity calculation comprises two measures, the first being a proximity measure wherein a proportion of uncharged portions on said simulated receptors being sufficiently close to non-polar regions on said molecular structure to generate effective London dispersion forces is estimated, and the second being the summed strengths of charge-dipole electrostatic force interactions generated between charged portions of said simulated receptor and dipoles present in said molecular structure.

41. The method according to claim 40 wherein said sum affinity correlation coefficient is $r_{SA}^2$, said maximal affinity correlation coefficient is $r_{MA}^2$, and wherein said fitness coefficient is $F=(r_{SA}^2 \times r_{MA}^2)^{0.5}$, and wherein said preselected fitness coefficient is substantially unity.

42. The method according to claim 40 wherein said sum affinity correlation coefficient is $r_{SA-MA}^2$, said maximal affinity correlation coefficient is $r_{MA}^2$, and wherein said fitness coefficient is $F=(r_{MA}^2 \times (1-r_{SA-MA}^2))^{0.5}$, and wherein said preselected fitness coefficient is substantially unity.

43. A computer-based method of designing chemical structures having a preselected functional characteristic, comprising the steps of:

(a) providing a physical model of a receptor and a set of target molecules, the target molecules sharing at least one quantifiable functional characteristic;

(b) for each target molecule;

(i) calculating an affinity between the receptor and the target molecule in each of a plurality of orientations using an effective affinity calculation;

(ii) calculating a sum affinity by summing the calculated affinities;

(iii) identifying a maximal affinity;

(c) using the calculated sum and maximal affinities to:

(i) calculate a maximal affinity correlation coefficient between the maximal affinities and the quantifiable functional characteristic;

(ii) calculate a sum affinity correlation coefficient between the sum affinities and the quantifiable functional characteristic;

(d) using the maximal correlation coefficient and sum correlation coefficient to calculate a fitness coefficient;

(e) altering the structure of the receptor and repeating steps (b) through (d) until a population of receptors having a preselected fitness coefficient are obtained;

(f) providing a physical model of a chemical structure, calculating an affinity between the chemical structure and each receptor in a plurality of orientations using said effective affinity calculation, using calculated affinities to calculate an affinity fitness score;

(g) altering the chemical strucutre to produce a variant of the chemical structure and repeating step (f); and (h) retaining and further altering those variants of the chemical structure whose affinity score approaches a preselected affinity score.

44. The method according to claim 43 wehrein the step of providing a physical model of a receptor comprises generating a receptor linear character sequence which codes for spatial occupancy and charge, and wherein the step of producing a physical model of a chemical structure comprises generating a linear character sequence which codes for spatial occupancy and charge.

45. The method according to claim 44 wherein said linear character sequences for said chemical structure comprises a plurality of sequential character triplets, a first character of said triplet being randomly selected from a first character set specifying position and identity of an occupying atom incular skeleton of said chemical strucute, a second character of said triplet being randomly selected from a second character set specifying the identity of a substituent group attached to said occupying atom, and a third character of said triplet being randomly selected from a third character set specifying the location of said substituent on the atom specified by said first character of the triplet.

46. The method according to claim 45 wherein the chemical structure linear character sequence is decoded using an effective molecular assembly algorithm which sequentially translates each triplet from said olecular linear sequence and thereafter fills unfilled positions on said molecular skeleton with hydrogen atoms.

47. A method of encoding a chemical structure comprising atomic elements, the method comprising providing a linear character sequence which codes for spatial occupancy, relative atomic position, bond type and charge for each atom to define a unique three dimensional conformation of said chemical structure.

48. The method according to claim 47 wherein said linear character sequence for said chemical structure comprises a plurality of sequential character triplets, a first character of said triplet being selected from a first character set specifying position and identity of an occupying atom in a molecular skeleton of said chemical structure, a second character of said triplet being selected from a second character set specifying the identity of a substituent group attached to said occupying atom, and a third character of said triplet being selected from a third character set specifying the location of said substituent on the atom specified by said first character of the triplet.

49. The method according to claim 45 wherein the linear character sequence is decoded using an effective molecular assembly algorithm which sequentially translates each triplet from said linear character sequence and thereafter fills unfilled positions on said molecular skeleton with preselected atoms.

50. The method according to claim 49 including the step of storing said linear character sequence in a storage means accessible by a computer.

51. The method according to claim 19 wherein said functional characteristic is biological toxicity.

52. The method according to claim 19 wherein said functional characteristic is catalytic activity.

* * * * *